(12) United States Patent
Danjo et al.

(10) Patent No.: US 11,332,455 B2
(45) Date of Patent: May 17, 2022

(54) α,β-UNSATURATED AMIDE COMPOUND

(71) Applicant: KYOWA KIRIN CO., LTD., Tokyo (JP)

(72) Inventors: Tomohiro Danjo, Chiyoda-ku (JP); Katsuaki Fujiwara, Chiyoda-ku (JP); Tomoyuki Nishikawa, Chiyoda-ku (JP); Takahiro Nakajima, Chiyoda-ku (JP); Nobumasa Otsubo, Chiyoda-ku (JP); Toshihiro Seike, Chiyoda-ku (JP)

(73) Assignee: KYOWA KIRIN CO., LTD., Tokyo (JP)

( * ) Notice: Subject to any disclaimer, the term of this patent is extended or adjusted under 35 U.S.C. 154(b) by 0 days.

(21) Appl. No.: 17/034,604

(22) Filed: Sep. 28, 2020

(65) Prior Publication Data

US 2021/0380551 A1    Dec. 9, 2021

Related U.S. Application Data

(63) Continuation of application No. 16/065,937, filed as application No. PCT/JP2016/088476 on Dec. 22, 2016, now Pat. No. 10,787,428.

(30) Foreign Application Priority Data

Dec. 24, 2015 (JP) .................. 2015-252234

(51) Int. Cl.
| | | |
|---|---|---|
| *C07D 311/68* | (2006.01) | |
| *C07D 401/04* | (2006.01) | |
| *C07D 405/12* | (2006.01) | |
| *C07D 311/74* | (2006.01) | |
| *A61K 31/5377* | (2006.01) | |
| *A61K 31/353* | (2006.01) | |
| *C07D 215/38* | (2006.01) | |
| *A61K 31/4433* | (2006.01) | |
| *A61K 31/4709* | (2006.01) | |
| *A61K 31/47* | (2006.01) | |
| *C07D 213/74* | (2006.01) | |

(Continued)

(52) U.S. Cl.
CPC .......... *C07D 311/68* (2013.01); *A61K 31/353* (2013.01); *A61K 31/4433* (2013.01); *A61K 31/47* (2013.01); *A61K 31/4709* (2013.01); *A61K 31/5377* (2013.01); *C07D 213/74* (2013.01); *C07D 213/75* (2013.01); *C07D 215/24* (2013.01); *C07D 215/38* (2013.01); *C07D 311/74* (2013.01); *C07D 401/04* (2013.01); *C07D 401/12* (2013.01); *C07D 405/12* (2013.01)

(58) Field of Classification Search
CPC .. C07D 311/68; C07D 213/74; C07D 213/75; C07D 215/24; C07D 215/38; C07D 401/04; C07D 401/12; C07D 405/12; A61K 31/353; A61K 31/4433; A61K 31/47; A61K 31/4709; A61K 31/5377

See application file for complete search history.

(56) References Cited

U.S. PATENT DOCUMENTS

| 6,002,008 A | 12/1999 | Wissner et al. |
| RE40,418 E | 7/2008 | Rabindran et al. |

(Continued)

FOREIGN PATENT DOCUMENTS

| CN | 101638383 B | 7/2013 |
| CN | 103450133 B | 7/2015 |

(Continued)

OTHER PUBLICATIONS

International Search Report and Written Opinion dated Apr. 4, 2017 in PCT/JP2016/088476 (with English translation of the Search Report only), 16 pages.

(Continued)

*Primary Examiner* — D Margaret M Seaman

(74) *Attorney, Agent, or Firm* — Oblon, McClelland, Maier & Neustadt, L.L.P.

(57) ABSTRACT

The present invention provides an α,β-unsaturated amide compound or a pharmaceutically acceptable salt or the like thereof having anticancer activity and the like represented by the following formula (I):

[Chemical formula 1]

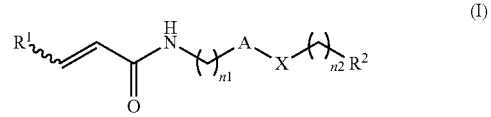

(I)

[wherein, "A" represents optionally substituted heterocyclic diyl, $R^1$ represents hydrogen atom or optionally substituted lower alkyl, $R^2$ represents optionally substituted aryl, optionally substituted cycloalkyl, optionally substituted aliphatic heterocyclic group or optionally substituted aromatic heterocyclic group, X represents —O—, —S—, —$SO_2$—, —$NR^{X1}$— (wherein, $R^{X1}$ represents hydrogen atom or lower alkyl), —$CHR^{X2}$— (wherein, $R^{X2}$ represents hydrogen atom or hydroxy), —CH=CH—, —CO— or —NH—CO—, and n1 and n2 are the same or different, and each represents 0 or 1].

3 Claims, No Drawings

(51) Int. Cl.
    *C07D 213/75*  (2006.01)
    *C07D 215/24*  (2006.01)
    *C07D 401/12*  (2006.01)

(56) References Cited

U.S. PATENT DOCUMENTS

| | | | |
|---|---|---|---|
| RE41,084 E | 1/2010 | Considine et al. | |
| RE41,253 E | 4/2010 | Rabindran et al. | |
| 9,302,991 B2 * | 4/2016 | Yamagishi | A61P 25/24 |
| 9,353,062 B2 | 5/2016 | Zhang | |
| 9,670,231 B2 | 6/2017 | Zhou | |
| 9,849,176 B2 | 12/2017 | Govindan | |
| 2002/0165229 A1 | 11/2002 | Wissner et al. | |
| 2003/0050222 A1 | 3/2003 | Rabindran et al. | |
| 2003/0229125 A1 | 12/2003 | Haaf et al. | |
| 2005/0059678 A1 | 3/2005 | Wissner et al. | |
| 2007/0197581 A1 | 8/2007 | Asberom et al. | |
| 2008/0319011 A1 | 12/2008 | Wissner et al. | |
| 2010/0016296 A1 | 1/2010 | Singh et al. | |
| 2010/0168142 A1 | 7/2010 | Guo et al. | |
| 2012/0252818 A1 | 10/2012 | Chiosis et al. | |
| 2012/0316135 A1 | 12/2012 | Dalgarno et al. | |
| 2014/0128417 A1 | 5/2014 | Shen et al. | |
| 2014/0162983 A1 | 6/2014 | Hodous et al. | |
| 2014/0206679 A1 | 7/2014 | Cheng et al. | |
| 2014/0323463 A1 | 10/2014 | Matsuya et al. | |
| 2016/0031860 A1 | 2/2016 | Shen et al. | |
| 2016/0207905 A1 | 7/2016 | Venkateshappa et al. | |
| 2017/0112833 A1 | 4/2017 | Wu | |
| 2017/0197962 A1 | 7/2017 | Huang et al. | |
| 2017/0253594 A1 | 9/2017 | Huang et al. | |
| 2018/0093975 A1 | 4/2018 | Shen et al. | |
| 2019/0218212 A1 | 7/2019 | Huang et al. | |

FOREIGN PATENT DOCUMENTS

| | | | |
|---|---|---|---|
| CN | 104761544 A | 7/2015 | |
| EP | 0 409 565 A1 | 1/1991 | |
| EP | 2 116 540 A1 | 11/2009 | |
| JP | 2002-543198 A | 12/2002 | |
| JP | 2004-536094 A | 12/2004 | |
| JP | 2009-528980 A | 8/2009 | |
| JP | 2012-524123 A | 10/2012 | |
| JP | 2013-502424 A | 1/2013 | |
| JP | 2014-514348 A | 6/2014 | |
| JP | 2014-517016 A | 7/2014 | |
| WO | WO 99/48859 A1 | 9/1999 | |
| WO | WO 2002/004445 | 1/2002 | |
| WO | WO 2004/032909 A2 | 4/2004 | |
| WO | WO 2004/106308 | 12/2004 | |
| WO | WO 2009/051822 A1 | 4/2009 | |
| WO | WO 2010/036928 A1 | 4/2010 | |
| WO | WO 2011/022440 A9 | 2/2011 | |
| WO | WO 2012/122058 A2 | 9/2012 | |
| WO | WO 2012/167600 A1 | 12/2012 | |
| WO | WO 2013/108754 A1 | 7/2013 | |
| WO | WO 2014/040555 A1 | 3/2014 | |
| WO | WO 2014/182829 A1 | 11/2014 | |
| WO | WO 2015/025197 A1 | 2/2015 | |
| WO | WO 2015/158310 A1 | 10/2015 | |
| WO | WO 2015/188777 A1 | 12/2015 | |
| WO | WO 2015/195228 A1 | 12/2015 | |
| WO | WO 2016/015453 A1 | 2/2016 | |
| WO | WO 2016/118951 A2 | 7/2016 | |

OTHER PUBLICATIONS

International Preliminary Report on Patentability and Written Opinion dated Jul. 5, 2018 in PCT/JP2016/088476 (submitting English translation only), 14 pages.

Kuramochi, T., et al., "Synthesis and Structure-Activity Relationships of Phenoxypyridine Derivatives as Novel Inhibitors of the Sodium-Calcium Exchanger", Bioorganic & Medicinal Chemistry, vol. 12, 2004, pp. 5039-5056.

Partial Supplementary European Search Report dated Jul. 9, 2019 in Patent Application No. 16878962.6, 15 pages.

Extended European Search Report dated Oct. 29, 2019 in Patent Application No. 16878962.6, 17 pages.

Asberom, T. et al. "Preparation of benzenesulfonyl-chromane, thiochromane, tetrahydronaphthalene and related gamma secretase inhibitors" Chemical Abstract Service, XP002791258, 2007, 4 pages (submitting abstract only).

Carmi, C. et al. "Irreversible Inhibition of Epidermal Growth Factor Receptor Activity by 3-Aminopropanamides" Journal of Medicinal Chemistry, vol. 55, No. 5, XP055623654, Feb. 2012, pp. 2251-2264.

Kluter, Chem Bio Chem, vol. 11, 2557-2566, 2010. (Year: 2010).
Sos, Cancer Res, vol. 70(3), 868-874, 2010. (Year: 2010).
Pawar, J Med Chem, vol. 53, 2892-2901, 2010. (Year: 2010).
Kotra, J Mol Graphics and Modeling, vol. 27, 244-254, 2008. (Year: 2008).

* cited by examiner

α,β-UNSATURATED AMIDE COMPOUND

CROSS-REFERENCE TO RELATED APPLICATION

The present patent application is a continuation of U.S. application Ser. No. 16/065,937, filed on Jun. 25, 2018, which is a national stage patent application of international patent application PCT/JP2016/088476, filed on Dec. 22, 2016, the text of which is incorporated herein by reference, and claims priority to Japanese Patent Application No. 2015-252234 filed on Dec. 24, 2015, the entire disclosure of which is incorporated herein by reference.

FIELD OF THE INVENTION

The present invention relates to an α,β-unsaturated amide compound or a pharmaceutically acceptable salt or the like thereof having anticancer activity and the like.

BACKGROUND ART

Mesothelioma is the general term for tumors derived from mesothelial cells, wherein the sites of occurrence are mainly pleura, peritoneum and pericardium. Although there are malignant and benign types, malignant mesothelioma is associated with poor prognosis and a 5-year survival rate of 10% or less. Therefore, the establishment of its treatment modality is strongly desired.

Most mesothelioma occurring in pleura and peritoneum is caused by exposure to asbestos, and it is known that the average incubation period of mesothelioma is 40 years or more (Annals of Oncology, 2015, 26, 1649-1660). Furthermore, mesothelioma is often treatment-resistant and has low response to surgical remedy, radiotherapy or chemotherapy. For chemotherapy, a combination therapy of cisplatin and pemetrexed is used (Journal of Clinical Oncology, 2003, 21, 2636-2644), but the mean survival time is only approximately 12 months.

Lung cancer is defined as canceration of part of cells belonging to trachea, bronchi, or alveoli of lung for some reason. Early detection is difficult, and the 5-year survival rate is 15% or less with poor prognosis (OncoTargets and Therapy, 2016, 9, 1023-1028). The establishment of a further treatment modality is desired.

Ovarian cancer occurs in ovaries which sit at both sides of the uterus, and there is a great variety of types of ovarian cancers such as epithelial, germ cell or sex cord-stromal tumor depending on the site of occurrence. However, 90% or more of ovarian cancer cases are epithelial tumors. The 5-year survival rate is 45% or less. It is reported that there are 15,000 fatal cases among ovarian cancers each year in the world (Best Practice & Research Clinical Obstetrics and Gynaecology, 2016, S1521-6934, 30091-30098). The establishment of a treatment modality is desired.

Liver cancer is classified roughly into two types: primary liver cancer and metastatic liver cancer that has metastasized from other organs. Primary liver cancer is classified as hepatoma and cholangioma. Most primary liver cancer is hepatoma. Primary liver cancer has a poor-prognosis, and it has been reported that the 5-year survival rate is 12 to 28% for hepatoma and, 25 to 40% for cholangioma (Journal of Gastrointestinal surgery, 2014, 18, 2136-2148). There are many cases of recurrence and the disease is resistant to systemic chemotherapy. Therefore, the establishment of a further treatment modality is desired.

As α,β-unsaturated amide compounds, known are, for example, an α,β-unsaturated amide compound having a phenyl group substituted with an aryloxy group as a melatonin receptor agonist (refer to patent document 1), an α,β-unsaturated amide compound having a phenyl group substituted with an aryloxy group as a synthetic rubber component (refer to patent document 2), an α,β-unsaturated amide compound having a phenyl group substituted with a heteroarylamino group as a protein kinase inhibitor (refer to patent document 3), an α,β-unsaturated amide compound having a phenyl group substituted with a heteroarylthio group as a Heat shock protein 70 inhibitor (refer to patent document 4), an α,β-unsaturated amide compound having a pyridyl group substituted with an aryloxy group as a sodium-potassium exchanger inhibitor (refer to non-patent document 1), an α,β-unsaturated amide compound having a quinolyl group substituted with an anilino group as an epidermal growth factor receptor inhibitor (refer to patent document 5), an α,β-unsaturated amide compound having a 3-cyanoquinolyl group as a tyrosine kinase inhibitor (refer to patent document 6), and an α,β-unsaturated amide compound having an aminopyrimidyl group as an epidermal growth factor receptor inhibitor (refer to patent document 7).

PRIOR ART DOCUMENTS

Patent Documents

[Patent Document 1] WO 1999/048859
[Patent Document 2] EP 409565(A1)
[Patent Document 3] WO 2009/051822
[Patent Document 4] WO 2011/022440
[Patent Document 5] WO 2004/032909
[Patent Document 6] U.S. Pat. No. 6,002,008
[Patent Document 7] WO 2015/188777

Non-Patent Documents

[Non-patent Document 1] Bioorganic & Medicinal Chemistry, 2004, Vol. 12, p. 5039-5056.

SUMMARY OF THE INVENTION

An object of the present invention is to provide an α,β-unsaturated amide compound or a pharmaceutically acceptable salt or the like thereof having anticancer activity and the like.

The present invention relates to the following clauses (1) to (37).

(1) An α,β-unsaturated amide compound or a pharmaceutically acceptable salt thereof represented by the following formula (I):

[Chemical formula 1]

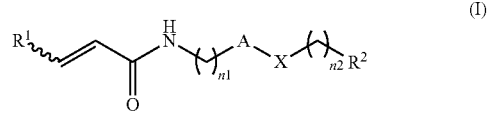

[wherein,
"A" represents optionally substituted heterocyclic diyl,
$R^1$ represents hydrogen atom or optionally substituted lower alkyl, $R^2$ represents optionally substituted aryl, optionally substituted cycloalkyl, optionally substituted aliphatic heterocyclic group or optionally substituted aromatic heterocyclic group, X represents —O—, —S—, —SO$_2$—, —NR$^{X1}$— (wherein, R$^{X1}$ represents hydrogen atom or lower alkyl), —CHR$^{X2}$— (wherein, R$^{X2}$ represents hydrogen atom or hydroxy), —CH=CH—, —CO— or —NH—CO—, and n1 and n2 are the same or different, and each represents 0 or 1].

(2) The α,β-unsaturated amide compound or a pharmaceutically acceptable salt thereof according to clause (1), wherein the heterocyclic diyl in the optionally substituted heterocyclic diyl is heterocyclic diyl selected from the group consisting of chromanediyl, 5,6,7,8-tetrahydroquinolinediyl, quinolinediyl, pyridinediyl, isoquinolinediyl, naphthyridinediyl, and 5,6,7,8-tetrahydroisoquinolinediyl.

(3) The α,β-unsaturated amide compound or a pharmaceutically acceptable salt thereof according to clause (1), wherein the heterocyclic diyl in the optionally substituted heterocyclic diyl is chromanediyl.

(4) The α,β-unsaturated amide compound or a pharmaceutically acceptable salt thereof according to clause (1), wherein the heterocyclic diyl in the optionally substituted heterocyclic diyl is heterocyclic diyl selected from the group consisting of the following formulae (A1-1), (A1-2), (A1-3), (A1-4), (A1-5), (A1-6), (A1-7) and (A1-8):

[Chemical formula 2]

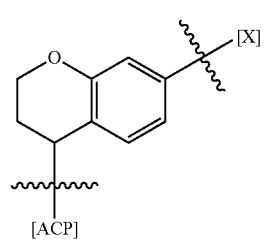

(A1-1)

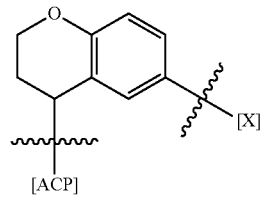

(A1-2)

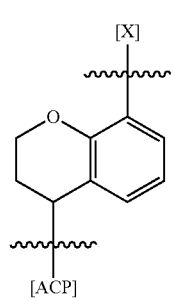

(A1-3)

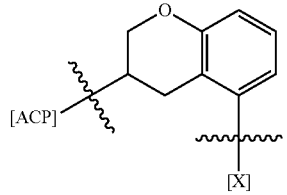

(A1-4)

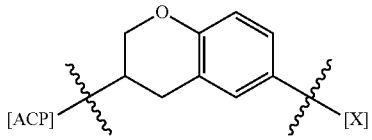

(A1-5)

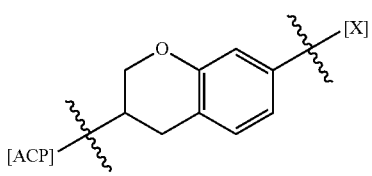

(A1-6)

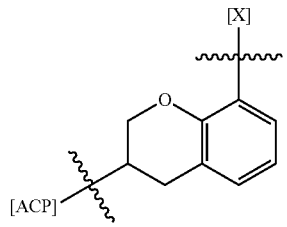

(A1-7)

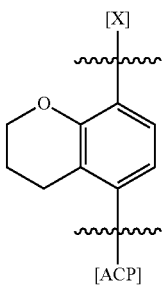

(A1-8)

{wherein, —[X] represents bonding position of the group represented in formula (A-1):

[Chemical formula 3]

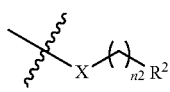

(A-1)

(wherein, X, R$^2$ and n2 are each the same as the definition described in clause (1))

-[ACP] represents bonding position of the group represented in formula (A-2):

[Chemical formula 4]

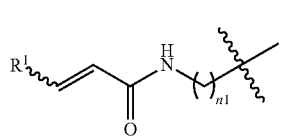
(A-2)

(wherein, $R^1$ and n1 are each the same as the definition described in clause (1))}.

(5) The α,β-unsaturated amide compound or a pharmaceutically acceptable salt thereof according to clause (1), wherein the heterocyclic diyl in the optionally substituted heterocyclic diyl is 5,6,7,8-tetrahydroquinolinediyl.

(6) The α,β-unsaturated amide compound or a pharmaceutically acceptable salt thereof according to clause (1), wherein the heterocyclic diyl in the optionally substituted heterocyclic diyl is heterocyclic diyl represented by the following formula (A2-1) or (A2-2):

[Chemical formula 5]

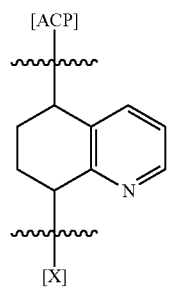
(A2-1)

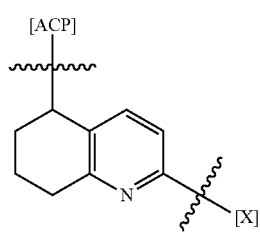
(A2-2)

(wherein, —[X] and -[ACP] are each the same as the definition described in clause (4)).

(7) The α,β-unsaturated amide compound or a pharmaceutically acceptable salt thereof according to clause (1), wherein the heterocyclic diyl in the optionally substituted heterocyclic diyl is quinolinediyl.

(8) The α,β-unsaturated amide compound or a pharmaceutically acceptable salt thereof according to clause (1), wherein the heterocyclic diyl in the optionally substituted heterocyclic diyl is heterocyclic diyl selected from the group consisting of the following formulae (A3-1), (A3-2), (A3-3), (A3-4), (A3-5), (A3-6), (A3-7), (A3-8) and (A3-9):

[Chemical formula 6]

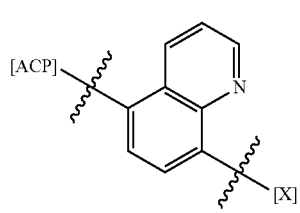
(A3-1)

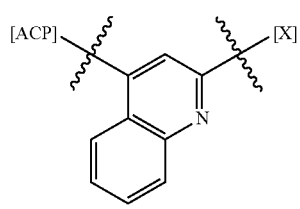
(A3-2)

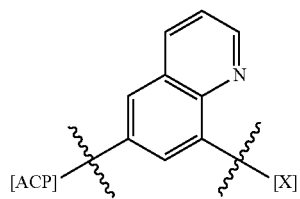
(A3-3)

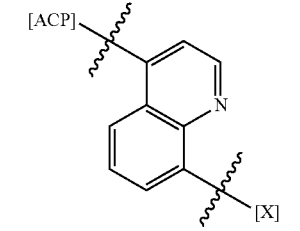
(A3-4)

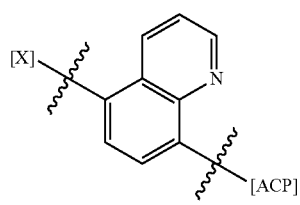
(A3-5)

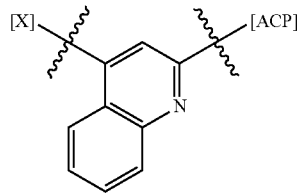
(A3-6)

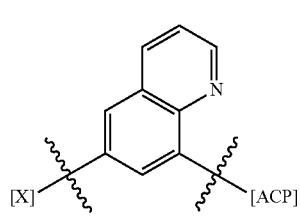
(A3-7)

-continued

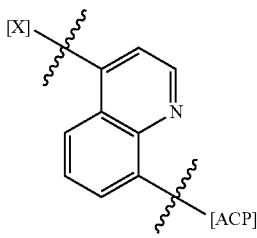
(A3-8)

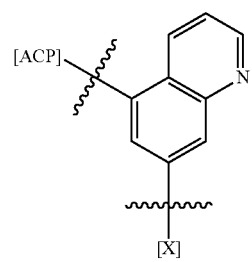
(A3-9)

(wherein, —[X] and -[ACP] are each the same as the definitions described in clause (4)).

(9) The α,β-unsaturated amide compound or a pharmaceutically acceptable salt thereof according to clause (1), wherein the heterocyclic diyl in the optionally substituted heterocyclic diyl is pyridinediyl.

(10) The α,β-unsaturated amide compound or a pharmaceutically acceptable salt thereof according to clause (1), wherein the heterocyclic diyl in the optionally substituted heterocyclic diyl is heterocyclic diyl selected from the group consisting of the following formulae (A4-1), (A4-2), (A4-3), and (A4-4):

[Chemical formula 7]

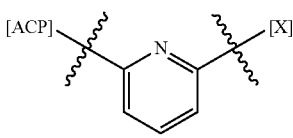
(A4-1)

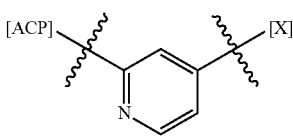
(A4-2)

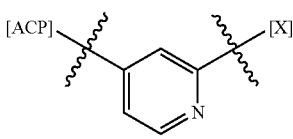
(A4-3)

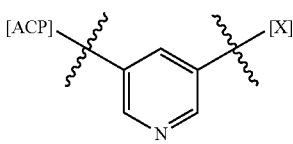
(A4-4)

(wherein, —[X] and -[ACP] are each the same as the definition described in clause (4)).

(11) The α,β-unsaturated amide compound or a pharmaceutically acceptable salt thereof according to clause (1), wherein the heterocyclic diyl in the optionally substituted heterocyclic diyl is isoquinolinediyl.

(12) The α,β-unsaturated amide compound or a pharmaceutically acceptable salt thereof according to clause (1), wherein the heterocyclic diyl in the optionally substituted heterocyclic diyl is heterocyclic diyl selected from the group consisting of the following formulae (A5-1), (A5-2), (A5-3) and (A5-4):

[Chemical formula 8]

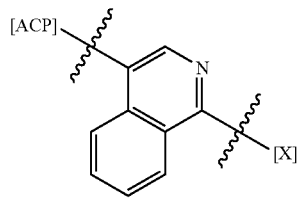
(A5-1)

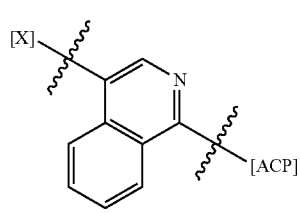
(A5-2)

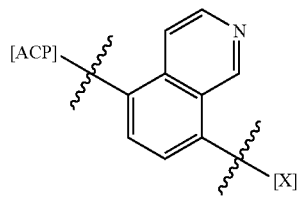
(A5-3)

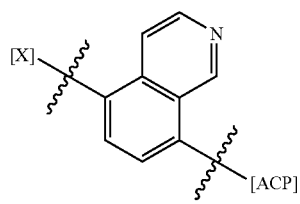
(A5-4)

(wherein, —[X] and -[ACP] are each the same as the definition described in clause (4)).

(13) The α,β-unsaturated amide compound or a pharmaceutically acceptable salt thereof according to clause (1), wherein the heterocyclic diyl in the optionally substituted heterocyclic diyl is naphthyridinediyl.

(14) The α,β-unsaturated amide compound or a pharmaceutically acceptable salt thereof according to clause (1), wherein the heterocyclic diyl in the optionally substituted heterocyclic diyl is heterocyclic diyl represented by the following formula (A6-1):

[Chemical formula 9]

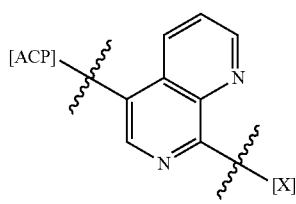

(A6-1)

(wherein, —[X] and -[ACP] are each the same as the definition described in clause (4)).

(15) The α,β-unsaturated amide compound or a pharmaceutically acceptable salt thereof according to clause (1), wherein the heterocyclic diyl in the optionally substituted heterocyclic diyl is 5,6,7,8-tetrahydroisoquinolinediyl.

(16) The α,β-unsaturated amide compound or a pharmaceutically acceptable salt thereof according to clause (1), wherein the heterocyclic diyl in the optionally substituted heterocyclic diyl is heterocyclic diyl represented by the following formula (A7-1):

[Chemical formula 10]

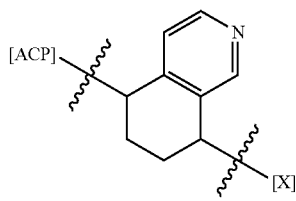

(A7-1)

(wherein, —[X] and -[ACP] are each the same as above).

(17) The α,β-unsaturated amide compound or a pharmaceutically acceptable salt thereof according to any one of clauses (1) to (16), wherein $R^1$ is hydrogen atom.

(18) The α,β-unsaturated amide compound or a pharmaceutically acceptable salt thereof according to any one of clauses (1) to (17), wherein $R^2$ is optionally substituted aryl or optionally substituted aromatic heterocyclic group.

(19) The α,β-unsaturated amide compound or a pharmaceutically acceptable salt thereof according to any one of clauses (1) to (18), wherein n1 is 0.

(20) The α,β-unsaturated amide compound or a pharmaceutically acceptable salt thereof according to any one of clauses (1) to (18), wherein n1 is 1.

(21) The α,β-unsaturated amide compound or a pharmaceutically acceptable salt thereof according to any one of clauses (1) to (20), wherein n2 is 0.

(22) The α,β-unsaturated amide compound or a pharmaceutically acceptable salt thereof according to any one of clauses (1) to (21), wherein X is —O—.

(23) A pharmaceutical composition comprising the α,β-unsaturated amide compound or a pharmaceutically acceptable salt thereof according to any one of clauses (1) to (22) and a carrier.

(24) The pharmaceutical composition according to clause (23) for the treatment or prevention of cancer.

(25) The pharmaceutical composition according to clause (24), wherein the cancer is one or two or more selected from the group consisting of mesothelioma, lung cancer, ovarian cancer, and liver cancer.

(26) A method for the treatment or prevention comprising administration of the α,β-unsaturated amide compound or a pharmaceutically acceptable salt thereof according to any one of clauses (1) to (22) to a subject.

(27) The method for the treatment or prevention according to clause (26), wherein the method is a method for the treatment or prevention of cancer.

(28) The method for the treatment or prevention according to clause (27), wherein the cancer is one or two or more selected from the group consisting of lung cancer, ovarian cancer, and liver cancer.

(29) The α,β-unsaturated amide compound or a pharmaceutically acceptable salt thereof according to any one of clauses (1) to (22) for use as a medicine.

(30) The α,β-unsaturated amide compound or a pharmaceutically acceptable salt thereof according to any one of clauses (1) to (22) for use in the treatment or prevention of cancer.

(31) The α,β-unsaturated amide compound or a pharmaceutically acceptable salt thereof according to clause (30), wherein the cancer is one or two or more selected from the group consisting of lung cancer, ovarian cancer, and liver cancer.

(32) Use of the α,β-unsaturated amide compound or a pharmaceutically acceptable salt thereof according to any one of clauses (1) to (22) for the manufacture of a medicine for treating or preventing cancer.

(33) The use according to clause (32), wherein the cancer is one or two or more selected from the group consisting of lung cancer, ovarian cancer, and liver cancer.

(34) Use of the α,β-unsaturated amide compound or a pharmaceutically acceptable salt thereof according to any one of clauses (1) to (22) for treating or preventing cancer.

(35) The use according to clause (34), wherein the cancer is one or two or more selected from the group consisting of lung cancer, ovarian cancer, and liver cancer.

(36) A medicine comprising the α,β-unsaturated amide compound or a pharmaceutically acceptable salt thereof according to any one of clauses (1) to (22) as an active ingredient.

(37) A prophylactic or therapeutic agent comprising the α,β-unsaturated amide compound or a pharmaceutically acceptable salt thereof according to any one of clauses (1) to (21) as an active ingredient.

The present invention provides an α,β-unsaturated amide compound or a pharmaceutically acceptable salt thereof or the like thereof having anticancer activity and the like.

DETAILED DESCRIPTION OF THE INVENTION

According to the present invention, an α,β-unsaturated amide compound or a pharmaceutically acceptable salt thereof represented by the following formula (I) is provided:

[Chemical formula 11]

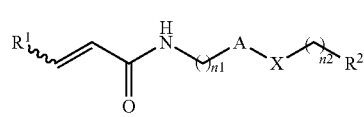

(I)

[wherein,
"A" represents optionally substituted heterocyclic diyl,
$R^1$ represents hydrogen atom or optionally substituted lower alkyl, R² represents optionally substituted aryl, optionally substituted cycloalkyl, optionally substituted aliphatic heterocyclic group or optionally substituted aromatic heterocyclic group, X represents —O—, —S—, —SO₂—, —NR$^{X1}$— (wherein, R$^{X1}$ represents hydrogen atom or lower alkyl), —CHR$^{X2}$— (wherein, R$^{X2}$ represents hydrogen atom or hydroxy), —CH=CH—, —CO— or —NH—CO—, and n1 and n2 are the same or different, and each represents 0 or 1.]

A compound represented by general formula (I) is hereinafter referred to as compound (I). The same applies to a compound of other formula number.

In the above general formula (I), "A" represents optionally substituted heterocyclic diyl.

A heterocyclic diyl group includes, for example, a group formed by removing one hydrogen atom from the group exemplified in the aliphatic heterocyclic group and the aromatic heterocyclic group in R² mentioned below, and more specifically aziridinediyl, azetidinediyl, pyrrolidinediyl, piperidinediyl, azepanediyl, 1,2,5,6-tetrahydropyridinediyl, imidazolidinediyl, pyrazolidinediyl, piperazinediyl, homopiperazinediyl, pyrazolinediyl, oxiranediyl, tetrahydrofurandiyl, tetrahydro-2H-pyrandiyl, 5,6-dihydro-2H-pyrandiyl, oxazolidinediyl, morpholinediyl, thioxazolidinediyl, thiomorpholinediyl, 2H-oxazolediyl, 2H-thioxazolediyl, dihydroindolediyl, dihydroisoindolediyl, dihydrobenzofurandiyl, benzimidazolinediyl, dihydrobenzoxazolediyl, dihydrobenzothioxazolediyl, benzodioxolediyl, 1,2,3,4-tetrahydroquinolinediyl, 5,6,7,8-tetrahydroquinolinediyl, 1,2,3,4-tetrahydroisoquinolinediyl, chromanediyl, isochromanediyl, coumarinediyl, isocoumarinediyl, 1,2,3,4-tetrahydroquinoxalinediyl, 5,6,7,8-tetrahydroquinoxalinediyl, 5,6,7,8-tetrahydroquinazolinediyl, benzodioxanediyl, furandiyl, thiophenediyl, pyrrolediyl, imidazolediyl, pyrazolediyl, oxazolediyl, isoxazoledlyl, oxadiazolediyl, thiazolediyl, isothiazolediyl, thiadiazolediyl, triazolediyl, tetrazolediyl, pyridinediyl, pyridazinediyl, pyrimidinediyl, pyrazinediyl, triazinediyl, benzofurandiyl, benzothiophenediyl, benzoxazolediyl, benzothiazolediyl, isoindolediyl, indolediyl, indazolediyl, benzimidazolediyl, benzotriazolediyl, oxazolopyrimidinediyl, thiazolopyrimidinediyl, pyrrolopyridinediyl, pyrrolopyrimidinediyl imidazopyridinediyl purinediyl quinolinediyl isoquinolinediyl cinnolinediyl phthalazinediyl quinazolinediyl, quinoxalinediyl, naphthyridinediyl, and the like. The one hydrogen atom removed may be any hydrogen atom on the aliphatic heterocyclic group or the aromatic heterocyclic group.

The heterocyclic diyl in the optionally substituted heterocyclic diyl is preferably heterocyclic diyl selected from the group consisting of chromanediyl, 5,6,7,8-tetrahydroquinolinediyl, quinolinediyl, pyridinediyl, isoquinolinediyl, naphthyridinediyl and 5,6,7,8-tetrahydroisoquinolinediyl. When the heterocyclic diyl in the optionally substituted heterocyclic diyl is chromanediyl, quinolinediyl or isoquinolinediyl, higher growth inhibition is exerted to a mesothelioma cell strain.

When the heterocyclic diyl in the optionally substituted heterocyclic diyl is chromanediyl, the chromanediyl is preferably selected from the group consisting of the following formulae (A1-1), (A1-2), (A1-3), (A1-4), (A1-5), (A1-6), (A1-7), and (A1-8):

[Chemical Formula 12]

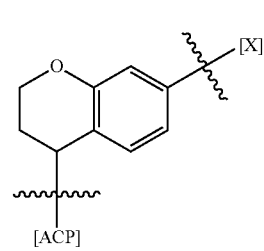
(A1-1)

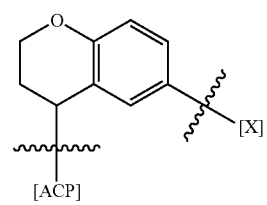
(A1-2)

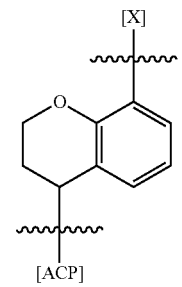
(A1-3)

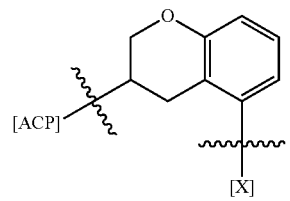
(A1-4)

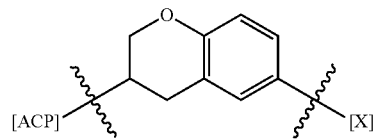
(A1-5)

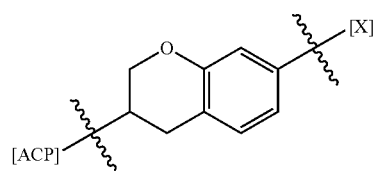
(A1-6)

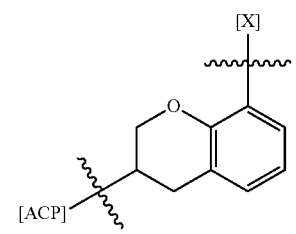
(A1-7)

-continued (A1-8)

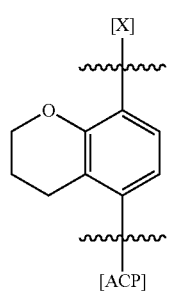

{wherein, —[X] represents bonding position of the group represented in formula (A-1):

[Chemical Formula 13]

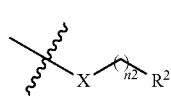
(A-1)

(wherein, X, R² and n2 are each the same as the definition described in the above formula (I))

-[ACP] represents bonding position of the group represented in formula (A-2):

[Chemical formula 14]

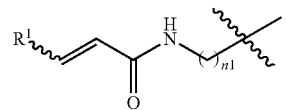
(A-2)

(wherein, R¹ and n1 are each the same as the definition described in the above formula (I))}.

When the heterocyclic diyl in the optionally substituted heterocyclic diyl is 5,6,7,8-tetrahydroquinolinediyl, the 5,6,7,8-tetrahydroquinolinediyl is preferably represented by the following formula (A2-1) or (A2-2):

[Chemical formula 15]

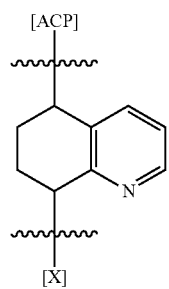
(A2-1)

-continued

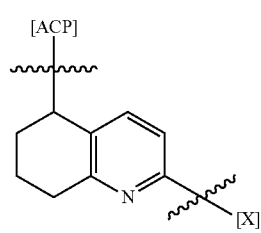
(A2-2)

(wherein, —[X] and -[ACP] are each the same as the definition described above).

When the heterocyclic diyl in the optionally substituted heterocyclic diyl is quinolinedlyl, the quinolinedlyl is preferably selected from the group consisting of the following formulae (A3-1), (A3-2), (A3-3), (A3-4), (A3-5), (A3-6), (A3-7), (A3-8), and (A3-9):

[Chemical formula 16]

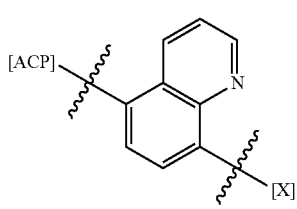
(A3-1)

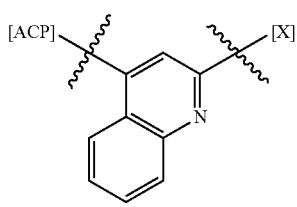
(A3-2)

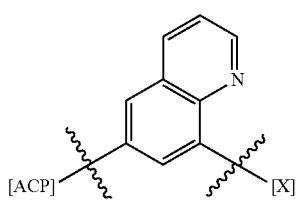
(A3-3)

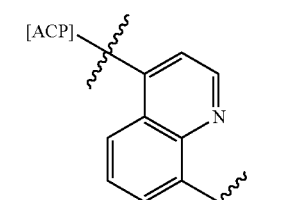
(A3-4)

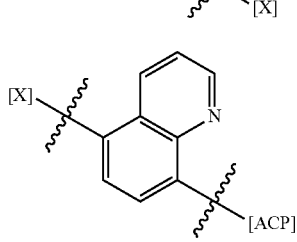
(A3-5)

(A3-6)

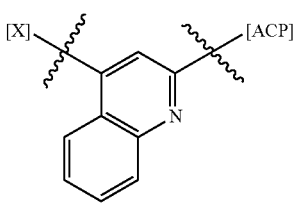

(A3-7)

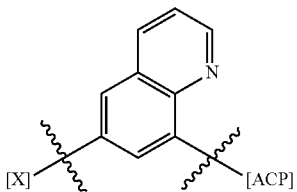

(A3-8)

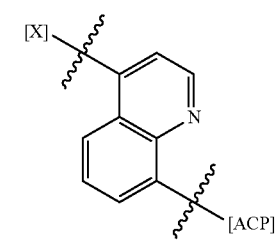

(A3-9)

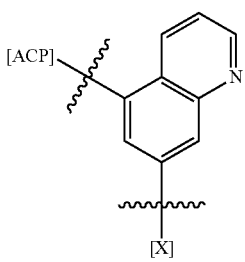

(wherein, —[X] and -[ACP] are each the same as the definitions described above).

When the heterocyclic diyl in the optionally substituted heterocyclic diyl is a pyridinediyl, the pyridinediyl is preferably selected from the group consisting of the following formulae (A4-1), (A4-2), (A4-3), and (A4-4):

[Chemical formula 17]

(A4-1)

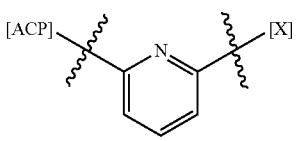

(A4-2)

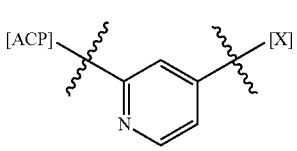

(A4-3)

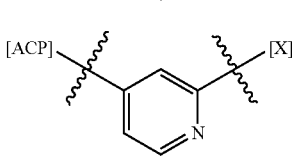

(A4-4)

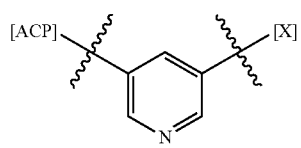

(wherein, —[X] and -[ACP] are each the same as the definition described above).

When the heterocyclic diyl in the optionally substituted heterocyclic diyl is isoquinolinediyl, the isoquinolinediyl is selected from the group consisting of the following formulae (A5-1), (A5-2), (A5-3), and (A5-4)

[Chemical formula 18]

(A5-1)

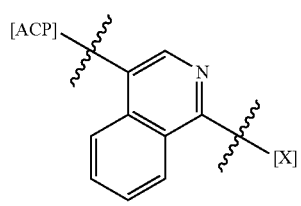

(A5-2)

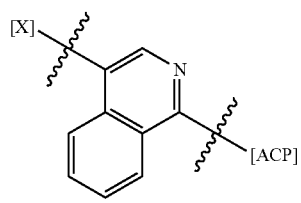

(A5-3)

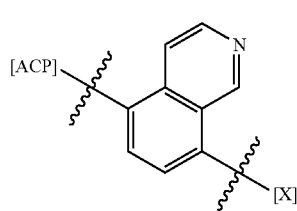

(A5-4)

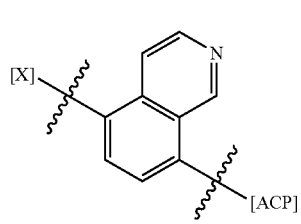

(wherein, —[X] and -[ACP] are each the same as the definition described above).

When the heterocyclic diyl in the optionally substituted heterocyclic diyl is naphthyridinediyl, the naphthyridinediyl is preferably represented by the following formula (A6-1):

[Chemical formula 19]

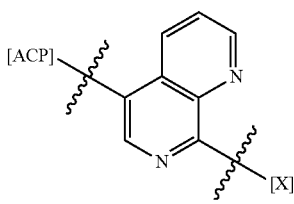

(A6-1)

(wherein, —[X] and -[ACP] are each the same as the definition described above).

When the heterocyclic diyl in the optionally substituted heterocyclic diyl is 5,6,7,8-tetrahydroisoquinolinediyl, the 5,6,7,8-tetrahydroisoquinolinediyl is preferably represented by the following formula (A7-1):

[Chemical formula 20]

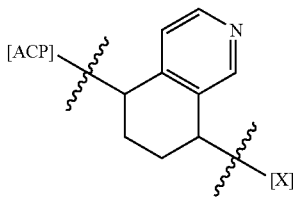

(A7-1)

(wherein, —[X] and -[ACP] are each the same as the definition described above).

In general formula (I) mentioned above, $R^1$ represents hydrogen atom or optionally substituted lower alkyl, and is preferably hydrogen atom.

Lower alkyl in the present description includes, for example, straight or branched chain alkyl having 1-10 carbon atoms and more specifically includes methyl, ethyl, propyl, isopropyl, butyl, isobutyl, sec-butyl, tert-butyl, pentyl, isopentyl, neopentyl, hexyl, heptyl, octyl, nonyl, decyl and the like.

Lower alkyl in $R^1$ is preferably straight chain alkyl having 1-3 carbon atoms, and more preferably methyl.

In general formula (I) mentioned above, $R^2$ represents optionally substituted aryl, optionally substituted cycloalkyl, optionally substituted aliphatic heterocyclic group or optionally substituted aromatic heterocyclic group, and preferably optionally substituted aryl or optionally substituted aromatic heterocyclic group.

Aryl in the present description includes, for example, aryl having 6-14 carbon atoms, and more specifically includes phenyl, naphthyl, azulenyl, and anthryl and the like.

Aryl in $R^2$ is preferably phenyl.

Cycloalkyl in the present description includes, for example, cycloalkyl having 3-10 carbon atoms, and more specifically includes cyclopropyl, cyclobutyl, cyclopentyl, cyclohexyl, cycloheptyl, cyclooctyl, cyclononyl, and cyclodecanyl and the like.

Cycloalkyl in $R^2$ is preferably cycloalkyl having 5-7 carbon atoms, and more preferably cyclohexyl.

Aliphatic heterocyclic group in the present description includes, for example, 5- or 6-membered monocyclic aliphatic heterocyclic group containing at least one atom selected from nitrogen atom, oxygen atom, and sulfur atom, and ring-fused aliphatic heterocyclic group and the like formed by fusing 3- to 8-membered rings in a bicyclic or tricyclic ring and containing at least one atom selected from nitrogen atom, oxygen atom, and sulfur atom; and more specifically includes aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, dioxanyl, 5,6-dihydro-2H-pyranyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzimidazolinyl, dihydrobenzoxazolyl, dihydrobenzothioxazolyl, benzodioxolyl, 1,2,3,4-tetrahydroquinolyl, 5,6,7,8-tetrahydroquinolyl, 1,2,3,4-tetrahydroisoquinolyl, chromanyl, isochromanyl, 2H-chromenyl, 4H-chromenyl, 1,2,3,4-tetrahydroquinoxalinyl, 5,6,7,8-tetrahydroquinoxalinyl, 5,6,7,8-tetrahydroquinazolinyl, and benzodioxanyl and the like.

Aliphatic heterocyclic group in $R^2$ is preferably 6-membered monocyclic aliphatic heterocyclic group containing 1-3 oxygen atom(s), and more preferably tetrahydro-2H-pyranyl.

Aromatic heterocyclic group in the present description includes, for example, 5- or 6-membered monocyclic aromatic heterocyclic group containing at least one atom selected from nitrogen atom, oxygen atom, and sulfur atom, and ring-fused aromatic heterocyclic group and the like formed by fusing 3- to 8-membered rings in a bicyclic or tricyclic ring and containing at least one atom selected from nitrogen atom, oxygen atom and sulfur atom, and more specifically includes furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzoxazolyl, benzothiazolyl, isoindolyl, indolyl, indazolyl, benzimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl, and the like.

Aromatic heterocyclic group in $R^2$ is preferably furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyrimidinyl, pyridazinyl, pyrazinyl, triazinyl, isoindolyl, indolyl, indazolyl, benzimidazolyl, benzotriazolyl, oxazolopyrimidinyl, thiazolopyrimidinyl, pyrrolopyridinyl, pyrrolopyrimidinyl, imidazopyridinyl, and purinyl, and more preferably a monocyclic aromatic heterocyclic group containing one or two nitrogen atom(s) (however, in general formula (I) mentioned above, $R^2$ is not pyrimidinyl when X=NH), and more preferably pyridyl, pyrimidinyl, pyridazinyl or pyrazinyl (however, in general formula (I) mentioned above, $R^2$ is not pyrimidinyl when X=NH).

Substituents in the optionally substituted lower alkyl are the same or different, and each include, for example, with the number of substitution of 1-3, a substituent selected from the group consisting of halogen, hydroxy, mercapto, nitro, cyano, carboxy, carbamoyl, $C_{3-10}$ cycloalkyl, $C_{6-14}$ aryl, aliphatic heterocyclic group, aromatic heterocyclic group, $C_{1-10}$ alkoxy, $C_{3-10}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylthio, —$NR^XR^Y$ (wherein, $R^X$ and $R^Y$ are the same or different and each represent hydrogen atom, $C_{1-10}$ alkyl, $C_{3-10}$ cycloalkyl, $C_{6-14}$ aryl, aromatic heterocyclic group, $C_{7-16}$ aralkyl, $C_{2-11}$ alkanoyl, $C_{7-15}$ aroyl, $C_{1-10}$ alkoxycarbonyl or $C_{7-16}$ aralkyloxycarbonyl), $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl, and di-$C_{1-10}$ alkylcarbamoyl.

Substituents in the optionally substituted lower alkyl in $R^1$ are preferably halogen with the number of substitution of 1-3, and more preferably fluorine atom with the number of substitution of 3.

Substituents in the aryl optionally substituted and the optionally substituted aromatic heterocyclic group are the same or different, and each include, for example, with the number of substitution of 1-3, a substituent selected from the group consisting of halogen, hydroxy, mercapto, nitro, cyano, carboxy, carbamoyl, optionally substituted $C_{1-10}$ alkyl (substituents in the optionally substituted $C_{1-10}$ alkyl are the same or different, and each include, for example, halogen with the number of substitution of 1-3 and the like), $C_{2-10}$ alkenyl, $C_{2-10}$ alkynyl, p-toluenesulfonyloxy, methanesulfonyloxy, trifluoromethanesulfonyl, trifluoromethanesulfonyloxy, $C_{3-10}$ cycloalkyl, $C_{6-14}$ aryl, aliphatic heterocyclic group, aromatic heterocyclic group, optionally substituted $C_{1-10}$ alkoxy (substituents in the optionally substituted $C_{1-10}$ alkoxy are the same or different, and each include, for example, halogen with the number of substitution of 1-3 and the like), $C_{3-10}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylthio optionally substituted (substituents in the $C_{1-10}$ alkylthio optionally substituted are the same or different, and each include, for example, halogen with the number of substitution of 1-3), —$NR^{Xa}R^{Ya}$ (wherein, $R^{Xa}$ and $R^{Ya}$ are the same or different, and each represent hydrogen atom, $C_{1-10}$ alkyl (substituents in the optionally substituted $C_{1-10}$ alkyl are the same or different, and each include, for example, with the number of substitution of 1-3, —$NR^{Xa1}R^{Ya1}$ (wherein, $R^{Xa1}$ and $R^{Ya1}$ are the same or different, and each represent hydrogen atom or $C_{1-10}$ alkyl)) and the like, $C_{3-10}$ cycloalkyl, $C_{6-14}$ aryl, aromatic heterocyclic group, $C_{7-16}$ aralkyl, $C_{2-11}$ alkanoyl, $C_{7-15}$ aroyl, $C_{1-10}$ alkoxycarbonyl or $C_{7-16}$ aralkyloxycarbonyl), $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl, and di-$C_{1-10}$ alkylcarbamoyl.

Substituents in the optionally substituted aryl are preferably, with the number of substitution of 1 or 2, halogen (preferably chlorine atom or fluorine atom), cyano, $C_{1-3}$ alkyl, trifluoromethyl, $C_{3-5}$ cycloalkyl, optionally substituted $C_{1-5}$ alkoxy (substituents in the optionally substituted $C_{1-5}$ alkoxy include fluorine atom with the number of substitution of 3), $C_{7-9}$ aralkyloxy, optionally substituted $C_{1-3}$ alkylthio (substituents in the optionally substituted $C_{1-10}$ alkylthio include fluorine atom with the number of substitution of 3) or —$NR^{Xa}R^{Ya}$ (wherein, $R^{Xa}$ and $R^{Ya}$ are the same or different and represent $C_{1-3}$ alkyl).

Substituents in the optionally substituted aromatic heterocyclic group in $R^2$ are preferably, with the number of substitution of 1 or 2, halogen (preferably chlorine atom or fluorine atom), $C_{1-3}$ alkyl, trifluoromethyl or $C_{1-5}$ alkoxy.

Substituents in the optionally substituted cycloalkyl and the optionally substituted aliphatic heterocyclic group are the same or different, and each include, for example, with the number of substitution of 1-3, a substituent selected from the group consisting of oxo, halogen (preferably fluorine atom), hydroxy, mercapto, nitro, cyano, carboxy, carbamoyl, $C_{1-10}$ alkyl, fluoromethyl, difluoromethyl, trifluoromethyl, $C_{3-10}$ cycloalkyl, $C_{6-14}$ aryl, optionally substituted aliphatic heterocyclic group (substituents in the optionally substituted aliphatic heterocyclic group are the same or different, and include, for example, halogen with the number of substitution of 1-3 and the like), aromatic heterocyclic group, $C_{1-10}$ alkoxy, $C_{3-10}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylthio, —$NR^{Xb}R^{Yb}$ (wherein, $R^{Xb}$ and $R^{Yb}$ are the same or different, and each represent hydrogen atom, $C_{1-10}$ alkyl, $C_{3-10}$ cycloalkyl, $C_{6-14}$ aryl, aromatic heterocyclic group, $C_{7-16}$ aralkyl, $C_{2-11}$ alkanoyl, $C_{7-15}$ aroyl, $C_{1-10}$ alkoxycarbonyl or $C_{7-16}$ aralkyloxycarbonyl), $C_{2-11}$ alkanoyl, $C_{7-15}$ aroyl, $C_{1-10}$ alkoxycarbonyl, $C_{6-14}$ aryloxy carbonyl, $C_{1-10}$ alkylcarbamoyl and di-$C_{1-10}$ alkylcarbamoyl.

Substituents in the optionally substituted cycloalkyl in $R^2$ preferably are optionally substituted with trifluoromethyl or two fluorine atoms.

Substituents in the optionally substituted aliphatic heterocyclic group in $R^2$ are optionally substituted with $C_{1-3}$ alkyl.

Substituents in the optionally substituted heterocyclic diyl are the same or different, and each include, for example, with the number of substitution of 1-3, a substituent selected from the group consisting of halogen (preferably chlorine atom, fluorine atom or bromine atom), hydroxy, mercapto, nitro, cyano, carboxy, carbamoyl, $C_{1-10}$ alkyl, $C_{2-10}$ alkenyl, $C_{2-10}$ alkynyl, trifluoromethyl, p-toluenesulfonyloxy, methanesulfonyloxy, trifluoromethanesulfonyloxy, $C_{3-10}$ cycloalkyl, $C_{6-14}$ aryl, optionally substituted aliphatic heterocyclic group (substituents in the optionally substituted aliphatic heterocyclic group are the same or different, and each include, for example, halogen with the number of substitution of 1-3 and the like), aromatic heterocyclic group, optionally substituted $C_{1-10}$ alkoxy (substituents in the optionally substituted $C_{1-10}$ alkoxy are the same or different, and each include, for example, halogen with the number of substitution of 1-3 and the like), $C_{3-10}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylthio, —$NR^{Xc}R^{Yc}$ (wherein, $R^{Xc}$ and $R^{Yc}$ are the same or different, and each represent hydrogen atom, optionally substituted $C_{1-10}$ alkyl (substituents in the optionally substituted $C_{1-10}$ alkyl are the same or different, and each include for example, with the number of substitution of 1-3, $C_{1-10}$ alkylamino, and di-$C_{1-10}$ alkylamino and the like), $C_{3-10}$ cycloalkyl, $C_{6-14}$ aryl, aromatic heterocyclic group, $C_{7-16}$ aralkyl, $C_{2-11}$ alkanoyl, $C_{7-15}$ aroyl, $C_{1-10}$ alkoxycarbonyl or $C_{7-16}$ aralkyloxycarbonyl), $C_{2-11}$ alkanoyl, $C_{7-15}$ aroyl, $C_{1-10}$ alkoxycarbonyl, $C_{6-14}$ aryloxy carbonyl, $C_{1-10}$ alkylcarbamoyl, and di-$C_{1-10}$ alkylcarbamoyl.

Substituents in the optionally substituted heterocyclic diyl preferably are not cyano group, and more preferably are, with the number of substitution of 1-3, a substituent selected from the group consisting of halogen (preferably chlorine atom, fluorine atom or bromine atom), hydroxy, mercapto, nitro, carboxy, carbamoyl, $C_{1-10}$ alkyl, $C_{2-10}$ alkynyl, trifluoromethyl, p-toluenesulfonyloxy, methanesulfonyloxy, trifluoromethanesulfonyloxy, $C_{3-10}$ cycloalkyl, $C_{6-14}$ aryl, optionally substituted aliphatic heterocyclic group (substituents in the optionally substituted aliphatic heterocyclic group are the same or different, and each include, for example, halogen with the number of substitution of 1-3 and the like), aromatic heterocyclic group, optionally substituted $C_{1-10}$ alkoxy (substituents in the optionally substituted $C_{1-10}$ alkoxy are the same or different, and each include, for example, halogen with the number of substitution of 1-3 and the like), $C_{3-10}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylthio, —$NR^{Xc}R^{Yc}$ (wherein, $R^{Xc}$ and $R^{Yc}$ are the same or different, and each represent hydrogen atom, optionally substituted $C_{1-10}$ alkyl (substituents in the optionally substituted $C_{1-10}$ alkyl are the same or different, and each include, for example, di-$C_{1-10}$ alkylamino with the number of substitution of 1-3 and the like), $C_{3-10}$ cycloalkyl, $C_{6-14}$ aryl, aromatic heterocyclic group, $C_{7-16}$ aralkyl, $C_{2-11}$ alkanoyl, $C_{7-15}$ aroyl, $C_{1-10}$ alkoxycarbonyl or $C_{7-16}$ aralkyloxycarbonyl), $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl and the di-$C_{1-10}$ alkylcarbamoyl; and are more preferably, with the number of substitution of 1 or 2, halogen (preferably chlorine atom, fluorine atom or bromine atom), hydroxy, cyano, $C_{1-3}$ alkyl, $C_{3-5}$ cycloalkyl, oxo, $C_{1-3}$ alkoxy, —$NR^{Xa}R^{Ya}$ (wherein, $R^{Xa}$ and $R^{Ya}$ are the same or different, and include $C_{1-3}$ alkyl), optionally substituted 4- to 6-membered monocyclic aliphatic heterocyclic group having one nitrogen atom and/or one oxygen atom (substituents in the optionally substituted 4- to 6-membered monocyclic aliphatic heterocyclic group include fluorine atom with the number of substitution of 2) or optionally substituted $C_{1-3}$ alkyl (substituents in the optionally substituted $C_{1-3}$ alkyl include di-$C_{1-3}$ alkylamino with the number of substitution of 1-3 and the like).

In general formula (I) mentioned above, X represents —O—, —S—, —$SO_2$—, —$NR^{X1}$— (wherein, $R^{X1}$ represents hydrogen atom or lower alkyl), —$CHR^{X2}$— (wherein, $R^{X2}$ represents hydrogen atom or hydroxy), —CH=CH—, —CO— or —NH—CO—, preferably —O—, —S—, —$NR^{X1}$— (wherein, $R^{X1}$ represents hydrogen atom or lower alkyl), —$CHR^{X2}$— (wherein, $R^{X2}$ represents hydrogen atom), —CH=CH— or —CO, and more preferably —O—.

In general formula (I) mentioned above, n1 and n2 are the same or different, and each represent 0 or 1. n2 is preferably 0.

When substituents in the optionally substituted heterocyclic diyl are bonded, in the heterocyclic diyl, to an aliphatic heterocycle moiety (the aliphatic heterocycle includes, for example, an aliphatic heterocycle formed by bonding hydrogen atom to a bonding group of the above-exemplified aliphatic heterocyclic groups) and/or a cycloalkane moiety (the cycloalkane includes, for example, a cycloalkane formed by bonding hydrogen atom to a bonding group of the above-exemplified cycloalkyl groups), the above substituent may be, for example, oxo with the number of substitution of 1-3.

That is, when substituents in the optionally substituted heterocyclic diyl are bonded to an $sp^3$ carbon constituting the heterocyclic diyl, the above substituent may be, for example, substituted with oxo with the number of substitution of 1-3. Here, the $sp^3$ carbon refers to a carbon atom forming an $sp^3$ hybrid orbit. In the present description, a $sp^2$ carbon also similarly refers to a carbon atom forming $sp^2$ hybrid orbit.

Alkyl moieties of $C_{1-3}$ alkyl and $C_{1-10}$ alkyl, $C_{1-3}$ alkoxy, $C_{1-5}$ alkoxy, $C_{1-5}$ alkoxy, $C_{2-11}$ alkanoyloxy, $C_{1-3}$ alkylthio, $C_{1-10}$ alkylthio, $C_{2-11}$ alkanoyl, $C_{1-10}$ alkoxycarbonyl, $C_{1-10}$ alkylamino, di-$C_{1-3}$ alkylamino, di-$C_{1-10}$ alkylamino, $C_{1-10}$ alkylcarbamoyl, and di-$C_{1-10}$ alkylcarbamoyl, as shown here, are exemplified, for example, by the groups given in the above lower alkyl examples. Two alkyl moieties in di-$C_{1-3}$ alkylamino, di-$C_{1-10}$ alkylamino, and di-$C_{1-10}$ alkylcarbamoyl may be the same or different.

Cycloalkyl moieties of $C_{3-5}$ cycloalkyl and $C_{3-10}$ cycloalkyl and $C_{3-10}$ cycloalkoxy are exemplified, for example, by the groups given in the above cycloalkyl examples.

Aryl moieties of $C_{6-14}$ aryl and $C_{6-14}$ aryloxy, $C_{7-15}$ aroyl, $C_{7-15}$ aroyloxy and $C_{6-14}$ aryloxycarbonyl are exemplified by the groups given in the above aryl examples.

Aryl moieties of $C_{7-9}$ aralkyloxy, $C_{7-16}$ aralkyloxy, $C_{7-16}$ aralkyl, and $C_{7-16}$ aralkyloxycarbonyl are exemplified by the groups given in the above aryl examples. Alkyl moiety thereof include, for example, $C_{1-10}$ alkylene, and more specifically a group formed by removing one hydrogen atom from the groups given in the above lower alkyl examples.

$C_{2-10}$ alkenyl represents, for example, straight or branched chain alkenyl having 2-10 carbon atoms, and more specifically includes vinyl, propenyl, butenyl, pentenyl, hexenyl, heptenyl, octenyl, nonenyl, and decenyl and the like.

In the present description, $C_{2-10}$ alkynyl represents, for example, straight or branched chain alkynyl having 2-10 carbon atoms, and more specifically includes ethynyl, propynyl, butynyl, pentynyl, hexynyl, heptynyl, octynyl, nonynyl, and decynyl and the like.

In the present description, aliphatic heterocyclic group and aromatic heterocyclic group are the same as defined above, respectively.

In the present description, halogen means fluorine, chlorine, bromine or iodine atom.

According to a preferred embodiment of the compound (compound (I)) represented by general formula (I), in the above formula (I), "A" represents optionally substituted heterocyclic diyl, wherein the heterocyclic diyl is heterocyclic diyl selected from the group consisting of chromanediyl, 5,6,7,8-tetrahydroquinolinediyl, quinolinediyl, pyridinediyl, isoquinolinediyl, naphthyridinediyl, and 5,6,7,8-tetrahydroisoquinolinediyl, the heterocyclic diyl is optionally substituted with, with the number of substitution of 1 or 2, halogen (preferably chlorine atom, fluorine atom or bromine atom), hydroxy, cyano, trifluoromethyl, $C_{2-5}$ alkanoyloxy, $C_{1-3}$ alkyl, $C_{3-5}$ cycloalkyl, oxo, $C_{1-3}$ alkoxy, —$NR^{Xa}R^{Ya}$ (wherein, $R^{Xa}$ and $R^{Ya}$ are the same or different, and include $C_{1-3}$ alkyl), optionally substituted 4- to 6-membered monocyclic aliphatic heterocyclic group having one nitrogen atom and/or one oxygen atom (substituents in the optionally substituted 4- to 6-membered monocyclic aliphatic heterocyclic group include fluorine atom with the number of substitution of 2) or optionally substituted $C_{1-3}$ alkyl (substituents in the optionally substituted $C_{1-3}$ alkyl include di-$C_{1-3}$ alkylamino with the number of substitution of 1-3 and the like), $R^1$ represents hydrogen atom or optionally substituted $C_{1-3}$ alkyl (preferably trifluoromethyl), $R^2$ represents optionally substituted aryl, optionally substituted cycloalkyl, optionally substituted aliphatic heterocyclic group or optionally substituted aromatic heterocyclic group, wherein, the optionally substituted aryl is optionally substituted phenyl, and the phenyl is optionally substituted with, with the number of substitution of 1 or 2, halogen (preferably chlorine atom or fluorine atom), cyano, $C_{1-3}$ alkyl, trifluoromethyl, $C_{3-5}$ cycloalkyl, optionally substituted $C_{1-5}$ alkoxy (substituents in the optionally substituted $C_{1-5}$ alkoxy include fluorine atom with the number of substitution of 3), $C_{7-9}$ aralkyloxy, optionally substituted $C_{1-3}$ alkylthio (substituents in the optionally substituted $C_{1-3}$ alkylthio include fluorine atom with the number of substitution of 3), —$NR^{Xa}R^{Ya}$ (wherein, $R^{Xa}$ and $R^{Ya}$ are the same or different and represent $C_{1-3}$ alkyl) or trifluoromethane sulfonyl, the optionally substituted cycloalkyl is optionally substituted cycloalkyl having 5-7 carbon atoms (preferably cyclohexyl), and the cycloalkyl is optionally unsubstituted or substituted with trifluoromethyl or two fluorine atoms, the optionally substituted aliphatic heterocyclic group is optionally substituted 6-membered monocyclic aliphatic heterocyclic group having one oxygen atom (preferably tetrahydro-2H-pyranyl group), and the aliphatic heterocyclic group is optionally substituted with $C_{1-3}$ alkyl, the optionally substituted aromatic heterocyclic group is monocyclic aromatic heterocyclic group having one or two nitrogen atom(s) (preferably pyridyl, pyrimidinyl, pyridazinyl or pyrazinyl) (however, in general formula (I) mentioned above, $R^2$ is not pyrimidinyl when X=NH), and the aromatic heterocyclic group is optionally substituted, with the number of substitution of 1 or 2, with halogen (preferably chlorine atom or fluorine atom), oxo, $C_{1-3}$ alkyl, trifluoromethyl or $C_{1-5}$ alkoxy, X represents —O—, and n1 and n2 are the same or different and each represent 0 or 1.

According to a more preferred embodiment of the compound (compound (1)) represented by general formula (I), in the above formula (I), "A" represents optionally substituted heterocyclic diyl, wherein the heterocyclic diyl in the optionally substituted heterocyclic diyl is heterocyclic diyl selected from the group consisting of chromanediyl, 5,6,7,8-tetrahydroquinolinediyl, quinolinediyl, pyridinediyl, isoquinolinediyl, naphthyridinediyl and 5,6,7,8-tetrahydroisoquinolinediyl, the heterocyclic diyl is optionally substituted with, with the number of substitution of 1 or 2, halogen (preferably chlorine atom, fluorine atom or bromine atom), hydroxy, cyano, trifluoromethyl, $C_{2-5}$ alkanoyloxy, $C_{1-3}$ alkyl, $C_{3-5}$ cycloalkyl, oxo, $C_{1-3}$ alkoxy, —NR$^{Xa}$R$^{Ya}$ (wherein, R$^{Xa}$ and R$^{Ya}$ are the same or different, and include $C_{1-3}$ alkyl), optionally substituted 4- to 6-membered monocyclic aliphatic heterocyclic group having one nitrogen atom and/or one oxygen atom (substituents in the optionally substituted 4- to 6-membered monocyclic aliphatic heterocyclic group include fluorine atom with the number of substitution of 2) or optionally substituted $C_{1-3}$ alkyl (substituents in the optionally substituted $C_{1-3}$ alkyl include di-$C_{1-3}$ alkylamino with the number of substitution of 1-3 and the like), $R^1$ represents hydrogen atom or optionally substituted $C_{1-3}$ alkyl (preferably trifluoromethyl), $R^2$ represents optionally substituted aryl, optionally substituted cycloalkyl, optionally substituted aliphatic heterocyclic group or optionally substituted aromatic heterocyclic group, wherein, the optionally substituted aryl is optionally substituted phenyl, and the phenyl is optionally substituted with, with the number of substitution of 1 or 2, halogen (preferably chlorine atom or fluorine atom), cyano, $C_{1-3}$ alkyl, trifluoromethyl, $C_{3-5}$ cycloalkyl, optionally substituted $C_{1-5}$ alkoxy (substituents in the optionally substituted $C_{1-5}$ alkoxy include fluorine atom with the number of substitution of 3), $C_{7-9}$ aralkyloxy, optionally substituted $C_{1-3}$ alkylthio (substituents in the optionally substituted $C_{1-10}$ alkylthio include fluorine atom with the number of substitution of 3) or —NR$^{Xa}$R$^{Ya}$ (wherein, R$^{Xa}$ and R$^{Ya}$ are the same or different and represent $C_{1-3}$ alkyl), the optionally substituted cycloalkyl is optionally substituted cycloalkyl having 5-7 carbon atoms (preferably cyclohexyl), and the cycloalkyl is optionally unsubstituted or substituted with trifluoromethyl or two fluorine atoms, the optionally substituted aliphatic heterocyclic group is optionally substituted 6-membered monocyclic aliphatic heterocyclic group having one oxygen atom (preferably tetrahydro-2H-pyranyl group), and the aliphatic heterocyclic group is optionally substituted with $C_{1-3}$ alkyl, the optionally substituted aromatic heterocyclic group is a monocyclic aromatic heterocyclic group having one or two nitrogen atom(s) (preferably pyridyl, pyrimidinyl, pyridazinyl or pyrazinyl) (however, in general formula (I) mentioned above, $R^2$ is not pyrimidinyl when X=NH), and the aromatic heterocyclic group is optionally substituted, with the number of substitution of 1 or 2, with halogen (preferably chlorine atom or fluorine atom), $C_{1-3}$ alkyl, trifluoromethyl or $C_{1-5}$ alkoxy, X represents —O—, and n1 and n2 are the same or different and each represent 0 or 1.

According to a more preferred embodiment of the compound (compound (I)) represented by general formula (I), in the above formula (I), "A" represents optionally substituted chromanediyl, wherein the chromanediyl is optionally substituted with, with the number of substitution of 1 or 2, halogen (preferably chlorine atom, fluorine atom or bromine atom), oxo, hydroxy, trifluoromethyl, $C_{2-5}$ alkanoyloxy, $C_{1-3}$ alkoxy, $C_{1-3}$ alkyl or —NR$^{Xa}$R$^{Ya}$ (wherein, R$^{Xa}$ and R$^{Ya}$ are the same or different, and include $C_{1-3}$ alkyl), $R^1$ represents hydrogen atom or optionally substituted $C_{1-3}$ alkyl (preferably trifluoromethyl), $R^2$ represents optionally substituted aryl or optionally substituted cycloalkyl, wherein, the optionally substituted aryl is optionally substituted phenyl, and the phenyl is optionally substituted with, with the number of substitution of 1 or 2, halogen (preferably chlorine atom or fluorine atom), cyano, $C_{1-3}$ alkyl, trifluoromethyl, optionally substituted $C_{1-5}$ alkoxy (substituents in the optionally substituted $C_{1-5}$ alkoxy include fluorine atom with the number of substitution of 3), optionally substituted $C_{1-3}$ alkylthio (substituents in the optionally substituted $C_{1-3}$ alkylthio include fluorine atom with the number of substitution of 3) or trifluoromethanesulfonyl, the optionally substituted cycloalkyl is a optionally substituted cycloalkyl having 5-7 carbon atoms (preferably cyclohexyl), and the cycloalkyl is optionally unsubstituted or substituted with two fluorine atoms, X represents —O—, and n1 and n2 are the same or different and each represent 0 or 1.

According to another more preferred embodiment of the compound (compound (1)) represented by general formula (I), in the above formula (I), "A" represents optionally substituted chromanediyl, wherein the chromanediyl is optionally substituted with, with the number of substitution of 1 or 2, halogen (preferably chlorine atom, fluorine atom or bromine atom), oxo, hydroxy, trifluoromethyl, $C_{2-5}$ alkanoyloxy, $C_{1-3}$ alkoxy, $C_{1-3}$ alkyl or —NR$^{Xa}$R$^{Ya}$ (wherein, R$^{Xa}$ and R$^{Ya}$ are the same or different, and include $C_{1-3}$ alkyl), $R^1$ represents hydrogen atom or optionally substituted $C_{1-3}$ alkyl (preferably trifluoromethyl), $R^2$ represents optionally substituted aromatic heterocyclic group, wherein the optionally substituted aromatic heterocyclic group is a monocyclic aromatic heterocyclic group having one or two nitrogen atom(s) (preferably pyridyl, pyrimidinyl, pyridazinyl or pyrazinyl), and the aromatic heterocyclic group is optionally substituted, with the number of substitution of 1 or 2, with halogen (preferably chlorine atom or fluorine atom), $C_{1-3}$ alkyl, trifluoromethyl or $C_{1-5}$ alkoxy, X represents —O—, and n1 and n2 are the same or different and each represent 0 or 1.

According to a further preferred embodiment of the compound (compound (1)) represented by general formula (I), in the above formula (I), "A" represents unsubstituted chromanediyl, $R^1$ represents hydrogen atom, $R^2$ represents optionally substituted phenyl, wherein the phenyl is optionally substituted with, with the number of substitution of 1 or 2, halogen (preferably chlorine atom or fluorine atom), cyano, $C_{1-3}$ alkyl, trifluoromethyl, optionally substituted $C_{1-5}$ alkoxy (substituents in the optionally substituted $C_{1-5}$ alkoxy include fluorine atom with the number of substitution of 3) or optionally substituted $C_{1-3}$ alkylthio (substituents in the optionally substituted $C_{1-3}$ alkylthio include fluorine atom with the number of substitution of 3), X represents —O—, and n1 and n2 are the same or different and each represent 0 or 1 (n2 preferably represents 0).

According to another further preferred embodiment of the compound (compound (I)) represented by general formula (I), in the above formula (I), "A" represents unsubstituted chromanediyl, $R^1$ represents hydrogen atom, $R^2$ represents optionally substituted aromatic heterocyclic group, wherein the optionally substituted aromatic heterocyclic group is a monocyclic aromatic heterocyclic group having one or two nitrogen atom(s) (preferably pyridyl, pyrimidinyl, pyridazinyl or pyrazinyl), and the aromatic heterocyclic group is optionally substituted, with the number of substitution of 1 or 2, with halogen (preferably chlorine atom or fluorine atom), $C_{1-3}$ alkyl, trifluoromethyl or $C_{1-5}$ alkoxy, X represents —O—, and n1 and n2 are the same or different and each represent 0 or 1 (n2 preferably represents 0).

According to another more preferred embodiment of the compound (compound (I)) represented by general formula (I), in the above formula (I), "A" represents optionally substituted quinolinediyl, wherein the quinolinedlyl is optionally substituted with, with the number of substitution of 1 or 2, halogen (preferably chlorine atom), hydroxy or $C_{1-3}$ alkyl, $R^1$ represents hydrogen atom, $R^2$ represents optionally substituted aryl, wherein the optionally substituted aryl is optionally substituted phenyl, and the phenyl is optionally substituted with, with the number of substitution of 1 or 2, halogen (preferably chlorine atom or fluorine atom), $C_{2-5}$ alkynyl, cyano, $C_{1-3}$ alkyl, trifluoromethyl, $C_{3-5}$ cycloalkyl, optionally substituted $C_{1-5}$ alkoxy (substituents in the optionally substituted $C_{1-5}$ alkoxy include fluorine atom with the number of substitution of 3), $C_{7-9}$ aralkyloxy, optionally substituted $C_{1-3}$ alkylthio (substituents in the optionally substituted $C_{1-10}$ alkylthio include fluorine atom with the number of substitution of 3), or —$NR^{Xa}R^{Ya}$ (wherein, $R^{Xa}$ and $R^{Ya}$ are the same or different and represent $C_{1-3}$ alkyl), X represents —O—, and n1 and n2 are the same or different and each represent 0 or 1.

According to another more preferred embodiment of the compound (compound (I)) represented by general formula (I), in the above formula (I), "A" represents optionally substituted quinolinediyl, wherein the quinolinediyl is optionally substituted with, with the number of substitution of 1 or 2, halogen (preferably chlorine atom), hydroxy or $C_{1-3}$ alkyl, $R^1$ represents hydrogen atom, $R^2$ represents optionally substituted aromatic heterocyclic group, wherein the optionally substituted aromatic heterocyclic group is a monocyclic aromatic heterocyclic group having one or two nitrogen atom(s) (preferably pyridyl, pyrimidinyl, pyridazinyl or pyrazinyl) (however, in general formula (I) mentioned above, $R^2$ is not pyrimidinyl when X=NH), and the aromatic heterocyclic group is optionally substituted, with the number of substitution of 1 or 2, with halogen (preferably chlorine atom or fluorine atom), $C_{1-3}$ alkyl, trifluoromethyl or $C_{1-5}$ alkoxy, X represents —O—, and n1 and n2 are the same or different and each represent 0 or 1.

According to another further preferred embodiment of the compound (compound (I)) represented by general formula (I), in the above formula (I), "A" represents unsubstituted quinolinediyl, $R^1$ represents hydrogen atom, $R^2$ represents optionally substituted phenyl, wherein the phenyl is optionally substituted with, with the number of substitution of 1 or 2, halogen (preferably chlorine atom), $C_{2-5}$ alkynyl, trifluoromethyl, or $C_{3-5}$ cycloalkyl, X represents —O—, and n1 and n2 are the same or different and each represent 0 or 1 (n2 preferably represents 0).

According to another further preferred embodiment of the compound (compound (I)) represented by general formula (I), in the above formula (I), "A" represents unsubstituted quinolinediyl, $R^1$ represents hydrogen atom, $R^2$ represents optionally substituted aromatic heterocyclic group, wherein the optionally substituted aromatic heterocyclic group is a monocyclic aromatic heterocyclic group having one or two nitrogen atom(s) (preferably pyridyl, pyrimidinyl, pyridazinyl or pyrazinyl), and the aromatic heterocyclic group is optionally substituted, with the number of substitution of 1 or 2, with halogen (preferably chlorine atom or fluorine atom), $C_{1-3}$ alkyl, trifluoromethyl or $C_{1-5}$ alkoxy, X represents —O—, and n1 and n2 are the same or different and each represent 0 or 1 (n2 preferably represents 0).

According to another more preferred embodiment of the compound (compound (1)) represented by general formula (I), in the above formula (I), "A" represents optionally substituted pyridinedlyl, wherein the pyridinediyl is optionally substituted with, with the number of substitution of 1 or 2, halogen (preferably chlorine atom), hydroxy or $C_{1-3}$ alkyl, $R^1$ represents hydrogen atom or a $C_{1-3}$ alkyl (preferably methyl), $R^2$ represents optionally substituted aryl, wherein the optionally substituted aryl is optionally substituted phenyl, and the phenyl is optionally substituted with, with the number of substitution of 1 or 2, halogen (preferably chlorine atom or fluorine atom), cyano, $C_{1-3}$ alkyl, trifluoromethyl, $C_{3-5}$ cycloalkyl, optionally substituted $C_{1-5}$ alkoxy (substituents in the optionally substituted $C_{1-5}$ alkoxy include fluorine atom with the number of substitution of 3), $C_{7-9}$ aralkyloxy, $C_{1-3}$ alkylthio optionally substituted (substituents in the optionally substituted $C_{1-10}$ alkylthio include fluorine atom with the number of substitution of 3) or —$NR^{Xa}R^{Ya}$ (wherein, $R^{Xa}$ and $R^{Ya}$ are the same or different and represent $C_{1-3}$ alkyl), X represents —O—, and n1 and n2 are the same or different and each represent 0 or 1.

According to another further preferred embodiment of the compound (compound (I)) represented by general formula (I), in the above formula (I), "A" represents unsubstituted pyridinediyl, $R^1$ represents hydrogen atom or methyl, $R^2$ represents optionally substituted phenyl, wherein the phenyl is optionally substituted with, with the number of substitution of 1 or 2, halogen (preferably chlorine atom or fluorine atom), cyano, trifluoromethyl, optionally substituted $C_{1-5}$ alkoxy (substituents in the optionally substituted $C_{1-5}$ alkoxy include fluorine atom with the number of substitution of 3) or $C_{7-9}$ aralkyloxy, X represents —O—, and n1 and n2 are the same or different and each represent 0 or 1 (n2 preferably represents 0).

According to another more preferred embodiment of the compound (compound (I)) represented by general formula (I), in the above formula (I), "A" represents optionally substituted isoquinolinediyl, wherein the isoquinolinediyl is optionally substituted with, with the number of substitution of 1 or 2, halogen (preferably chlorine atom), hydroxy or $C_{1-3}$ alkyl, $R^1$ represents hydrogen atom or $C_{1-3}$ alkyl (preferably methyl), $R^2$ represents optionally substituted aryl, wherein the optionally substituted aryl is optionally substituted phenyl, and the phenyl is optionally substituted with, with the number of substitution of 1 or 2, halogen (preferably chlorine atom or fluorine atom), cyano, $C_{1-3}$ alkyl, trifluoromethyl, $C_{3-5}$ cycloalkyl, optionally substituted $C_{1-5}$ alkoxy (substituents in the optionally substituted $C_{1-5}$ alkoxy include fluorine atom with the number of substitution of 3), $C_{7-9}$ aralkyloxy, optionally substituted $C_{1-3}$ alkylthio (substituents in the optionally substituted $C_{1-10}$ alkylthio include fluorine atom with the number of substitution of 3) or —NR$^{Xa}$R$^{Ya}$ (wherein, R$^{Xa}$ and R$^{Ya}$ are the same or different and represent $C_{1-3}$ alkyl), X represents —O—, and n1 and n2 are the same or different and each represent 0 or 1.

According to another further preferred embodiment of the compound (compound (I)) represented by general formula (I), in the above formula (I), "A" represents unsubstituted isoquinolinediyl, $R^1$ represents hydrogen atom, $R^2$ represents optionally substituted phenyl, wherein the phenyl is optionally substituted with, with the number of substitution of 1 or 2, halogen (preferably chlorine atom), $C_{2-5}$ alkynyl, trifluoromethyl or $C_{3-5}$ cycloalkyl, X represents —O—, and n1 and n2 are the same or different and each represent 0 or 1 (n2 preferably represents 0).

According to another further preferred embodiment of the compound (compound (1)) represented by general formula (I), in the above formula (I), "A" represents unsubstituted isoquinolinedyl $R^1$ represents hydrogen atom, $R^2$ represents optionally substituted aromatic heterocyclic group, wherein the optionally substituted aromatic heterocyclic group is a monocyclic aromatic heterocyclic group having one or two nitrogen atom(s) (preferably pyridyl, pyrimidinyl, pyridazinyl or pyrazinyl), and the aromatic heterocyclic group is optionally substituted, with the number of substitution of 1 or 2, with halogen (preferably chlorine atom or fluorine atom), $C_{1-3}$ alkyl, trifluoromethyl or $C_{1-5}$ alkoxy, X represents —O—, and n1 and n2 are the same or different and each represent 0 or 1 (n2 preferably represents 0).

The pharmaceutically acceptable salt of compound (I) includes, for example, pharmaceutically acceptable acid addition salt, metal salt, ammonium salt, organic amine addition salt, and amino acid addition salt and the like. Pharmaceutically acceptable acid addition salt of compound (I) includes, for example, inorganic acid salt such as hydrochloride, hydrobromide, nitrate, sulfate, and phosphate and the like, and organic acid salt such as acetate, oxalate, maleate, fumarate, citrate, benzoate, and methanesulfonate and the like; pharmaceutically acceptable metal salt includes, for example, alkali metal salt such as sodium salt and potassium salt and the like, and alkali earth metal salt such as magnesium salt, and calcium salt and the like, aluminum salt, and zinc salt and the like; pharmaceutically acceptable ammonium salt include, for example, salt of such as ammonium and tetramethylammonium and the like; pharmaceutically acceptable organic amine addition salt includes, for example, addition salt of such as morpholine and piperidine and the like; pharmaceutically acceptable amino acid addition salt includes, for example, addition salt of such as lysine, glycine, phenylalanine, aspartic acid, and glutaminic acid and the like.

The wavy line between $R^1$ and the carbon atom adjacent to $R^1$ in compound (I) indicates a cis- or trans-configuration.

Next, manufacturing methods of compound (I) will be explained.

For the manufacturing method described below, when the defined groups are altered under the conditions of the manufacturing method or the method is not appropriate to conduct, target compounds can be manufactured by using a method of introducing or removing a protecting group commonly used in organic synthetic chemistry [e.g., a method described in Protective Groups in Organic Synthesis, third edition by T. W. Greene, John Wiley & Sons Inc. (1999), and the like] and the like. Furthermore, the order of the reaction steps such as the introduction of substituents and the like can be changed as needed.

The compounds (I) can be manufactured according to the following steps.

Manufacturing Method 1

In manufacturing method 10, among compounds (II) that are precursors of compounds (I), compounds (II-a), (II-b) and (II-c) as 4-aminochromane derivatives and compound (II-d) as a 4-aminomethylchromane derivative can be manufactured according to the following steps:

[Chemical formula 21]
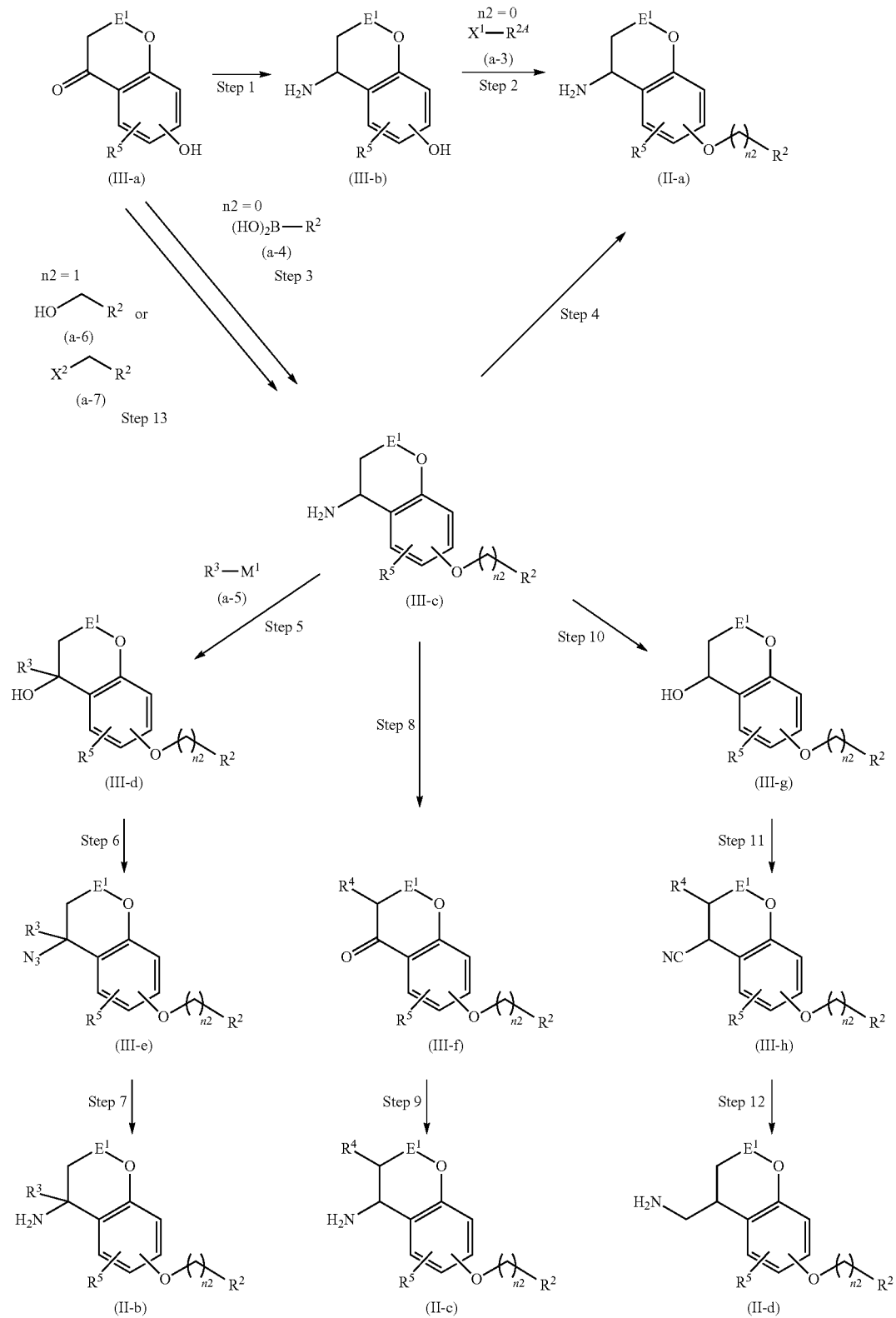
(wherein $R^2$ and n2 are the same as the definition described above; $R^{2A}$ represents optionally substituted aryl or option- ally substituted aromatic heterocyclic group in $R^2$; $R^3$ represents lower alkyl; $R^4$ represents lower alkyl, fluorine atom, chlorine atom, bromine atom or iodine atom; $R^5$ represents the substituent mentioned above as the substituent of optionally substituted heterocyclic diyl or hydrogen atom; $E^1$ represents $CR^aR^b$ (wherein $R^a$ and $R^b$ are the same or different, and each represents the substituent mentioned above as the substituent of optionally substituted heterocyclic diyl or hydrogen atom); $X^1$ and $X^2$ are the same or different, and each represents a leaving group such as chlorine atom, bromine atom, iodine atom, p-toluenesulfonyloxy, methanesulfonyloxy, or trifluoromethanesulfonyloxy or the like; and $M^1$ represents MgI, MgBr, MgCl, Li, and the like).

Step 1

Compound (III-b) can be manufactured by reacting compound (III-a) in a solvent with an ammonia source preferably in 1 to 10 equivalent amount, for 5 minutes to 72 hours in the presence of a reducing agent preferably in 1 to 10 equivalent amount, an acid preferably in 1 to 10 equivalent amount, and if needed, a metallic catalyst preferably in 0.01 to 1 equivalent amount, at a temperature between −20° C. and the boiling point of the solvent used.

Compound (III-a) can be obtained as a commercially available product, or by well-known methods (e.g., WO2015/051447, WO2001/18006, WO1998/13356, Bioorganic & Medicinal Chemistry, 2007, 17, 1288-1290, and the like) or their equivalent methods.

The ammonia sources include, for example, ammoniacal water, ammonium formate, and ammonium acetate and the like.

The reducing agents include, for example, sodium triacetoxyborohydride, and sodium cyanoborohydride and the like.

The acids include, for example, hydrochloric acid, sulfuric acid, formic acid, acetic acid, trifluoroacetic acid, and p-toluenesulfonic acid and the like.

The metallic catalysts include, for example, chloro[N-{4-(dimethylamino)phenyl}-2-pyridine carboxyamidate](pentamethylcyclopentadienyl)iridium(III) and the like.

The solvents include, for example, methanol, ethanol, dichloromethane, chloroform, 1,2-dichloroethane, toluene, ethyl acetate, acetonitrile, diethyl ether, tetrahydrofuran (THF), 1,2-dimethoxyethane (DME), dioxane, N,N-dimethylformamide (DMF), N,N-dimethyl acetamide (DMA), N-methyl-2-pyrrolidone (NMP), and water and the like. They are used alone or in mixtures.

Step 2

Compound (II-a), wherein n2 is 0 and $R^2$ is optionally substituted aryl or optionally substituted aromatic heterocyclic group, can be manufactured by reacting compound (III-b) in a solvent with compound (a-3) preferably in 1 to 10 equivalent amount, for 5 minutes to 72 hours in the presence of a copper reagent in preferably 0.01 to 1 equivalent amount, a ligand in preferably 0.01 to 1 equivalent amount, and a base in preferably 1 to 10 equivalent amount, at a temperature between −20° C. and the boiling point of the solvent used.

Compound (a-3) can be obtained as a commercially available product.

The copper reagents include, for example, copper(0), copper(I) iodide, copper(II) acetate, copper(II) oxide, and copper(I) chloride and the like.

The ligands include, for example, phenanthroline, trans-1,2-cyclohexanediamine, and picolinic acid and the like.

The bases include, for example, potassium carbonate, cesium carbonate, lithium chloride, potassium chloride, potassium tert-butoxide, sodium tert-butoxide, triethylamine, potassium acetate, sodium ethoxide, sodium carbonate, sodium hydroxide, potassium phosphate, ethylenediamine, glycine, N-methylpyrrolidine, pyridine, and 1,2-diaminocyclohexane and the like.

The solvents include, for example, methanol, ethanol, THF, pyridine, collidine, dichloromethane, 1,2-dichloroethane, DMF, acetonitrile, dioxane, N,N-dimethylsulfoxide (DMSO), DMA, NMP, toluene, and hexamethylphosphoric triamide (HMPA). They are used alone or in mixtures and the like.

Step 3

Compound (III-c) wherein n2 is 0 can be manufactured by reacting compound (III-a) in a solvent with compound (a-4) preferably in 1 to 10 equivalent amount, for 5 minutes to 72 hours in the presence of a copper reagent preferably in 1 to 10 equivalent amount and a base in 1 to 10 equivalent amount, at a temperature between −20° C. and the boiling point of the solvent used.

Compound (a-4) can be obtained as a commercially available product, or by well-known methods [e.g., "Jikken Kagaku Koza 18, 5th Ed., Synthesis of organic compounds VI, Organic synthesis using metals" p. 97, Maruzen (2005)] or its equivalent methods.

Copper reagents include, for example, copper(0), copper(I) iodide, copper(II) acetate, copper(II) oxide, and copper(I) chloride and the like.

The bases include, for example, potassium carbonate, cesium carbonate, lithium chloride, potassium chloride, potassium tert-butoxide, sodium tert-butoxide, triethylamine, potassium acetate, sodium ethoxide, sodium carbonate, sodium hydroxide, potassium phosphate, ethylenediamine, glycine, N-methylpyrrolidine, pyridine, and 1,2-diaminocyclohexane and the like.

The solvents include, for example, methanol, ethanol, THF, pyridine, collidine, dichloromethane, 1,2-dichloroethane, DMF, acetonitrile, dioxane, DMSO, DMA, NMP, toluene, and HMPA and the like. They are used alone or in mixtures.

Step 4

Compound (II-a) can be manufactured using compound (III-c) by a method similar to step 1.

Step 5

Compound (III-d) can be manufactured by reacting compound (III-c) in a solvent with compound (a-5) preferably in 1 to 10 equivalent amount, for 5 minutes to 72 hours at a temperature between −78° C. and the boiling point of the solvent used.

Compound (a-5) can be obtained as a commercially available product, or by well-known methods [e.g., "Jikken Kagaku Koza 18, 5th Ed., Synthesis of organic compounds VI, organic synthesis using metals" p. 59, Maruzen (2005)] or its equivalent methods.

The solvents include, for example, toluene, diethyl ether, THF, DME, dioxane, and hexane and the like. They are used alone or in mixtures.

Step 6

Compound (III-e) can be manufactured by reacting compound (III-d) in a solvent with an azidation reagent preferably in 1 equivalent to a large excess amount, for 5 minutes to 72 hours in the presence of, if needed, a base preferably in 1 equivalent to a large excess amount or if needed, an acid preferably in 1 equivalent to a large excess amount, at a temperature between 0° C. and the boiling point of the solvent used.

The azidation agents include, for example, sodium azide, potassium azide, and diphenylphosphoryl azide and the like.

The bases include, for example, potassium carbonate, sodium carbonate, potassium bicarbonate, sodium bicarbonate, triethylamine, diisopropylethylamine, N-methylmorpholine, pyridine, and 1,8-diazabicyclo[5.4.0]-7-undecene (DBU) and the like.

The acids include, for example, trifluoroacetic acid and the like.

The solvents include, for example, THF, DME, benzene, toluene, xylene, 1,4-dioxane, DMF, DMA, and NMP and the like. They are used alone or in mixtures.

Step 7

Compound (II-b) can be manufactured by reacting compound (III-e) in a solvent with a reducing agent preferably in 1 to 10 equivalent amount for 5 minutes to 72 hours at a temperature between −78° C. and the boiling point of the solvent used.

The reducing agents include, for example, lithium aluminum hydride, borane dimethyl sulfide complex, triphenylphosphine, and tetrabutyltin hydride and the like.

The solvents include, for example, methanol, ethanol, dichloromethane, chloroform, 1,2-dichloroethane, toluene, diethyl ether, THF, DME, dioxane, DMF, DMA, and NMP and the like. They are used alone or in mixtures.

Furthermore, as an alternative method, compound (II-b) can be manufactured by reacting compound (III-e) in a solvent (i) with a hydrogen source preferably in 2 equivalents to a large excess amount for 5 minutes to 72 hours, or (ii) with hydrogen under the hydrogen atmosphere preferably at 1 to 20 atmospheric pressure for 5 minutes to 72 hours, in the presence of a catalyst preferably in 0.01 to 50% by weight relative to compound (III-e), at a temperature between −20° C. and the boiling point of the solvent used.

The catalysts include, for example, palladium carbon, and palladium hydroxide and the like.

The hydrogen sources include, for example, formic acid, ammonium formate, sodium formate, cyclohexadiene, and hydrazine and the like.

The solvents include, for example, methanol, ethanol, toluene, ethyl acetate, acetonitrile, diethyl ether, THF, DME, dioxane, DMF, DMA, NMP, and water and the like. They are used alone or in mixtures.

Step 8

Compound (III-f) can be manufactured using compound (III-c), for example, by methods equivalent to a method described in "Jikken Kagaku Koza 13, 5th Ed., Synthesis of organic compounds I, hydrogen/halogen compounds", Maruzen (2005), "Jikken Kagaku Koza 15, 5th Ed., Synthesis of organic compounds III, aldehydes/ketones/quinones", Maruzen (2005), and the like.

Compound (III-f) can be manufactured by reacting compound (III-c) in a solvent with 1 equivalent to a large excess amount of a halogenating agent or an alkylating agent for 5 minutes to 72 hours at a temperature between −78° C. and the boiling point of the solvent used.

The halogenating agents include, for example, (diethylamino)sulfur trifluoride (DAST), bis(2-methoxyethyl)aminosulfur trifluoride, 1-fluoro-4-hydroxy-1,4-diazabicyclo[2.2.2]octane-1,4-diium tetrafluoroborate, N-chlorosuccinimide, N-bromosuccinimide, N-iodosuccinimide, chlorine, bromine, and iodine and the like. Alkylating agents include, for example, methyl iodide, ethyl iodide, and methyl trifluoromethanesulfonate and the like.

The solvents include, for example, dichloromethane, 1,2-dichloroethane, and methanol and the like. They are used alone or in mixtures.

Step 9

Compound (II-c) can be manufactured by a method similar to step 1 using compound (III-f).

Step 10

Compound (III-g) can be manufactured by reacting compound (III-c) in a solvent with a reducing agent preferably in 1 to 10 equivalent amount for 5 minutes to 72 hours at a temperature between −78° C. and the boiling point of the solvent used.

The reducing agents include, for example, lithium aluminum hydride, diisobutylaluminium hydride, bis(2-methoxyethoxy)aluminum sodium hydride, borane dimethyl sulfide complex, lithium borohydride, and sodium borohydride and the like.

The solvents include, for example, methanol, ethanol, dichloromethane, chloroform, 1,2-dichloroethane, toluene, diethyl ether, THF, DME, dioxane, DMF, DMA, and NMP and the like. They are used alone or in mixtures.

Step 11

Compound (III-h) can be manufactured by reacting compound (III-g) in a solvent with a cyanating agent preferably in 1 to 10 equivalent amount for 5 minutes to 72 hours in the presence of, if needed, an additive preferably in 1 to 10 equivalent amount at a temperature between 0° C. and the boiling point of the solvent used.

The additives include, for example, zinc iodide and the like.

The cyanating agents include, for example, sodium cyanide, potassium cyanide, tetrabutyl ammonium cyanide, and trimethylsilyl cyanide and the like.

The solvents include, for example, dichloromethane, 1,2-dichloroethane, THF, DME, 1,4-dioxane, DMF, DMA, NMP, DMSO, and toluene and the like. They are used alone or in mixtures.

Step 12

Compound (II-d) can be manufactured by reacting compound (III-h) in a solvent with a reducing agent preferably in 1 to 10 equivalent amount for 5 minutes to 72 hours at a temperature between 0° C. and the boiling point of the solvent used.

The reducing agents include, for example, lithium aluminum hydride, and diborane and the like.

The solvents include, for example, toluene, diethyl ether, THF, DME, dioxane, and the like. They are used alone or in mixtures.

Furthermore, as an alternative method, compound (II-d) can be manufactured by reacting compound (III-h) in a solvent or without solvent (i) with a hydrogen source preferably in 2 equivalents to a large excess amount for 5 to 72 hours, or (ii) with hydrogen under the hydrogen atmosphere preferably at 1 to 20 atmospheric pressure for 5 minutes to 72 hours, by adding, if needed, an acid preferably in 1 equivalent to a large excess amount or if needed, an ammonia-alcoholic solution preferably in 1 equivalent to a large excess amount, in the presence of a catalyst preferably in 0.01 to 50% by weight relative to compound (III-h), at a temperature between −20° C. and the boiling point of the solvent used (between 0° C. and 150° C. when without solvent).

The acids include, for example, acetic acid, and hydrochloric acid and the like.

The ammonia-alcoholic solutions include, for example, an ammonia-methanol solution, an ammonia-ethanol solution, and an ammonia-2-propanol solution and the like.

The catalysts include, for example, palladium carbon, and Raney nickel and the like.

The hydrogen sources include, for example, formic acid, ammonium formate, sodium formate, cyclohexadiene, and hydrazine and the like.

The solvents include, for example, methanol, ethanol, toluene, ethyl acetate, acetonitrile, diethyl ether, THF, DME, dioxane, DMF, DMA, NMP, and water and the like. They are used alone or in mixtures.

Step 13

Compound (III-c) wherein n2 is 1 can be manufactured by reacting compound (III-a) in a solvent with compound (a-6) preferably in 1 to 10 equivalent amount, for 5 minutes to 72 hours in the presence of a phosphine compound preferably in 1 to 10 equivalent amount and an azo compound preferably in 1 to 10 equivalent amount, at a temperature between −78° C. and the boiling point of the solvent used.

Compound (a-6) can be obtained as a commercially available product.

The phosphine compounds include, for example, triphenylphosphine, and tributylphosphine and the like.

The azo compounds include, for example, diethyl azodicarboxylate (DEAD), di-tert-butyl azadicarboxylate, diisopropyl azadicarboxylate, N,N,N',N'-tetramethyl azadicarboxamide, 1,1'-(azadicarbonyl)dipiperazine, and N,N,N',N'-tetraisopropyl azadicarboxamide and the like.

The solvents include, for example, toluene, ethyl acetate, acetonitrile, diethyl ether, THF, DME, dioxane, DMF, DMA, and NMP and the like. They are used alone or in mixtures.

Furthermore, as an alternative method, compound (III-c) can be manufactured by reacting compound (III-a) in a solvent with compound (a-7) preferably in 1 to 10 equivalent amount, in the presence of a base preferably in 1 to 10 equivalent amount, at a temperature between −20° C. and the boiling point of the solvent used for 5 minutes to 72 hours.

Compound (a-7) can be obtained as a commercially available product.

The bases include, for example, sodium carbonate, potassium carbonate, potassium hydroxide, sodium hydroxide, potassium tert-butoxide, diisopropylethylamine, and DBU and the like.

The solvents include, for example, methanol, ethanol, toluene, ethyl acetate, acetonitrile, diethyl ether, THF, DME, dioxane, DMF, and water and the like. They are used alone or in mixtures.

Manufacturing Method 2

Among compounds (II), compound (II-i) that is a 3-aminochromane derivative wherein X is —O— can be manufactured according to the following steps:

[Chemical formula 22]

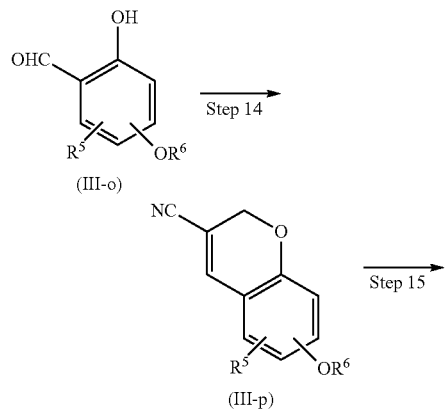

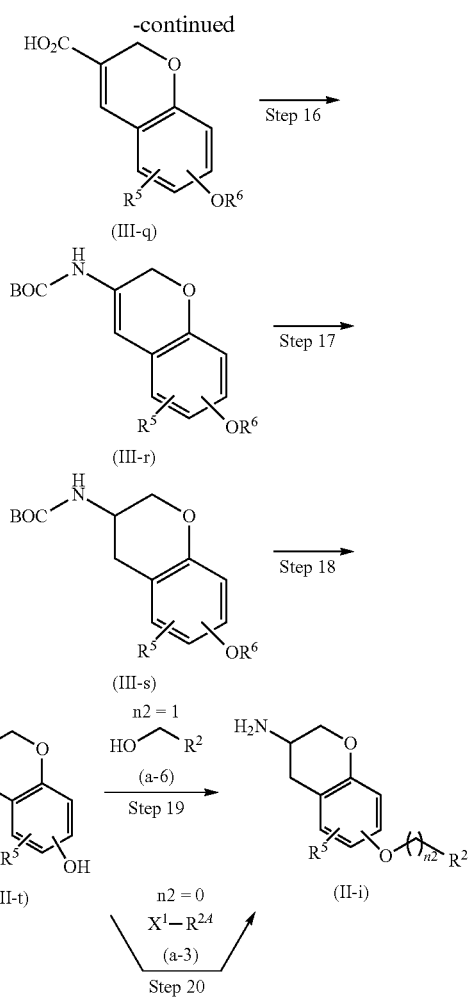

(wherein $R^2$, $R^{2A}$, $R^5$, $X^1$ and n2 are the same as the definition described above; $R^6$ represents lower alkyl; and BOC represents tert-butoxycarbonyl).

Step 14

Compound (III-p) can be manufactured by reacting compound (III-o) in a solvent or without solvent with acrylonitrile preferably in 1 equivalent to a large excess amount, in the presence of a base preferably in 1 to 10 equivalent amount, at a temperature between 0° C. and the boiling point of the solvent used (at 0° C. and 150° C. when without solvent) for 5 minutes to 72 hours.

Compound (III-o) can be obtained as a commercially available product, or by well-known methods (e.g., "Jikken Kagaku Koza 15, 5th Ed., Synthesis of organic compounds III, aldehydes/ketones/quinones" p. 78, Maruzen (2005)] or by its equivalent methods.

The bases include, for example, 1,4-diazabicyclo[2.2.2]octane and the like.

The solvents include, for example, methanol, ethanol, dichloromethane, chloroform, 1,2-dichloroethane, toluene, acetonitrile, DMF, and water and the like. They are used alone or in mixtures.

Step 15

Compound (III-q) can be manufactured by treating compound (III-p) in a solvent with a base preferably in 1 equivalent to a large excess amount, for 5 minutes to 72 hours at a temperature between 0° C. and the boiling point of the solvent used.

The bases include, for example, potassium carbonate, lithium hydroxide, potassium hydroxide, sodium hydroxide, and sodium methoxide and the like.

The solvents include, for example, methanol, ethanol, dichloromethane, chloroform, 1,2-dichloroethane, toluene, ethyl acetate, acetonitrile, diethyl ether, THF, DME, dioxane, DMF, DMA, NMP, and pyridine and the like. They are used by mixing with water, or mixing each solvent and further adding water thereto.

Step 16

Compound (III-r) can be manufactured by reacting compound (III-q) in a solvent or without solvent with an azidation reagent preferably in 1 equivalent to a large excess amount and tert-butanol preferably in 1 equivalent to a large excess amount, in the presence of, if needed, a base preferably in 1 equivalent to a large excess amount, at a temperature between 0° C. and the boiling point of the solvent used (between 0° C. and 150° C. when without solvent) for 5 minutes to 72 hours.

The azidation reagents include, for example, sodium azide, potassium azide, and diphenylphosphoryl azide and the like.

The bases include, for example, potassium carbonate, sodium carbonate, potassium bicarbonate, sodium bicarbonate, triethylamine, diisopropylethylamine, N-methylmorpholine, pyridine, and DBU and the like.

The solvents include, for example, THF, DME, benzene, toluene, xylene, 1,4-dioxane, DMF, DMA, and NMP and the like. They are used alone or in mixtures.

Step 17

Compound (III-s) can be manufactured by reacting compound (III-r) in a solvent (i) with hydrogen under the hydrogen atmosphere preferably at 1 to 20 atmospheric pressure for 5 minutes to 72 hours, or (ii) with a hydrogen source preferably in 2 equivalent to a large excess amount, in the presence of preferably 0.01 to 50% by weight of a catalyst, at a temperature between −20° C. and the boiling point of the solvent used, for 5 minutes to 72 hours.

The catalysts include, for example, palladium carbon, palladium, palladium hydroxide, palladium acetate, and palladium black and the like.

The hydrogen sources include, for example, formic acid, ammonium formate, sodium formate, cyclohexadiene, and hydrazine and the like.

The solvents include, for example, methanol, ethanol, toluene, ethyl acetate, acetonitrile, diethyl ether, THF, DME, dioxane, DMF, DMA, NMP, and water and the like. They are used alone or in mixtures.

Step 18

Compound (III-t) can be manufactured by treating compound (III-s) in a solvent or without solvent with an additive preferably in 1 equivalent to a large excess amount, at a temperature between 0° C. and the boiling point of the solvent used (between 0° C. and 150° C. when without solvent), or if needed, using a microwave reaction device and at a temperature between 0° C. and 200° C. for one minute to 72 hours.

The additives include, for example, pyridine hydrochloride, boron tribromide, boron trifluoride diethyl ether complex, and aluminum chloride and the like.

The solvents include, for example, dichloromethane, chloroform, 1,2-dichloroethane, toluene, ethyl acetate, acetonitrile, diethyl ether, THF, DME, dioxane, DMF, DMA, and NMP and the like. They are used alone or in mixtures.

Step 19

Compound (II-i) wherein n2 is 1 can be manufactured using compounds (III-t) and (a-6) by a method similar to step 13.

Step 20

Compound (II-i), wherein n2 is 0 and $R^2$ is optionally substituted aryl or optionally substituted aromatic heterocyclic group, can be manufactured using compounds (III-t) and (a-3) by a method similar to step 2.

Manufacturing method 3

Among compounds (III-r) described in manufacturing method 2, compound (III-r-2) can be also manufactured according to the following step:

[Chemical formula 23]

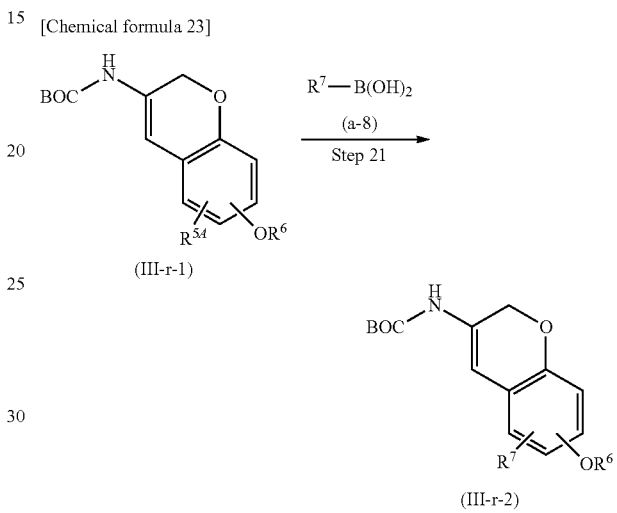

(wherein $R^{54}$ represents chlorine atom, bromine atom, iodine atom, p-toluene sulfonyloxy, methanesulfonyloxy or trifluoro-methanesulfonyloxy, and the like; $R^6$ is the same as the definition described above; and $R^7$ represents lower alkyl in $R^5$).

Step 21

Compound (III-r-2) can be manufactured by reacting compound (III-r-1) in a solvent with compound (a-8) preferably in 1 to 5 equivalent amount, for 5 minutes to 72 hours in the presence of a base preferably in 0.1 to 10 equivalent amount and a palladium catalyst preferably in 0.001 to 0.5 equivalent amount, at a temperature between −20° C. and the boiling point of the solvent used.

Compound (III-r-1) can be obtained according to step 16 of manufacturing method 2.

Compound (a-8) can be obtained as a commercially available product, or by well-known methods [e.g., Jikken Kagaku Koza 18, 5th Ed., Synthesis of organic compounds VI, Organic synthesis using metals" p. 97, Maruzen (2005)] or by its equivalent methods.

The bases include, for example, sodium carbonate, potassium carbonate, potassium phosphate, potassium hydroxide, sodium hydroxide, potassium tert-butoxide, triethylamine, diisopropylethylamine, N-methylmorpholine, pyridine, and DBU and the like.

The palladium catalysts include, for example, palladium acetate, tris(dibenzylidene acetone)dipalladium, tetrakis(triphenylphosphine)palladium, and 1,1'-bis(diphenylphosphino)ferrocene dichloropalladium/dichloromethane 1:1 adduct and the like.

The solvents include, for example, methanol, ethanol, toluene, ethyl acetate, acetonitrile, diethyl ether, THF, DME, dioxane, DMF, DMA, NMP, and water and the like. They are used alone or in mixtures.

Manufacturing Method 4

Among compounds (II), compound (II-j), that is a 3-aminochroman-4-one derivative, can be manufactured according to the following steps:

[Chemical formula 24]

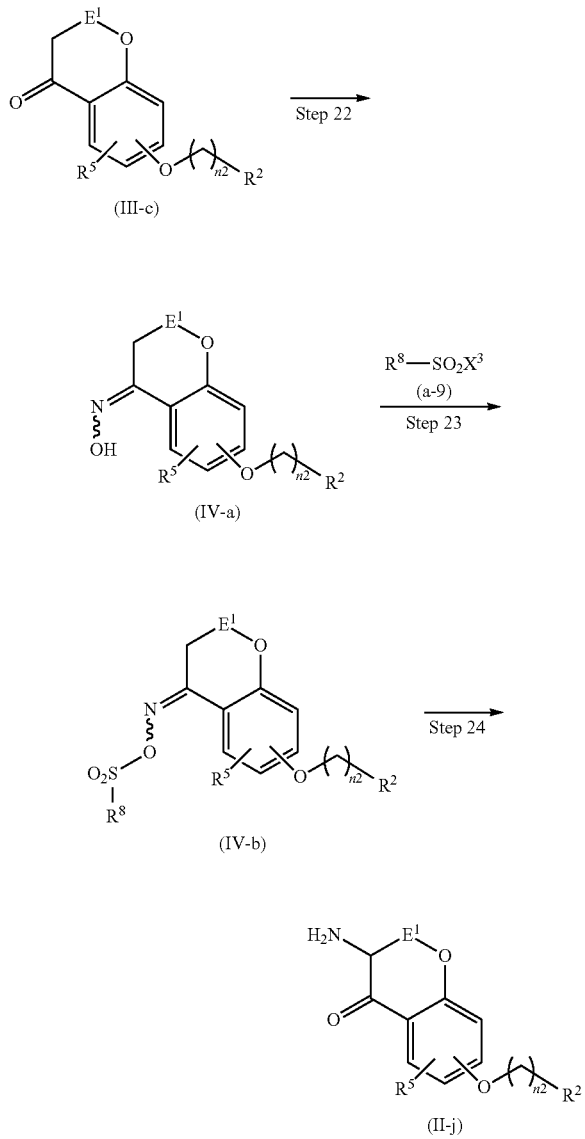

(wherein $R^2$, $R^5$, n2 and $E^1$ are each the same as the definition described above; $R^8$ represents phenyl optionally substituted with a substituent selected from the group consisting of fluorine atom, chlorine atom, bromine atom, iodine atom, lower alkyl and lower alkoxy; and $X^3$ represents chlorine atom, bromine atom or iodine atom).

Step 22

Compound (IV-a) can be manufactured by reacting compound (III-c) obtained in step 3 or step 13 of manufacturing method 1 in a solvent with hydroxylamine or a salt thereof preferably in 1 to 10 equivalent amount, for 5 minutes to 72 hours in the presence of a base or acid preferably in 1 to 10 equivalent amount, at a temperature between −20° C. and the boiling point of the solvent used.

The bases include, for example, potassium carbonate, potassium phosphate, potassium hydroxide, sodium hydroxide, potassium tert-butoxide, triethylamine, diisopropylethylamine, N-methylmorpholine, pyridine, and DBU and the like.

The acids include, for example, hydrochloric acid, and acetic acid and the like.

The solvents include, for example, methanol, ethanol, dichloromethane, chloroform, 1,2-dichloroethane, toluene, acetonitrile, acetone, diethyl ether, THF, DME, dioxane, DMF, DMA, NMP, pyridine, and water and the like. They are used alone or in mixtures.

The hydroxylamine or salts thereof include, for example, hydroxylamine, hydroxylamine hydrochloride, and hydroxylamine sulfate and the like. Also, an aqueous hydroxylamine solution can be used.

Step 23

Compound (IV-b) can be manufactured by reacting compound (IV-a) in a solvent with compound (a-9) preferably in 1 to 10 equivalent amount, for 5 minutes to 72 hours in the presence of a base preferably in 1 to 10 equivalent amount, at a temperature between −20° C. and the boiling point of the solvent used.

Compound (a-9) can be obtained as a commercially available product.

The bases include, for example, potassium carbonate, potassium hydroxide, sodium hydroxide, sodium bicarbonate, sodium hydride, sodium methoxide, potassium tert-butoxide, triethylamine, diisopropylethylamine, N-methylmorpholine, pyridine, and DBU and the like.

The solvents include, for example, methanol, ethanol, dichloromethane, chloroform, 1,2-dichloroethane, toluene, ethyl acetate, acetonitrile, acetone, diethyl ether, THF, DME, dioxane, DMF, DMA, NMP, pyridine, and water and the like. They are used alone or in mixtures.

Step 24

Compound (II-j) can be manufactured by treating compound (IV-b) in a solvent with a base preferably in 1 to 10 equivalent amount for 5 minutes to 72 hours at a temperature between −20° C. and the boiling point of the solvent used.

The bases include, for example, potassium hydroxide, sodium hydroxide, sodium methoxide, sodium ethoxide, potassium methoxide, potassium ethoxide, potassium tert-butoxide, and pyridine and the like.

The solvents include, for example, methanol, ethanol, dichloromethane, chloroform, 1,2-dichloroethane, toluene, ethyl acetate, acetonitrile, acetone, diethyl ether, THF, DME, dioxane, DMF, DMA, NMP, and pyridine and the like. They are used by mixing with water or mixing each solvent and further adding water thereto.

Manufacturing Method 5

Among compounds (II), compound (II-k), that is a 5,6,7,8-tetrahydroquinoline derivative, can be manufactured according to the following steps:

[Chemical formula 25]

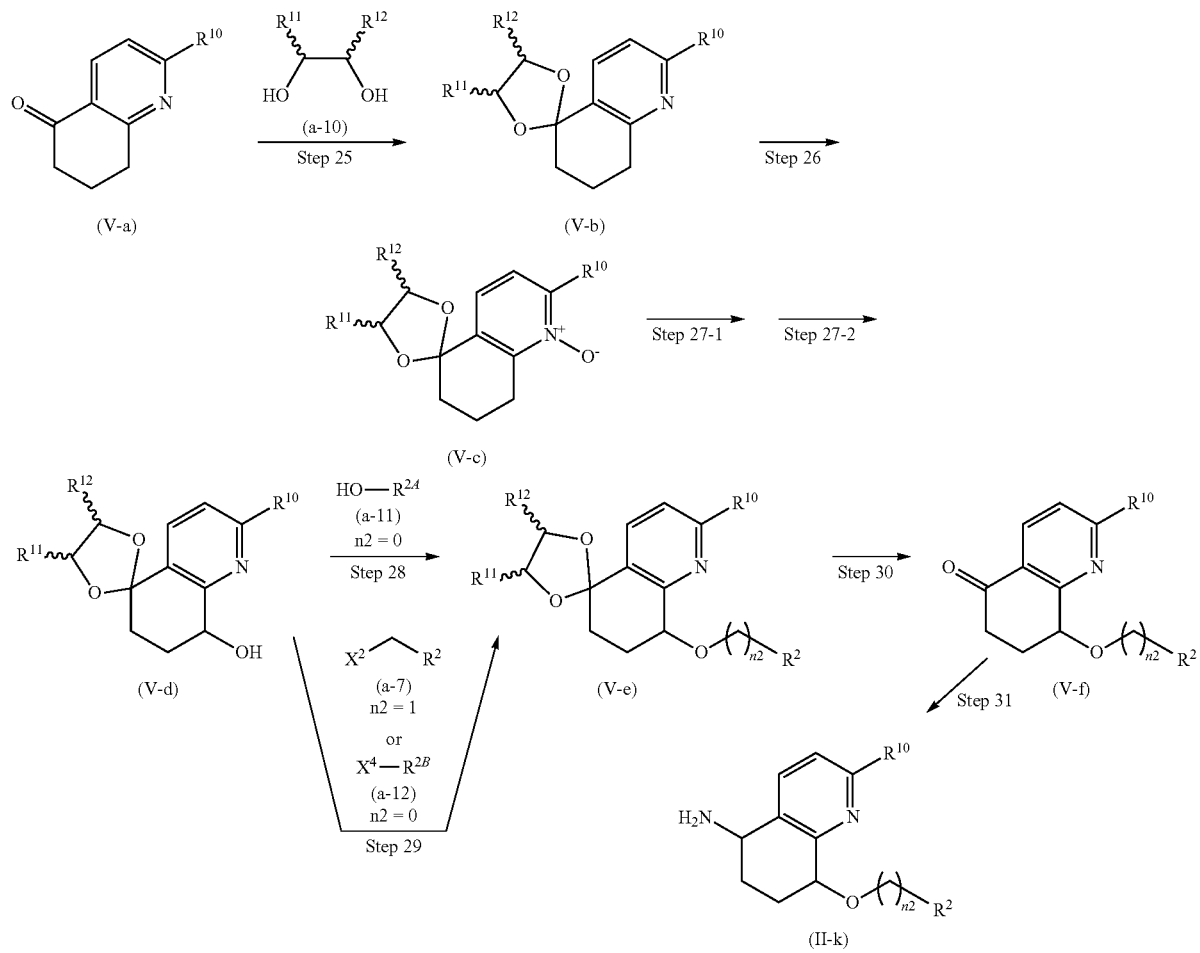

[wherein $R^2$, $R^{2A}$, $X^2$ and n2 each are the same as the definition described above; in $R^2$, $R^{2B}$ represents (i) optionally substituted cycloalkyl, or (ii) aliphatic heterocyclic group wherein $X^4$ is bonded to the sp$^3$ carbon constituting the aliphatic heterocyclic group among optionally substituted aliphatic heterocyclic groups; $X^4$ represents leaving group such as chlorine atom, bromine atom, iodine atom, p-toluene sulfonyloxy, methanesulfonyloxy or trifluoromethanesulfonyloxy, or the like; $R^{10}$ represents the substituent mentioned above as a substituent of optionally substituted heterocyclic diyl or hydrogen atom; and $R^{11}$ and $R^{12}$ are the same or different, and each represents hydrogen atom or lower alkyl].

Step 25

Compound (V-b) can be manufactured by reacting compound (V-a) in a solvent with compound (a-10) preferably in 1 to 10 equivalent amount, for 5 minutes to 72 hours in the presence of an additive preferably in 0.1 to 10 equivalent amount, at a temperature between −20° C. and the boiling point of the solvent used.

The additives include, for example, pyridinium p-toluenesulfonate, p-toluenesulfonic acid, hydrochloric acid, and acetic acid and the like.

The solvents include, for example, dichloromethane, chloroform, 1,2-dichloroethane, toluene, ethyl acetate, and acetonitrile and the like.

Compound (V-a) can be obtained as a commercially available product, or by well-known methods (e.g., Synthetic Communications, 2010 Vol. 40, p. 1708-1716) or its equivalent methods.

Compound (a-10) can be obtained as a commercially available product. Other than the methods above, compound (V-b), for example, can be manufactured by methods equivalent to a method described in Protective Groups in Organic Synthesis, the third edition, by T. W. Greene, John Wiley & Sons Inc. (1999) and the like.

Step 26

Compound (V-c) can be manufactured by reacting compound (V-b) in a solvent with an oxidizing agent preferably in 1 to 10 equivalent amount, for 5 minutes to 72 hours at a temperature between −20° C. and the boiling point of the solvent used.

The oxidizing agents include, for example m-chloroperoxybenzoic acid (m-CPBA), benzoyl peroxide, peracetic acid, and hydrogen peroxide and the like.

The solvents include, for example, methanol, ethanol, dichloromethane, chloroform, 1,2-dichloroethane, toluene, ethyl acetate, acetonitrile, diethyl ether, THF, DME, dioxane, DMF, DMA, NMP, and water and the like. They are used alone or in mixtures.

Steps 27-1 and 27-2

Compound (V-d) can be manufactured by the following method.

Step 27-1

Compound (V-c) is subjected to a reaction in a solvent with an acid anhydride preferably in 1 to 10 equivalent amount, for 5 minutes to 72 hours in the presence of a base preferably in 1 to 10 equivalent amount, at a temperature between −78° C. and the boiling point of the solvent used.

Step 27-2

The compound obtained in step 27-1 is subjected to a reaction in a solvent with a base in 1 equivalent to a large excess amount relative to compound (V-c) for 5 minutes to 72 hours at a temperature between 0° C. and the boiling point of the solvent used.

The acid anhydrides include acetic anhydride, and trifluoroacetic acid anhydride and the like.

The bases used in steps 27-1 and 27-2 are the same or different, and each include, for example, potassium carbonate, potassium hydroxide, sodium hydroxide, triethylamine, diisopropylethylamine, N-methylmorpholine, and pyridine and the like.

The solvents used in step 27-1 are the same or different, and each include, for example, dichloromethane, chloroform, 1,2-dichloroethane, toluene, acetonitrile, diethyl ether, THF, DME, dioxane, DMF, DMA, NMP, pyridine and the like. They are used alone or in mixtures.

The solvents used in step 27-2 are the same or different, and each include, for example, methanol, ethanol, dichloromethane, chloroform, 1,2-dichloroethane, toluene, acetonitrile, diethyl ether, THF, DME, dioxane, DMF, DMA, NMP, pyridine, and water and the like. They are used alone or in mixtures.

Step 28

Compound (V-e), wherein n2 is 0 and $R^2$ is optionally substituted aryl or optionally substituted aromatic heterocyclic group, can be manufactured by reacting compound (V-d) in a solvent with compound (a-11) preferably in 1 to 10 equivalent amount, for 5 minutes to 72 hours in the presence of a phosphine compound preferably in 1 to 10 equivalent amount and an azo compound preferably in 1 to 10 equivalent amount, at a temperature between −78° C. and the boiling point of the solvent used.

Compound (a-11) can be obtained as a commercially available product.

The phosphine compounds include, for example, triphenylphosphine, and tributylphosphine and the like.

The azo compounds include, for example, DEAD, di-tertbutyl azadicarboxylate, diisopropyl azadicarboxylate, N,N,N',N'-tetramethyl azadicarboxamide, and 1,1'-(azadicarbonyl)dipiperazine, N,N,N',N'-tetraisopropyl azadicarboxamide and the like.

The solvents include, for example, toluene, ethyl acetate, acetonitrile, diethyl ether, THF, DME, dioxane, DMF, DMA, and NMP and the like. They are used alone or in mixtures.

Step 29

Compound (V-e) wherein n2 is 1 can be manufactured by reacting compound (V-d) in a solvent with compound (a-7) preferably in 1 to 10 equivalent amount, for 5 minutes to 72 hours in the presence of a base preferably in 1 to 10 equivalent amount, at a temperature between −20° C. and the boiling point of the solvent used.

Compound (a-7) can be obtained as a commercially available product.

The bases include, for example, sodium carbonate, potassium carbonate, cesium carbonate, potassium hydroxide, sodium hydroxide, sodium hydride, potassium tert-butoxide, diisopropylethylamine, and DBU and the like.

The solvents include, for example, toluene, ethyl acetate, acetonitrile, diethyl ether, THF, DME, DMF, dioxane, and water and the like. They are used alone or in mixtures.

Compound (V-e) wherein n2 is 0 and $R^2$ is optionally substituted cycloalkyl, or compound (V-e) wherein n2 is 0 and $R^2$ is optionally substituted aliphatic heterocyclic group wherein the sp³ carbon constituting the aliphatic heterocyclic group is bonded to —O—, can be manufactured by reacting compound (V-d) in a solvent with compound (a-12) preferably in 1 to 10 equivalent amount, in the presence of a base preferably in 1 to 10 equivalent amount at a temperature between −20° C. and the boiling point of the solvent used for 5 minutes to 72 hours.

Compound (a-12) can be obtained as a commercially available product.

The bases include, for example, sodium carbonate, potassium carbonate, cesium carbonate, potassium hydroxide, sodium hydroxide, sodium hydride, potassium tert-butoxide, diisopropylethylamine, and DBU and the like.

The solvents include, for example, toluene, ethyl acetate, acetonitrile, diethyl ether, THF, DME, DMF, dioxane, and water and the like. They are used alone or in mixtures.

Step 30

Compound (V-f) can be manufactured using compound (V-e), for example, by methods equivalent to a method described in Protective Groups in Organic Synthesis, third edition by T. W. Greene, John Wiley & Sons Inc. (1999), and the like.

Step 31

Compound (II-k) can be manufactured using compound (V-f) by a method similar to step 1.

Manufacturing Method 6

Among compounds (II-k), compound (II-L) wherein in the position 2 of 5,6,7,8-tetrahydroquinoline is lower alkoxy or —$NR^cR^d$ [wherein $R^c$ and $R^d$ are the same or different, and each represent hydrogen atom or low alkyl, or form an optionally substituted nitrogen-containing heterocyclic group together with the adjacent nitrogen atom (the nitrogen-containing heterocyclic groups include, for example, aziridinyl, azetidinyl, pyrrolidinyl, piperidino, azepanyl, pyrrolyl, imidazolidinyl, imidazolyl, pyrazolidinyl, pyrazolinyl, pyrazolyl, piperazinyl, homopiperazinyl, oxazolidinyl, 2H-oxazolyl, thioxazolidinyl, 2H-thioxazolyl, morpholino, and thiomorpholinyl and the like; and the substituents of the optionally substituted nitrogen-containing heterocyclic group together with the adjacent nitrogen atom are the same or different, and each include, for example, the substituent exemplified as the substituent of the aliphatic heterocyclic group optionally substituted with the number of substitution of 1-3)] can also be manufactured according to the following steps:

[Chemical formula 26]

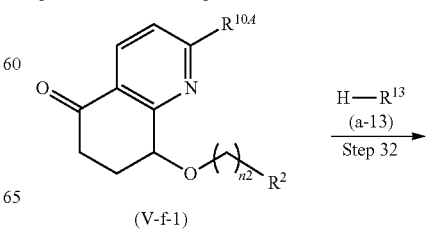

(V-f-1)

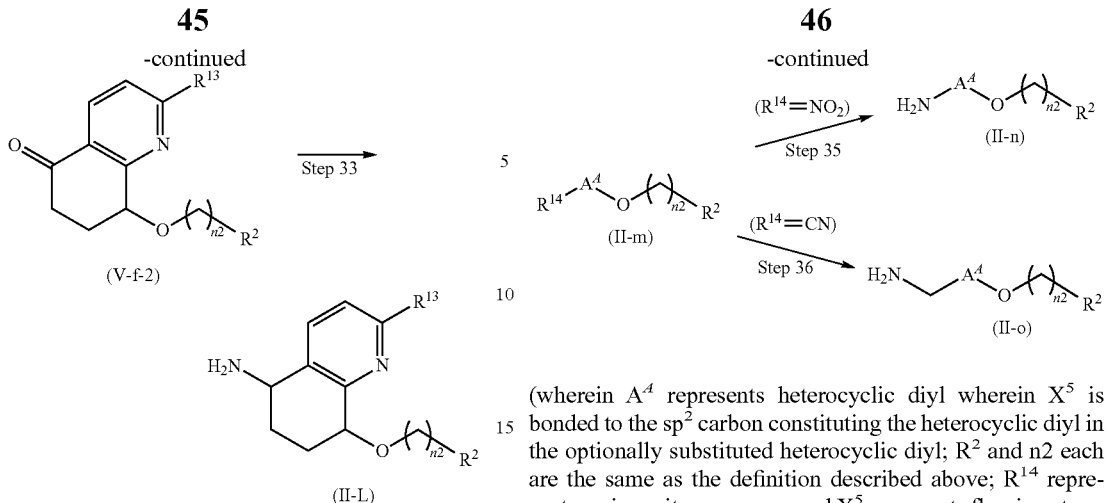

(V-f-2)

(II-L)

(wherein $R^2$ and n2 are the same as the definition described above; $R^{10A}$ corresponds to $R^{10}$ of compound (V-f), and represents fluorine atom, chlorine atom, bromine atom or iodine atom in $R^{10}$, $R^{13}$ represents lower alkoxy or —$NR^cR^d$ [wherein $R^c$ and $R^d$ each are the same as the definition described above] in $R^{10}$).

Step 32

Compound (V-f-2) can be manufactured by reacting compound (V-f-1) in a solvent with compound (a-13) or an alkali metal salt of compound (a-13) preferably in 1 to 10 equivalent amount, in the presence of, if needed, a base preferably in 1 to 10 equivalent amount, at a temperature between 0° C. and the boiling point of the solvent used, or if needed, using a microwave reaction device and at a temperature between 0° C. and 200° C. for one minute to 72 hours.

The bases include, for example, potassium carbonate, potassium hydroxide, sodium hydroxide, sodium methoxide, potassium tert-butoxide, triethylamine, diisopropylethylamine, N-methylmorpholine, pyridine, and DBU and the like.

Compound (V-f-1) can be obtained according to step 30 of manufacturing method 5. Compound (a-13) or an alkali metal salt of compound (a-13) can be obtained as a commercially available product.

The alkali metal salts of compound (a-13) include, for example, lithium salt, sodium salt or potassium salt or the like of compound (a-13).

The solvents include, for example, toluene, ethyl acetate, acetonitrile, diethyl ether, THF, DME, dioxane, DMF, DMA, NMP, pyridine, and water and the like. They are used alone or in mixtures.

Step 33

Compound (II-L) can be manufactured using compound (V-f-2) by a method similar to step 1.

Manufacturing Method 7

Among compounds (II), compounds (II-m), (II-n) and (II-o) can be manufactured according to the following steps:

[Chemical formula 27]

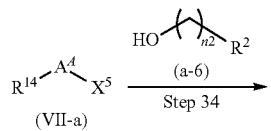

(VII-a)

(II-m)

(II-n)

(II-o)

(wherein $A^A$ represents heterocyclic diyl wherein $X^5$ is bonded to the $sp^2$ carbon constituting the heterocyclic diyl in the optionally substituted heterocyclic diyl; $R^2$ and n2 each are the same as the definition described above; $R^{14}$ represents amino, nitro or cyano; and $X^5$ represents fluorine atom, chlorine atom, bromine atom or iodine atom).

Step 34

Compound (II-m) can be manufactured by reacting compound (VII-a) in a solvent or without solvent with compound (a-6) preferably in 1 to 10 equivalent amount for one minute to 72 hours, if needed, in the presence of sodium iodide or potassium iodide preferably in 1 to 10 equivalent amount, and if needed, in the presence of a base preferably in 1 to 10 equivalent amount, at a temperature between −20° C. and the boiling point of the solvent used (between −20° C. and 180° C. when without solvent), or if needed, using a microwave reaction device and at a temperature between 0° C. and 200° C.

Compound (VII-a) can be obtained as a commercially available product or manufactured by methods equivalent to a method described in well-known methods [e.g., Chemistry of Heterocyclic Compounds, Volume 1-64, John Wiley & Sons Inc. (2008), CN101983961A, WO2007/036743, and the like].

Compound (a-6) can be obtained as a commercially available product.

The bases include, for example, potassium carbonate, cesium carbonate, potassium hydroxide, sodium hydroxide, potassium tert-butoxide, triethylamine, diisopropylethylamine, N-methylmorpholine, pyridine, and DBU and the like.

The solvents include, for example, toluene, acetonitrile, diethyl ether, THF, DME, dioxane, DMF, DMA, NMP, pyridine, and water and the like. They are used alone or in mixtures.

Furthermore, as an alternative method, when reacting with compound (a-6), wherein n2 is 0 and $R^2$ is an optionally substituted aromatic heterocyclic group or optionally substituted aryl, a method similar to step 2 of manufacturing method 1 can be used.

Step 35

Compound (II-n) can be manufactured by reacting compound (II-m), wherein $R^{14}$ is nitro, in a solvent, (i) with hydrogen under the hydrogen atmosphere preferably at 1 to 20 atmospheric pressure for 5 minutes to 72 hours, or (ii) with a hydrogen source preferably 2 equivalent to a large excess amount relative to compound (II-m), in the presence of a catalyst preferably in 0.01 to 50% by weight, at a temperature between −20° C. and the boiling point of the solvent used, for 5 minutes to 72 hours.

The catalysts include, for example, palladium carbon, palladium, palladium hydroxide, palladium acetate, palladium black, platinum oxide, and Raney nickel and the like.

The hydrogen sources include, for example, formic acid, ammonium formate, sodium formate, cyclohexadiene, and hydrazine and the like.

The solvents include, for example, methanol, ethanol, toluene, ethyl acetate, diethyl ether, THF, DME, dioxane, DMF, DMA, NMP, and water and the like. They are used alone or in mixtures.

Furthermore, as an alternative method, compound (II-n) can be manufactured by reacting compound (II-m) in a solvent with a metal or metal salt preferably in 1 to 10 equivalent amount, in the presence of an additive preferably in 1 equivalent to large excess amount, at a temperature between 0° C. and the boiling point of the solvent used for 5 minutes to 72 hours.

The metals or metal salts include, for example, tin, zinc, iron, samarium, indium, and tin dichloride and the like.

The additives include, for example, hydrochloric acid, acetic acid, and ammonium chloride and the like.

The solvents include, for example, methanol, ethanol, toluene, ethyl acetate, acetonitrile, diethyl ether, THF, DME, dioxane, DMF, DMA, NMP, and water and the like. They are used alone or in mixtures.

Step 36

Compound (II-e) can be manufactured using compound (II-m) wherein $R^{14}$ is cyano by a method similar to step 12.

Manufacturing Method 8

Among compounds (II), compound (II-n) can also be manufactured according to the following steps:

[Chemical formula 28]

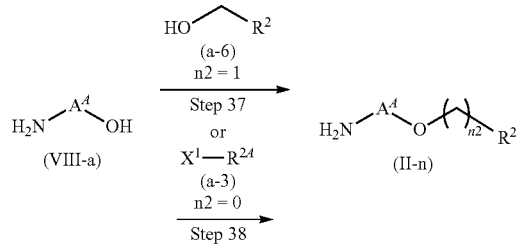

(wherein $A^A$, $R^2$, $R^{2A}$, $X^1$ and n2 are each the same as the definition described above).

Step 37

Compound (II-n) wherein n2 is 1 can be manufactured by reacting compound (VIII-a) in a solvent with compound (a-6) preferably in 1 to 10 equivalent amount, for 5 minutes to 72 hours in the presence of a phosphine compound preferably in 1 to 10 equivalent amount and an azo compound preferably in 1 to 10 equivalent amount, at a temperature between −78° C. and the boiling point of the solvent used.

Compound (a-6) can be obtained as a commercially available product.

Compound (VIII-a) can be obtained as a commercially available product or manufactured by methods equivalent to a method described in well-known methods [e.g., Chemistry of Heterocyclic Compounds, Volume 1-64, John Wiley & Sons Inc. (2008), WO2011/025546, and the like].

The phosphine compounds include, for example, triphenylphosphine, and tributylphosphine and the like.

The azo compounds include, for example, DEAD, di-tert-butyl azadicarboxylate, diisopropyl azadicarboxylate, N,N,N',N'-tetramethyl azadicarboxamide, 1,1'-(azadicarbonyl) dipiperazine, and N,N,N',N'-tetraisopropyl azadicarboxamide and the like.

The solvents include, for example, toluene, ethyl acetate, acetonitrile, diethyl ether, THF, DME, dioxane, DMF, DMA, and NMP and the like. They are used alone or in mixtures.

Step 38

Compound (II-n) wherein n2 is 0 and $R^2$ is optionally substituted aryl or optionally substituted aromatic heterocyclic group can be manufactured by a method similar to step 2 of manufacturing method 1 using compounds (VIII-a) and (a-3).

Compound (VIII-a) can be obtained in the method similar to the above.

Compound (a-3) can be obtained as a commercially available product.

Manufacturing Method 9

Among compounds (II), compound (II-n) can also be manufactured according to the following steps:

[Chemical formula 29]

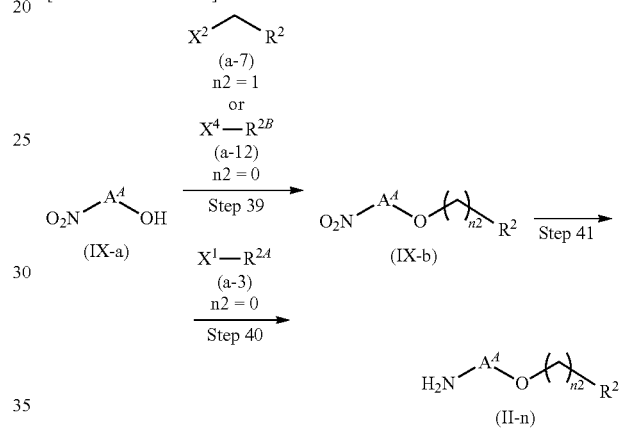

(wherein $A^A$, $R^2$, $R^{2A}$, $R^{2B}$, $X^1$, $X^2$, $X^4$ and n2 are each the same as the definition described above).

Step 39

Compound (IX-b) wherein n2 is 1 can be manufactured by reacting compound (IX-a) in a solvent with compound (a-7) preferably in 1 to 10 equivalent amount, for 5 minutes to 72 hours in the presence of a base preferably in 1 to 10 equivalent amount, at a temperature between −20° C. and the boiling point of the solvent used.

Compound (a-7) can be obtained as a commercially available product.

Compound (IX-a) can be obtained as a commercially available product or manufactured by methods equivalent to a method described in well-known methods [e.g., Chemistry of Heterocyclic Compounds, Volume 1-64, John Wiley & Sons Inc. (2008), and the like].

The bases include, for example, sodium carbonate, potassium carbonate, cesium carbonate, potassium hydroxide, sodium hydroxide, potassium tert-butoxide, diisopropylethylamine, and DBU and the like.

The solvents include, for example, methanol, ethanol, toluene, ethyl acetate, acetonitrile, diethyl ether, THF, DME, DMF, dioxane, water, and the like. They are used alone or in mixtures.

Compound (IX-b) wherein n2 is 0 and $R^2$ is optionally substituted cycloalkyl, or compound (IX-b) wherein n2 is 0 and $R^2$ is optionally substituted aliphatic heterocyclic group wherein the sp³ carbon constituting the aliphatic heterocyclic group is bonded to —O—, can be manufactured by reacting compound (IX-a) in a solvent with compound (a-12) preferably in 1 to 10 equivalent amount, in the presence of a base preferably in 1 to 10 equivalent amount, at a temperature between −20° C. and the boiling point of the solvent used for 5 minutes to 72 hours.

Compound (a-12) can be obtained as a commercially available product.

The bases include, for example, sodium carbonate, potassium carbonate, cesium carbonate, potassium hydroxide, sodium hydroxide, potassium tert-butoxide, diisopropylethylamine, and DBU and the like.

The solvents include, for example, methanol, ethanol, toluene, ethyl acetate, acetonitrile, diethyl ether, THF, DME, DMF, dioxane, and water and the like. They are used alone or in mixtures.

Step 40

Compound (IX-b), wherein n2 is 0 and $R^2$ is optionally substituted aryl or optionally substituted aromatic heterocyclic group, can be manufactured using compounds (IX-a) and (a-3) by a method similar to step 2 of manufacturing method 1.

Step 41

Compound (II-n) can be manufactured by a method similar to step 34 using compound (IX-b).

Manufacturing Method 10

Compound (I) can be manufactured according to the following manufacturing method.

[Chemical formula 30]

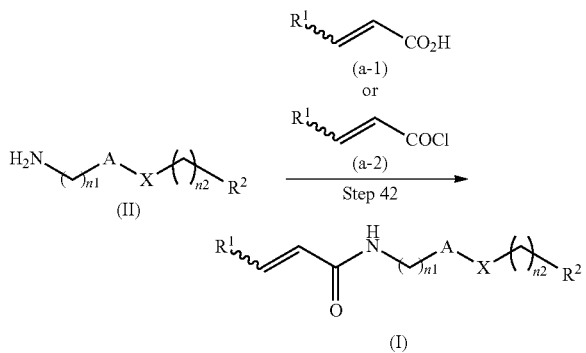

(wherein $R^Z$, $R^2$, X, n1, n2 and A are each the same as the definition described above, and the wavy line part between $R^1$ and the adjacent carbon atom represents cis or trans configuration).

Step 42

Compound (I) can be manufactured by reacting compound (II) in a solvent with compound (a-1) preferably in 1 to 5 equivalent amount, for 5 minutes to 72 hours in the presence of a condensation agent preferably in 1 to 5 equivalent amount, and if needed, in the presence of an additive preferably in 1 to 5 equivalent amount, at a temperature between −20° C. and the boiling point of the solvent used.

Compound (a-1) can be obtained as a commercially available product or also manufactured by methods equivalent to a method described in well-known methods [e.g., "Jikken Kagaku Koza 16, 5th Ed., Synthesis of organic compounds IV, carboxylic acid, amino acid, peptide" Maruzen (2005), and the like].

Compound (II) can be manufactured according to any one of manufacturing methods 1, 2, 4-9, 11-15, or 17-19.

The condensation agents include, for example, 1,3-dicyclohexane carbodiimide (DCC), 1-ethyl-3-(3-dimethylaminopropyl)carbodiimide hydrochloride (EDC), carbonyldiimidazole (CDI), and 2-chloro-1-methyl pyridinium iodide and the like.

The additives include, for example, 1-hydroxybenzotriazole monohydrate (HOBt) and the like.

The solvents include, for example, toluene, ethyl acetate, acetonitrile, diethyl ether, THF, DME, dioxane, DMF, DMA, NMP, and pyridine and the like. They are used alone or in mixtures.

Furthermore, as an alternative method, compound (I) can be manufactured by reacting compound (II) in a solvent or without solvent with compound (a-2) preferably in 1 to 10 equivalent amount, if needed, in the presence of a base preferably in 1 to 10 equivalent amount, at a temperature between −20° C. and the boiling point of the solvent used (between −20° C. and 150° C. when without solvent) for 5 minutes to 72 hours.

Compound (a-2) can be obtained as a commercially available product, or obtained by well-known methods [e.g., "Jikken Kagaku Koza 16, 5th Ed., Synthesis of organic compounds IV" p. 101, Maruzen (2005)] or by its equivalent methods.

The bases include, for example, potassium carbonate, potassium hydroxide, sodium hydroxide, potassium tert-butoxide, triethylamine, diisopropylethylamine, N-methylmorpholine, pyridine, DBU, and 4-dimethylaminopyridine (DMAP) and the like.

The solvents include, for example, dichloromethane, chloroform, 1,2-dichloroethane, toluene, ethyl acetate, acetonitrile, diethyl ether, THF, DME, dioxane, DMF, DMA, NMP, and pyridine and the like. They are used alone or in mixtures.

Manufacturing Method 11

Among compounds (II), compound (II-p), (II-q) or (II-r) as a 5-aminochromane derivative or a 5-aminomethylchromane derivative can be manufactured according to the following steps:

[Chemical formula 31]

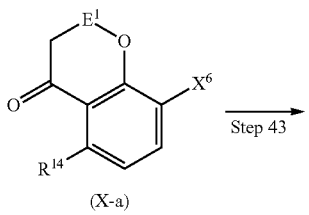

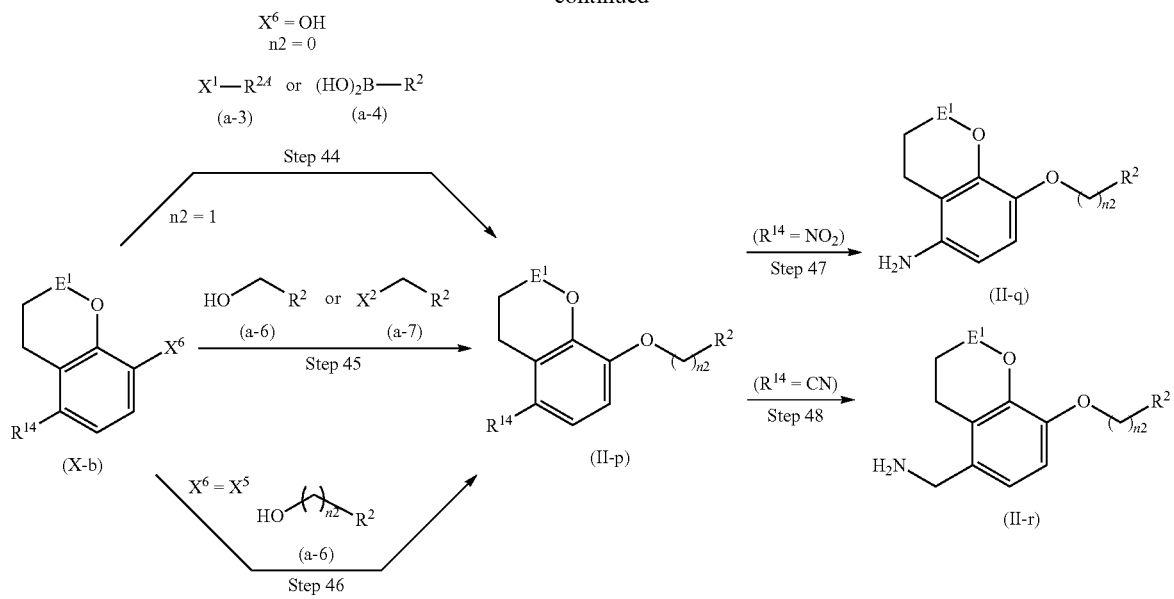

(wherein $R^2$, $R^{2A}$, $R^{14}$, $X^1$, $X^2$, $X^5$, n2 and $E^1$ are the same as the definition described above; and $X^6$ represents hydroxy, fluorine atom, chlorine atom, bromine atom or iodine atom).

Step 43

Compound (X-b) can be manufactured by reacting compound (X-a) in a solvent or without solvent, (i) with 1 equivalent to a large excess amount of a reducing agent for 5 minutes to 72 hours in the presence of 1 equivalent to a large excess amount of an acid at a temperature between −20° C. and the boiling point of the solvent used, or (ii) with hydrogen under the hydrogen atmosphere at 1 to 20 atmospheric pressure or with 2 equivalents to a large excess amount of a hydrogen source for 5 minutes to 72 hours in the presence of a catalyst preferably in 0.01 to 50% by weight, at a temperature between −20° C. and the boiling point of the solvent used.

Compound (X-a) can be obtained as a commercially available product, or obtained by well-known methods [Chemistry of Heterocyclic Compounds, Volume 31, John Wiley & Sons Inc. (2008) and the like] or their equivalent methods.

The acids include, for example, acetic acid, hydrochloric acid, and trifluoroacetic acid and the like.

The reducing agents include, for example, triethylsilane, and zinc amalgam and the like.

The catalysts include, for example, palladium carbon, palladium, palladium hydroxide, palladium acetate, palladium black, platinum oxide, and Raney nickel and the like.

The hydrogen sources include, for example, formic acid, ammonium formate, sodium formate, cyclohexadiene, and hydrazine and the like.

The solvents include, for example, methanol, ethanol, toluene, ethyl acetate, diethyl ether, THF, DME, dioxane, DMF, DMA, NMP, and water and the like. They are used alone or in mixtures.

Step 44

Compound (II-p) wherein n2 is 0 can be manufactured using compound (X-b) wherein $X^6$ is hydroxy by a method similar to step 2 or 3 of manufacturing method 1.

Step 45

Compound (II-p) wherein n2 is 1 can be manufactured by a method similar to step 13 of manufacturing method 1 using compound (X-b) wherein $X^6$ is hydroxy.

Step 46

Compound (II-p) can be manufactured by a method similar to step 34 using compound (X-b) wherein $X^6$ is fluorine atom, chlorine atom, bromine atom or iodine atom.

Step 47

Compound (II-q) can be manufactured by a method similar to step 35 using compound (II-p) wherein $R^{14}$ is nitro.

Step 48

Compound (II-r) can be manufactured by a method similar to step 12 using compound (II-p) wherein $R^{14}$ is cyano.

Manufacturing Method 12

Among compounds (II), compound (II-s) that is a 5,6,7,8-tetrahydroquinoline derivative can be manufactured according to the following steps:

[Chemical formula 32]

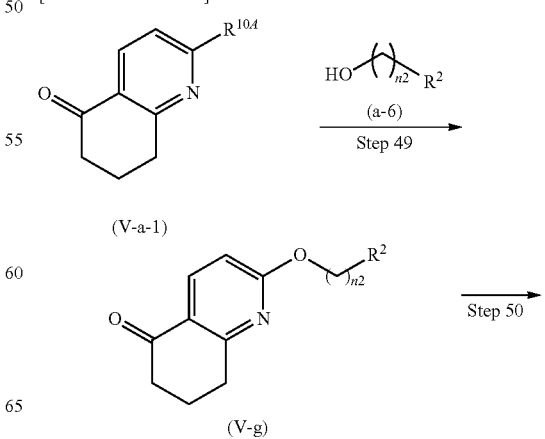

-continued

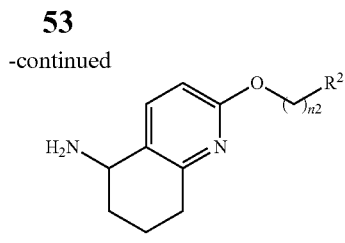

(wherein $R^2$, $R^{10A}$ and n2 are the same as the definition described above).

Step 49

Compound (V-g) can be manufactured by a method similar to step 34 of manufacturing method 7 using compound (V-a-1).

Compound (V-a-1) can be obtained as a commercially available product, or by well-known methods [e.g., Synthetic Communications, 2010 Vol. 40, p. 1708-1716] or its equivalent methods.

Step 50

Compound (II-s) can be manufactured by a method similar to step 1 of manufacturing method 1 using compound (V-g).

Manufacturing Method 13

Among compounds (II), compound (II-t) that is a 5,6,7,8-tetrahydroisoquinoline derivative can be manufactured according to the following steps:

[Chemical formula 33]

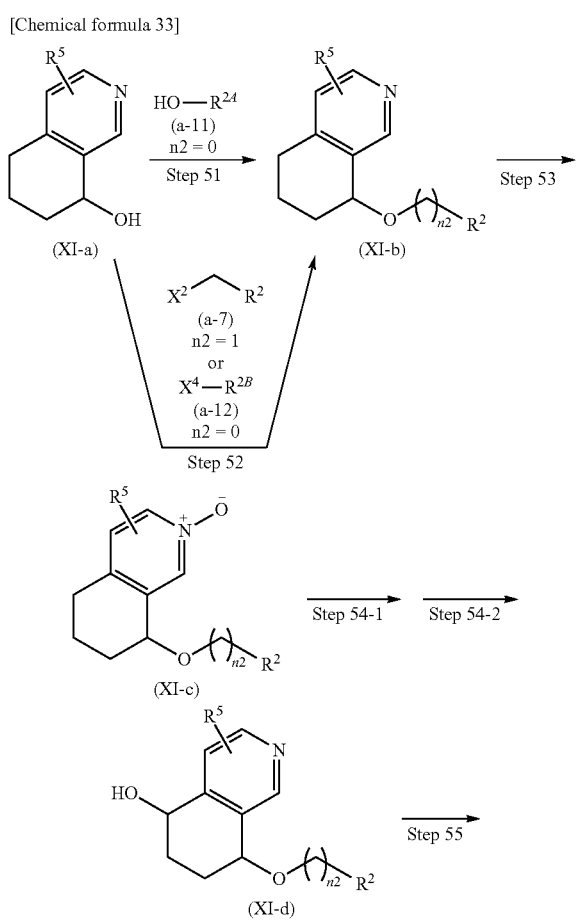

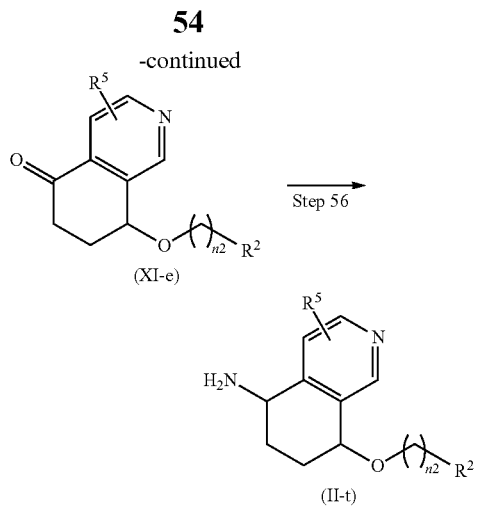

(wherein $R^2$, $R^{2A}$, $R^{2B}$, $R^5$, $X^2$, $X^4$ and n2 are the same as the definition described above).

Step 51

Compound (XI-b), wherein n2 is 0 and $R^2$ is optionally substituted aryl or optionally substituted aromatic heterocyclic group, can be manufactured by a method similar to step 28 of manufacturing method 5 using compound (XI-a).

Compound (XI-a) can be obtained as a commercially available product or by well-known methods [e.g., US2013/0274287, WO2013/079452 and the like] or its equivalent methods.

Step 52

Compound (XI-b) wherein n2 is 1 and $R^2$ is optionally substituted cycloalkyl or optionally substituted aliphatic heterocyclic group, and compound (XI-b) wherein n2 is 0 and $R^2$ is optionally substituted cycloalkyl, or compound (XI-b) wherein n2 is 0 and $R^2$ is aliphatic heterocyclic group wherein the sp³ carbon constituting the aliphatic heterocyclic group is bonded to —O—, can be manufactured by a method similar to step 29 of manufacturing method 5 using compound (XI-a).

Step 53

Compound (XI-c) can be manufactured by a method similar to step 26 of manufacturing method 5 using compound (XI-b).

Steps 54-1 and 54-2

Compound (XI-d) can be manufactured by a method similar to steps 27-1 and 27-2 of manufacturing method 5 using compound (XI-c).

Step 55

Compound (XI-e) can be manufactured by treating compound (XI-d) in a solvent with an oxidation agent preferably in 1 to 10 equivalent amount for 5 minutes to 72 hours at a temperature between −20° C. and the boiling point of the solvent used.

The oxidizing agent includes, for example, manganese dioxide, chromic acid, pyridinium chlorochromate (PCC), pyridinium dichlorochromate (PDC), potassium permanganate, sulfur trioxide-pyridine, Oxone (registered trademark), DMSO/oxalyl chloride, and Dess-Martin periodinane and the like.

The solvents include, for example, dichloromethane, chloroform, 1,2-dichloroethane, toluene, ethyl acetate, acetonitrile, diethyl ether, THF, DME, dioxane, DMF, DMA, NMP, DMSO, pyridine, hydrochloric acid, acetic acid, propionic acid, acetic anhydride, sulfuric acid, and water and the like. They are used alone or in mixtures.

Step 56

Compound (II-t) can be manufactured by a method similar to step 1 of manufacturing method 1 using compound (XI-e).

Manufacturing Method 14

Among compounds (II), compounds (II-u), (II-v), (II-w), (II-x) and (II-y), wherein X is —O—, —S—, —NR$^{X1}$— (wherein R$^{X1}$ represents hydrogen atom or lower alkyl), —CH═CH—, —NH—CO— or —SO$_2$—; and X is bonded to the sp$^3$ carbon constituting A; can be manufactured according to the following steps:

[Chemical formula 34]

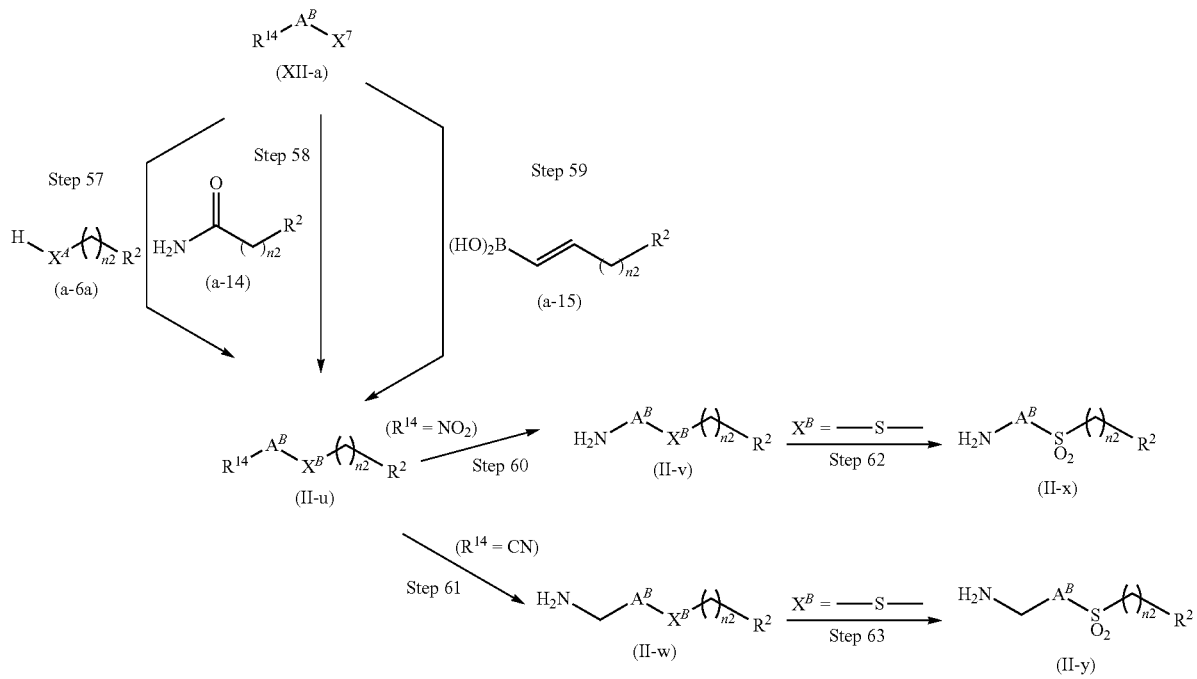

[wherein R$^2$, R$^{14}$ and n2 are the same as the definition described above; AB represents heterocyclic diyl wherein X$^7$ is bonded to the sp$^3$ carbon constituting the heterocyclic diyl among optionally substituted heterocyclic diyl groups; X$^7$ represents fluorine atom, chlorine atom, bromine atom, iodine atom, p-toluene sulfonyloxy, methanesulfonyloxy or trifluoromethanesulfonyloxy; X$^7$ represents —O—, —S— or —NR$^{X1}$— (wherein R$^{X1}$ represents hydrogen atom or lower alkyl); and X$^B$ represents —O—, —S—, —NR$^{X1}$— (wherein R$^{X1}$ represents hydrogen atom or lower alkyl), —CH═CH— or —NH—CO—)].

Step 57

Compound (II-u) wherein X$^B$ is X$^A$ can be manufactured by a method similar to step 29 of manufacturing method 5 using compounds (XII-a) and (a-6a).

Compound (XII-a) can be obtained as a commercially available product or manufactured by methods equivalent to a method described in well-known methods [e.g., Chemistry of Heterocyclic Compounds, Volume 1-64, John Wiley & Sons Inc. (2008), and the like].

Compound (a-6a) can be obtained as a commercially available product.

Step 58

Compound (II-u) wherein X$^B$ is —NH—CO— can be manufactured by reacting compound (XII-a) in a solvent with compound (a-14) preferably in 1 to 10 equivalent amount under exposure of light, for 5 minutes to 72 hours in the presence of a copper reagent preferably in 0.01 to 1 equivalent amount and a base preferably in 1 to 10 equivalent amount at a temperature between −20° C. and the boiling point of the solvent used.

The copper reagents include, for example, copper(0), copper(I) iodide, copper(II) acetate, copper(II) oxide, and copper(I) chloride and the like.

The bases include, for example, potassium carbonate, cesium carbonate, potassium phosphate, potassium tert-butoxide, sodium tert-butoxide, lithium tert-butoxide, and potassium phosphate and the like.

The solvents include, for example, toluene, ethyl acetate, acetonitrile, diethyl ether, THF, DME, DMF, HMPA, DMSO, dioxane, and water and the like. They are used alone or in mixtures.

Compound (a-14) can be obtained as a commercially available product.

Step 59

Compound (II-u) wherein X$^B$ is —CH═CH— can be manufactured by reacting compound (XII-a) in a solvent with compound (a-15) preferably in 1 to 5 equivalent amount, for 5 minutes to 72 hours in the presence of a base preferably in 0.1 to 10 equivalent amount and a metallic catalyst preferably 0.001 to 0.5 equivalent amount at a temperature between −20° C. and the boiling point of the solvent used.

Compound (a-15) can be obtained as a commercially available product or by well-known methods [e.g., "Jikken Kagaku Koza 18, 5th Ed., Synthesis of organic compounds VI, Organic synthesis using metals" p. 97, Maruzen (2005)], or its equivalent methods.

The bases include, for example, potassium carbonate, potassium phosphate, potassium hydroxide, sodium hydroxide, potassium tert-butoxide, triethylamine, diisopropylethylamine, N-methylmorpholine, pyridine, DBU, and sodium hexamethyldisilazide and the like.

The metallic catalysts include, for example, palladium acetate, tris(dibenzylidene acetone)dipalladium, tetrakis(triphenylphosphine)palladium, 1,1'-bis(diphenylphosphino)ferrocene dichloropalladium/dichloromethane 1:1 adduct, nickel dicyclooctadiene, nickel chloride, nickel bromide, and nickel iodide and the like.

The solvents include, for example, methanol, ethanol, dichloromethane, chloroform, 1,2-dichloroethane, toluene, ethyl acetate, acetonitrile, diethyl ether, THF, DME, dioxane, DMF, DMA, NMP, and water and the like. They are used alone or in mixtures.

[Chemical formula 35]

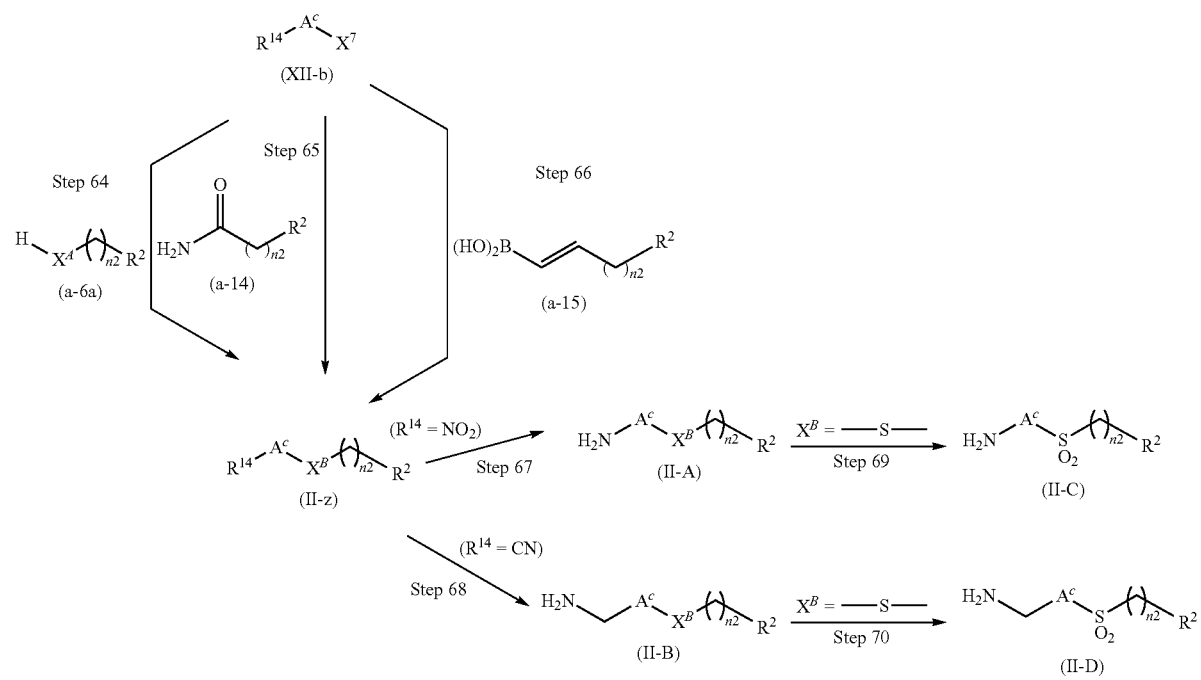

Step 60

Compound (II-v) can be manufactured by a method similar to step 35 of manufacturing method 7 using compound (II-u) wherein $R^{14}$ is nitro.

Step 61

Compound (II-w) can be manufactured by a method similar to step 12 of manufacturing method 1 using compound (II-u) wherein $R^{14}$ is cyano.

Step 62

Compound (II-x) can be manufactured by treating compound (II-v) wherein $X^F$ is —S— in a solvent with an oxidizing agent preferably in 2 to 10 equivalent amount for 5 minutes to 72 hours at a temperature between 0° C. and the boiling point of the solvent used.

The oxidizing agents include, for example, m-chloroperoxybenzoic acid, benzoyl peroxide, peracetic acid, hydrogen peroxide solution, sodium periodate, and potassium permanganate and the like.

The solvents include, for example, methanol, ethanol, dichloromethane, chloroform, 1,2-dichloroethane, toluene, ethyl acetate, acetonitrile, diethyl ether, THF, DME, dioxane, DMF, DMA, NMP, pyridine, and water and the like. They are used alone or in mixtures.

Step 63

Compound (II-y) can be manufactured by a method similar to step 62 using compound (II-w) wherein $X^B$ is —S—.

Manufacturing Method 15

Among compounds (II), compounds (II-z), (II-A), (II-B), (II-C) and (II-D), wherein X is —O—, —S—, —NR$^{X1}$— (wherein $R^{X1}$ represents hydrogen atom or lower alkyl), —CH=CH—, —NH—CO— or —SO$_2$—; and X is bonded to the sp$^2$ carbon constituting A; can be manufactured according to the following steps:

(wherein $R^2$, $R^{14}$, $X^7$, $X^A$, $X^B$ and n2 are the same as the definition described above; $A^c$ represents a heterocyclic diyl wherein $X^7$ is bonded to the sp$^2$ carbon constituting the heterocyclic diyl among the optionally substituted heterocyclic diyl groups).

Step 64

Compound (II-u) wherein $X^B$ is $X^A$ can be manufactured by a method similar to step 34 using compounds (XII-b) and (a-6a).

Compound (XII-b) can be obtained as a commercially available product, or manufactured by methods equivalent to a method described in well-known methods [e.g., Chemistry of Heterocyclic Compounds, Volume 1-64, John Wiley & Sons Inc. (2008), and the like].

Step 65

Compound (II-z) wherein $X^B$ is —NH—CO— can be manufactured by reacting compound (XII-b) in a solvent with compound (a-14) preferably in 1 to 10 equivalent amount, for 5 minutes to 72 hours in the presence of a copper reagent preferably 0.01 to 1 equivalent amount or palladium catalyst in 0.001 to 0.5 equivalent amount, a ligand preferably in 0.001 to 1 equivalent amount and a base preferably in 1 to 10 equivalent amount at a temperature between −20° C. and the boiling point of the solvent used.

The copper reagents include, for example, copper(0), copper(I) iodide, copper(II) acetate, copper(II) oxide, and copper(I) chloride and the like.

The palladium catalysts include, for example, palladium acetate, tris(dibenzylidene acetone)dipalladium, tetrakis(triphenylphosphine)palladium, and 1,1'-bis(diphenylphosphino)ferrocene dichloropalladium/dichloromethane 1:1 adduct and the like.

The ligands include, for example, phenanthroline, trans-1,2-cyclohexane diamine, picolinic acid, 2,2'-bis(diphenylphosphino)-1,1'-binaphthyl, o-tolylphosphine, tributylphosphine, di-tert-butydiphenylphosphine, 2-(di-tert-butylphosphino)biphenyl, and 2-(dicyclohexylphosphino)biphenyl and the like.

The bases include, for example, potassium carbonate, cesium carbonate, potassium phosphate, potassium tert-butoxide, sodium tert-butoxide, sodium disilazide, triethylamine, potassium acetate, sodium ethoxide, sodium carbonate, sodium hydroxide, potassium phosphate, ethylenediamine, glycine, N-methylpyrrolidine, pyridine, and 1,2-diaminocyclohexane and the like.

The solvents include, for example, toluene, ethyl acetate, acetonitrile, diethyl ether, THF, DME, DMF, HMPA, DMSO, dioxane, and water and the like. They are used alone or in mixtures.

Step 66

Compound (II-z) wherein $X^B$ is —CH═CH— can be manufactured by reacting in a solvent compound (XII-b) with compound (a-15) preferably in 1 to 5 equivalent amount, for 5 minutes to 72 hours in the presence of a base preferably in 0.1 to 10 equivalent amount and a palladium catalyst preferably in 0.001 to 0.5 equivalent amount at a temperature between −20° C. and the boiling point of the solvent used.

The bases include, for example, potassium carbonate, potassium phosphate, potassium hydroxide, sodium hydroxide, potassium tert-butoxide, triethylamine, diisopropylethylamine, N-methylmorpholine, pyridine, and DBU and the like.

The palladium catalysts include, for example, palladium acetate, tris(dibenzylidene acetone)dipalladium, tetrakis(triphenylphosphine)palladium, and 1,1'-bis(diphenylphosphino)ferrocene dichloropalladium/dichloromethane 1:1 adduct and the like.

The solvents include, for example, methanol, ethanol, dichloromethane, chloroform, 1,2-dichloroethane, toluene, ethyl acetate, acetonitrile, diethyl ether, THF, DME, dioxane, DMF, DMA, NMP, and water and the like. They are used alone or in mixtures.

Step 67

Compound (II-A) can be manufactured by a method similar to step 35 of manufacturing method 7 using compound (II-z) wherein $R^{14}$ is nitro.

Step 68

Compound (II-B) can be manufactured by a method similar to step 12 of manufacturing method 1 using compound (II-z) wherein $R^{14}$ is cyano.

Step 69

Compound (II-C) can be manufactured by a method similar to step 62 of manufacturing method 14 using compound (II-A) wherein $X^B$ is —S—.

Step 70

Compound (II-D) can be manufactured by a method similar to step 62 of manufacturing method 14 using compound (II-B) wherein $X^B$ is —S—.

Manufacturing Method 16

Among compounds (XII-a) and (XII-b), compound (XII-d) wherein X % is p-toluenesulfonyloxy, methanesulfonyloxy or trifluoromethanesulfonyloxy, can be manufactured according to the following step:

[Chemical formula 36]

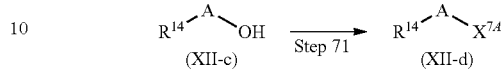

(wherein A and $R^{14}$ are the same as the definition described above; $X^{7A}$ represents p-toluenesulfonyloxy, methanesulfonyloxy or trifluoromethanesulfonyloxy).

Step 71

Compound (XII-d) can be manufactured by treating compound (XII-c) in a solvent or without solvent with a sulfonylation agent preferably in 1 to 10 equivalent amount, for 5 minutes to 72 hours if needed, in the presence of a base preferably in the equal amount of a catalyst to 10 equivalent amount at a temperature between −20° C. and 150° C.

The sulfonylation agents include, for example, anhydrous trifluoromethanesulfonic acid, anhydrous methanesulfonic acid, methanesulfonyl chloride, and p-toluenesulfonyl chloride and the like.

The bases include, for example, triethylamine, diisopropylethylamine, and pyridine and the like.

The solvents include, for example, dichloromethane, chloroform, 1,2-dichloroethane, toluene, ethyl acetate, acetonitrile, diethyl ether, THF, DME, dioxane, DMF, DMA, NMP, and pyridine and the like. They are used alone or in mixtures.

Compound (XII-c) can be obtained as a commercially available product, or also manufactured by methods equivalent to a method described in well-known methods [e.g., Chemistry of Heterocyclic Compounds, Volume 1-64, John Wiley & Sons Inc. (2008), WO2011/025546, and the like].

Manufacturing Method 17

Among compounds (II), compound (II-E) wherein X is —CH(OH)— or —CH═CH— can be manufactured according to the following steps:

[Chemical formula 37]

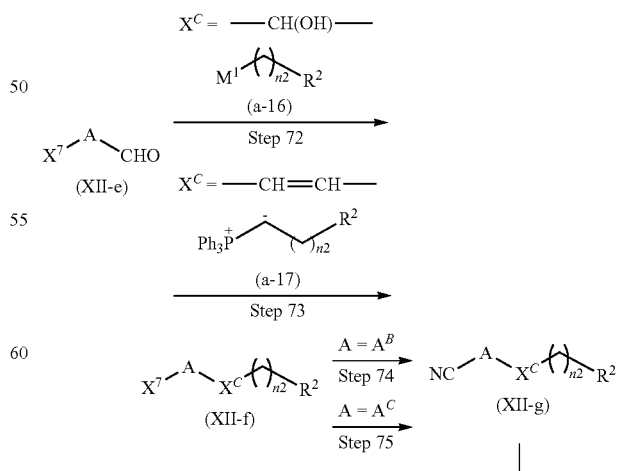

-continued $$H_2N \diagup A \diagdown X^C \diagup_{n2} R^2$$

(II-E)

[wherein A, $A^B$, $A^C$, $R^2$, $X^7$, $M^1$ and n2 are the same as the definition described above; and $X^C$ represents —CH(OH)— or —CH=CH—].

Step 72

Compound (XII-f) wherein $X^C$ is —CH(OH)— can be manufactured by reacting compound (XII-e) in a solvent with compound (a-16) preferably in 1 to 10 equivalent amount, for 5 minutes to 72 hours at a temperature between −78° C. and the boiling point of the solvent used.

Compound (XII-e) can be obtained as a commercially available product or also manufactured by methods equivalent to a method described in well-known methods [e.g., Chemistry of Heterocyclic Compounds, Volume 1-64, John Wiley & Sons Inc. (2008), and the like].

Compound (a-16) can be obtained as a commercially available product or by well-known methods [e.g., "Jikken Kagaku Koza 18, 5th Ed., Synthesis of organic compounds VI, Organic synthesis using metal" p. 59, Maruzen (2005)] or its equivalent methods.

The solvents include, for example, toluene, diethyl ether, THF, DME, dioxane, and hexane and the like. They are used alone or in mixtures.

Step 73

Compound (XII-f) wherein $X^C$ is —CH=CH— can be manufactured by reacting compound (XII-e) in a solvent with compound (a-17) preferably in 1 to 10 equivalent amount, for 5 minutes to 72 hours in the presence of a base preferably in 0.1 to 10 equivalent amount at a temperature between −78° C. and the boiling point of the solvent used.

The bases include, for example, potassium acetate, sodium bicarbonate, potassium carbonate, potassium hydroxide, sodium hydroxide, sodium methoxide, potassium tert-butoxide, triethylamine, diisopropylethylamine, N-methylmorpholine, pyridine, and DBU and the like.

The solvents include, for example, methanol, ethanol, dichloromethane, chloroform, 1,2-dichloroethane, toluene, ethyl acetate, acetonitrile, diethyl ether, THF, DME, dioxane, DMF, DMA, and NMP. They are used alone or in mixtures.

Compound (a-17) can be obtained as a commercially available product, or by well-known methods [e.g., "Jikken Kagaku Koza 24, 4th Ed." p. 252, Maruzen (2000)] or its equivalent methods.

Step 74

When compound (XII-f) wherein $X^7$ is bonded to the sp$^3$ carbon constituting A is used, compound (XII-g) can be manufactured by reacting compound (XII-f) in a solvent with a cyanating agent preferably in 1 to 10 equivalent amount, for 5 minutes to 72 hours in the presence of, if needed, a base preferably in 1 to 10 equivalent amount at a temperature between −20° C. and 150° C.

The cyanating agents include, for example, sodium cyanide, potassium cyanide, tetrabutylammonium cyanide, and trimethylsilyl cyanide and the like.

The bases include, for example, potassium carbonate, potassium hydroxide, sodium hydroxide, sodium methoxide, potassium tert-butoxide, triethylamine, diisopropylethylamine, N-methylmorpholine, pyridine, and DBU and the like.

The solvents include, for example, dichloromethane, chloroform, 1,2-dichloroethane, toluene, ethyl acetate, acetonitrile, diethyl ether, THF, DME, dioxane, DMF, DMA, and NMP and the like. They are used alone or in mixtures.

Step 75

When compound (XII-f) wherein $X^7$ is bonded to the sp$^2$ carbon constituting A is used, compound (XII-g) can be manufactured by reacting compound (XII-f) in a solvent with a cyanating agent preferably in 1 equivalent to 10 equivalent amount, in the presence of a base preferably in 0.1 to 10 equivalent amount and a palladium catalyst preferably in 0.001 to 0.5 equivalent amount at a temperature between −20° C. and the boiling point of the solvent used, or if needed, using a microwave reaction device and at a temperature between 0° C. and 200° C. for 5 minutes to 72 hours.

The cyanating agents include, for example, zinc cyanide, sodium cyanide, and potassium cyanide and the like.

The bases include, for example, sodium carbonate, potassium carbonate, potassium phosphate, potassium hydroxide, sodium hydroxide, potassium tert-butoxide, triethylamine, diisopropylethylamine, N-methylmorpholine, pyridine, and DBU and the like.

The palladium catalysts include, for example, palladium acetate, tris(dibenzylidene acetone)dipalladium, tetrakis(triphenylphosphine)palladium, and 1,1'-bis(diphenylphosphino)ferrocene dichloropalladium/dichloromethane 1:1 adduct and the like.

The solvents include, for example, methanol, ethanol, toluene, ethyl acetate, acetonitrile, diethyl ether, THF, DME, dioxane, DMF, DMA, NMP, and water and the like. They are used alone or in mixtures.

Manufacturing Method 18

Among compounds (II), compounds (II-F), (II-G) and (II-H) wherein X is —CHR$^{X2}$— (wherein R$^{X2}$ represents hydrogen atom or hydroxy) or —CO— can be manufactured according to the following steps:

[Chemical formula 38]

$$NC \diagup A \diagdown \underset{OH}{\diagup}\diagdown_{n2} R^2 \xrightarrow{\text{Step 79}} NC \diagup A \diagdown \underset{O}{\diagup}\diagdown_{n2} R^2 \xrightarrow{\text{Step 80}} H_2N \diagup A \diagdown \underset{O}{\diagup}\diagdown_{n2} R^2$$

(XII-g-1)          (XII-i)          (II-H)

Step 76 ↓    Step 77 ↘

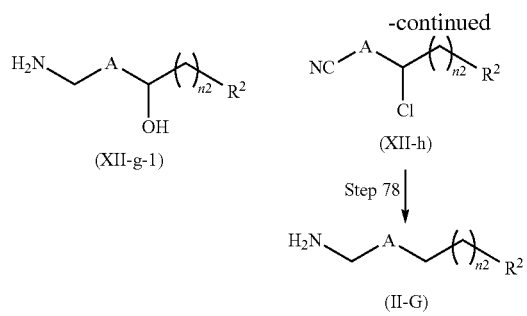

(wherein A, $R^2$ and n2 are the same as the definition described above).

Step 76

Compound (II-F) can be manufactured by a method similar to step 12 of manufacturing method 1 using compound (XII-g-1).

Compound (XII-g-1) can be obtained according to step 72 of manufacturing method 17.

Step 77

Compound (XII-h) can be manufactured by treating compound (XII-g-1) in a solvent or without solvent with a chlorinating agent preferably in 1 to a large excess amount, in the presence of, if needed, an additive preferably in the equal amount of a catalyst to 1 equivalent amount at a temperature between −20° C. and 150° C. for 5 minutes to 72 hours.

The chlorinating agents include, for example, phosphorus oxychloride, phosphorus pentachloride, phosphorus trichloride, and thionyl chloride and the like.

The additives include, for example, DMF, pyridine, and diisopropylethylamine and the like.

The solvents include, for example, dichloromethane, chloroform, 1,2-dichloroethane, toluene, diethyl ether, THF, DME, dioxane, DMF, DMA, NMP, and pyridine and the like. They are used alone or in mixtures.

Step 78

Compound (II-G) can be manufactured by a method similar to step 12 of manufacturing method 1 using compound (XII-h).

Step 79

Compound (XII-i) can be manufactured by a method similar to step 55 of manufacturing method 13 using compound (XII-g-1).

Step 80

Compound (II-H) can be manufactured by a method similar to step 12 of manufacturing method 1 using compound (XII-i).

Manufacturing Method 19

Among compounds (II), compound (II-J) wherein n is 1 and X is —$CH_2$— can be manufactured according to the following step:

[Chemical formula 39]

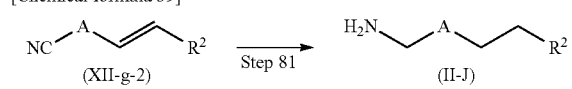

(wherein A and $R^2$ are the same as the definition described above).

Step 81

Compound (II-1) can be manufactured by a method similar to step 12 using compound (XII-g-2).

Compound (XII-g-2) can be obtained according to the method of step 73 of manufacturing method 17.

Manufacturing Method 20

Among compounds (I), compound (I-b) wherein X is —$SO_2$— can also be manufactured according to the following step:

[Chemical formula 40]

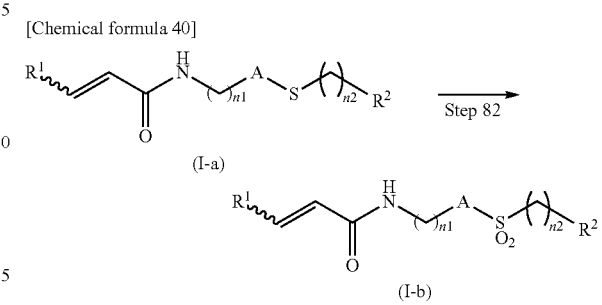

(wherein $R^1$, $R^2$, n1, n2 and A are each the same as the definition described above, and the wavy line part between $R^1$ and the adjacent carbon atom indicates cis or trans configuration).

Compound (I-a) can be obtained according to the method of step 42 of manufacturing method 10.

Step 82

Compound (1-b) can be manufactured by a method similar to step 62 using compound (I-a).

Conversion of functional groups contained in $R^1$ or $R^2$ of compound (I) can be conducted by well-known methods [methods described in Comprehensive Organic Transformations 2nd Ed., by R. C. Larock, Vch Verlagsgesellschaft Mbh (1999), and the like] or their equivalent methods.

The intermediate and the target compound in each manufacturing method mentioned above can be isolated and purified by an isolation/purification procedure commonly used in organic synthetic chemistry, for example, by subjecting to filtration, extraction, washing, drying, concentration, recrystallization, and various chromatography and the like. Furthermore, the intermediates can be supplied to the next reactions without being particularly purified.

Among compounds (1), stereoisomers such as geometric isomer, optical isomer, and the like, and tautomer and the like can be present, but the present invention includes all possible isomers and mixtures thereof.

A part or all of each atom in compound (I) may be substituted with the corresponding isotope, and the present invention includes these compounds substituted with these isotopes. For example, a part or all of hydrogen atom(s) in compound (I) may be hydrogen atom having an atomic weight of 2 (deuterium atom).

Compound (I), wherein a part or all of each atom is substituted with the corresponding isotope, can be manufactured by a method similar to the manufacturing method mentioned above using commercially available building blocks. Furthermore, a compound wherein a part or all of each hydrogen atom in compound (I) is substituted with deuterium can be synthesized by, for example, 1) a method by which carboxylic acid and the like are deuterated under the basic conditions using deuterium peroxide (refer to U.S. Pat. No. 3,849,458), 2) a method by which alcohol, carboxylic acid and the like are deuterated using an iridium complex as a catalyst and heavy water as a deuterium source [refer to J. Am. Chem. Soc., Vol. 124, No. 10, 2092 (2002)], 3) a method by which aliphatic acid is deuterated using palladium carbon as a catalyst and only deuterium gas as a deuterium source [refer to LIPIDS, Vol. 9, No. 11, 913 (1974)], 4) a method by which acrylic acid, methyl acrylate, methacrylic acid, methyl methacrylate, and the like are deuterated using a metal such as platinum, palladium, rhodium, ruthenium, iridium, and the like, and using heavy water or heavy water and deuterium gas as a deuterium source (refer to Japanese Examined Patent Application 5-19536, Japanese Unexamined Patent Application Publication No. 61-277648 and Japanese Unexamined Patent Application Publication No. 61-275241), 5) a method by which acrylic acid, methyl methacrylate, and the like are deuterated using a catalyst such as palladium, nickel, copper or copper chromite, and the like, and heavy water as a deuterium source (refer to Japanese Unexamined Patent Application Publication No. 63-198638), and the like.

When a salt of compound (I) is desired, in the case where compound (I) is obtained in the form of a salt, it can be purified as it is, or in the case where it is obtained in a free form, compound (I) can be dissolved or suspended in a suitable solvent and an acid or a base may be added to form a salt thereof followed by isolation and purification.

Furthermore, compound (I) and a pharmaceutically acceptable salt thereof may be present in the form of an adduct with water or various solvents, but these adducts are also included in the present invention.

Compounds represented in formula (I) of the present invention (compounds (I)) are preferably compounds described in the following Tables 1 to 26.

TABLE 1

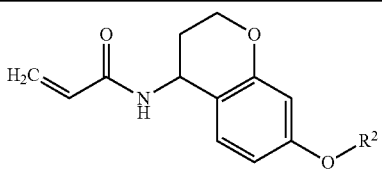

| Compound No. | R² |
|---|---|
| 1 | 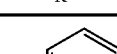 |
| 2 | 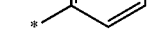 |

TABLE 1-continued

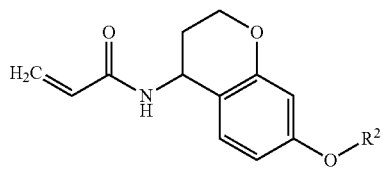

| Compound No. | R² |
|---|---|
| 3 |  |
| 4 |  |
| 5 |  |
| 6 |  |
| 7 |  |
| 8 |  |
| 9 |  |
| 10 |  |
| 11 |  |
| 12 | Compund with retention time of 4.17 minutes amoung two enaantiomers contained in compund 3 |
| 13 | Compund with retention time of 3.31 minutes amoung two enaantiomers contained in compund 3 |
| 14 | 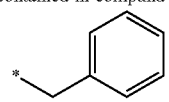 |

TABLE 1-continued

[Structure: acrylamide-NH-chroman-7-O-R²]

| Compound No. | R² |
|---|---|
| 15 | 4-chlorobenzyl (*-CH₂-C₆H₄-Cl) |
| 16 | cyclohexylmethyl (*-CH₂-cyclohexyl) |

TABLE 2

| Compound No. | Structure |
|---|---|
| 17 | N-(4-methyl-7-phenoxychroman-4-yl)acrylamide |
| 18 | N-(7-(4-chlorophenoxy)-2,2-dimethylchroman-4-yl)acrylamide |
| 19 | N-(2-methyl-7-(4-(trifluoromethyl)phenoxy)chroman-4-yl)acrylamide |
| 20 | N-(2-methyl-7-(4-(trifluoromethyl)phenoxy)chroman-4-yl)acrylamide (stereoisomer) |
| 21 | N-(3-fluoro-7-(4-(trifluoromethyl)phenoxy)chroman-4-yl)acrylamide |

TABLE 2-continued
| Compound No. | |
|---|---|
| 22 | 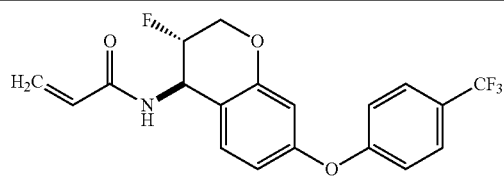 |
| 23 | 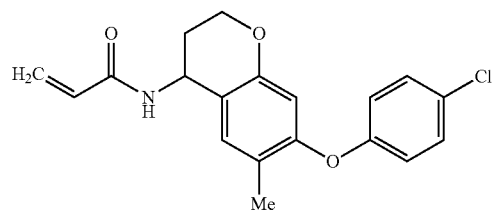 [SMILES: C=CC(=O)NC1CCOc2cc(Oc3ccc(Cl)cc3)c(C)cc21] |
| 24 | 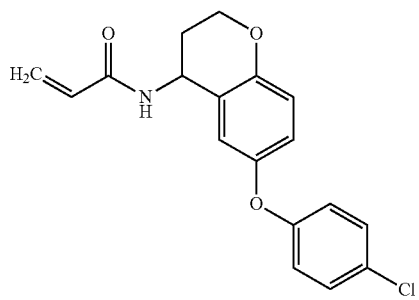 [SMILES: C=CC(=O)NC1CCOc2ccc(Oc3ccc(Cl)cc3)cc21] |
| 25 | 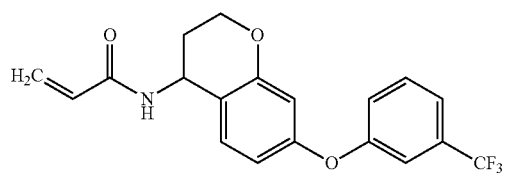 [SMILES: C=CC(=O)NC1CCOc2cc(Oc3cccc(C(F)(F)F)c3)ccc21] |
| 26 | 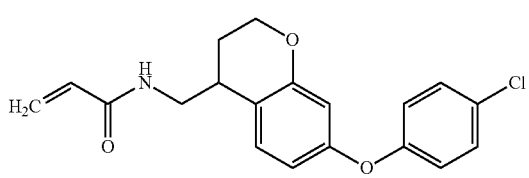 [SMILES: C=CC(=O)NCC1CCOc2cc(Oc3ccc(Cl)cc3)ccc21] |
TABLE 3
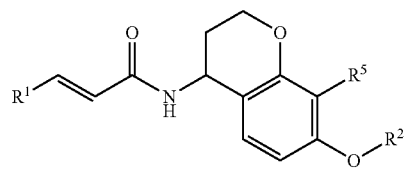
| Compound No. | $R^1$ | $R^5$ | $R^2$ |
|---|---|---|---|
| 27 | H | Me | 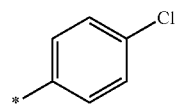 [SMILES: *c1ccc(Cl)cc1] |
TABLE 3-continued
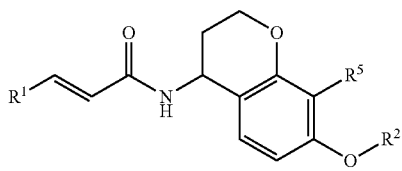
| Compound No. | $R^1$ | $R^5$ | $R^2$ |
|---|---|---|---|
| 28 | H | Me | 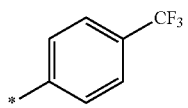 [SMILES: *c1ccc(C(F)(F)F)cc1] |

TABLE 3-continued
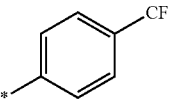
| Compound No. | R¹ | R⁵ | R² |
|---|---|---|---|
| 29 | CF₃ | Me | 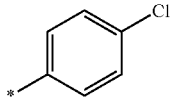 4-CF₃-phenyl |
| 30 | H | F | 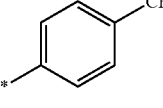 4-Cl-phenyl |
| 31 | H | F | 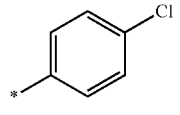 [SMILES: *c1ccc(Cl)cc1] 4-CF₃-phenyl |
| 32 | H | OMe | 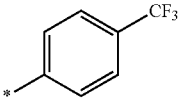 [SMILES: *c1ccc(C(F)(F)F)cc1] 4-Cl-phenyl |
| 33 | H | OMe | 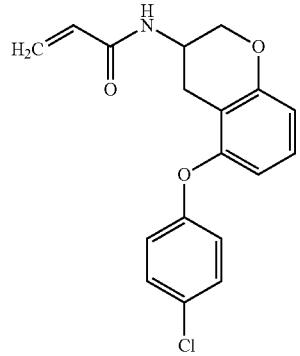 4-CF₃-phenyl |
TABLE 4
| Compound No. | |
|---|---|
| 34 | 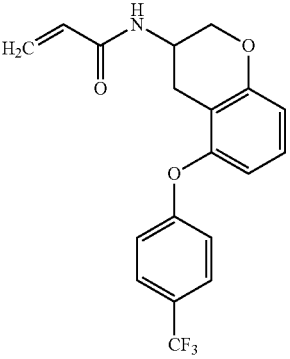 [SMILES: C=CC(=O)NC1COc2cccc(Oc3ccc(C(F)(F)F)cc3)c2C1] |
| 35 | |

TABLE 4-continued
| Compound No. | |
|---|---|
| 36 | 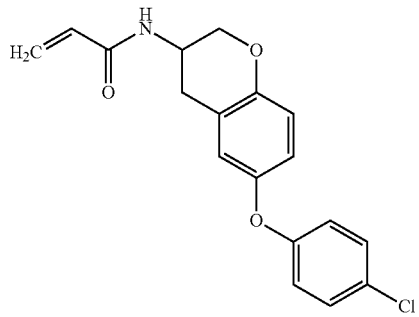 [SMILES: C=CC(=O)NC1COc2ccc(Oc3ccc(Cl)cc3)cc2C1] |
| 37 | 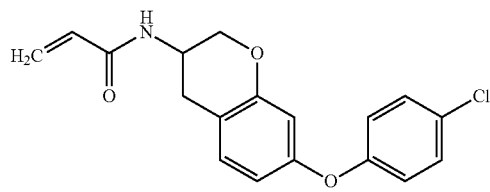 [SMILES: C=CC(=O)NC1COc2cc(Oc3ccc(Cl)cc3)ccc2C1] |
| 38 | 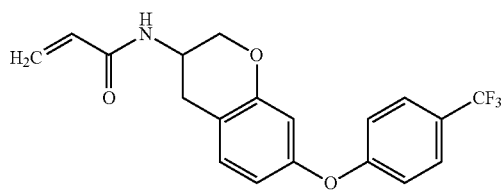 [SMILES: C=CC(=O)NC1COc2cc(Oc3ccc(C(F)(F)F)cc3)ccc2C1] |
| 39 | 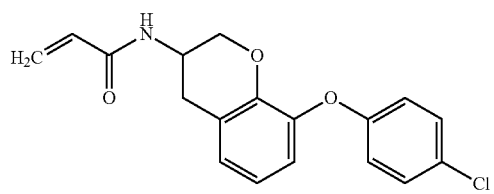 [SMILES: C=CC(=O)NC1COc2c(cccc2Oc2ccc(Cl)cc2)C1] |
| 40 | 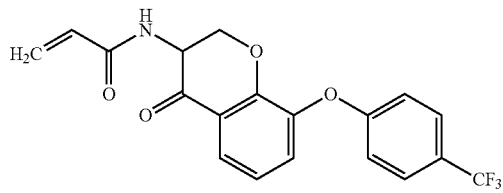 [SMILES: C=CC(=O)NC1COc2c(Oc3ccc(C(F)(F)F)cc3)cccc2C1=O] |
| 41 | 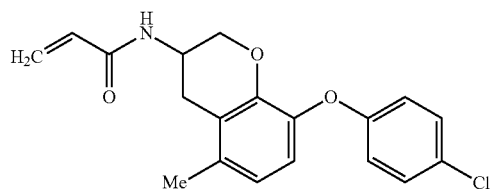 [SMILES: C=CC(=O)NC1COc2c(Oc3ccc(Cl)cc3)ccc(C)c2C1] |

TABLE 5

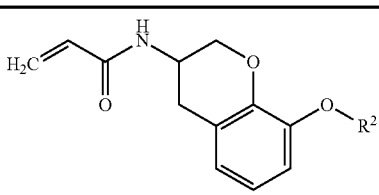

| Compound No. | R² |
|---|---|
| 42 | *-C₆H₄-Cl (4-Cl) |
| 43 | *-C₆H₄-CF₃ (3-CF₃) |
| 44 | *-C₆H₄-CF₃ (4-CF₃) |
| 45 | *-C₆H₄-OCF₃ (4-OCF₃) |
| 46 | *-C₆H₃-(3,4-diCl) |
| 47 | *-C₆H₃-(3-CF₃, 4-Cl) |
| 48 | *-pyridin-2-yl, 5-Cl |
| 49 | *-pyridin-3-yl, 6-Cl |
| 50 | *-pyridin-2-yl, 5-CF₃ |
| 51 | *-pyridin-3-yl, 6-CF₃ |
| 52 | *-pyridin-2-yl, 4,5-diCl |

TABLE 5-continued

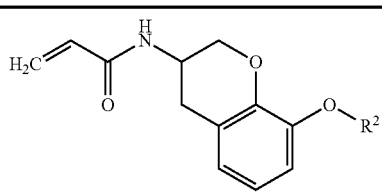

| Compound No. | R² |
|---|---|
| 53 | *-pyridin-6-yl, 2,3-diCl |
| 54 | *-pyridin-6-yl, 2-Me, 3-Cl |
| 55 | *-pyridin-2-yl, 4-Me, 5-Cl |
| 56 | *-pyridin-5-yl, 3-Me, 2-Cl |
| 57 | *-pyridin-6-yl, 2-Cl, 3-CF₃ |
| 58 | *-pyridin-2-yl, 4-CF₃, 5-CF₃ |

TABLE 6

| Compound No. | |
|---|---|
| 59 | Compound with retention time of 3.48 minutes among two enantiomers contained in compound 42 |
| 60 | Compound with retention time of 4.57 minutes among two enantiomers contained in compound 42 |
| 61 | Compound with retention time of 4.17 minutes among two enantiomers contained in compound 44 |
| 62 | Compound with retention time of 5.74 minutes among two enantiomers contained in compound 44 |
| 63 | Compound with retention time of 5.95 minutes among two enantiomers contained in compound 50 |
| 64 | Compound with retention time of 7.82 minutes among two enantiomers contained in compound 50 |

TABLE 6-continued
| Compound No. | |
|---|---|
| 65 | Compound with retention time of 6.65 minutes among two enantiomers contained in compound 35 |
| 66 | Compound with retention time of 8.25 minutes among two enantiomers contained in compound 35 |
TABLE 7
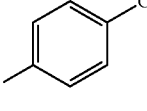
| Compound No. | R¹⁰ | R² |
|---|---|---|
| 67 | H | 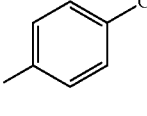 |
| 68 | H | 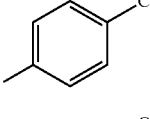 |
| 69 | H |  |
| 70 | Cl | 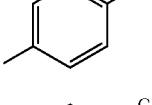 |
| 71 | OMe | 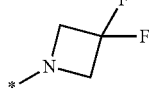 |
| 72 | 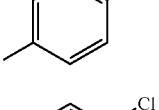 | 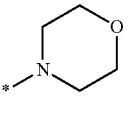 |
| 73 | 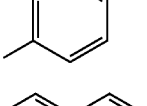 | 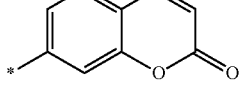 |
| 74 | 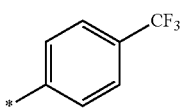 | 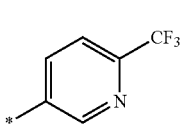 |
| 75 | Cl |  |
TABLE 7-continued
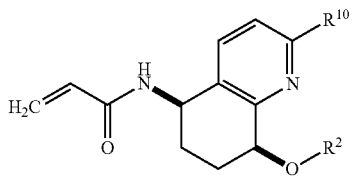
| Compound No. | R¹⁰ | R² |
|---|---|---|
| 76 | Cl | 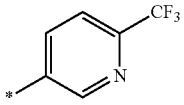 |
| 77 | Cl | 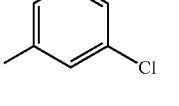 |
| 78 | 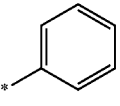NMe₂ | 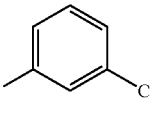 |
TABLE 8
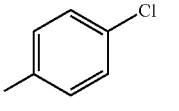
| Compound No. | R¹⁰ | R² |
|---|---|---|
| 79 | H | 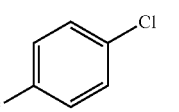 |
| 80 | H | 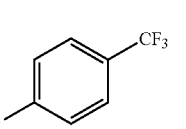 |
| 81 | OMe | |
| 82 | Cl | |

TABLE 9

Structure: R¹-CH=CH-C(=O)-NH-A-O-C₆H₄-Cl (para)

| Compound No. | R¹ | A |
|---|---|---|
| 83 | H | pyridine-2,6-diyl |
| 84 | H | pyridine-2,4-diyl |
| 85 | H | pyridine-4,2-diyl |
| 86 | H | 3-Me-pyridine-2,6-diyl |
| 87 | H | 4-Me-pyridine-2,6-diyl |
| 88 | H | 6-Me-pyridine-2,4-diyl |
| 89 | H | 5-Me-pyridine-2,4-diyl |
| 90 | Me | pyridine-2,4-diyl |
| 91 | H | 6-Me-pyridine-2,4-diyl |
| 92 | H | 2-Me-pyridine-3,5-diyl |
| 93 | H | 2-Me-pyridine-3,5-diyl |

TABLE 10

Structure: H₂C=CH-C(=O)-NH-(pyridin-3-yl)-5-O-R²

| Compound No. | R² |
|---|---|
| 94 | 4-Cl-phenyl |
| 95 | 3-CF₃-phenyl |
| 96 | 4-CF₃-phenyl |
| 97 | 3-OMe-phenyl |
| 98 | 4-OMe-phenyl |
| 99 | 4-CN-phenyl |
| 100 | 4-OCF₃-phenyl |

TABLE 10-continued

[Structure: H2C=CH-C(=O)-NH- attached to pyridine with -O-R² substituent]

| Compound No. | R² |
|---|---|
| 101 | *-C6H4-OEt (meta) |
| 102 | *-C6H4-OEt (para) |
| 103 | *-C6H4-OiPr (para) |
| 104 | *-C6H4-OBn (para) |
| 105 | *-C6H3-Cl,Cl (3,4-dichlorophenyl) |
| 106 | *-C6H3-F,CF3 |
| 107 | *-pyridyl-CF3 |
| 108 | *-pyridyl-CF3 |
| 109 | *-pyridyl-CF3 |
| 110 | *-pyridyl-OiPr |

TABLE 11

[Structure: H2C=CH-C(=O)-NH- attached to quinoline with R¹⁵ and -O-R²]

| Compound No. | R¹⁵ | R² |
|---|---|---|
| 111 | H | *-phenyl |
| 112 | Me | *-phenyl |
| 113 | H | *-C6H4-Cl (ortho) |
| 114 | H | *-C6H4-Cl (meta) |
| 115 | Me | *-C6H4-Cl (meta) |
| 116 | H | *-C6H4-Cl (para) |
| 117 | Me | *-C6H4-Cl (para) |
| 118 | H | *-C6H3-Cl,Cl (3,4-dichlorophenyl) |
| 119 | H | *-cyclohexyl |
| 120 | H | *-4,4-difluorocyclohexyl |
| 121 | H | *-tetrahydropyran-4-yl |
| 122 | H | *-tetrahydropyran-3-yl |

TABLE 12

[Structure: H2C=CH-C(O)-NH- attached to quinoline (with N) having 8-O-CH2-R2 substituent]

| Compound No. | R² |
|---|---|
| 123 | *-phenyl |
| 124 | *-(4-ethynylphenyl) |
| 125 | *-cyclohexyl |
| 126 | *-(4,4-difluorocyclohexyl) |
| 127 | *-(4-CF3-cyclohexyl) (cis) |
| 128 | *-(4-CF3-cyclohexyl) (trans) |
| 129 | *-(tetrahydropyran-4-yl) |
| 130 | *-(tetrahydropyran-3-yl) |
| 131 | *-(tetrahydropyran-2-yl) |
| 132 | *-(2,2-dimethyltetrahydropyran-4-yl) |

TABLE 13

[Structure: R1-CH=CH-C(O)-NH-CH2- attached to quinoline with R15 at 2-position and 8-O-R2]

| Compound No. | R¹ | R¹⁵ | R² |
|---|---|---|---|
| 133 | H | H | *-(3-chlorophenyl) |
| 134 | H | H | *-(4-chlorophenyl) |
| 135 | CF₃ | H | *-(4-chlorophenyl) |
| 136 | H | H | *-(4-cyclopropylphenyl) |
| 137 | H | H | *-(3-CF3-phenyl) |
| 138 | H | H | *-(4-CF3-phenyl) |
| 139 | H | Cl | *-(4-CF3-phenyl) |
| 140 | H | H | *-(3,4-dichlorophenyl) |
| 141 | H | H | *-(3,5-dichlorophenyl) |
| 142 | H | H | *-(6-chloropyridin-3-yl) |
| 143 | H | H | *-(6-CF3-pyridin-3-yl) |

TABLE 14

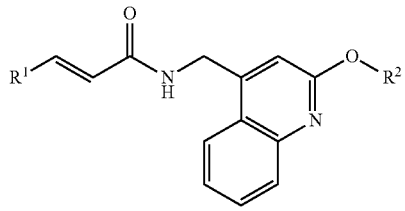

| Compound No. | R¹ | R² |
|---|---|---|
| 144 | H | 4-chlorophenyl |
| 145 | CF₃ | 4-chlorophenyl |
| 146 | H | 4-(trifluoromethyl)phenyl |
| 147 | CF₃ | 4-(trifluoromethyl)phenyl |
| 148 | H | 6-chloropyridin-3-yl |
| 149 | H | 6-(trifluoromethyl)pyridin-3-yl |
| 150 | H | 2-chloropyridin-4-yl |
| 151 | H | 2-(trifluoromethyl)pyridin-4-yl |

TABLE 15

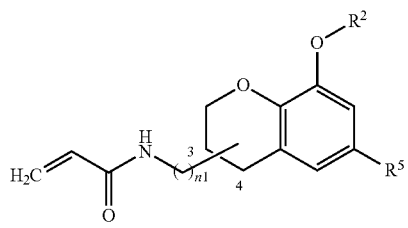

| Compound No. | Substitution position of acrylamide | n1 | R² | R⁵ |
|---|---|---|---|---|
| 152 | 4 | 1 | 4-chlorophenyl | H |
| 153 | 3 | 0 | 6-(trifluoromethyl)pyridin-3-yl | Br |
| 154 | 3 | 0 | 6-isopropoxypyridin-3-yl | H |
| 155 | 3 | 0 | 2-(trifluoromethyl)pyrimidin-5-yl | H |
| 156 | 3 | 0 | 6-(trifluoromethyl)pyridazin-3-yl | H |
| 157 | 3 | 0 | 5-(trifluoromethyl)pyrazin-2-yl | H |
| 158 | 3 | 0 | 4-(trifluoromethylthio)phenyl | H |
| 159 | 3 | 0 | 4-(trifluoromethylsulfonyl)phenyl | H |
| 160 | 3 | 0 | (4,4-difluorocyclohexyl)methyl | H |
| 161 | 3 | 0 | 5-chloropyrimidin-2-yl | H |

TABLE 15-continued

Structure: H2C=CH-C(=O)-NH-(CH2)n1-[chroman with R2O at position 8 and R5 at position 6, positions 3 and 4 marked]

| Compound No. | Substitution position of acrylamide | n1 | R² | R⁵ |
|---|---|---|---|---|
| 162 | 3 | 0 | *-5-(2-CF₃-pyridyl) | CF₃ |

TABLE 16

Structure: H2C=CH-C(=O)-NH-[chroman-4-yl with R5 at position 8 and OR2 at position 7]

| Compound No. | R² | R⁵ |
|---|---|---|
| 163 | *-5-(2-CF₃-pyridyl) | OMe |
| 164 | *-(3,4-difluorophenyl) | OMe |
| 165 | *-CH₂-(4,4-difluorocyclohexyl) | OMe |

TABLE 16-continued

Structure: H2C=CH-C(=O)-NH-[chroman-4-yl with R5 at position 8 and OR2 at position 7]

| Compound No. | R² | R⁵ |
|---|---|---|
| 166 | *-CH₂-phenyl (benzyl) | F |
| 167 | *-(3-fluorophenyl) | F |
| 168 | *-5-(2-CF₃-pyridyl) | Cl |
| 169 | *-5-(2-CF₃-pyridyl) | Br |
| 170 | *-5-(2-CF₃-pyridyl) | OH |
| 171 | *-5-(2-CF₃-pyrimidyl) | F |
| 172 | *-5-(2-CF₃-pyridyl) | OEt |
| 173 | *-5-(2-CF₃-pyridyl) | NMe₂ |

TABLE 17

| Compound No. | |
|---|---|
| 174 | Structure: H2C=CH-C(=O)-NH-CH₂-[chroman with OC(=O)Me at position 3 and O-(4-chlorophenyl) at position 8, acrylamidomethyl at position 5] |

TABLE 17-continued
Compound No.
175 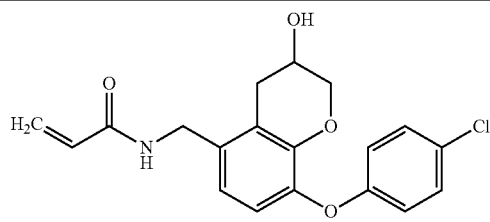
176 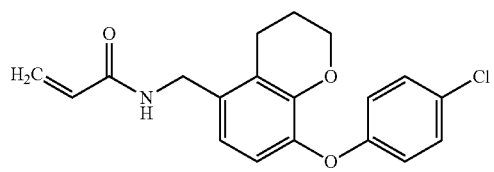 [SMILES: C=CC(=O)NCc1ccc(Oc2ccc(Cl)cc2)c2c1CCCO2]
177 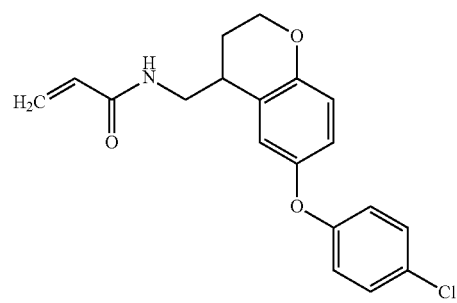 [SMILES: C=CC(=O)NCC1CCOc2ccc(Oc3ccc(Cl)cc3)cc21]
| TABLE 18 | | | TABLE 18-continued | | |
|---|---|---|---|---|---|
| 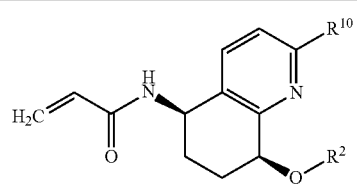 | | | 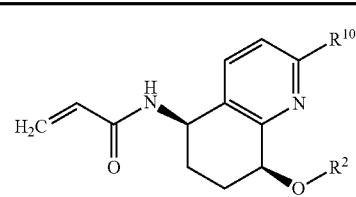 | | |
| Compound No. | R² | R¹⁰ | Compound No. | R² | R¹⁰ |
| 178 | 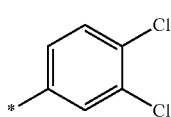 | Cl | 182 | 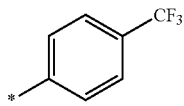 [SMILES: *c1ccc(C(F)(F)F)cc1] | CN |
| 179 | 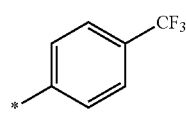 | OMe | 183 | 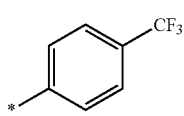 [SMILES: *c1ccc(C(F)(F)F)cc1] | Me |
| 180 | 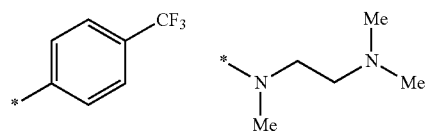 | | (Optically active substane of 184) | | |
| 181 | 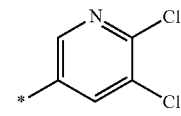 [SMILES: *c1cnc(Cl)c(Cl)c1] | Cl | 184 | 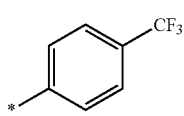 [SMILES: *c1ccc(C(F)(F)F)cc1] | Me |

TABLE 18-continued
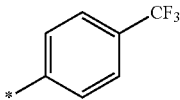
| Compound No. | R² | R¹⁰ |
|---|---|---|
| 185 | 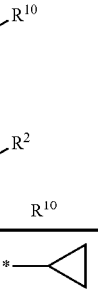 4-CF₃-phenyl | cyclopropyl |
| 186 | 4-CF₃-phenyl | Et |
| 187 | 3-F-4-CF₃-phenyl | Cl |
| 188 | 4-CF₃-phenyl | OEt |
| 189 | 5-CF₃-pyridin-2-yl | Cl |
TABLE 19
| Compound No. |
|---|
| 190 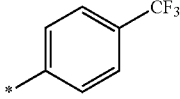 [SMILES: *c1ccc(C(F)(F)F)cc1] |
| 191 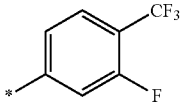 |
TABLE 20
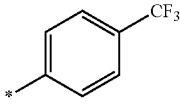 [SMILES: *c1ccc(C(F)(F)F)cc1]
| Compound No. | R² |
|---|---|
| 192 | 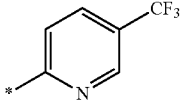 (4,4-difluorocyclohexyl)methyl |
| 193 | 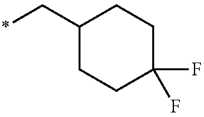 4-(trifluoromethyl)pyrimidin-2-yl |
| 194 | 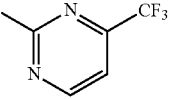 4,4-difluorocyclohexyl |

TABLE 21
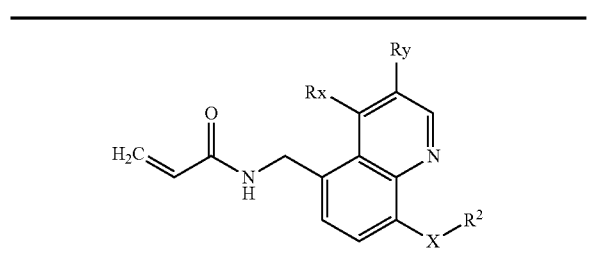
| Compound No. | R² | Rx | Ry | X |
|---|---|---|---|---|
| 195 | 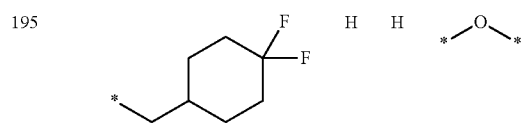 | H | H | *—O—* |
| 196 | 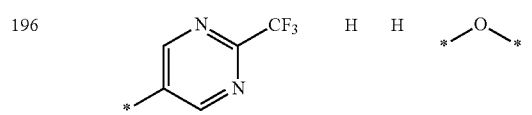 | H | H | *—O—* |
| 197 | 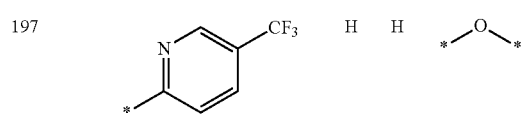 | H | H | *—O—* |
| 198 | 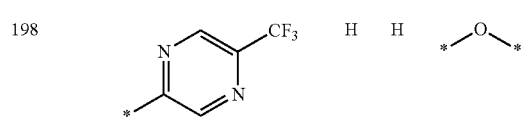 | H | H | *—O—* |
| 199 | 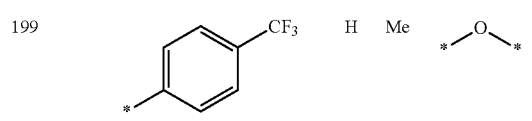 | H | Me | *—O—* |
| 200 | 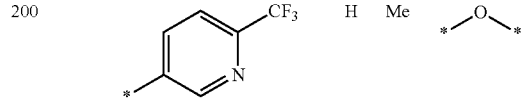 | H | Me | *—O—* |
| 201 | 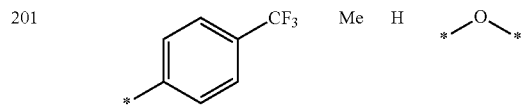 | Me | H | *—O—* |
| 202 | 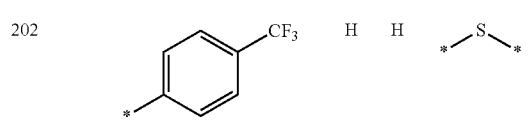 | H | H | *—S—* |
| 203 | 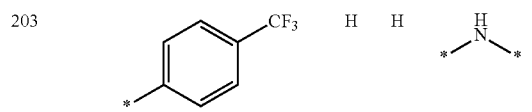 | H | H | *—NH—* |
TABLE 21-continued
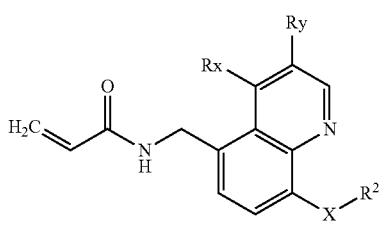
| Compound No. | R² | Rx | Ry | X |
|---|---|---|---|---|
| 204 | 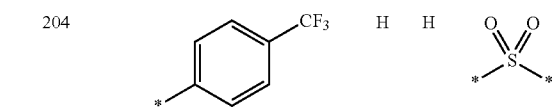 | H | H | *—SO₂—* |
TABLE 22
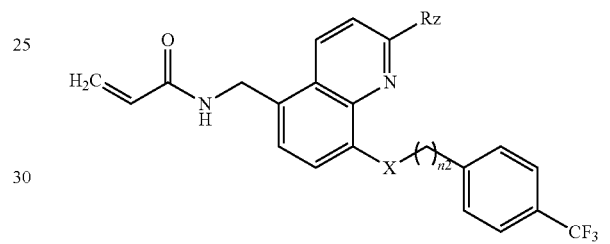
| Compound No. | Rz | X | n2 |
|---|---|---|---|
| 205 | H |  N(Me) | 0 |
| 206 | H | 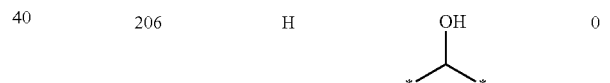 CH(OH) | 0 |
| 207 | H | 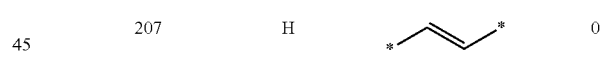 CH=CH | 0 |
| 208 | H |  C(=O) | 0 |
| 209 | H | 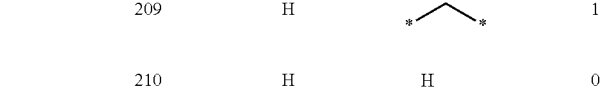 | 1 |
| 210 | H |  NHC(=O) | 0 |
| 211 | H |  CH₂ | 0 |
| 212 | Me | 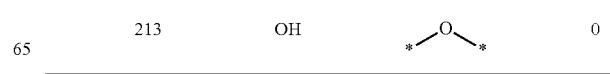 O | 0 |
| 213 | OH | 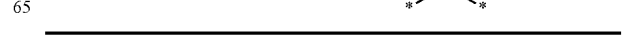 O | 0 |

TABLE 23
| Compound No. | |
|---|---|
| 214 | 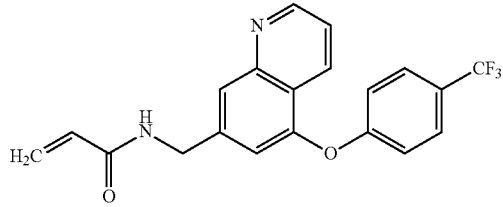 [SMILES: C=CC(=O)NCc1cc(Oc2ccc(C(F)(F)F)cc2)c2cccnc2c1] |
| 215 | 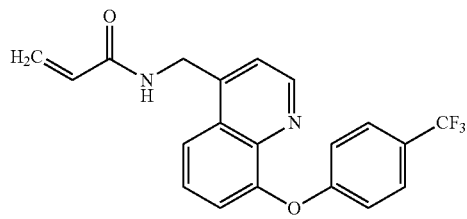 |
| 216 |  |
| 217 | 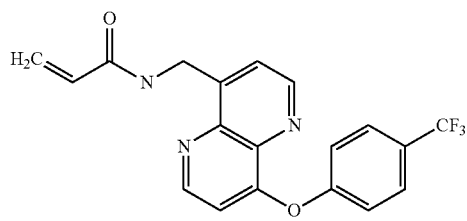 [SMILES: C=CC(=O)NCc1ccnc2c(Oc3ccc(C(F)(F)F)cc3)ccnc12] |
| 218 | 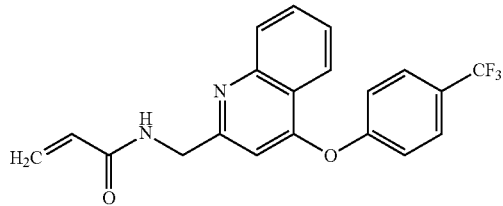 [SMILES: C=CC(=O)NCc1cc(Oc2ccc(C(F)(F)F)cc2)c2ccccc2n1] |
| 219 | 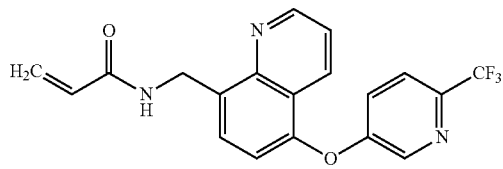 |
| 220 | 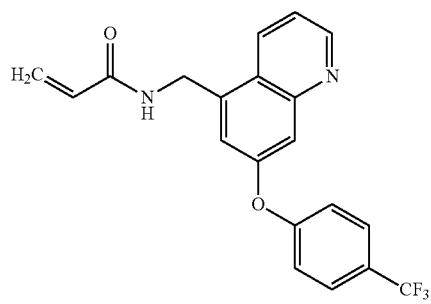 [SMILES: C=CC(=O)NCc1cc(Oc2ccc(C(F)(F)F)cc2)cc2ncccc12] |

TABLE 23-continued
| Compound No. |
|---|
| 221 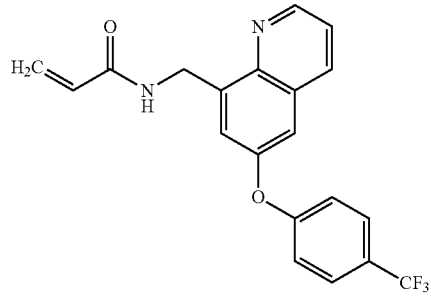 [SMILES: C=CC(=O)NCc1cc(Oc2ccc(C(F)(F)F)cc2)cc2cccnc12] |
TABLE 24
| Compound No. |
|---|
| 222 |
| 223 |
| 224 |
| 225 |
TABLE 25
| Compound No. |
|---|
| 226 |

TABLE 25-continued

Compound No.

227

228

TABLE 26

| Compound No. | |
|---|---|
| 229 | Compound with retention time of 2.61 minutes among two enantiomers contained in compound 51 |
| 230 | Compound with retention time of 3.28 minutes among two enantiomers contained in compound 51 |
| 231 | Compound with retention time of 2.44 minutes among two enantiomers contained in compound 153 |
| 232 | Compound with retention time of 3.24 minutes among two enantiomers contained in compound 153 |
| 233 | Compound with retention time of 4.56 minutes among two enantiomers contained in compound 40 |
| 234 | Compound with retention time of 5.07 minutes among two enantiomers contained in compound 40 |
| 235 | Compound with retention time of 3.67 minutes among two enantiomers contained in compound 41 |
| 236 | Compound with retention time of 4.35 minutes among two enantiomers contained in compound 41 |
| 237 | Compound with retention time of 5.14 minutes among two enantiomers contained in compound 33 |
| 238 | Compound with retention time of 6.79 minutes among two enantiomers contained in compound 33 |
| 239 | Compound with retention time of 6.19 minutes among two enantiomers contained in compound 31 |
| 240 | Compound with retention time of 7.43 minutes among two enantiomers contained in compound 31 |
| 241 | Compound with retention time of 2.73 minutes among two enantiomers contained in compound 76 |

TABLE 26-continued

| Compound No. | |
|---|---|
| 242 | Compound with retention time of 3.41 minutes among two enantiomers contained in compound 76 |

Compound (I) or a pharmaceutically acceptable salt thereof can be administered alone, but generally it is desirable to provide it as various pharmaceutical preparations. In addition, these pharmaceutical preparations are used for animals or humans, preferably humans.

The pharmaceutical preparation related to the present invention can contain compound (I) or a pharmaceutically acceptable salt thereof as an active ingredient by itself, or as a mixture with any other active ingredients used for the treatment. Furthermore, those pharmaceutical preparations are manufactured by a well-known method in the technical field of pharmaceutics by mixing the active ingredient with one kind or more pharmaceutically acceptable carriers (e.g., an attenuant, a solvent, a diluent and the like).

The most effective administration route is desirably used for the treatment. For example, it includes an oral or parental administration route such as intravenous injection and the like.

Administration forms include, for example, tablets, injection and the like.

Suitable formulation for the oral administration, for example, such as tablets, can be manufactured using a diluent such as lactose, a disintegrant such as starch, a lubricant such as magnesium stearate, a binder such as hydroxypropylcellulose, and the like.

Suitable formulation for the parenteral administration, for example, such as injection, can be manufactured using an attenuant such as a salt solution, glucose solution or mixed solution of saline and glucose solutions; a solvent or the like.

Dose and frequency of administration of compound (I) or a pharmaceutically acceptable salt thereof differ depending on administration form, age of the patient, body weight or the nature of the symptoms to be treated or severity of them or the like. Generally, they are administered for oral administration at a dosage of 0.01 to 1000 mg per adult, preferably at a dosage of 0.05 to 100 mg once daily or several times a day. In the case of parenteral administrations such as intravenous administration, they are administered at a dosage of 0.001 to 1000 mg per adult, preferably at a dosage of 0.01 to 100 mg once daily or several times a day. However, the dose and frequency of the administration vary depending on the above-mentioned conditions.

According to another embodiment of the present invention, provided is a pharmaceutical composition comprising compound (I) or a pharmaceutically acceptable salt thereof and a carrier. The pharmaceutical composition of the present invention is used in administration routes and dosage forms and the like similar to the pharmaceutical preparation mentioned above. Furthermore, the carrier contained in the pharmaceutical composition of the present invention may be an attenuant, solvent, diluent, and the like that are similar to the case of the pharmaceutical preparation mentioned above. Furthermore, the pharmaceutical composition of the present invention is used preferably for the treatment or prevention of cancers, more preferably for the treatment or prevention of one or two or more cancers selected from the group consisting of mesothelioma, lung cancer, ovarian cancer and liver cancer. Here, prevention means that the clinical condition of a disease, the outcome of biological symptoms or the severity of the disease is substantially reduced, or that development of such condition or the biological symptoms is delayed, and the like. The situation is similar to the following prevention.

According to another embodiment of the present invention, provided is a method for the treatment or prevention comprising administering compound (I) of the present invention or a pharmaceutically acceptable salt thereof to a subject (preferably a subject in need thereof). The subject includes, for example, an animal other than a human, but is preferably a human. This is also the same in the following subjects. The method for the treatment or prevention in the present invention is preferably used for the treatment or prevention of cancers, more preferably is used for the treatment or prevention of one or two or more cancers selected from the group consisting of mesothelioma, lung cancer, ovarian cancer and liver cancer.

According to another embodiment, provided is compound (I) of the present invention or a pharmaceutically acceptable salt thereof for use as a medicament.

According to another embodiment, provided is compound (I) of the present invention or a pharmaceutically acceptable salt thereof for use of treating or preventing cancers. Here, cancers are preferably one or two or more cancers selected from the group consisting of lung cancer, ovarian cancer and liver cancer.

According to another embodiment, provided is use of compound (I) of the present invention or a pharmaceutically acceptable salt thereof for the manufacture of drugs for the treatment or prevention of cancers. Here, cancers are preferably one or two or more cancers selected from the group consisting of lung cancer, ovarian cancer and liver cancer.

According to another embodiment, provided is use of compound (I) of the present invention or a pharmaceutically acceptable salt thereof for the treatment or prevention of cancers.

According to another embodiment, provided is a medicament comprising compound (I) of the present invention or a pharmaceutically acceptable salt thereof as an active ingredient.

According to another embodiment, provided is a preventive or therapeutic agent for cancers comprising compound (I) of the present invention or a pharmaceutically acceptable salt thereof as an active ingredient.

EXAMPLES

The present invention will be explained by examples more specifically below, but the scope of the present invention is not limited to these examples.

The pharmacological action of the typical compound (I) will be specifically explained by a test example.

Test Example 1

Cell growth inhibitory effect on human mesothelioma, human liver cancer, human ovarian cancer, and human liver cancer cell lines NCI-H226 cells, a human mesothelioma cell line (ATCC, CRL-5826), NCI-H322 cells, a human lung cancer cell line (the European Collection of Authenticated Cell Cultures, 95111734), OVTOKO cells, a human ovarian cancer cell line (JCRB cell bank, JCRB1048) and HuH28, a human liver cancer cell line (JCRB cell bank, JCRB0426) were each subcultured by keeping the cell density under 80% in a RPMI1640 culture medium with 10% fetal bovine serum (FBS). NCI-H226 cells, NCI-H322 cells and SSP-25 cells were each suspended in the RPMI1640 culture medium mentioned above, and plated to a 96-well flat-bottom plate at 500 cells/well in each well, and incubated at 37° C. in an incubator with 5% $CO_2$ for one day. After the incubation, the evaluation of cell growth inhibitory activity was started. OVTOKO cells were suspended in the RPMI1640 culture medium mentioned above, and plated to a 96-well flat-bottom plate at 250 cells/well in each well, and incubated it at 37° C. in an incubator with 5% $CO_2$ for one day. After the incubation, the evaluation of the cell growth inhibitory activity was started. The next day, a test compound was serially diluted to 5 times of its final concentration in the RPMI1640 culture medium mentioned above, and the diluted solution was added to each well. In this case, the final concentration of DMSO in each well was adjusted to 0.1%. After the test compound was added, cells were incubated at 37° C. in an incubator with 5% $CO_2$ for 6 days. At the addition of the test compound and 6 days after the addition, the cell counting measurement was performed using a cell counting kit 8 (made by DOJINDO) according to a protocol equivalent to DOJINDO's recommendation. A reagent contained in the kit was added to each plate and color reaction was performed for 2 or 3 hours at 37° C. in an incubator with 5% $CO_2$. After the reaction, an absorbance at wavelength of 450 nm was measured using a microplate reader. A growth inhibition rate was calculated according to the following formula, from which the concentration of a test compound at which cell growth was inhibited by 50% ($GI_{50}$ value) was determined.

[Mathematical formula 1]

$$\text{Inhibition rate of growth (\%)} = \frac{\begin{pmatrix} \text{Absorbance of well} \\ \text{without addition of a} \\ \text{test compund} \end{pmatrix} - \begin{pmatrix} \text{Absorbance of well} \\ \text{with addition of a} \\ \text{test compound} \end{pmatrix}}{\begin{pmatrix} \text{Absorbance of well} \\ \text{without addition of a} \\ \text{test compund} \end{pmatrix} - \begin{pmatrix} \text{Absorbance of well} \\ \text{before addition of a} \\ \text{test compound} \end{pmatrix}} \times 100$$

Among compounds described in examples, compounds 1, 3, 5, 11, 19-22, 27, 28, 30-35, 39-44, 50, 51, 56, 59, 60, 68, 70, 71, 76, 82, 95, 96, 100, 107-109, 111, 112, 114, 117, 126, 133, 134, 137-139, 143, 149-151, 155, 157, 163, 167, 168, 169, 176, 178, 179, 184, 185, 187, 189, 190, 199, 200, 201, 202, 203, 211, 212, 214, 216, 219, 222, 223, 224, 225, 226, 227, 229, 230, 231, 232, 233, 234, 235, 236, 237, 238, 239, 240 and 241 exhibited a $GI_{50}$ value of less than 100 nmol/L and compounds 14, 16, 23, 24, 26, 29, 49, 67, 81, 92-94, 101-103, 105, 106, 110, 116, 120, 123, 135, 136, 142, 144, 146, 147, 153, 156, 159, 162, 164, 166, 172, 181, 186, 192, 196, 206, 208, 220 and 221 exhibited a $GI_{50}$ value of 100 nmol/L to 1 μmol/L against the human mesothelioma cell line, NCI-H226 cells.

Among compounds described in examples, compounds 5, 21, 22, 27, 28, 31-33, 35, 37, 40-42, 44, 50, 51, 59, 61, 64, 68, 70, 71, 76, 82, 95, 96, 106-109, 111, 112, 114, 117, 126, 134, 137-139, 143, 149-151, 155, 157, 162-164, 168, 169, 176, 179, 184, 185, 187, 189, 190, 192, 199-203, 206, 208, 211, 212, 214, 216, 219, 220, 222-230 and 241 exhibited a $GI_{50}$ value of less than 1000 nmol/L against the human lung cancer cell line, NCI-H322 cells.

Among compounds described in examples, compounds 5, 21, 22, 27, 28, 31-33, 35, 37, 40-42, 44, 51, 59, 61, 68, 70, 71, 76, 82, 95, 96, 100, 105-109, 111, 112, 114, 117, 126, 134, 137, 138, 143, 149-151, 155, 157, 162-164, 168, 169, 176, 179, 184, 185, 187, 189, 190, 192, 199, 200-203, 206, 208, 211, 212, 216, 219, 222-224, 226, 227, 229, 230, 241 exhibited a $GI_{50}$ value of 3000 nmol/L to 1 μmol/L against the human ovarian cancer cell line, OVTOKO cells.

Among compounds described in examples, compounds 5, 22, 28, 31, 33, 40, 68, 95, 96, 107, 108, 111, 112, 114, 117, 126, 134, 137, 138, 139, 143, 149-151, 155, 163, 164, 168, 169, 176, 179, 185, 187, 189, 190, 192, 199, 200-203, 206, 208, 211, 212 and 222-227 exhibited a $GI_{50}$ value of less than 3000 nmol/L against human liver cancer cell line, HuH28 cells.

As mentioned above, compound (I) of the present invention represented in test compounds exhibited a high growth inhibitory effect on NCI-H226 cells as the human mesothelioma cell line, on NCI-H322 cells as the human lung cancer cell line, on OVTOKO cells as the human ovarian cancer cell line, and on HuH28 cells as the human liver cancer cell line. Therefore, compound (I) of the present invention was found to be useful as a preventive or therapeutic agent or the like for cancers.

The proton nuclear magnetic resonance spectrum ($^1$H NMR) used in the following examples is measured at 300 MHz or 400 MHz, and sometimes an exchangeable proton may not be clearly observed depending on compounds and measurement conditions. In addition, commonly used notation is used as one for the multiplicity of signals, but br expresses an apparent wide signal.

Example 1

Step 1

3-Chloro-1-(2, 4-dihydroxyphenyl)propan-1-one (Compound 1-1)

To a mixture of resorcinol (5.00 g, 45.4 mmol) and 3-chloropropionic acid (4.90 g, 45.4 mmol), trifluoromethanesulfonic acid (15 mL) was added, and the mixture was stirred at 80° C. for 0.5 hours. A reaction liquid obtained by adding dichloromethane (100 mL) to the mixture left to cool to room temperature was gradually added to water (100 mL). The organic layer was extracted with dichloromethane, dried over anhydrous sodium sulfate, and concentrated under reduced pressure to obtain compound 1-1 (6.00 g) as a crude product.

$^1$H NMR (400 MHz, CDCl$_3$, δ): 12.48 (s, 1H), 7.62 (d, J=11.6 Hz, 1H), 6.43-6.39 (m, 2H), 3.90 (t, J=9.2 Hz, 2H), 3.40 (t, J=9.2 Hz, 2H).

Step 2

7-Hydroxychroman-4-one (Compound 1-2)

To compound 1-1 (6.00 g), a 2 mol/L aqueous sodium hydroxide solution (250 mL) was added at −5° C., and the mixture was stirred at room temperature for 2 hours. The mixture was cooled to −5° C., and 2 mol/L sulfuric acid was added to the mixture to adjust pH to 2. The organic layer was extracted with ethyl acetate, dried over anhydrous sodium sulfate, and concentrated under reduced pressure to obtain compound 1-2 (3.00 g, 40% over two steps).

$^1$H NMR (400 MHz, DMSO-d$_6$, δ): 12.48 (s, 1H), 7.62 (d, J=11.6 Hz, 1H), 6.43-6.39 (m, 2H), 3.90 (t, J=9.2 Hz, 2H), 3.40 (t, J=9.2 Hz, 2H).

Step 3

7-Phenoxychroman-4-one (Compound 1-3)

Compound 1-2 (0.50 g, 3.04 mmol) was dissolved in dichloromethane (15 mL), and phenylboronic acid (0.74 g, 6.09 mmol), pyridine (1.22 mL, 15.2 mmol), and copper(II) acetate (0.82 g, 4.57 mmol) were added to the solution. The solution was stirred at room temperature for 18 hours. Dichloromethane (30 mL) was added to the mixture, followed by filtration with Celite®, and the solid on the Celite was washed with dichloromethane (50 mL). The organic layer in the filtrate was washed with 2 mol/L hydrochloric acid, dried over anhydrous sodium sulfate, and concentrated under reduced pressure. The residue was purified by silica gel column chromatography (hexane/ethyl acetate=100/0→70/30) to obtain compound 1-3 (0.075 g, 10%).

$^1$H NMR (400 MHz, CDCl$_3$, δ): 7.87 (d, J=8.8 Hz, 1H), 7.42-7.38 (m, 2H), 7.09-7.07 (m, 2H), 6.84-6.82 (m, 1H), 6.63 (dd, J=8.8, 2.4 Hz, 1H), 6.42 (d, J=2.4 Hz, 1H), 4.50 (t, J=6.4 Hz, 2H), 2.76 (t, J=6.4 Hz, 2H);

ESIMS m/z: [M+H]$^+$ 241.

Step 4

7-Hydroxychroman-4-amine (Compound 1-4)

Compound 1-3 (0.05 g, 0.21 mmol) was dissolved in methanol (3 mL), and ammonium acetate (0.24 g, 3.12 mmol) and sodium cyanoborohydride (0.04 g, 0.62 mmol) were added to the solution. The mixture was stirred at 80° C. for 18 hours in a sealed tube. The mixture was left to cool to room temperature, and water was added to the mixture. The organic layer was extracted with ethyl acetate, dried over anhydrous sodium sulfate, and concentrated under reduced pressure to obtain compound 1-4 (0.03 g, 60%).

$^1$H NMR (400 MHz, CDCl$_3$, δ): 7.39-7.34 (m, 3H), 7.12 (t, J=7.6 Hz, 1H), 6.99-6.97 (m, 2H), 6.50 (dd, J=8.4, 2.4 Hz, 1H), 6.30 (d, J=2.4 Hz, 1H), 4.26-4.20 (m, 11H), 4.14-4.09 (m, 1H), 3.86 (t, J=5.2 Hz, 1H), 2.01-1.94 (m, 1H), 1.75-1.68 (m, 1H).

Step 5

N-(7-phenoxychroman-4-yl)acrylamide (Compound 1)

Compound 1-4 (0.15 g, 0.62 mmol) was dissolved in dichloromethane (5 mL), and diisopropylethylamine (0.23 mL, 1.24 mmol) and acryloyl chloride (0.075 mL, 0.93 mmol) were added to the solution under cooling at 0° C. The mixture was stirred at 0° C. for 0.5 hours. A saturated aqueous sodium bicarbonate solution was added to the mixture. The organic layer was extracted with dichloromethane, dried over anhydrous sodium sulfate, and concentrated under reduced pressure. The residue was purified by silica gel column chromatography (hexane/ethyl acetate=90/10→50/50) to obtain compound 1 (0.08 g, 44%).

$^1$H NMR (400 MHz, DMSO-$d_6$, δ): 8.55 (d, J=8.0 Hz, 1H), 7.41-7.36 (m, 2H), 7.16-7.13 (m, 2H), 7.00-6.98 (m, 2H), 6.54 (dd, J=8.4, 2.4 Hz, 1H), 6.38 (d, J=2.4 Hz, 1H), 6.26 (dd, J=16.8, 9.6 Hz, 1H), 6.15 (dd, J=16.8, 2.4 Hz, 1H), 5.62 (dd, J=10.0, 2.4 Hz, 1H), 5.04 (q, J=5.6 Hz, 1H), 4.26-4.13 (m, 2H), 2.10-1.86 (m, 2H)

ESIMS m/z: [M−70]$^+$ 225.

The following compounds were synthesized in accordance with the synthesis method of compound 1.

N-{7-(3-chlorophenoxy)chroman-4-yl}acrylamide (Compound 2)

ESIMS m/z: [M−70]$^+$ 259,

N-{7-(p-tolyloxy)chroman-4-yl}acrylamide (Compound 4)

ESIMS m/z: [M−70]$^+$ 239.

Example 2

Step 1

7-(4-Chlorophenoxy)chroman-4-one (Compound 2-1)

Compound 2-1 (0.26 g, 26%) was obtained in the same manner as step 3 of example 1, using compound 1-2.

$^1$H NMR (300 MHz, CDCl$_3$, δ): 7.87 (d, J=8.7 Hz, 1H), 7.36 (dd, J=6.9, 2.1 Hz, 2H), 7.01 (dd, J=6.9, 2.4 Hz, 2H), 6.62 (dd, J=9.0, 2.4 Hz, 1H), 6.42 (d, J=2.1 Hz, 1H), 4.51 (t, J=6.3 Hz, 2H), 2.77 (t, J=6.3 Hz, 2H).

Step 2

7-(4-Chlorophenoxy)chroman-4-amine (Compound 2-2)

Compound 2-2 (0.20 g, 80%) was obtained in the same manner as in step 4 of example 1, using compound 2-1 obtained in step 1.

$^1$H NMR (400 MHz, CDCl$_3$, δ): 7.28-7.24 (m, 3H), 6.95-6.93 (m, 2H), 6.55 (dd, J=8.4, 2.4 Hz, 1H), 6.43 (d, J=2.4 Hz, 1H), 4.30-4.18 (m, 2H), 4.04-4.02 (m, 1H), 2.18-2.10 (m, 1H), 1.86-1.79 (m, 1H).

Step 3

N-{7-(4-Chlorophenoxy)chroman-4-yl}acrylamide (Compound 3)

Compound 3 (0.11 g, 55%) was obtained in the same manner as step 5 of example 1, using compound 2-2.

$^1$H NMR (400 MHz, DMSO-$d_6$, δ): 8.58 (d, J=8.0 Hz, 1H), 7.43 (d, J=8.8 Hz, 2H), 7.16 (d, J=8.4 Hz, 1H), 6.99 (d, J=8.8 Hz, 1H), 6.57 (dd, J=8.4, 2.4 Hz, 1H), 6.44 (d, J=2.0 Hz, 1H), 6.29-6.13 (m, 2H), 5.63 (dd, J=10.0, 2.4 Hz, 1H), 5.07-5.02 (m, 1H), 4.26-4.14 (m, 2H), 2.10-1.87 (m, 2H);

ESIMS m/z: [M−70]$^+$ 259.

Step 4

N-{7-(4-Chlorophenoxy)chroman-4-yl}acrylamide (Compounds 12 and 13)

Compound 3 was optically resolved under the following chiral preparative conditions to obtain compound 13 (17 mg, 34%) having a retention time of 3.31 minutes and compound 12 (15 ng, 31%) having a retention time of 4.17 minutes.

Compound 12: ESIMS m/z: [M+H]$^+$ 330.
Compound 13: ESIMS m/z: [M+H]$^+$ 330.

Chiral Preparative Conditions
Apparatus used: SFC30 manufactured by Waters
Column used: CHIRALPAK® IB/SFC 10 mmφ×250 mm, 5 μM
Temperature: 40° C.
Liquid feeding condition: 90% carbon dioxide/10% methanol
Preparative time: 6 minutes
Flow rate: 30 mL/minute
Retention time: 4.17 minutes (compound 12), 3.31 minutes (compound 13)

Example 3

7-{4-(Trifluoromethyl)phenoxy}chronan-4-one (Compound 3-1)

Step 1

Compound 1-2 (0.80 g, 4.87 mmol) was dissolved in dichloromethane (20 mL), and 4-trifluoromethylphenylboronic acid (7.40 g, 39.0 mmol), pyridine (1.96 mL, 24.4 mmol), and copper(II) acetate (1.77 g, 9.75 mmol) were added to the solution. The mixture was stirred at room temperature overnight. A saturated aqueous ammonium chloride solution was added to the mixture. The mixture was filtered with Celite®. The organic layer in the filtrate was extracted with ethyl acetate, washed with saturated saline, and dried over anhydrous magnesium sulfate. The solvent was distilled off under reduced pressure. The residue was purified by silica gel column chromatography (heptane/ethyl acetate=80/20→20/80) to obtain compound 3-1 (0.18 g, 12%).

$^1$H NMR (400 MHz, CDCl$_3$, δ): 7.91 (d, J=8.8 Hz, 1H), 7.65 (d, J=8.5 Hz, 2H), 7.16 (d, J=8.5 Hz, 2H), 6.67 (dd, J=8.8, 2.2 Hz, 1H), 6.51 (d, J=2.2 Hz, 1H), 4.54 (t, J=6.5 Hz, 2H), 2.80 (t, J=6.5 Hz, 2H).

Step 2

7-{4-(Trifluoromethyl)phenoxy}chroman-4-amine (Compound 3-2)

Compound 3-1 (0.45 g, 1.44 mmol) was dissolved in methanol (14 mL). Added to the solution were ammonium formate (1.82 g, 28.9 mmol), acetic acid (0.12 mL, 2.17 mmol), and chloro[N-{4-(dimethylamino)phenyl}-2-pyridinecarboxyamidate](pentamethylcyclopentadienyl)iridium (III) (0.026 g, 0.043 mmol), and the mixture was stirred at 80° C. for 2.5 hours. The mixture was left to cool to room temperature, methanol was concentrated under reduced pressure, and water and ethyl acetate were added to the mixture. The mixture was filtered with Presep ((R); diatomaceous earth, granular type M, 4.5 g/25 mL), and the filtrate was concentrated under reduced pressure. The residue was purified by silica gel column chromatography (heptane/ethyl acetate=50/50→chloroform/methanol=90/10) to obtain compound 3-2 (0.43 g, 97%).

Step 3

N-[7-{4-(trifluoromethyl)phenoxy}chroman-4-yl]acrylamide (Compound 5)

Compound 5 (0.26 g, 51%) was obtained in the same manner as step 5 of example 1, using compound 3-2.

$^1$H NMR (400 MHz, CDCl$_3$, δ): 7.58 (d, J=8.8 Hz, 2H), 7.21 (d, J=8.6 Hz, 1H), 7.06 (d, J=8.8 Hz, 2H), 6.61 (dd, J=8.6, 2.4 Hz, 1H), 6.51 (d, J=2.4 Hz, 1H), 6.36 (dd, J=17.0, 1.2 Hz, 1H), 6.11 (dd, J=17.0, 10.4 Hz, 1H), 5.77 (d, J=6.8 Hz, 1H), 5.72 (dd, J=10.4, 1.2 Hz, 1H), 5.26-5.20 (m, 1H), 4.33-4.26 (m, 1H), 4.20-4.13 (m, 1H), 2.28-2.23 (m, 1H), 2.16-2.08 (m, 1H);

ESIMS m/z: [M−H]$^+$ 362.

The following compounds were synthesized in accordance with the synthesis method of compound 5.

N-[7-{4-Chloro-3-(trifluoromethyl)phenoxy}chroman-4-yl]acrylamide (Compound 8)

ESIMS m/z: [M−H]$^+$ 396.

N-[7-{4-(Trifluoromethoxy)phenoxy}chroman-4-yl]acrylamide (Compound 9)

ESIMS m/z: [M−H]$^+$ 378.

N-{7-(4-Chloro-3-fluorophenoxy)chroman-4-yl]acrylamide (Compound 10)

ESIMS m/z: [M−H]$^+$ 346.

Example 4

Step 1

7-(Benzyloxy)chroman-4-one (Compound 4-1)

Compound 1-2 (1.50 g, 9.14 nmol) was dissolved in DMF (15 mL). Benzyl bromide (1.62 g, 13.7 mmol) and potassium carbonate (3.78 g, 27.4 mmol) were added to the solution, and the mixture was stirred at room temperature for 3 hours. Water was added to the mixture. The organic layer was extracted with ethyl acetate, dried over anhydrous sodium sulfate, and concentrated under reduced pressure. The residue was purified by silica gel column chromatography (hexane/ethyl acetate=100/0→85/15) to obtain compound 4-1 (2.00 g, 86%).

$^1$H NMR (300 MHz, DMSO-d$_6$, δ): 7.68 (d, J=8.7 Hz, 1H), 7.45-7.30 (m, 5H), 6.70 (dd, J=8.7, 2.4 Hz, 1H), 6.20 (d, J=2.4 Hz, 1H), 5.17 (s, 2H), 4.50 (t, J=6.3 Hz, 2H), 2.70 (t, J=6.3 Hz, 2H).

Step 2

7-(Benzyloxy)chroman-4-amine (Compound 4-2)

Compound 4-2 (1.50 g, 75%) was obtained in the same manner as step 4 of example 1, using compound 4-1.

$^1$H NMR (300 MHz, DMSO-d$_6$, δ): 7.39-7.30 (m, 5H), 7.22 (d, J=8.7 Hz, 1H), 6.51 (dd, J=8.4, 2.4 Hz, 1H), 6.33 (d, J=2.4 Hz, 1H), 5.03 (s, 2H), 4.22-4.16 (m, 1H), 4.10-4.05 (m, 1H), 3.80 (t, J=5.1 Hz, 1H), 1.97-1.88 (m, 1H), 1.72-1.64 (m, 1H).

Step 3

4-Aminochroman-7-ol (Compound 4-3)

Compound 4-2 (1.50 g, 5.88 mmol) was dissolved in ethanol (50 mL), and 10% palladium carbon (0.15 g) was added to the solution. The mixture was stirred under hydrogen atmosphere at a pressure of 60 psi at room temperature for 16 hours. The mixture was filtered with Celite®, and the filtrate was concentrated under reduced pressure to obtain compound 4-3 (0.60 g, 61%).

$^1$H NMR (400 MHz, DMSO-d$_6$, δ): 7.10 (d, J=8.4 Hz, 1H), 6.27 (dd, J=8.1, 2.4 Hz, 1H), 6.09 (d, J=2.4 Hz, 1H), 4.20-4.08 (m, 1H), 4.07-4.02 (m, 1H), 3.80 (t, J=5.1 Hz, 1H), 1.96-1.92 (m, 1H), 1.72-1.64 (m, 1H).

Step 4

7-{4-(Dimethylamino)phenoxy}chroman-4-amine (Compound 4-4)

4-Iodo-N,N-dimethylaniline (0.20 g, 1.21 mmol) was dissolved in DMSO (10 mL), and compound 4-3 (0.44 g, 1.81 mmol), tripotassium phosphate (0.51 g, 2.42 mmol), picolinic acid (0.014 g, 0.12 mmol), and copper(I) iodide (0.012 g, 0.06 mmol) were added to the solution under argon atmosphere. The mixture was stirred at 90° C. for 16 hours. Water was added to the mixture, and the mixture was filtered with Celite®. The organic layer in the filtrate was extracted with ethyl acetate, dried over anhydrous sodium sulfate, and concentrated under reduced pressure. The residue was purified by silica gel column chromatography (hexane/ethyl acetate=60/40→40/60) to obtain compound 4-4 (0.13 g, 37%).

$^1$H NMR (400 MHz, DMSO-d$_6$, δ): 7.27 (d, J=7.2 Hz, 1H), 6.88 (d, J=9.2 Hz, 2H), 6.74 (d, J=9.2 Hz, 2H), 6.39 (dd, J=8.0, 2.4 Hz, 1H), 6.15 (d, J=2.4 Hz, 1H), 4.22-4.18 (m, 1H), 4.09-4.07 (m, 1H), 3.80-3.78 (m, 1H), 2.86 (s, 6H), 1.98-1.95 (m, 1H), 1.72-1.70 (m, 1H).

Step 5

N-[7-{4-(Dimethylamino)phenoxy}chroman-4-yl]acrylamide (Compound 6)

Compound 6 (0.055 g, 35%) was obtained in the same manner as step 5 of example 1, using compound 4-4.

$^1$H NMR (400 MHz, DMSO-d$_6$, δ): 8.51 (d, J=7.6 Hz, 1H), 7.06 (d, J=8.8 Hz, 1H), 6.88 (d, J=9.2 Hz, 2H), 6.74 (d, J=8.8 Hz, 2H), 6.43 (dd, J=8.8, 2.8 Hz, 1H), 6.28-6.21 (m, 2H), 6.14 (dd, J=16.8, 2.4 Hz, 1H), 5.61 (dd, J=9.6, 2.4 Hz, 1H), 5.02-4.98 (m, 1H), 4.21-4.08 (m, 2H), 2.87 (m, 6H), 2.09-2.00 (m, 1H), 1.98-1.84 (m, 1H);

ESIMS m/z: [M+H]$^+$ 339.

The following compound was synthesized in accordance with the synthesis method of compound 6.

N-{7-(4-Cyanophenoxy)chroman-4-yl}acrylamide (Compound 7)

ESIMS m/z: [M−70]$^+$ 250.

Example 5

Step 1

7-[{6-Chloro-5-(trifluoromethyl)pyridin-2-yl}oxy]chroman-4-one (Compound 5-1)

Compound 1-2 (70.0 mg, 0.426 mmol) was dissolved in DMF (1 mL), and potassium carbonate (431 mg, 3.41 mmol) and 2,6-dichloro-3-(trifluoromethyl)pyridine (0.092 mL, 0.853 mmol) were added to the solution. The mixture was stirred at 50° C. overnight. Water and ethyl acetate were added to the mixture. The mixture was filtered with Presep ((R); diatomaceous earth, granular type M, 4.5 g/25 mL), and the filtrate was concentrated. The residue was purified by silica gel column chromatography (heptane/ethyl acetate=100/0→heptane/ethyl acetate=70/30) to obtain compound 5-1 (41.0 mg, 28%).

$^1$H NMR (400 MHz, CDCl$_3$, δ): 8.02 (d, J=8.2 Hz, 1H), 7.96 (d, J=8.2 Hz, 1H), 6.97 (d, J=8.2 Hz, 1H), 6.82 (d, J=2.3 Hz, 1H), 6.80-6.79 (m, 1H), 4.58 (t, J=6.6 Hz, 2H), 2.83 (t, J=6.6 Hz, 2H).

Step 2

7-[{6-Chloro-5-(trifluoromethyl)pyridin-2-yl}oxy]chroman-4-amine (Compound 5-2)

Compound 5-2 was obtained as a crude product in the same manner as step 2 of example 3, using compound 5-1, and used as it is in the next reaction.

ESIMS m/z: [M+H]$^+$ 344.

Step 3

N-(7-[{6-Chloro-5-(trifluoromethyl)pyridin-2-yl}oxy]chroman-4-yl)acrylamide (Compound 11)

Compound 11 (20.3 mg, 43% over two steps) was obtained in the same manner as step 5 of example 1, using compound 5-2.

$^1$H NMR (400 MHz, CDCl$_3$, δ): 7.96 (d, J=8.6 Hz, 1H), 7.25 (d, J=8.6 Hz, 1H), 6.88 (d, J=8.6 Hz, 1H), 6.70 (dd, J=8.6, 2.4 Hz, 1H), 6.64 (d, J=2.4 Hz, 1H), 6.36 (dd, J=16.8, 1.4 Hz, 1H), 6.13 (dd, J=16.8, 10.4 Hz, 1H), 5.98 (d, J=7.2 Hz, 1H), 5.71 (dd, J=10.4, 1.4 Hz, 1H), 5.25-5.23 (m, 1H), 4.32-4.29 (m, 1H), 4.21-4.15 (m, 1H), 2.30-2.20 (m, 1H), 2.16-2.09 (m, 1H);

ESIMS m/z: [M–H]$^+$397.

Example 6

N-{7-(Benzyloxy)chroman-4-yl}acrylamide (Compound 14)

Compound 14 (0.075 g, 45%) was obtained in the same manner as step 5 of example 1, using compound 4-2.

$^1$H NMR (400 MHz, CDCl$_3$, δ): 7.43-7.30 (m, 5H), 7.10 (d, J=8.4 Hz, 1H), 6.57 (dd, J=8.4, 2.6 Hz, 1H), 6.45 (d, J=2.6 Hz, 1H), 6.33 (dd, J=16.9, 1.5 Hz, 1H), 6.07 (dd, J=16.9, 10.3 Hz, 1H), 5.74 (d, J=7.3 Hz, 2H), 5.68 (dd, J=10.3, 1.5 Hz, 2H), 5.14 (dd, J=12.5, 5.1 Hz, 1H), 5.02 (s, 2H), 4.27-4.24 (m, 1H), 4.15-4.07 (m, 1H);

ESIMS m/z: [M+H]$^+$ 310.

The following compound was synthesized in accordance with the synthesis method of compound 14.

N-[7-{(4-Chlorobenzyl)oxy}chroman-4-yl}acrylamide (Compound 15)

ESIMS m/z: [M−70]$^+$ 273.

Example 7

Step 1

7-(Cyclohexylmethoxy)chroman-4-one (Compound 7-1)

Compound 1-2 (0.10 g, 0.61 mmol) was dissolved in THF (3 mL), and, triphenylphosphine (0.32 g, 1.22 mmol), diethyl azodicarboxylate (a 2.2 mol/L toluene solution, 0.55 mL, 1.22 mmol), and cyclohexanemethanol (0.15 mL, 1.22 mmol) were added to the solution. The mixture was stirred at room temperature for 3 hours. After the mixture was concentrated under reduced pressure, the mixture was purified by silica gel column chromatography (heptane/ethyl acetate=90/10) to obtain compound 7-1 as a crude product, which was used as it is in the next reaction.

Step 2

7-(Cyclohexylmethoxy)chroman-4-amine (Compound 7-2)

Compound 7-2 was obtained as a crude product in the same manner as step 4 of example 1, using compound 7-1, and used as it is in the next reaction.

Step 3

N-{7-(Cyclohexylmethoxy)chroman-4-yl}acrylamide (Compound 16)

Compound 16 (0.12 g, 62% in three stages) was obtained in the same manner as step 5 of example 1, using compound 7-2.

$^1$H NMR (300 MHz, CDCl$_3$, δ): 7.08 (d, J=8.4 Hz, 1H), 6.49 (dd, J=8.4, 2.6 Hz, 1H), 6.33 (dd, J=17.2, 1.8 Hz, 2H), 6.07 (dd, J=16.9, 10.3 Hz, 1H), 5.74 (d, J=7.0 Hz, 1H), 5.68 (dd, J=10.3, 1.5 Hz, 1H), 5.13 (dd, J=12.3, 4.9 Hz, 1H), 4.30-4.21 (m, 1H), 4.15-4.07 (m, 1H), 3.70 (d, J=6.2 Hz, 2H), 2.28-2.16 (m, 1H), 2.14-2.03 (m, 1H), 1.89-1.67 (m, 5H), 1.35-1.18 (m, 4H), 1.08-0.95 (m, 2H);

ESIMS m/z: [M+H]$^+$ 316.

Example 8

Step 1

4-Methyl-7-phenoxychroman-4-ol (Compound 8-1)

Compound 1-3 (0.10 g, 0.41 mmol) was dissolved in THF (3 mL), and a 1.6 mol/L methyllithium solution in diethyl ether (0.78 mL, 1.25 mmol) was added dropwise to the solution, at 0° C. under nitrogen atmosphere. The mixture was stirred at room temperature for 2 hours. A saturated aqueous ammonium chloride solution was added to the mixture. The organic layer was extracted with ethyl acetate, dried over anhydrous sodium sulfate, and concentrated under reduced pressure to obtain compound 8-1 (0.10 g, 95%).

$^1$H NMR (400 MHz, CDCl$_3$, δ): 7.45-7.36 (m, 3H), 7.15-7.11 (m, 1H), 6.99 (d, J=7.6 Hz, 2H), 6.52 (dd, J=8.8, 2.4 Hz, 1H), 6.30 (d, J=2.4 Hz, 1H), 5.10 (s, 1H), 4.25-4.11 (m, 2H), 1.97-1.88 (m, 2H), 1.46 (s, 3H).

Step 2

4-Azido-4-methyl-7-phenoxychromane (Compound 8-2)

Compound 8-1 (0.10 g, 0.39 mmol) was dissolved in chloroform (3 mL), and sodium azide (0.25 g, 3.90 mmol) was added to the solution. A mixed liquid of trifluoroacetic acid (0.15 mL, 1.95 mmol) and chloroform (3 mL) were added dropwise to the mixture at 0° C. The mixture was stirred at room temperature for 3 hours. Water was added to the mixture. The organic layer was extracted with dichloromethane, dried over anhydrous sodium sulfate, and concentrated under reduced pressure. The residue was purified by silica gel column chromatography (hexane/ethyl acetate=90/10→80/20) to obtain compound 8-2 (0.06 g, 51%).

$^1$H NMR (400 MHz, CDCl$_3$, δ): 7.48-7.36 (m, 3H), 7.20-7.16 (m, 1H), 7.05-7.00 (m, 2H), 6.59 (dd, J=8.4, 2.4 Hz, 1H), 6.39 (d, J=2.8 Hz, 1H), 4.28-4.11 (m, 2H), 2.18-1.89 (m, 2H), 1.65 (s, 3H).

Step 3

4-Methyl-7-phenoxychroman-4-amine (Compound 8-3)

Compound 8-2 (0.05 g, 0.17 mmol) was dissolved in THF (3 mL), and a 2 mol/L lithium aluminum hydride solution in THF (0.44 mL, 0.88 mmol) was added dropwise to the solution at 0° C. under nitrogen atmosphere. The mixture was stirred at room temperature for 3 hours. The mixture was cooled to 0° C., and water was added to the mixture. The organic layer was extracted with dichloromethane, dried over anhydrous sodium sulfate, and concentrated under reduced pressure to obtain compound 8-3 (0.02 g, 65%).

$^1$H NMR (400 MHz, CDCl$_3$, δ): 7.50 (d, J=8.4 Hz, 1H), 7.39-7.35 (m, 2H), 7.14-7.10 (m, 1H), 7.02-6.97 (m, 2H), 6.50 (dd, J=8.4, 2.4 Hz, 1H), 6.27 (d, J=2.8 Hz, 1H), 4.25-4.10 (m, 2H), 1.77-1.74 (m, 2H), 1.36 (s, 3H).

Step 4

N-(4-Methyl-7-phenoxychroman-4-yl)acrylamide (Compound 17)

Compound 17 (0.08 g, 40%) was obtained in the same manner as step 5 of example 1, using compound 8-3.

$^1$H NMR (400 MHz, DMSO-d$_6$, δ): 8.14 (s, 1H), 7.42-7.32 (m, 3H), 7.15 (t, J=7.2 Hz, 1H), 7.01 (d, J=8.0 Hz, 2H), 6.51 (dd, J=8.4, 2.0 Hz, 1H), 6.36-6.29 (m, 2H), 6.01 (dd, J=17.2, 2.0 Hz, 1H), 5.51 (dd, J=10.0, 1.6 Hz, 1H), 4.16-4.13 (m, 2H), 2.84-2.78 (m, 1H), 1.80-1.74 (m, 1H), 1.65 (s, 3H);

ESIMS m/z: [M−70]$^+$ 239.

Example 9

Step 1

7-(4-Chlorophenoxy)-2,2-dimethylchroman-4-one (Compound 9-1)

Compound 9-1 (170 mg, 72%) was obtained in the same manner as step 1 of example 3, using commercially available 7-hydroxy-2,2-dimethylchroman-4-one.

$^1$H NMR (400 MHz, CDCl$_3$, δ): 7.84 (d, J=8.6 Hz, 1H), 7.37-7.35 (m, 2H), 7.04-7.02 (m, 2H), 6.59 (dd, J=8.6, 2.3 Hz, 1H), 6.36 (d, J=2.3 Hz, 1H), 2.68 (s, 2H), 1.44 (s, 6H).

Step 2

7-(4-Chlorophenoxy)-2,2-dimethylchroman-4-amine (Compound 9-2)

Compound 9-2 was obtained as a crude product in the same manner as step 2 of example 3, using compound 9-1, and used as it is in the next reaction.

ESIMS m/z: [M−17]$^+$ 287.

Step 3

N-{7-(4-Chlorophenoxy)-2,2-dimethylchroman-4-yl}acrylamide (Compound 18)

Compound 18 (38.0 mg, 35% over two steps) was obtained in the same manner as step 5 of example 1, using compound 9-2.

$^1$H NMR (400 MHz, CDCl$_3$, δ): 7.31-7.26 (m, 2H), 7.16 (d, J=8.6 Hz, 1H), 6.96-6.93 (m, 2H), 6.54 (dd, J=8.6, 2.7 Hz, 1H), 6.38 (d, J=2.7 Hz, 1H), 6.34 (dd, J=17.0, 1.4 Hz, 1H), 6.14 (dd, J=17.0, 10.4 Hz, 1H), 5.81 (d, J=8.6 Hz, 1H), 5.70 (dd, J=10.4, 1.4 Hz, 1H), 5.35-5.32 (m, 1H), 2.23 (dd, J=13.3, 6.3 Hz, 1H), 1.71 (dd, J=13.3, 10.9 Hz, 1H), 1.40 (s, 3H), 1.33 (s, 3H);

ESIMS m/z: [M−H]$^+$356.

Example 10

Step 1

7-Hydroxy-2-methylchroman-4-one (Compound 10-1)

Trifluoromethanesulfonic acid (3.2 mL) was added to a mixture of resorcinol (500 mg, 4.54 mmol) and crotonic acid (430 mg, 4.99 mmol), and the mixture was stirred at 80° C. for 2 hours. The mixture left to cool to room temperature was gradually added to a 2 mol/L aqueous sodium hydroxide solution. The organic layer was extracted with ethyl acetate, dried over anhydrous magnesium sulfate, and concentrated under reduced pressure. The residue was purified by silica gel column chromatography (heptane/ethyl acetate=100/0→heptane/ethyl acetate=50/50) to obtain compound 10-1 (55.0 mg, 7%).

$^1$H NMR (400 MHz, DMSO-d$_6$, δ): 7.59 (d, J=8.6 Hz, 1H), 6.46 (dd, J=8.6, 2.3 Hz, 1H), 6.28 (d, J=2.3 Hz, 1H), 4.58-4.55 (m, 1H), 2.62-2.58 (m, 2H), 1.39 (d, J=6.3 Hz, 3H).

Step 2

2-Methyl-7-{4-(trifluoromethyl)phenoxy}chroman-4-one (Compound 10-2)

Compound 10-2 (66.5 mg, 83%) was obtained in the same manner as step 1 of example 3, using compound 10-1.

$^1$H NMR (400 MHz, CDCl$_3$, δ): 7.65 (d, J=8.5 Hz, 2H), 7.49 (d, J=8.5 Hz, 1H), 7.16 (d, J=8.5 Hz, 2H), 6.67 (dd, J=8.5, 2.5 Hz, 1H), 6.49 (d, J=2.5 Hz, 1H), 4.62-4.59 (m, 1H), 2.68-2.67 (m, 2H), 1.50 (d, J=6.3 Hz, 3H).

Step 3

2-Methyl-7-{4-(trifluoromethyl)phenoxy}chroman-4-amine (Compound 10-3)

Compound 10-3 was obtained as an unpurified crude product in the same manner as step 2 of example 3, using compound 10-2, and used as it is in the next reaction.

ESIMS m/z: [M−16]$^+$ 307.

Step 4 cis-N-[2-Methyl-7-{4-(trifluoromethyl)phenoxy}chroman-4-yl]acrylamide (Compound 19)

trans-N-[2-Methyl-7-{4-(trifluoromethyl)phenoxy}chroman-4-yl]acrylamide (Compound 20)

Compound 19 (16.8 mg, 22% over two steps) and compound 20 (12.9 mg, 17% over two steps) were obtained in the same manner as step 5 of example 1, using compound 10-3.

Compound 19: $^1$H NMR (400 MHz, CDCl$_3$, δ): 7.57 (d, J=8.6 Hz, 2H), 7.21 (dd, J=8.6, 0.9 Hz, 1H), 7.06 (d, J=8.6 Hz, 2H), 6.60 (dd, J=8.6, 2.5 Hz, 1H), 6.48 (d, J=2.5 Hz, 1H), 6.38 (dd, J=17.0, 1.1 Hz, 1H), 6.14 (dd, J=17.0, 10.4

Hz, 1H), 5.74 (dd, J=10.4, 1.4 Hz, 1H), 5.64 (d, J=8.6 Hz, 1H), 5.47-5.41 (m, 1H), 4.34-4.28 (m, 1H), 2.43-2.40 (m, 1H), 1.65-1.62 (m, 1H), 1.41 (d, J=6.3 Hz, 3H)

ESIMS m/z: [M−H]⁺376.

Compound 20: $^1$H NMR (400 MHz, CDCl$_3$, δ): 7.58 (d, J=8.6 Hz, 2H), 7.23 (d, J=8.6 Hz, 1H), 7.07 (d, J=8.6 Hz, 2H), 6.62 (dd, J=8.6, 2.5 Hz, 1H), 6.51 (d, J=2.5 Hz, 1H), 6.35 (dd, J=17.0, 1.4 Hz, 1H), 6.08 (dd, J=17.0, 10.4 Hz, 1H), 5.81 (d, J=6.8 Hz, 1H), 5.70 (dd, J=10.4, 1.4 Hz, 1H), 5.15-5.11 (m, 1H), 4.20-4.13 (m, 1H), 2.23 (dt, J=14.3, 2.0 Hz, 1H), 1.90-1.86 (m, 1H), 1.43 (d, J=6.3 Hz, 3H)

ESIMS m/z: [M−H]⁺376.

Example 11

Step 1

3-Fluoro-7-(4-(trifluoromethyl)phenoxy)chroman-4-one (Compound 11-1)

Compound 3-1 (110 mg, 0.357 mmol) was dissolved in methanol (1 mL), and 1-fluoro-4-hydroxy-1,4-diazabicyclo[2.2.2]octane-1,4-diium tetrafluoroborate (50% on aluminum oxide, 276 mg, 0.428 mmol) was added to the solution. The mixture was stirred at 80° C. for 2 hours, followed by filtration, and the filtrate was concentrated under reduced pressure. The residue was purified by silica gel column chromatography (heptane/ethyl acetate=100/0→heptane/ethyl acetate=60/40) to obtain compound 11-1 (90.0 mg, 77%).

$^1$H NMR (400 MHz, CDCl$_3$, δ): 7.94 (d, J=8.6 Hz, 1H), 7.68 (d, J=8.6 Hz, 2H), 7.17 (d, J=8.6 Hz, 2H), 6.74 (dd, J=8.6, 2.3 Hz, 1H), 6.52 (d, J=2.3 Hz, 1H), 5.11 (ddd, J=47.1, 4.2, 2.1 Hz, 1H), 4.62-4.56 (m, 2H).

Step 2

3-Fluoro-7-(4-(trifluoromethyl)phenoxy)chroman-4-amine (Compound 11-2)

Compound 11-2 was obtained as a crude product in the same manner as step 2 of example 3, using compound 11-1, and used as it is in the next reaction.

Step 3 cis-N-[3-Fluoro-7-{4-(trifluoromethyl)phenoxy}chroman-4-yl]acrylamide (Compound 21)

trans-N-[3-Fluoro-7-{4-(trifluoromethyl)phenoxy}chroman-4-yl]acrylamide (Compound 22)

Compound 21 (44.5 mg, 41% over two steps) and compound 22 (5.5 mg, 5% over two steps) were obtained in the same manner as step 5 of example 1, using compound 11-2.

Compound 21: $^1$H NMR (400 MHz, CDCl$_3$, δ): 7.58 (d, J=8.6 Hz, 2H), 7.20 (d, J=8.6 Hz, 1H), 7.06 (d, J=8.6 Hz, 2H), 6.65 (dd, J=8.6, 2.7 Hz, 1H), 6.55 (d, J=2.7 Hz, 1H), 6.43 (dd, J=17.0, 0.9 Hz, 1H), 6.23 (dd, J=17.0, 10.2 Hz, 1H), 6.10 (d, J=9.1 Hz, 1H), 5.80 (dd, J=10.2, 0.9 Hz, 1H), 5.58 (ddd, J=29.9, 9.5, 3.2 Hz, 1H), 5.02 (dt, J=48.5, 3.2 Hz, 1H), 4.59-4.52 (m, 1H), 4.26 (dd, J=39.0, 13.1 Hz, 1H);

ESIMS m/z: [M−H]⁺380.

Compound 22: $^1$H NMR (400 MHz, CDCl$_3$, δ): 7.59 (d, J=8.6 Hz, 2H), 7.23 (d, J=8.2 Hz, 1H), 7.08 (d, J=8.6 Hz, 2H), 6.68 (dd, J=8.4, 2.5 Hz, 1H), 6.58 (d, J=2.3 Hz, 1H), 6.38 (dd, J=16.8, 1.4 Hz, 1H), 6.09 (dd, J=17.0, 10.2 Hz, 1H), 5.75 (dd, J=10.4, 1.4 Hz, 1H), 5.65 (d, J=5.4 Hz, 1H), 5.21-5.19 (m, 1H), 5.03 (dtd, J=45.2, 3.4, 1.4 Hz, 1H), 4.49-4.42 (m, 1H), 4.15 (ddd, J=36.0, 12.9, 1.1 Hz, 1H);

ESIMS m/z: [M−H]⁺380.

Example 12

Step 1

3-Chloro-1-(2,4-dihydroxy-5-methylphenyl)propan-1-one (Compound 12-1)

Compound 12-1 (0.25 g, 48%) was obtained in the same manner as step 1 of example 1, using 4-methylbenzene-1,3-diol.

$^1$H NMR (300 MHz, DMSO-d$_6$, δ): 10.68 (s, 1H), 12.29 (s, 1H), 7.66 (s, 1H), 6.31 (s, 1H), 3.91 (t, J=6.3 Hz, 2H), 3.48 (t, J=6.3 Hz, 2H), 2.06 (s, 3H).

Step 2

7-Hydroxy-6-methylchroman-4-one (Compound 12-2)

Compound 12-2 (0.15 g, 72%) was obtained in the same manner as step 2 of example 1, using compound 12-1.

$^1$H NMR (300 MHz, DMSO-d$_6$, δ): 10.54 (s, 1H), 7.46 (s, 1H), 6.34 (s, 1H), 4.42 (t, J=6.3 Hz, 2H), 2.63 (t, J=6.3 Hz, 2H), 2.05 (s, 3H).

Step 3

7-(Benzyloxy)-6-methylchroman-4-one (Compound 12-3)

Compound 12-3 (0.55 g, 76%) was obtained in the same manner as step 1 of example 4, using compound 12-2.

$^1$H NMR (300 MHz, DMSO-d$_6$, δ): 7.53 (s, 1H), 7.47-7.31 (m, 5H), 6.62 (s, 1H), 5.19 (s, 2H), 4.47 (t, J=6.3 Hz, 2H), 2.67 (t, J=6.3 Hz, 2H), 2.13 (s, 3H).

Step 4

7-(Benzyloxy)-6-methylchroman-4-amine (Compound 12-4)

Compound 12-4 (0.40 g, 78%) was obtained in the same manner as step 4 of example 1, using compound 12-3.

$^1$H NMR (300 MHz, DMSO-d$_6$, δ): 7.43-7.30 (m, 5H), 7.09 (s, 1H), 6.34 (s, 1H), 5.04 (s, 2H), 4.20-4.02 (m, 2H), 3.77 (t, J=5.1 Hz, 1H), 2.10 (s, 3H), 2.10-1.83 (m, 1H), 1.96-1.83 (m, 1H).

Step 5

4-Amino-6-methylchroman-7-ol (Compound 12-5)

Compound 12-5 (0.18 g, 65%) was obtained in the same manner as step 3 of example 4, using compound 12-4.

$^1$H NMR (400 MHz, DMSO-d$_6$, δ): 7.02 (s, 1H), 6.18 (s, 1H), 4.17-3.99 (m, 2H), 3.92 (bs, 1H), 2.01 (s, 3H), 1.96-1.92 (m, 1H), 1.84-1.71 (m, 1H).

Step 6

7-(4-Chlorophenoxy)-6-methylchroman-4-amine (Compound 12-6)

Compound 12-6 (0.09 g, 56%) was obtained in the same manner as step 4 of example 4, using compound 12-5.

ESIMS m/z: [M−16]⁺ 273.

Step 7

N-{7-(4-Chlorophenoxy)-6-methylchroman-4-yl}acrylamide (Compound 23)

Compound 23 (0.025 g, 23%) was obtained in the same manner as step 5 of example 1, using compound 12-6.

$^1$H NMR (400 MHz, DMSO-d$_6$, δ): 8.56 (d, J=8.0 Hz, 1H), 7.40 (d, J=9.2 Hz, 2H), 7.08 (s, 1H), 6.89 (d, J=9.2 Hz, 2H), 6.34-6.24 (m, 2H), 6.16 (d, J=17.2, 2.4 Hz, 1H), 5.63 (dd, J=10.0, 2.4 Hz, 1H), 5.06-5.01 (m, 1H), 4.23-4.10 (m, 2H), 2.09-2.03 (m, 4H), 1.92-1.85 (m, 1H)
ESIMS m/z: [M−70]$^+$ 273.

Example 13

Step 1

6-Hydroxychroman-4-one (Compound 13-1)

A 33% hydrogen bromide solution in acetic acid (10.0 mL) was added to commercially available 6-methoxychroman-4-one (030 g, 1.68 mmol), and the mixture was stirred at 100° C. for 12 hours. The mixture was cooled to room temperature, a saturated aqueous sodium bicarbonate solution was added to the mixture. The organic layer was extracted with ethyl acetate, dried over anhydrous sodium sulfate, and concentrated under reduced pressure. The residue was purified by silica gel column chromatography (heptane/ethyl acetate=70/30→60/40) to obtain compound 13-1 (0.20 g, 72%).

$^1$H NMR (300 MHz, DMSO-d$_6$, δ): 9.36 (s, 1H), 7.07 (d, J=3.0 Hz, 1H), 6.99 (dd, J=8.7, 3.0 Hz, 1H), 6.87 (d, J=9.0 Hz, 1H), 4.42 (t, J=6.6 Hz, 2H), 2.72 (t, J=6.6 Hz, 2H).
Step 2

6-(4-Chlorophenoxy)chroman-4-one (Compound 13-2)

Compound 13-2 (0.310 g, 32%) was obtained in the same manner as step 3 of example 1, using compound 13-1.

$^1$H NMR (300 MHz, DMSO-d$_6$, δ): 7.44-7.41 (m, 2H), 7.34 (dd, J=9.0, 3.3 Hz, 1H), 7.25 (d, J=3.0 Hz, 1H), 7.11 (d, J=9.0 Hz, 1H), 7.11-6.99 (m, 2H), 4.54 (t, J=6.3 Hz, 2H), 2.79 (t, J=6.3 Hz, 2H).
Step 3

6-(4-Chlorophenoxy)chroman-4-amine (Compound 13-3)

Compound 13-3 was obtained as a crude product in the same manner as step 4 of example 1, using compound 13-2, and used as it is in the next reaction.
ESIMS m/z: [M−16]$^+$ 259.
Step 4

N-{6-(4-Chlorophenoxy)chroman-4-yl}acrylamide (Compound 24)

Compound 24 (0.120 g, 35% over two steps) was obtained in the same manner as step 5 of example 1, using compound 13-3.

$^1$H NMR (300 MHz, DMSO-d$_6$, δ): 8.59 (d, J=8.1 Hz, 1H), 7.37 (d, J=9.0 Hz, 2H), 6.94-6.89 (m, 3H), 6.85-6.83 (m, 2H), 6.28-6.19 (m, 1H), 6.15-6.09 (m, 1H), 5.61 (dd, J=9.6, 2.4 Hz, 1H), 5.10-5.03 (m, 1H), 4.24-4.18 (m, 2H), 2.09-2.06 (m, 1H), 1.95-1.87 (m, 1H)
ESIMS m/z: [M+H]$^+$ 330.

Example 14

Step 1

4-Aminochroman-8-ol Hydrobromide (Compound 14-1)

A saturated aqueous sodium bicarbonate solution was added to commercially available 8-methoxychroman-4-amine hydrochloride (500 mg, 2.32 mol). The organic layer was extracted with chloroform and filtered with Presep ((R); diatomaceous earth, granular type M, 4.5 g/25 mL). The filtrate was concentrated under reduced pressure. The residue was dissolved in dichloromethane (4 mL) and the solution was cooled to −78° C. A 1 mol/L boron tribromide solution in dichloromethane (4.64 mL, 4.64 mmol) was added to the solution, and the mixture was stirred at −78° C. for 2 hours. To the reaction liquid, methanol was added at −78° C., and the mixture was concentrated under reduced pressure. The residue was purified by silica gel column chromatography (chloroform/methanol=90/10→chloroform/methanol=70/30) to obtain compound 14-1 (403 mg, 71%).

$^1$H NMR (400 MHz, DMSO-d$_6$, δ): 8.35 (br, 2H), 6.89-6.88 (m, 1H), 6.78 (s, 1H), 6.77 (s, 1H), 4.49-4.48 (m, 1H), 4.27-4.22 (m, 2H), 2.28-2.23 (m, 1H), 2.12-2.05 (m, 1H).
Step 2

8-(4-(Trifluoromethyl)phenoxy)chroman-4-anine (Compound 14-2)

Compound 14-2 (20.7 mg, 17%) was obtained in the same manner as step 4 of example 4, using compound 14-1 and 1-iodo-4-(trifluoromethyl)benzene.

$^1$H NMR (400 MHz, CDCl$_3$, δ): 7.53 (d, J=8.6 Hz, 2H), 7.21 (dd, J=6.3, 3.2 Hz, 1H), 6.98 (d, J=8.6 Hz, 2H), 6.92-6.91 (m, 2H), 4.31-4.20 (m, 2H), 4.12 (t, J=5.0 Hz, 1H), 2.20-2.12 (m, 1H), 1.90-1.82 (m, 1H).
Step 3

N-[8-{4-(Trifluoromethyl)phenoxy}chroman-4-yl]acrylamide (Compound 25)

Compound 25 (17.3 mg, 87%) was obtained in the same manner as step 5 of example 1, using compound 14-2.

$^1$H NMR (400 MHz, CDCl$_3$, δ): 7.55 (d, J=8.5 Hz, 2H), 7.13 (dt, J=7.6, 0.9 Hz, 1H), 6.98 (d, J=8.1 Hz, 3H), 6.93-6.91 (m, 1H), 6.38 (d, J=16.8 Hz, 1H), 6.12 (dd, J=16.8, 10.5 Hz, 1H), 5.79-5.77 (m, 1H), 5.74 (d, J=10.5 Hz, 1H), 5.32 (dd, J=13.2, 5.6 Hz, 1H), 4.32-4.26 (m, 1H), 4.18-4.14 (m, 1H), 2.29-2.26 (m, 1H), 2.14-2.11 (m, 1H)
ESIMS m/z: [M−H]$^+$362.

Example 15

Step 1

7-(4-Chlorophenoxy)chroman-4-ol (Compound 15-1)

Compound 2-1 (0.24 g, 0.87 mmol) was dissolved in methanol (5 mL), and sodium borohydride (0.16 g, 4.37 mmol) was added to the solution at 0° C. The mixture was stirred at room temperature for 2 hours. Water was added to the mixture. The organic layer was extracted with dichloromethane, dried over anhydrous sodium sulfate, and concentrated under reduced pressure to obtain compound 15-1 (0.10 g, 41%).

$^1$H NMR (300 MHz, DMSO-d$_6$, δ): 7.42 (dd, J=6.6, 2.1 Hz, 2H), 7.31 (d, J=8.4 Hz, 1H), 7.00 (d, J=6.9 Hz, 2H), 6.54 (dd, J=8.1, 2.4 Hz, 1H), 6.38 (d, J=2.4 Hz, 1H), 5.37 (d, J=4.5 Hz, 1H), 4.61-4.59 (m, 1H), 4.20-4.16 (m, 2H), 2.04-1.81 (m, 2H).

Step 2

7-(4-Chlorophenoxy)chroman-4-carbonitrile (Compound 15-2)

Compound 15-1 (0.10 g, 0.36 mmol) was dissolved in dichloromethane (3 mL), and zinc(II) iodide (0.34 g, 1.08 mmol) and trimethylsilyl cyanide (0.06 mL, 0.54 mmol) were added to the solution. The mixture was stirred at room temperature for 18 hours. Water was added to the mixture. The organic layer was extracted with ethyl acetate, dried over anhydrous sodium sulfate, and concentrated under reduced pressure to obtain compound 15-2 (0.06 g, 58%).

$^1$H NMR (400 MHz, DMSO-d$_6$, δ): 7.20 (d, J=8.8 Hz, 2H), 7.09 (d, J=8.8 Hz, 1H), 6.82 (d, J=9.2 Hz, 2H), 6.39 (dd, J=8.4, 2.0 Hz, 1H), 6.23 (d, J=2.4 Hz, 1H), 4.19 (t, J=6.0 Hz, 1H), 3.99-3.95 (m, 2H), 2.09-1.94 (m, 2H).

Step 3

{7-(4-Chlorophenoxy)chroman-4-yl}methanamine (Compound 15-3)

Compound 15-2 (0.06 g, 0.21 mmol) was dissolved in ethanol (5 mL), and Raney nickel (0.05 g) and ammonia water (0.1 mL) were added to the solution. The mixture was stirred under hydrogen atmosphere at room temperature for 2 hours. The mixture was filtered with Celite®, and the filtrate was concentrated under reduced pressure to obtain compound 15-3 (0.06 g) as a crude product.

ESIMS m/z: [M+H]$^+$ 290.

Step 4

N-[{7-(4-Chlorophenoxy)chroman-4-yl}methyl]acrylamide (Compound 26)

Compound 26 (0.03 g, 42% over two steps) was obtained in the same manner as step 5 of example 1, using compound 15-3.

$^1$H NMR (400 MHz, DMSO-d$_6$, δ): 8.34 (bs, 1H), 7.42 (d, J=8.8 Hz, 2H), 7.19 (d, J=8.4 Hz, 1H), 7.01 (d, J=8.8 Hz, 2H), 6.54 (dd, J=8.0, 2.0 Hz, 1H), 6.4 (d, J=2.0 Hz, 1H), 6.26 (dd, J=17.2, 10.0 Hz, 1H), 6.10 (dd, J=17.2, 2.0 Hz, 1H), 5.61 (dd, J=10.0, 1.6 Hz, 1H), 4.18-4.09 (m, 2H), 3.49-3.44 (m, 1H), 3.30-3.25 (m, 1H), 2.91-2.90 (m, 1H), 1.93-1.88 (m, 1H), 1.81-1.78 (m, 1H);

ESIMS m/z: [M+H]$^+$ 344.

Example 16

Step 1

3-Chloro-1-(2,4-dihydroxy-3-methylphenyl)propan-1-one (Compound 16-1)

Compound 16-1 (0.60 g, 34%) was obtained in the same manner as step 1 of example 1, using 2-methylbenzene-1,3-diol.

ESIMS m/z: [M+H]$^+$ 214.

Step 2

7-Hydroxy-8-methylchroman-4-one (Compound 16-2)

Compound 16-2 (0.30 g, 60%) was obtained in the same manner as step 2 of example 1, using compound 16-1.

$^1$H NMR (300 MHz, DMSO-d$_6$, δ): 10.4 (s, 1H), 7.48 (d, J=8.7 Hz, 1H), 6.55 (d, J=8.7 Hz, 1H), 4.50-4.46 (m, 2H), 2.65 (t, J=6.0 Hz, 2H), 1.97 (s, 3H).

Step 3

7-(4-Chlorophenoxy)-8-methylchroman-4-one (Compound 16-3)

Compound 16-3 (0.20 g, 45%) was obtained in the same manner as step 3 of example 1, using compound 16-2.

$^1$H NMR (300 MHz, DMSO-d$_6$, δ): 7.46 (d, J=8.7 Hz, 1H), 7.18 (d, J=8.7 Hz, 2H), 7.03 (d, J=8.7 Hz, 1H), 6.76 (d, J=8.7 Hz, 2H), 4.60 (t, J=6.3 Hz, 2H), 3.39 (t, J=6.0 Hz, 1H), 2.77 (d, 1=6.3 Hz, 1H), 2.09 (s, 3H).

Step 4

7-(4-Chlorophenoxy)-8-methylchroman-4-amine (Compound 16-4)

Compound 16-4 (0.30 g, 60%) was obtained in the same manner as step 4 of example 1, using compound 16-3.

$^1$H NMR (300 MHz, DMSO-d$_6$, δ): 7.36 (d, J=9.0 Hz, 2H), 7.25 (d, J=8.4 Hz, 1H), 6.85 (d, J=9.0 Hz, 2H), 6.50 (d, J=8.4 Hz, 1H), 4.35-4.18 (m, 2H), 3.88 (t, J=5.1 Hz, 1H), 2.00-1.94 (m, 1H), 1.92 (s, 3H), 1.79-1.70 (m, 1H).

Step 5

N-{7-(4-Chlorophenoxy)-8-methylchroman-4-yl}acrylamide (Compound 27)

Compound 27 (0.17 g, 48%) was obtained in the same manner as step 5 of example 1, using compound 16-4.

$^1$H NMR (300 MHz, DMSO-d$_6$, δ): 8.60 (d, J=7.8 Hz, 1H), 7.38 (d, J=8.7 Hz, 2H), 7.03 (d, J=8.4 Hz, 1H), 6.86 (d, J=8.7 Hz, 2H), 6.54 (d, J=8.7 Hz, 1H), 6.30-6.12 (m, 2H), 5.63 (dd, J=9.6, 2.7 Hz, 1H), 5.10-5.08 (m, 1H), 4.34-4.09 (m, 2H), 2.11-2.06 (m, 1H), 1.96-1.88 (m, 4H)

ESIMS m/z: [M−70]$^+$ 273.

Example 17

Step 1

8-Methyl-7-{4-(trifluoromethyl)phenoxy}chroman-4-one (Compound 17-1)

Compound 17-1 (177 mg, 65%) was obtained in the same manner as step 1 of example 3, using compound 16-2.

$^1$H NMR (400 MHz, CDCl$_3$, δ): 7.78 (d, J=8.8 Hz, 1H), 7.60 (d, J=8.6 Hz, 2H), 7.03 (d, J=8.6 Hz, 2H), 6.56 (d, J=8.8 Hz, 1H), 4.61 (t, 3=6.3 Hz, 2H), 2.82 (t, 3=6.3 Hz, 2H), 2.14 (s, 3H).

Step 2

8-Methyl-7-{4-(trifluoromethyl)phenoxy}chroman-4-amine (Compound 17-2)

Compound 17-2 (140 mg, 73%) was obtained in the same manner as step 2 of example 3, using compound 17-1.

¹H NMR (400 MHz, CDCl₃, δ): 7.52 (d, J=8.6 Hz, 2H), 7.16 (d, J=8.3 Hz, 1H), 6.93 (d, J=8.6 Hz, 2H), 6.57 (d, J=8.3 Hz, 1H), 4.38-4.28 (m, 2H), 4.08 (t, J=5.1 Hz, 1H), 2.18-2.15 (m, 1H), 2.02 (s, 3H), 1.89-1.82 (m, 1H).

Step 3

N-[8-Methyl-7-{4-(trifluoromethyl) phenoxy}chroman-4-yl]acrylamide (Compound 28)

Compound 17-2 (70 mg, 0.22 mmol) was dissolved in DMA (2 mL), and acryloyl chloride (0.026 mL, 0.33 mmol) was added to the mixed solution. The mixture was stirred at room temperature for 2 hours. Water was added to the mixture, and a precipitated solid was filtered off, washed with water, and dried to obtain a crude product. The crude product was purified by silica gel column chromatography (heptane/ethyl acetate=80/20→50/50) to obtain compound 28 (34 mg, 42%).

¹H NMR (400 MHz, CDCl₃, δ): 7.53 (d, 1=8.6 Hz, 2H), 7.08 (d, J=8.8 Hz, 1H), 6.93 (d, J=8.6 Hz, 2H), 6.56 (d, J=8.8 Hz, 1H), 6.36 (dd, J=17.0, 1.5 Hz, 1H), 6.10 (dd, J=17.0, 10.4 Hz, 1H), 5.77 (s, 1H), 5.71 (dd, J=10.4, 1.5 Hz, 1H), 5.25-5.22 (m, 1H), 4.39-4.34 (m, 1H), 4.24-4.18 (m, 1H), 2.30-2.22 (m, 1H), 2.17-2.10 (m, 1H), 2.03 (s, 3H)

ESIMS m/z: [M–H]⁺376.

Example 18

(E)-4,4,4-Trifluoro-N-[8-methyl-7-{4-(trifluoromethyl)phenoxy}chroman-4-yl]-2-butenamide (Compound 29)

Compound 29 (61 mg, 63%) was obtained in the same manner as step 3 of example 17, using compound 17-2 and commercially available (E)-4,4,4-trifluoro-2-butenoyl chloride.

¹H NMR (400 MHz, CDCl₃, δ): 7.54 (d, J=8.8 Hz, 2H), 7.05 (d, J=8.3 Hz, 1H), 6.93 (d, J=8.8 Hz, 2H), 6.85-6.81 (m, 1H), 6.57 (d, J=8.3 Hz, 1H), 6.50-6.46 (m, 1H), 6.00 (d, J=7.8 Hz, 1H), 5.25-5.22 (m, 1H), 4.41-4.37 (m, 1H), 4.23-4.17 (m, 1H), 2.31-2.26 (m, 1H), 2.17-2.11 (m, 1H), 2.04 (s, 3H);

ESIMS m/z: [M–H]⁺ 444.

Example 19

Step 1

2-Fluorobenzene-1,3-diol (Compound 19-1)

2-Fluoro-3-methoxyphenol (0.50 g, 3.52 mmol) was dissolved in dichloromethane (10 mL). A 1 mol/L boron tribromide in dichloromethane (17.6 mL, 17.6 mmol) was added dropwise to the mixture at −78° C. under nitrogen atmosphere, and the mixture was stirred at room temperature for 18 hours. The mixture was cooled to −78° C., and water was added to the mixture. The organic layer was extracted with dichloromethane, dried over anhydrous sodium sulfate, and concentrated under reduced pressure to obtain compound 19-1 (0.45 g, 89%).

¹H NMR (400 MHz, DMSO-d₆, δ): 9.57 (s, 2H), 6.73-6.68 (m, 1H), 6.38-6.34 (m, 2H).

Step 2

3-Chloro-1-(3-fluoro-2,4-dihydroxyphenyl)propan-1-one (Compound 19-2)

Compound 19-2 (0.65 g, 85%) was obtained in the same manner as step 1 of example 1, using compound 19-1.

¹H NMR (400 MHz, DMSO-d₆, δ): 12.24 (s, 1H), 11.18 (s, 1H), 7.64-7.61 (m, 1H), 6.56-6.52 (m, 1H), 3.91 (t, J=6.4 Hz, 2H), 3.52 (t, J=6.4 Hz, 2H).

Step 3

8-Fluoro-7-hydroxychroman-4-one (Compound 19-3)

Compound 19-3 (0.45 g, 83%) was obtained in the same manner as step 2 of example 1, using compound 19-2.

¹H NMR (400 MHz, DMSO-d₆, δ): 11.05 (s, 1H), 7.44-7.41 (m, 1H), 6.66-6.62 (m, 1H), 4.57 (t, J=6.4 Hz, 2H), 2.73 (t, J=6.4 Hz, 2H).

Step 4

7-(4-Chlorophenoxy)-8-fluorochroman-4-one (Compound 19-4)

Compound 19-4 was obtained as a crude product in the same manner as step 1 of example 3, using compound 19-3.

¹H NMR (300 MHz, DMSO-d₆, δ): 7.57 (dd, J=9.0, 2.1 Hz, 1H), 7.49 (d, J=8.7 Hz, 2H), 7.16 (d, J=8.7 Hz, 2H), 6.72-6.67 (m, 1H), 4.68 (t, J=6.3 Hz, 2H), 2.85 (t, J=6.6 Hz, 2H).

Step 5

7-(4-Chlorophenoxy)-8-fluorochroman-4-amine (Compound 19-5)

Compound 19-5 was obtained as a crude product in the same manner as step 4 of example 1, using compound 19-4.

¹H NMR (400 MHz, DMSO-d₆, δ): 7.40-7.30 (m, 3H), 6.95 (d, J=8.8 Hz, 2H), 6.68-6.64 (m, 1H), 4.34-4.09 (m, 3H), 2.04-2.00 (m, 1H), 1.80-1.76 (m, 1H);

ESIMS m/z: [M–16]⁺ 277.

Step 6

N-{7-(4-Chlorophenoxy)-8-fluorochroman-4-yl}acrylamide (Compound 30)

Compound 30 (0.025 g, 4% in three stages) was obtained in the same manner as step 5 of example 1, using compound 19-5.

¹H NMR (400 MHz, CDCl₃, δ): 7.29-7.25 (m, 2H), 6.97-6.89 (m, 3H), 6.59-6.55 (m, 1H), 6.36 (dd, J=16.8, 1.2 Hz, 1H), 6.10 (dd, J=16.8, 10.0 Hz, 1H), 5.81-5.71 (m, 2H), 5.30-5.20 (m, 1H), 4.43-4.38 (m, 1H), 4.29-4.23 (m, 1H), 2.32-2.24 (m, 1H), 2.18-2.11 (m, 1H);

ESIMS m/z: [M–70]⁺ 277.

Example 20

Step 1

8-Fluoro-7-{4-(trifluoromethyl)phenoxy}chroman-4-one (Compound 20-1)

Compound 20-1 (0.02 g, 11%) was obtained in the same manner as step 1 of example 3, using compound 19-3.

¹H NMR (400 MHz, CDCl₃, δ): 7.70-7.62 (m, 3H), 7.12 (d, J=8.4 Hz, 2H), 6.69-6.65 (m, 1H), 4.70-4.66 (m, 2H), 2.89-2.86 (m, 2H).

Step 2

8-Fluoro-7-{4-(trifluoromethyl)phenoxy}chroman-4-amine (Compound 20-2)

Compound 20-2 (0.12 g, 67%) was obtained in the same manner as step 4 of example 1, using compound 20-1.

¹H NMR (300 MHz, CDCl₃, δ): 7.57-7.11 (m, 3H), 7.02 (d, J=8.7 Hz, 2H), 6.68-6.62 (m, 1H), 4.41-4.08 (m, 3H), 2.25-2.15 (m, 1H), 1.95-1.87 (m, 1H).

Step 3

N-[8-Fluoro-7-{4-(trifluoromethyl)phenoxy}chroman-4-yl]acrylamide (Compound 31)

Compound 31 (0.05 g, 39%) was obtained in the same manner as step 5 of example 1, using compound 20-2.

¹H NMR (400 MHz, DMSO-d₆, δ): 8.66 (d, J=7.6 Hz, 1H), 7.74 (d, J=8.4 Hz, 2H), 7.11 (d, J=8.4 Hz, 2H), 7.05 (d, J=8.8 Hz, 1H), 6.82 (t, J=7.6 Hz, 1H), 6.30-6.15 (m, 2H), 5.66 (dd, J=9.6, 2.4 Hz, 1H), 5.15-5.13 (m, 1H), 4.39-4.30 (m, 2H), 2.16-2.12 (m, 1H), 1.98-1.96 (m, 1H);

ESIMS m/z: [M−70]⁺ 311.

Example 21

Step 1

2-Methoxybenzene-1,3-diol (Compound 21-1)

Benzene-1,2,3-triol (2.00 g, 15.87 mmol) was dissolved in acetone (20 mL), and potassium hydrogen carbonate (1.74 g, 17.46 mmol) and methyl iodide (2.25 g, 15.83 mmol) were added to the solution. The mixture was stirred at 50° C. for 24 hours. The mixture was filtered with Celite®, and the filtrate was concentrated under reduced pressure. The residue was purified by silica gel column chromatography (hexane/ethyl acetate=100/0→70/30) to obtain compound 21-1 (0.50 g, 22%).

¹H NMR (400 MHz, DMSO-d₆, δ): 8.98 (s, 2H), 6.65 (t, J=8.4 Hz, 1H), 6.27 (d, J=8.0 Hz, 2H), 3.65 (s, 3H).

Step 2

3-Chloro-1-(2,4-dihydroxy-3-methoxyphenyl)propan-1-one (Compound 21-2)

Compound 21-2 (0.77 g, 46%) was obtained in the same manner as step 1 of example 1, using compound 21-1.

¹H NMR (400 MHz, DMSO-d₆, δ): 12.39 (s, 1H), 10.50 (s, 1H), 7.57 (d, J=8.8 Hz, 1H), 6.46 (d, J=8.8 Hz, 1H), 3.90-3.88 (m, 2H), 3.71 (s, 3H), 3.51-3.48 (m, 2H).

Step 3

7-Hydroxy-8-methoxychroman-4-one (Compound 21-3)

Compound 21-3 (0.10 g, 59%) was obtained in the same manner as step 2 of example 1, using compound 21-2.

¹H NMR (400 MHz, DMSO-d₆, δ): 10.30 (s, 1H), 7.38 (d, J=8.8 Hz, 1H), 6.55 (d, J=8.8 Hz 1H), 4.52 (t, J=6.4 Hz, 2H), 3.70 (s, 3H), 2.68 (t, J=5.6 Hz, 2H).

Step 4

7-(4-Chlorophenoxy)-8-methoxychroman-4-one (Compound 21-4)

Compound 21-4 (0.30 g, 58%) was obtained in the same manner as step 1 of example 3, using compound 21-3.

¹H NMR (300 MHz, DMSO-d₆, δ): 7.54-7.46 (m, 3H), 7.06 (d, J=8.7 Hz, 2H), 6.63 (d, J=9.0 Hz, 1H), 4.62 (t, J=6.6 Hz, 2H), 3.73 (s, 3H), 2.80 (t, J=6.3 Hz, 2H).

Step 5

7-(4-Chlorophenoxy)-8-methoxychroman-4-amine (Compound 21-5)

Compound 21-5 (0.20 g, 70%) was obtained in the same manner as step 4 of example 1, using compound 21-4.

¹H NMR (300 MHz, DMSO-d₆, δ): 7.36 (d, J=9.0 Hz, 2H), 7.15 (d, J=9.0 Hz, 1H), 6.88 (d, J=9.0 Hz, 2H), 6.58 (d, J=8.7 Hz, 1H), 4.32-4.10 (m, 2H), 3.90-3.86 (m, 1H), 3.59 (s, 3H), 2.03-1.96 (m, 1H), 1.79-1.71 (m, 1H).

Step 6

N-{7-(4-Chlorophenoxy)-8-methoxychroman-4-yl}acrylamide (Compound 32)

Compound 32 (0.09 g, 38%) was obtained in the same manner as step 5 of example 1, using compound 21-5.

¹H NMR (300 MHz, DMSO-d₆, δ): 8.62 (d, J=8.1 Hz, 1H), 7.38 (d, J=9.0 Hz, 2H), 6.91-6.88 (m, 3H), 6.62 (d, J=8.7 Hz, 1H), 6.31-6.12 (m, 2H), 5.63 (dd, J=8.7, 2.7 Hz, 1H), 5.08 (d, J=7.8 Hz, 1H) 4.36-4.20 (m, 2H), 3.6 (s, 3H), 2.12-2.06 (m, 1H), 1.94-1.90 (m, 1H);

ESIMS m/z: [M−70]⁺ 289.

Example 22

Step 1

8-Methoxy-7-{4-(trifluoromethyl)phenoxy}-chroman-4-one (Compound 22-1)

Compound 22-1 (0.38 g, 66%) was obtained in the same manner as step 1 of example 3, using compound 21-3.

¹H NMR (300 MHz, DMSO-d₆, δ): 7.75 (d, J=8.4 Hz, 2H), 7.58 (d, J=8.4 Hz, 1H), 7.17 (d, J=8.4 Hz, 2H), 6.79 (d, J=8.7 Hz, 1H), 4.65 (t, J=6.6 Hz, 2H), 3.72 (s, 3H), 2.82 (t, J=6.6 Hz, 2H).

Step 2

8-Methoxy-7-{4-(trifluoromethyl)phenoxy}-chroman-4-amine (Compound 22-2)

Compound 22-2 (0.34 g, 90%) was obtained in the same manner as step 4 of example 1, using compound 22-1.

¹H NMR (300 MHz, DMSO-d₆, δ): 7.60 (d, J=8.7 Hz, 2H), 7.20 (d, J=8.4 Hz, 1H), 7.02 (d, J=8.4 Hz, 2H), 6.67 (d, J=8.4 Hz, 1H), 4.34-4.19 (m, 2H), 3.92-3.88 (m, 1H), 3.59 (s, 3H), 2.06-1.99 (m, 1H), 1.82-1.73 (m, 1H).

Step 3

N-[8-Methoxy-7-{4-(trifluoromethyl)phenoxy}chroman-4-yl]acrylamide (Compound 33)

Compound 33 (0.12 g, 28%) was obtained in the same manner as step 5 of example 1, using compound 22-2.

¹H NMR (300 MHz, DMSO-d₆, δ): 8.60 (d, J=7.8 Hz, 1H), 7.70 (d, J=8.7 Hz, 2H), 7.00 (d, J=8.7 Hz, 2H), 6.90 (d, J=8.4 Hz, 1H), 6.70 (d, J=8.4 Hz, 1H), 6.32-6.13 (m, 2H), 5.64 (dd, J=9.6, 2.7 Hz, 1H), 5.13 (d, J=5.7 Hz, 1H), 4.37-4.22 (m, 2H), 3.60 (s, 3H), 2.14-2.08 (m, 1H) 1.99-1.91 (m, 1H);

ESIMS m/z: [M−70]⁺ 323.

Example 23

Step 1

5-Methoxy-2H-chromene-3-carbonitrle (Compound 23-1)

Acrylonitrile (10 mL) and 1,4-diazabicyclo[2.2.2]octane (0.55 g, 4.93 mmol) were added to commercially available 2-hydroxy-6-methoxybenzaldehyde (0.50 g, 3.28 mmol), and the mixture was stirred at 85° C. for 16 hours. The mixture was cooled to room temperature, and water was added to the mixture. The organic layer was extracted with ethyl acetate, dried over anhydrous sodium sulfate, and concentrated under reduced pressure. The residue was purified by silica gel column chromatography (hexane/ethyl acetate=80/20→70/30) to obtain compound 23-1 (0.30 g, 48%).

$^1$H NMR (400 MHz, DMSO-$d_6$, δ): 7.55 (d, J=0.8 Hz, 1H), 7.30 (t, 3=8.4 Hz, 1H), 6.67 (dd, J=8.4, 0.4 Hz, 1H), 6.52 (d, J=8.0 Hz, 1H), 4.80 (d, J=1.2 Hz, 2H), 3.83 (s, 3H)

Step 2

5-Methoxy-2H-chromene-3-carboxylic acid (Compound 23-2)

A 3 mol/L aqueous sodium hydroxide solution (10 mL) was added to compound 23-1 (0.30 g, 1.64 mmol), and the mixture was refluxed for 5 hours. The mixture was cooled to room temperature, and 2 mol/L hydrochloric acid (10.0 mL) was added to the mixture. The precipitated solid was filtered off, washed with water, and dried under reduced pressure to obtain compound 23-2 (0.25 g, 72%).

$^1$H NMR (400 MHz, DMSO-$d_6$, δ): 12.75 (s, 1H), 7.56 (d, J=0.8 Hz, 1H), 7.24 (t, J=8.4 Hz, 1H), 6.62 (dd, J=8.4, 0.4 Hz, 1H), 6.49-6.47 (m, 1H), 4.84 (d, J=1.6 Hz, 2H), 3.82 (s, 3H).

Step 3 tert-Butyl (5-methoxy-2H-chromen-3-yl)carbamate (Compound 23-3)

tert-Butanol (25 mL) and triethylamine (1.3 mL, 9.70 mmol) were added to compound 23-2 (0.50 g, 3.28 mmol). Diphenylphosphoryl azide (1.3 mL, 5.82 mmol) was added to the solution at room temperature, and the mixture was stirred at 90° C. for 16 hours. The mixture was cooled to room temperature, and concentrated under reduced pressure. The residue was purified by silica gel column chromatography (hexane/ethyl acetate=60/40→40/60) to obtain compound 23-3 (0.95 g, 73%).

$^1$H NMR (300 MHz, DMSO-$d_6$, δ): 8.97 (s, 1H), 6.93 (t, J=8.1 Hz, 1H), 6.72 (s, 1H), 6.54 (d, J=8.1 Hz, 1H), 6.30 (d, J=8.1 Hz, 1H), 4.60 (s, 2H), 3.76 (s, 3H), 1.44 (s, 9H).

Step 4 tert-Butyl (5-methoxy-2H-chroman-3-yl)carbamate (Compound 23-4)

Compound 23-3 (0.95 g, 3.42 mmol) was dissolved in ethanol (20 mL), and palladium/carbon (0.90 g) was added to the solution. The mixture was stirred under hydrogen atmosphere at room temperature for 16 hours. The reaction liquid was filtered with Celite®. The filtrate was concentrated under reduced pressure to obtain compound 23-4 as a crude product, which was used as it is in the next reaction.

$^1$H NMR (300 MHz, DMSO-$d_6$, δ): 7.04 (t, 3=8.1 Hz, 1H), 6.96 (d, J=6.6 Hz, 1H), 6.51 (d, J=8.1 Hz, 1H), 6.40 (d, J=8.1 Hz, 1H), 4.08-4.05 (m, 1H), 3.82 (s, 3H), 3.59-3.82 (m, 2H), 2.80 (dd, J=16.8, 5.4 Hz, 1H), 2.44-2.38 (m, 1H), 1.40 (s, 9H).

Step 5

3-Aminochroman-5-ol (Compound 23-5)

Pyridine hydrochloride (150 mg) was added to compound 23-4, and the mixture was stirred at 150° C. for 30 minutes using a microwave reactor, Initiator, manufactured by Biotage. The mixture was cooled to room temperature, and a saturated aqueous sodium bicarbonate solution was added to the mixture. The organic layer was extracted with dichloromethane, dried over anhydrous sodium sulfate, and concentrated under reduced pressure. The residue was purified by silica gel column chromatography (hexane/ethyl acetate=40/60→30/70) to obtain compound 23-5 (40.0 mg, 62% over two steps).

$^1$H NMR (300 MHz, DMSO-$d_6$, δ): 9.31 (s, 1H), 6.82 (t, J=8.1 Hz, 1H), 6.33 (d, J=7.8 Hz, 1H), 6.20 (d, J=8.1 Hz, 1H), 4.01-3.98 (m, 1H), 3.48 (t, J=9.0 Hz, 1H), 3.05-3.02 (m, 1H), 2.78 (dd, J=16.8, 4.8 Hz, 1H), 2.19-2.11 (m, 1H).

Step 6

5-(4-Chlorophenoxy)chroman-3-amine (Compound 23-6)

Compound 23-6 (0.110 g, 26%) was obtained in the same manner as step 4 of example 4, using compound 23-5.

ESIMS m/z: [M+H]$^+$ 276.

Step 7

N-{5-(4-Chlorophenoxy)chroman-3-yl}acrylamide (Compound 34)

Compound 34 (21 mg, 18%) was obtained in the same manner as step 5 of example 1, using compound 23-6.

$^1$H NMR (300 MHz, DMSO-$d_6$, δ): 8.25 (d, J=6.6 Hz, 1H), 7.40 (d, J=9.0 Hz, 2H), 7.14 (t, J=8.1 Hz, 1H), 6.96 (d, J=9.0 Hz, 2H), 6.70 (d, J=8.1 Hz, 1H), 6.50 (d, J=7.8 Hz, 1H), 6.26 (dd, J=17.1, 9.9 Hz, 1H), 6.10 (dd, J=17.1, 2.4 Hz, 1H), 5.59 (dd, J=9.9, 2.4 Hz, 1H), 4.21-4.13 (m, 2H), 3.93-3.88 (m, 1H), 2.87 (dd, J=17.1, 5.7 Hz, 1H), 2.57-2.50 (m, 1H); ESIMS m/z: [M+H]$^+$ 330.

The following compounds were synthesized in accordance with the synthesis method of compound 34.

N-{6-(4-Chlorophenoxy)chroman-3-yl}acrylamide (Compound 36)

ESIMS m/z: [M+H]$^+$ 330.

N-{7-(4-Chlorophenoxy)chroman-3-yl}acrylamide (Compound 37)

ESIMS m/z: [M+H]$^+$ 330.

N-[7-{4-(Trifluoromethyl)phenoxy}chroman-3-yl]acrylamide (Compound 38)

ESIMS m/z: [M+H]$^+$ 364.

Example 24

Step 1

5-{4-(Trifluoromethyl)phenoxy}chroman-3-amine (Compound 24-1)

Compound 24-1 (0.13 g, 46%) was obtained in the same manner as step 4 of example 4, using compound 23-5.
ESIMS m/z: [M+H]$^+$ 310.

Step 2

N-[5-{4-(Trifluoromethyl)phenoxy}chroman-3-yl] acrylamide (Compound 35)

Compound 35 (70 mg, 46%) was obtained in the same manner as step 5 of example 1, using compound 24-1.
$^1$H NMR (400 MHz, DMSO-d$_6$, δ): 8.26 (d, J=6.8 Hz, 1H), 7.71 (d, J=8.8 Hz, 2H), 7.20 (t, J=8.4 Hz, 1H), 7.08 (d, J=8.4 Hz, 2H), 6.78-6.76 (m, 1H), 6.64 (dd, J=8.0, 0.8 Hz, 1H), 6.24 (dd, J=17.2, 10.4 Hz, 1H), 6.09 (dd, J=16.8, 2.0 Hz, 1H), 5.59 (dd, J=10.0, 2.4 Hz, 1H), 4.20-4.15 (m, 2H), 3.94-3.89 (m, 1H), 2.83 (dd, J=16.8, 6.4 Hz, 1H), 2.56-2.54 (m, 1H);
ESIMS n/z: [M+H]$^+$ 364.

Step 3

N-[5-{4-(Trifluoromethyl)phenoxy}chroman-3-yl] acrylamide (Compounds 65 and 66)

Compound 35 was optically resolved under the following chiral preparative conditions to obtain compound 65 (17 mg, 25%) having a retention time of 6.65 minutes and compound 66 (19 mg, 29%) having a retention time of 8.25 minutes.
Compound 65: ESIMS m/z: [M+H]$^+$ 364.
Compound 66: ESIMS m/z: [M+H]$^+$ 364.

Chiral Preparative Conditions
Apparatus used: SFC30 manufactured by Waters
Column used: CHIRALPAK® IA/SFC 10 mmφ×250 mm, 5 μM
Temperature: 40° C.
Liquid feeding condition: 95% carbon dioxide/5% isopropanol
Preparative time: 15 minutes
Flow rate: 30 mL/minute
Retention time: 6.65 minutes (compound 65), 8.25 minutes (compound 66)

Example 25

Step 1

3-(2-Methoxyphenoxy)propionic acid (Compound 25-1)

DMF (10 mL) was added to sodium hydride (65% liquid paraffin dispersion, 1.73 g, 48.38 mmol). A solution prepared by adding DMF (20 mL) to 2-methoxyphenol (5.00 g, 40.32 mmol) was added dropwise to the mixture under nitrogen atmosphere at 0° C., and the mixture was stirred for 30 minutes. A solution prepared by adding DMF (20 mL) to 3-bromopropionic acid (7.40 g, 48.38 mmol) was added dropwise to the mixture, and the mixture was stirred under nitrogen atmosphere at room temperature for 18 hours. Water was added to the mixture. The mixture was acidified by the addition of a 2 mol/L aqueous hydrochloric acid solution (20 mL). The organic layer was extracted with ethyl acetate, dried over anhydrous sodium sulfate, concentrated under reduced pressure to obtain compound 25-1 as a crude product, which was used as it is in the next reaction.
$^1$H NMR (400 MHz, DMSO-d$_6$, δ): 12.34 (br, 1H), 6.97-6.86 (m, 2H), 6.76-6.73 (m, 1H), 4.13 (t, J=6.0 Hz, 2H), 3.73 (s, 3H), 2.68 (t, J=6.0 Hz, 2H).

Step 2

8-Methoxychroman-4-one (Compound 25-2)

Trifluoromethanesulfonic acid (1 mL) was added to compound 25-1, and the mixture was stirred at 80° C. for 30 minutes. A solution prepared by adding dichloromethane to the mixture left to cool to room temperature was slowly added to water. The organic layer was extracted with dichloromethane, dried over anhydrous sodium sulfate, and concentrated under reduced pressure. The residue was purified by silica gel column chromatography (hexane/ethyl acetate=100/0→70/30) to obtain compound 25-2 (0.15 g, 13% over two steps).
$^1$H NMR (400 MHz, DMSO-d$_6$, δ): 7.32-7.30 (m, 11H), 7.23-7.21 (m, 1H), 6.97 (t, J=8.0 Hz, 1H), 4.53 (t, J=6.4 Hz, 2H), 3.79 (s, 3H), 2.77 (t, J=6.8 Hz, 2H).

Step 3

8-Hydroxychroman-4-one (Compound 25-3)

Compound 25-2 (0.10 g, 0.56 mmol) was dissolved in dichloromethane (3 mL), and the solution was cooled to −78° C. A 1 mol/L boron tribromide solution in dichloromethane (2.80 mL, 2.80 mmol) was added dropwise to the solution under nitrogen atmosphere, and the mixture was stirred at room temperature for 2 hours. The mixture was cooled to −78° C., and water was added to the mixture. The organic layer was extracted with ethyl acetate, dried over anhydrous sodium sulfate, and concentrated under reduced pressure to obtain compound 25-3 as a crude product, which was used as it is in the next reaction.
$^1$H NMR (400 MHz, DMSO-d$_6$, δ): 9.52 (s, 1H), 7.19 (dd, J=8.0, 1.6 Hz, 1H), 7.04-7.02 (m, 1H), 6.84 (t, J=7.6 Hz, 1H), 4.53 (t, J=6.4 Hz, 2H), 2.77 (t, J=6.4 Hz, 2H).

Step 4

8-(4-chlorophenoxy)chroman-4-one (Compound 25-4)

Compound 25-4 (0.10 g, 39% over two steps) was obtained in the same manner as step 1 of example 3, using compound 25-3 and 4-chlorophenylboronic acid.
$^1$H NMR (400 MHz, DMSO-d$_6$, δ): 7.65 (dd, J=8.0, 1.2 Hz, 1H), 7.39-7.37 (m, 3H), 7.08 (t, J=8.0 Hz, 1H), 6.94 (d, J=8.8 Hz, 2H), 4.53 (t, J=6.4 Hz, 2H), 2.81 (t, J=6.4 Hz, 2H).

Step 5

8-(4-Chlorophenoxy)chroman-4-one oxime (Compound 25-5)

Compound 25-4 (0.10 g, 0.364 mmol) was dissolved in pyridine (2 mL), and hydroxylamine hydrochloride (0.05 g, 0.72 mmol) was added to the solution. The mixture was stirred at 80° C. for 2 hours. The mixture was cooled to room temperature, and a 2 mol/L aqueous hydrochloric acid solution (5 mL) was added to the mixture. The organic layer was extracted with dichloromethane, dried over anhydrous sodium sulfate, and concentrated under reduced pressure to obtained compound 25-5 as a crude product, which was used as it is in the next reaction.

¹H NMR (400 MHz, DMSO-d₆, δ): 11.39 (s, 1H), 7.69-7.67 (m, 1H), 7.35 (d, J=9.2 Hz, 2H), 7.08-7.06 (m, 1H), 7.00-6.96 (m, 1H), 6.89 (d, J=9.2 Hz, 2H), 4.14 (t, J=6.0 Hz, 2H), 2.83 (t, J=6.0 Hz, 2H).

Step 6

8-(4-Chlorophenoxy)chroman-4-one O-tosyl oxime (Compound 25-6)

A solution prepared by adding THF (2 mL) to compound 25-5 (0.10 g, 0.34 mmol) was added dropwise to a suspension solution prepared by adding THF (1 mL) to sodium hydride (65% liquid paraffin dispersion, 0.025 g, 0.69 mmol) under nitrogen atmosphere at room temperature, and the mixture was stirred for 30 minutes. A solution prepared by adding THF (2 mL) to p-toluenesulfonyl chloride (0.10 g, 0.519 mmol) was added dropwise to the mixture. The mixture was stirred under nitrogen atmosphere at room temperature for one hour. Water was added to the mixture. The organic layer was extracted with dichloromethane, dried over anhydrous sodium sulfate, and concentrated under reduced pressure to obtain compound 25-6 as a crude product, which was used as it is in the next reaction.

¹H NMR (400 MHz, DMSO-d₆, δ): 7.93 (d, J=8.0 Hz, 2H), 7.57-7.45 (m, 3H), 7.34 (d, J=8.0 Hz, 2H), 7.24-7.22 (m, 1H), 7.06-7.00 (m, 1H), 6.89 (d, J=8.8 Hz, 2H), 4.18 (t, J=6.0 Hz, 2H), 3.00 (t, J=6.4 Hz, 2H), 2.43 (s, 3H).

Step 7

3-Amino-8-(4-chlorophenoxy)chroman-4-one hydrochloride (Compound 25-7)

Compound 25-6 (0.10 g, 0.22 mmol) was dissolved in toluene (5 mL), and a 24% potassium ethoxide solution in ethanol (0.11 mL, 0.338 mmol) was added to the solution. The mixture was stirred under argon atmosphere at room temperature for 18 hours. tert-Butylmethyl ether (20 mL) was added to the mixture, and the mixture was filtered with Celite®. Concentrated hydrochloric acid (0.2 mL) was added to the filtrate, and the mixture was stirred at room temperature for one hour. The liquid mixture was concentrated under reduced pressure, and tert-butylmethyl ether was added to the residue for reslurrying to obtain compound 25-7 (0.02 g, 14% in three stages).

¹H NMR (400 MHz, DMSO-d₆, δ): 8.76 (s, 3H), 7.70 (dd, J=7.6, 1.2 Hz, 1H), 7.46 (dd, J=7.6, 1.2 Hz, 1H), 7.41 (d, J=8.8 Hz, 2H), 7.19 (t, J=8.0 Hz, 1H), 6.99 (d, J=8.8 Hz, 2H), 4.79-4.71 (m, 2H), 4.50-4.42 (m, 1H).

Step 8

N-{8-(4-Chlorophenoxy)-4-oxochroman-3-yl}acrylamide (Compound 39)

Compound 39 (0.11 g, 52%) was obtained in the same manner as step 5 of example 1, using compound 25-7.

¹H NMR (400 MHz, DMSO-d₆, δ): 8.58 (d, J=7.6 Hz, 1H), 7.68 (dd, J=7.6, 1.2 Hz, 1H), 7.42-7.38 (m, 3H), 7.14 (t, J=8.0 Hz, 1H), 6.98 (d, J=8.8 Hz, 2H), 6.35 (dd, J=17.2, 10.4 Hz, 1H), 6.15 (dd, J=17.2, 1.6 Hz, 1H), 5.69 (dd, J=10.0, 1.6 Hz, 1H), 5.02-4.96 (m, 1H), 4.55-4.51 (m, 1H), 4.36-4.30 (m, 1H);

ESIMS m/z: [M+H]⁺ 344.

Example 26

Step 1

8-{4-(Trifluoromethyl)phenoxy}chroman-4-one (Compound 26-1)

Compound 26-1 (0.05 g, 27%) was obtained in the same manner as step 1 of example 3, using compound 25-3 and 4-(trifluoromethyl)phenylboronic acid.

¹H-NMR (400 MHz, H, CDCl₃) δ: 7.80 (dd, J=8.0, 1.2 Hz, 1H), 7.57 (d, J=8.4 Hz, 2H), 7.28-7.26 (m, 1H), 7.06-6.91 (m, 3H), 4.54 (t, J=6.4 Hz, 2H), 2.85 (t, J=6.4 Hz, 2H).

Step 2

8-{4-(Trifluoromethyl)phenoxy}chroman-4-one oxime (Compound 26-2)

Compound 26-2 was obtained as a crude product in the same manner as step 5 of example 25, using compound 26-1, and used as it is in the next reaction.

¹H NMR (300 MHz, DMSO-d₆, δ): 11.43 (s, 1H), 7.74 (dd, J=7.8, 1.2 Hz, 1H), 7.68 (d, J=8.7 Hz, 2H), 7.18 (dd, J=8.1, 1.5 Hz, 1H), 7.05-7.03 (m, 3H), 4.14 (t, J=6.0 Hz, 2H), 2.83 (t, J=6.3 Hz, 2H).

Step 3

8-{4-(Trifluoromethyl)phenoxy}chroman-4-one O-tosyl oxime (Compound 26-3)

Compound 26-3 was obtained as a crude product in the same manner as step 6 of example 25, using compound 26-2, and used as it is in the next reaction.

¹H NMR (300 MHz, DMSO-d₆, δ): 7.94 (d, J=8.1 Hz, 2H), 7.80 (t, J=7.8 Hz, 1H), 7.68-7.61 (m, 2H), 7.52 (d, J=8.1 Hz, 2H), 7.36-7.33 (m, 1H), 7.10-7.01 (m, 3H), 4.18 (t, J=6.3 Hz, 2H), 3.01 (t, J=6.3 Hz, 2H), 2.43 (s, 3H).

Step 4

3-Amino-8-{4-(trifluoromethyl)phenoxy}chroman-4-one hydrochloride (Compound 26-4)

Compound 26-4 (0.03 g, 31% in three stages) was obtained in the same manner as step 7 of example 25, using compound 26-3.

¹H NMR (400 MHz, DMSO-d₆, δ): 8.90 (s, 3H), 7.78-7.71 (m, 3H), 7.59 (d, J=8.0 Hz, 1H), 7.23 (t, J=8.0 Hz, 1H), 7.13 (d, J=8.4 Hz, 2H), 4.80-4.72 (m, 2H), 4.52-4.46 (m, 1H).

Step 5

N-[4-Oxo-8-{4-(trifluoromethyl)phenoxy}chroman-3-yl]acrylamide (Compound 40)

Compound 40 (0.18 g, 69%) was obtained in the same manner as step 5 of example 1, using compound 26-4 (0.25 g, 0.70 mmol).

¹H NMR (400 MHz, DMSO-d₆, δ): 8.58 (d, J=7.6 Hz, 1H), 7.75-7.70 (m, 3H), 7.53-7.51 (m, 1H), 7.18 (t, J=7.6 Hz, 1H), 7.12 (d, J=8.8 Hz, 2H), 6.35 (dd, J=17.2, 10.0 Hz, 1H), 6.15 (dd, J=17.2, 1.6 Hz, 1H), 5.68 (dd, J=10.0, 1.2 Hz, 1H), 5.04-4.97 (m, 1H), 4.54-4.50 (m, 1H), 4.37-4.31 (m, 1H);

ESIMS m/z: [M+H]⁺ 378.

Example 27

Step 1

5-Bromo-8-methoxy-2H-chromene-3-carbonitrile (Compound 27-1)

Compound 27-1 (0.12 g, 21%) was obtained in the same manner as step 1 of example 23, using commercially available 6-bromo-2-hydroxy-3-methoxybenzaldehyde.

$^1$H NMR (300 MHz, DMSO-$d_6$, δ): 7.53 (s, 1H), 7.25 (d, J=9.0 Hz, 1H), 7.05 (d, J=8.7 Hz, 1H), 4.87 (d, J=1.2 Hz, 2H), 3.77 (s, 3H).

Step 2

5-Bromo-8-methoxy-2H-chromene-3-carboxylic acid (Compound 27-2)

Compound 27-2 (0.10 g, 85%) was obtained in the same manner as step 2 of example 23, using compound 27-1.

$^1$H NMR (300 MHz, DMSO-$d_6$, δ): 13.18 (br, 1H), 7.45 (s, 1H), 7.20 (d, J=8.7 Hz, 1H), 6.99 (d, J=8.7 Hz, 1H), 4.89 (d, J=1.2 Hz, 2H), 3.77 (s, 3H).

Step 3 tert-Butyl (5-bromo-8-methoxy-2H-chromen-3-yl)carbamate (Compound 27-3)

Compound 27-3 (0.10 g, 80%) was obtained in the same manner as step 3 of example 23, using compound 27-2.

$^1$H-NMR (300 MHz, DMSO-$d_6$, δ): 9.22 (s, 1H), 7.08 (d, J=9.0 Hz, 1H), 6.77 (s, 1H), 6.72 (d, J=8.7 Hz, 1H), 4.64 (s, 2H), 3.72 (s, 3H), 1.46 (s, 9H).

Step 4 tert-Butyl (8-methoxy-5-methyl-2H-chromen-3-yl)carbamate (Compound 27-4)

Compound 27-3 (0.90 g, 2.52 mmol) was dissolved in 1,4-dioxane (20 mL), and trimethylboroxine (0.41 g, 5.05 mmol), potassium carbonate (0.69 g, 5.05 mmol), and tetrakis(triphenylphosphine)palladium(0) (0.29 g, 0.25 mmol) were added to the solution. The mixture was stirred at 100° C. for 16 hours. The liquid mixture was filtered, and water was added to the filtrate. The organic layer was extracted with tert-butyl methyl ether, dried over anhydrous sodium sulfate, and concentrated under reduced pressure. The residue was purified by silica gel column chromatography (hexane/ethyl acetate=60/40→50/50) to obtain compound 27-4 (0.65 g, 88%).

$^1$H NMR (300 MHz, DMSO-$d_6$, δ): 9.06 (s, 1H), 6.64-6.61 (m, 3H), 4.58 (s, 2H), 3.68 (s, 3H), 2.12 (s, 3H), 1.45 (s, 9H).

Step 5 tert-Butyl (8-methoxy-5-methyl-2H-chroman-3-yl)carbamate (Compound 27-5)

Compound 27-5 was obtained as a crude product in the same manner as step 4 of example 23, using compound 27-4, and used as it is in the next reaction.

$^1$H NMR (400 MHz, DMSO-$d_6$, δ): 6.97 (d, J=6.80 Hz, 1H), 6.66 (q, J=8.4 Hz, 2H), 4.06 (d, J=9.6 Hz, 1H), 3.80-3.61 (m, 5H), 2.79 (dd, J=16.4, 5.6 Hz, 1H), 2.46-2.44 (m, 1H), 2.06 (s, 3H), 1.40 (s, 9H).

Step 6

3-Amino-5-methylchroman-8-ol hydrobromide (Compound 27-6)

Compound 27-5 was dissolved in dichloromethane (10 mL), and the solution was cooled to 0° C. A 1 mol/L boron tribromide solution in dichloromethane (8.5 mL, 8.53 mmol) was added dropwise to the solution under nitrogen atmosphere, and the mixture was stirred at room temperature for 2 hours. The mixture was cooled to 0° C., and methanol (15 mL) was added to the mixture. The mixture was concentrated under reduced pressure, and tert-butyl methyl ether was added to the residue for reslurrying to obtain compound 27-6 (0.38 g, 62% in three stages).

$^1$H NMR (400 MHz, DMSO-$d_6$, δ): 8.82 (br, 1H), 8.14 (br, 3H), 6.59 (q, J=8.0 Hz, 2H), 4.11 (s, 2H), 3.81 (br, 1H), 2.99 (dd, J=17.2, 5.6 Hz, 1H), 2.63-2.58 (m, 1H), 2.05 (s, 3H).

Step 7

8-(4-Chlorophenoxy)-5-methylchroman-3-amine (Compound 27-7)

Compound 27-7 (0.150 g, 39%) was obtained in the same manner as step 4 of example 4, using compound 27-6.

$^1$H NMR (300 MHz, DMSO-$d_6$, δ): 7.31 (d, J=9.0 Hz, 2H), 6.85-6.76 (m, 4H), 4.00-3.98 (m, 1H), 3.59-3.47 (m, 2H), 2.72 (br, 1H), 2.27-2.25 (m, 1H), 2.17 (s, 3H).

Step 8

N-{8-(4-Chlorophenoxy)-5-methylchroman-3-yl}acrylamide (Compound 41)

Compound 41 (0.18 g, 26%) was obtained in the same manner as step 5 of example 1, using compound 27-7.

$^1$H NMR (300 MHz, DMSO-$d_6$, δ): 8.28 (d, J=6.6 Hz, 1H), 7.31 (d, J=9.0 Hz, 2H), 6.91-6.78 (m, 4H), 6.28 (dd, J=17.1, 10.2 Hz, 1H), 6.11 (dd, J=17.1, 2.1 Hz, 1H), 5.60 (dd, J=9.9, 2.4 Hz, 1H), 4.24-4.20 (m, 1H), 4.04-3.99 (m, 1H), 3.86-3.80 (m, 1H), 3.00-2.93 (m, 1H), 2.64-2.56 (m, 1H), 2.18 (s, 3H);

ESIMS m/z: [M+H]$^+$ 344.

Example 28

Step 1

8-Methoxychroman-3-amine (Compound 28-1)

Compound 28-1 was obtained as a crude product in the same manner as step 4 of example 1, using commercially available 8-methoxychroman-3-one, and was used as it is in the next reaction.

$^1$H NMR (300 MHz, DMSO-$d_6$, δ): 6.74 (br, 2H), 6.62-6.61 (m, 1H), 4.09-4.03 (m, 1H), 3.66 (s, 3H), 3.79-3.66 (m, 1H), 3.08-3.06 (m, 1H), 2.96-2.83 (m, 1H), 2.61-2.41 (m, 1H).

Step 2

3-Aminochroman-8-ol hydrobromide (Compound 28-2)

Compound 28-2 (0.25 g, 30% over two steps) was obtained in the same manner as step 6 of example 27, using compound 28-1.

ESIMS m/z: [M+H]$^+$ 166,

Step 3

8-(4-Chlorophenoxy)chroman-3-amine (Compound 28-3)

Compound 28-3 (0.150 g, 36%) was obtained in the same manner as step 4 of example 4, using compound 28-2.
ESIMS m/z: [M+H]$^+$ 276.

Step 4

N-{8-(4-Chlorophenoxy)chroman-3-yl}acrylamide (Compound 42)

Compound 42 (35 mg, 19%) was obtained in the same manner as step 5 of example 1, using compound 28-3.
$^1$H NMR (300 MHz, DMSO-d$_6$, δ): 8.29 (d, J=6.9 Hz, 1H), 7.33 (d, J=8.7 Hz, 2H), 7.03-7.01 (m, 1H), 6.91-6.86 (m, 4H), 6.29 (dd, J=17.1, 10.2 Hz, 1H), 6.10 (dd, J=16.8, 2.1 Hz, 1H), 5.60 (dd, J=10.2, 2.4 Hz, 1H), 4.21-4.17 (m, 1H), 4.09-4.05 (m, 1H), 3.92-3.86 (m, 1H), 3.15-309 (m, 1H), 2.82-2.74 (m, 1H);
ESIMS m/z: [M+H]$^+$ 330.

The following compounds were synthesized in accordance with the synthesis method of compound 42.

N-[8-{3-(Trifluoromethyl)phenoxy}chroman-3-yl]acrylamide (Compound 43)

ESIMS m/z: [M−H]$^+$362.

N-[8-{4-(Trifluoromethoxy)phenoxy}chroman-3-yl]acrylamide (Compound 45)

ESIMS m/z: [M−H]$^+$378.

N-{8-(3,4-Dichlorophenoxy)chroman-3-yl}acrylamide (Compound 46)

ESIMS m/z: [M−H]$^+$362, 364.

N-[8-{4-Chloro-3-(trifluoromethyl)phenoxy}chroman-3-yl]acrylamide (Compound 47)

ESIMS m/z: [M−H]$^+$396.

N-[8-{(5-Chloropyridin-2-yl)oxy}chroman-3-yl]acrylamide (Compound 48)

ESIMS m/z: [M+H]$^+$ 331.

N-[8-{(6-Chloropyridin-3-yl)oxy}chroman-3-yl]acrylamide (Compound 49)

ESIMS m/z: [M+H]$^+$ 331.

N-[8-{(4,5-Dichloropyridin-2-yl)oxy}chroman-3-yl]acrylamide (Compound 52)

ESIMS m/z: [M+H]$^+$ 365, 367.

N-[8-{(5,6-Dichloropyridin-2-yl)oxy}chroman-3-yl]acrylamide (Compound 53)

ESIMS m/z: [M+H]$^+$ 365, 367.

N-[8-{(5-Chloro-6-methylpyridin-2-yl)oxy}chroman-3-yl]acrylamide (Compound 54)

ESIMS m/z: [M+H]$^+$ 345.

N-[8-{(5-Chloro-4-methylpyridin-2-yl)oxy}chroman-3-yl]acrylamide (Compound 55)

ESIMS m/z: [M+H]$^+$ 345.

N-(8-[{6-Chloro-5-(trifluoronethyl)pyridin-2-yl}oxy]chroman-3-yl)acrylamide (Compound 57)

ESIMS m/z: [M+H]$^+$ 399.

N-(8-[{4,5-Bis(trifluoronethyl)pyridin-2-yl}oxy]chroman-3-yl)acrylamide (Compound 58)

ESIMS m/z: [M+H]$^+$ 433.

N-[8-{(6-Isopropoxypyridin-3-yl)oxy}chroman-3-yl]acrylamide (Compound 154)

ESIMS m/z: [M+H]$^+$ 355.

Step 5

N-{8-(4-chlorophenoxy)chroman-3-yl}acrylamide (Compounds 59 and 60)

Compound 42 was optically resolved under the following chiral preparative conditions to obtain compound 59 (63 mg, 31%) having a retention time of 3.48 minutes and compound 60 (68 mg, 33%) having a retention time of 4.57 minutes.
Compound 59: ESIMS m/z: [M+H]$^+$ 330.
Compound 60: ESIMS m/z: [M+H]$^+$ 330.

Chiral Preparative Conditions
Apparatus used: SFC30 manufactured by Waters
Column used: CHIRALPAK® IB/SFC 10 mmφ×250 mm, 5 µM
Temperature: 40° C.
Liquid feeding condition: 90% carbon dioxide/10% methanol
Preparative time: 6 minutes
Flow rate: 30 mL/minute
Retention time: 3.48 minutes (compound 59), 4.57 minutes (compound 60)

Example 29

Step 1

8-{4-(trifluoromethyl)phenoxy}chroman-3-amine (Compound 29-1)

Compound 29-1 was obtained as a crude product in the same manner as step 4 of example 4, using compound 28-2, and used as it is in the next reaction.
ESIMS m/z: [M+H]$^+$ 310.

Step 2

N-[8-{4-(Trifluoromethyl)phenoxy}chroman-3-yl]acrylamide (Compound 44)

Compound 44 (0.17 g, 33% over two steps) was obtained in the same manner as step 5 of example 1, using compound 29-1.

¹H NMR (400 MHz, DMSO-d₆, δ): 8.28 (d, J=6.8 Hz, 1H), 7.65 (d, J=8.8 Hz, 2H), 7.08-6.92 (m, 5H), 6.28 (dd, J=17.2, 10.4 Hz, 1H), 6.10 (d, J=17.2, 2.0 Hz, 1H), 5.60 (dd, J=10.0, 2.0 Hz, 1H), 4.21-4.19 (m, 1H), 4.08-4.05 (m, 1H), 3.91-3.87 (m, 1H), 3.17-3.10 (m, 1H), 2.83-2.77 (m, 1H)
ESIMS m/z: [M+H]⁺ 364.
Step 3

N-[8-{4-(Trifluoromethyl)phenoxy}chroman-3-yl]acrylamide (Compounds 61 and 62)

Compound 44 was optically resolved under the following chiral preparative conditions to obtain compound 61 (46 mg, 34%) having a retention time of 4.17 minutes and compound 62 (66 mg, 48%) having a retention time of 5.74 minutes.
Compound 61: ESIMS m/z: [M+H]⁺ 364.
Compound 62: ESIMS m/z: [M+H]⁺ 364.
Chiral Preparative Conditions
Apparatus used: SFC30 manufactured by Waters
Column used: CHIRALPAK® IB/SFC 10 mmϕ×250 mm, 5 μM
Temperature: 40° C.
Liquid feeding condition: 93% carbon dioxide/3.5% methanol/3.5% chloroform
Preparative time: 10 minutes
Flow rate: 30 mL/minute
Retention time: 4.17 minutes (Compound 61), 5.74 minutes (Compound 62)

Example 30

Step 1

8-[{5-(Trifluoromethyl)pyridin-2-yl}oxy]chroman-3-amine (Compound 30-1)

Compound 30-1 was obtained as a crude product in the same manner as step 4 of example 4, using compound 28-2 and commercially available 2-chloro-5-(trifluoromethyl)pyridine, and used as it is in the next reaction.
ESIMS m/z: [M+H]⁺ 311.
Step 2

N-(8-[{5-(Trifluoromethyl)pyridin-2-yl}oxy]chroman-3-yl)acrylamide (Compound 50)

Compound 50 (82.0 mg, 55% over two steps) was obtained in the same manner as step 5 of example 1, using compound 30-1.
¹H NMR (400 MHz, CDCl₃, δ): 8.35 (br, 1H), 7.90 (dd, J=8.6, 2.5 Hz, 1H), 7.06 (d, J=8.6 Hz, 1H), 7.00-6.95 (m, 3H), 6.27 (dd, J=17.0, 1.6 Hz, 1H), 6.25-6.22 (m, 1H), 6.05 (dd, J=17.0, 10.2 Hz, 1H), 5.63 (dd, J=10.2, 1.6 Hz, 1H), 4.59-4.54 (m, 1H), 4.12 (ddd, J=10.9, 2.0, 1.0 Hz, 1H), 4.05 (dd, J=10.9, 2.0 Hz, 1H), 3.19 (dd, J=17.0, 5.2 Hz, 1H), 2.87-2.85 (m, 1H);
ESIMS m/z: [M+H]⁺ 365.
Step 3

N-(8-[{5-(Trifluoromethyl)pyridin-2-yl}oxy]chroman-3-yl)acrylamide (Compounds 63 and 64)

Compound 50 was optically resolved under the following chiral preparative conditions to obtain compound 63 (23 mg, 34%) having a retention time of 5.95 minutes and compound 64 (26 mg, 38%) having a retention time of 7.82 minutes.
Compound 63: ESIMS m/z: [M+H]⁺ 365.
Compound 64: ESIMS m/z: [M+H]⁺ 365,
Chiral Preparative Conditions
Apparatus used: SFC30 manufactured by Waters
Column used: CHIRALPAK® IA/SFC 10 mmϕ×250 mm, 5 μM Temperature: 40° C.
Liquid feeding condition: 93% carbon dioxide/7% isopropanol
Preparative time: 12 minutes
Flow rate: 30 mL/minute
Retention time: 5.95 minutes (Compound 63), 7.82 minutes (Compound 64)

Example 31

Step 1

8-[{6-(Trifluoromethyl)pyridin-3-yl}oxy]chroman-3-amine (Compound 31-1)

Compound 31-1 was obtained as a crude product in the same manner as step 4 of example 4, using compound 28-2 and commercially available 5-bromo-2-(trifluoromethyl)pyridine, and was used as it is in the next reaction.
ESIMS m/z: [M+H]⁺ 311.
Step 2

N-(8-[{6-(Trifluoromethyl)pyridin-3-yl}oxy]chroman-3-yl)acrylamide (Compound 51)

Compound 51 (43.4 mg, 29% over two steps) was obtained in the same manner as step 5 of example 1, using compound 31-1.
¹H NMR (400 MHz, CDCl₃, δ): 8.39 (d, J=2.7 Hz, 1H), 7.60 (d, J=8.6 Hz, 1H), 7.27 (dd, J=8.6, 2.7 Hz, 1H), 7.01-6.92 (m, 3H), 6.29 (dd, J=16.8, 1.4 Hz, 1H), 6.12 (d, J=8.2 Hz, 1H), 6.07 (dd, J=16.8, 10.4 Hz, 1H), 5.66 (dd, J=10.4, 1.4 Hz, 1H), 4.59-4.53 (m, 1H), 4.16 (ddd, J=11.1, 2.0, 1.0 Hz, 1H), 4.10 (dd, J=11.1, 2.0 Hz, 1H), 3.20 (dd, J=17.0, 5.4 Hz, 1H), 2.90 (dd, J=17.0, 2.0 Hz, 1H);
ESIMS m/z: [M+H]⁺ 365.

Example 32

Step 1

8-{(6-Chloro-5-methylpyridin-3-yl)oxy}chroman-3-amine (Compound 32-1)

Compound 32-1 was obtained as a crude product in the same manner as step 4 of example 4, using compound 28-2 and commercially available 2-chloro-5-iodo-3-methylpyridine, and used as it is in the next reaction.
ESIMS m/z: [M+H]⁺ 290.
Step 2

N-[8-{(6-Chloro-5-methylpyridin-3-yl)oxy}chroman-3-yl]acrylamide (Compound 56)

Compound 56 (2.7 mg, 7%) was obtained in the same manner as step 5 of example 1, using compound 32-1.
¹H NMR (400 MHz, CDCl₃, δ): 7.92 (d, J=3.2 Hz, 1H), 7.17 (d, J=3.2 Hz, 1H), 6.94-6.89 (m, 3H), 6.31 (dd, J=17.0, 1.4 Hz, 1H), 6.05 (dd, J=17.0, 10.2 Hz, 1H), 5.88 (d, J=8.2 Hz, 1H), 5.67 (dd, J=10.2, 1.1 Hz, 1H), 4.61-4.58 (m, 1H), 4.23 (ddd, J=11.1, 2.0, 1.0 Hz, 1H), 4.12 (dd, J=11.1, 2.0 Hz, 1H), 3.20 (dd, J=17.0, 5.2 Hz, 1H), 2.90 (dt, J=17.0, 2.5 Hz, 1H), 2.36 (s, 3H);
ESIMS m/z: [M+H]$^+$ 345, Example 33

Step 1

7',8'-Dihydro-6'H-spiro[[1,3]dioxolane-2,5'-quinoline] (Compound 33-1)

In toluene (34 mL), 7,8-dihydroquinolin-5(6H)-one (0.50 g, 3.40 mmol) was dissolved. Ethylene glycol (0.38 mL, 6.79 mmol) and p-toluenesulfonic acid monohydrate (0.13 mg, 0.679 mmol) were added to the solution. The mixture was refluxed overnight using a Dean-Stark apparatus. The mixture was left to cool to room temperature, and triethylamine (0.14 mL) was added to the mixture. The mixture was concentrated under reduced pressure. The residue was purified by aminosilica gel column chromatography (heptane/ethyl acetate=100/0→80/20) to obtain compound 33-1 (374 mg, 58%).
$^1$H NMR (400 MHz, CDCl$_3$, δ): 8.49 (dd, J=4.8, 1.8 Hz, 1H), 7.79 (dd, J=8.1, 1.8 Hz, 1H), 7.15 (ddt, J=8.1, 4.8, 0.7 Hz, 1H), 4.20-4.12 (m, 4H), 2.98-2.96 (m, 2H), 2.08-1.95 (m, 4H); ESIMS m/z: [M+H]$^+$ 192.

Step 2

7',8'-Dihydro-6'H-spiro[[1,3]dioxolane-2,5'-quinoline] 1'-oxide (Compound 33-2)

Compound 33-1 (0.374 g, 1.95 mmol) was dissolved in dichloromethane (20 mL), and m-chloroperoxybenzoic acid (674 mg, 2.93 mmol) was added to the solution. The mixture was stirred at room temperature for one hour. A saturated aqueous sodium bicarbonate solution and a saturated aqueous sodium thiosulfate solution were added to the mixture. The mixture was filtered with Presep ((R); diatomaceous earth, granular type M, 4.5 g/25 mL), and the filtrate was concentrated under reduced pressure to obtain compound 33-2 (415 mg) as a crude product.
ESIMS m/z: [M+H]$^+$ 208.

Step 3

7',8'-Dihydro-6'H-spiro[[1,3]dioxolane-2,5'-quinolin]-8'-ol (Compound 33-3)

Compound 33-2 (415 mg) as a crude product was dissolved in ethyl acetate (15 mL), and triethylamine (0.84 mL, 6.01 mmol) was added to the solution. Trifluoroacetic anhydride (0.57 mL, 4.01 mmol) dissolved in ethyl acetate (5 mL) was added to the mixture at −78° C. After stirred at −78° C. for one hour, the mixture was stirred at room temperature overnight. A saturated aqueous sodium bicarbonate solution was added to the mixture. The mixture was filtered with Presep ((R); diatomaceous earth, granular type M, 4.5 g/25 mL), and the filtrate was concentrated under reduced pressure. Ethanol (1.0 mL) and a 2 mol/L aqueous sodium hydroxide solution (1.0 mL) were added to the residue, and the mixture was stirred at room temperature for one hour. Water was added to the mixture. The organic layer was extracted with ethyl acetate, dried over anhydrous sodium sulfate, and concentrated under reduced pressure. The residue was purified by silica gel column chromatography (chloroform/methanol=97/3→93/7) to obtain compound 33-3 (325 mg, 78% over two steps).
$^1$H NMR (400 MHz, CDCl$_3$, δ): 8.56 (dd, J=4.8, 1.8 Hz, 1H), 7.81 (dd, J=8.2, 1.8 Hz, 1H), 7.27 (dd, J=8.2, 4.8 Hz, 1H), 4.69 (dd, J=9.1, 5.4 Hz, 1H), 4.25-4.06 (m, 4H), 3.98 (br, 1H), 2.39-2.36 (m, 1H), 2.22-2.19 (m, 1H), 2.01-1.94 (m, 2H);
ESIMS m/z: [M+H]$^+$ 208.

Step 4

8'-Phenoxy-7',8'-dihydro-6'H-spiro[[1,3]dioxolane-2,5'-quinoline](Compound 33-4)

Compound 33-3 (36.0 mg, 0.174 mmol), triphenylphosphine (91.0 mg, 0.347 mmol), and phenol (33.0 mg, 0.347 mmol) were dissolved in THF (0.7 mL), and diisopropyl azodicarboxylate (0.068 mL) was added to the solution. The mixture was stirred at room temperature overnight. The mixture was concentrated under reduced pressure. The residue was purified by silica gel column chromatography (heptane/ethyl acetate=80/20→50/50) to obtain compound 33-4 (93.0 mg) as a crude product.
ESIMS m/z: [M+H]$^+$ 284.

Step 5

8-Phenoxy-7,8-dihydroquinolin-5(6H)-one (Compound 33-5)

A 2 mol/L hydrochloric acid dioxane solution (1 mL) was added to compound 33-4 as a crude product, and the mixture was stirred at 50° C. overnight. The mixture was concentrated under reduced pressure. The residue was purified by silica gel column chromatography (heptane/ethyl acetate=90/10→70/30) to obtain compound 33-5 (16.3 mg, 39% over two steps).
$^1$H NMR (400 MHz, CDCl$_3$, δ): 8.80 (dd, J=4.8, 2.1 Hz, 1H), 8.35 (dd, J=7.9, 2.1 Hz, 1H), 7.45 (dd, J=7.9, 4.8 Hz, 1H), 7.32 (tt, J=7.9, 2.1 Hz, 2H), 7.16-7.15 (m, 2H), 7.01 (td, J=7.9, 1.1 Hz, 1H), 5.63 (t, J=3.4 Hz, 1H), 3.16-3.13 (m, 1H), 2.72-2.59 (m, 2H), 2.43-2.34 (m, 1H);
ESIMS m/z: [M+H]$^+$ 240.

Step 6

8-Phenoxy-5,6,7,8-tetrahydroquinolin-5-amine (Compound 33-6)

Compound 33-6 (13.8 mg) was obtained as a crude product in the same manner as step 4 of example 1, using compound 33-5 (15.0 mg, 0.063 mmol).
ESIMS m/z: [M+H]$^+$ 241.

Step 7 cis-N-(8-Phenoxy-5,6,7,8-tetrahydroquinolin-5-yl)acrylamide (Compound 67)

Compound 33-6(13.8 mg) as a crude product was dissolved in dichloromethane (0.6 mL), and triethylamine (0.03 mL, 0.189 mmol) and acryloyl chloride (0.075 mL, 0.93 mmol) were added to the solution. The mixture was stirred at 0° C. for one hour. A saturated aqueous sodium bicarbonate solution was added to the mixture. The mixture was filtered with Presep ((R); diatomaceous earth, granular type M, 4.5 g/25 mL), and the filtrate was concentrated under reduced pressure. The residue was purified by silica gel column chromatography (heptane/ethyl acetate=70/30→40/60) to obtain compound 67 (3.20 mg, 17% over two steps).
$^1$H NMR (400 MHz, CDCl$_3$, δ): 8.58 (dt, J=4.5, 1.5 Hz, 1H), 7.71 (dd, J=8.2, 4.5 Hz, 1H), 7.31-7.27 (m, 3H), 7.10 (dd, J=8.6, 1.1 Hz, 2H), 6.99 (tt, J=7.2, 1.1 Hz, 1H), 6.39

(dd, J=17.0, 1.4 Hz, 1H), 6.16 (dd, J=17.0, 10.2 Hz, 1H), 5.93 (d, J=9.1 Hz, 1H), 5.75 (dd, J=10.2, 1.4 Hz, 1H), 5.45-5.38 (m, 2H), 2.44-2.42 (m, 1H), 2.18-1.98 (m, 3H);
ESIMS m/z: [M+H]$^+$ 295.

Example 34

Step 1

8'-(3-Chlorophenoxy)-7',8'-dihydro-6'H-spiro[[1,3]dioxolane-2,5'-quinoline] (Compound 34-1)

Compound 34-1 (207 mg) was obtained as a crude product in the same manner as step 4 of example 33, using compound 33-3 (80.0 mg, 0.386 mmol) and 3-chlorophenol (99.0 mg, 0.772 mmol).
$^1$H NMR (400 MHz, CDCl$_3$, δ): 8.64 (dd, J=4.8, 1.8 Hz, 1H), 7.88 (dd, J=7.9, 1.8 Hz, 1H), 7.33 (dd, J=7.9, 4.8 Hz, 1H), 7.21 (t, J=7.9 Hz, 1H), 7.11 (t, J=2.3 Hz, 1H), 7.00-6.94 (m, 2H), 5.41 (t, J=3.4 Hz, 1H), 4.23-4.14 (m, 4H), 2.35-2.30 (m, 3H), 2.00-1.97 (m, 1H); ESIMS m/z: [M+H]$^+$318.

Step 2

8-(3-Chlorophenoxy)-7,8-dihydroquinolin-5(6H)-one (Compound 34-2)

Compound 34-2 (180 mg) was obtained as a crude product in the same manner as step 5 of example 33, using compound 34-1 (207 mg) as a crude product.
$^1$H NMR (400 MHz, CDCl$_3$, δ): 8.80 (dd, J=4.5, 1.8 Hz, 1H), 8.36 (dd, J=8.2, 1.8 Hz, 1H), 7.46 (dd, J=8.2, 4.5 Hz, 1H), 7.23 (t, J=8.2 Hz, 1H), 7.19 (t, J=2.3 Hz, 1H), 7.07-7.05 (m, 1H), 7.00-6.98 (m, 1H), 5.60 (t, J=3.9 Hz, 1H), 3.17-3.08 (m, 1H), 2.73-2.68 (m, 1H), 2.64-2.57 (m, 1H), 2.45-2.37 (m, 1H);
ESIMS m/z: [M+H]$^+$ 274.

Step 3

8-(3-Chlorophenoxy)-5,6,7,8-tetrahydroquinolin-5-amine (Compound 34-3)

Compound 34-3 (59.2 m g) was obtained as a crude product in the same manner as step 6 of example 33, using compound 34-2 (180 mg) as a crude product.
ESIMS m/z: [M+H]$^+$ 275.

Step 4 cis-N-{8-(3-Chlorophenoxy)-5,6,7,8-tetrahydroquinolin-5-yl}acrylamide (Compound 68)

trans-N-{8-(3-Chlorophenoxy)-5,6,7,8-tetrahydroquinolin-5-yl}acrylamide (Compound 79)

Compound 68 (26.8 mg, 38% in four stages) and compound 79 (5.50 mg, 8% in four stages) were obtained in the same manner as step 7 of example 33, using compound 34-3 (59.2 mg) as a crude product.
Compound 68: $^1$H NMR (400 MHz, CDCl$_3$, δ): 8.59 (d, J=4.9 Hz, 1H), 7.73 (d, J=7.8 Hz, 1H), 7.30 (d, J=4.9 Hz, 1H), 7.23 (t, J=8.3 Hz, 1H), 7.12-7.11 (m, 1H), 7.01-6.97 (m, 2H), 6.40 (dd, J=17.1, 1.5 Hz, 1H), 6.16 (dd, J=17.1, 10.2 Hz, 1H), 5.82 (d, J=10.0 Hz, 1H), 5.76 (dd, J=10.2, 1.5 Hz, 1H), 5.42-5.40 (m, 2H), 2.42-2.40 (m, 1H), 2.15-2.09 (m, 3H);
ESIMS m/z: [M+H]$^+$ 329.
Compound 79: $^1$H NMR (400 MHz, CDCl$_3$, δ): 8.62 (d, J=6.8 Hz, 1H), 7.74 (d, J=6.8 Hz, 1H), 7.22-7.14 (m, 3H), 7.00-6.98 (m, 2H), 6.37 (dd, J=17.1, 1.9 Hz, 1H), 6.08 (dd, J=17.1, 10.2 Hz, 1H), 5.74-5.71 (m, 2H), 5.46-5.44 (m, 2H), 2.45-2.42 (m, 1H), 2.27-2.18 (m, 2H), 1.96-1.90 (m, 1H);
ESIMS m/z: [M+H]$^+$ 329.

The following compounds were synthesized in accordance with the synthesis method aforementioned.

cis-N-{8-(4-Chlorophenoxy)-5,6,7,8-tetrahydroquinolin-5-yl}acrylamide (Compound 69)

ESIMS m/z: [M+H]$^+$ 329.

trans-N-{8-(4-Chlorophenoxy)-5,6,7,8-tetrahydroquinolin-5-yl}acrylamide (Compound 80)

ESIMS m/z: [M+H]$^+$ 329.

cis-N-{2-Chloro-8-(3,4-dichlorophenoxy)-5,6,7,8-tetrahydroquinolin-5-yl}acrylanide (Compound 178)

ESIMS m/z: [M+H]$^+$ 397.

Example 35

Step 1

2'-Chloro-7',8'-dihydro-6'H-spiro[[1,3]dioxolane-2,5-quinoline](Compound 35-1)

Commercially available 2-chloro-7,8-dihydroquinolin-5(6H)-one (1.50 g, 8.26 mmol) was dissolved in toluene (83 mL). Ethylene glycol (0.92 mL, 16.5 mmol) and pyridinium p-toluenesulfonate (208 mg, 0.826 mmol) were added to the solution. The mixture was refluxed for three hours using a Dean-Stark apparatus during which ethylene glycol (0.92 mL, 16.5 mmol) was added four times every 30 minutes. The mixture was cooled to 0° C., and triethylamine (0.35 mL) was added to the mixture. The mixture was concentrated under reduced pressure. The residue was purified by aminosilica gel column chromatography (heptane/ethyl acetate=90/10→70/30) to obtain compound 35-1 (1.75 g, 94%).
$^1$H NMR (400 MHz, CDCl$_3$, δ): 7.73 (d, J=8.2 Hz, 1H), 7.17 (d, J=8.2 Hz, 1H), 4.21-4.08 (m, 4H), 2.93 (t, J=6.1 Hz, 2H), 2.03-1.93 (m, 4H);
ESIMS m/z: [M+H]$^+$ 226.

Step 2

2'-Chloro-7',8'-dihydro-6'H-spiro[[1,3]dioxolane-2,5'-quinolin]-8'-ol (Compound 35-2)

Compound 35-1 (2.35 g, 10.4 mmol) was dissolved in dichloromethane (104 mL), and m-chloroperoxybenzoic acid (4.79 g, 20.8 mmol) was added to the solution. After the mixture was stirred at room temperature overnight, m-chloroperoxybenzoic acid (2.39 g, 10.4 mmol) was further added to the mixture. The mixture was stirred at room temperature for one hour. The mixture was basified by the addition of a 4 mol/L aqueous sodium hydroxide solution, and a saturated aqueous sodium thiosulfate solution was added to the mixture. The organic layer was extracted with chloroform, dried over anhydrous sodium sulfate, and concentrated under reduced pressure. The residue was dissolved in ethyl acetate (104 mL), and trifluoroacetic acid anhydride (0.57 mL, 4.01 mmol) was added to the mixture at −78° C. The mixture was stirred at room temperature overnight. The mixture was concentrated under reduced pressure. Ethanol (20 mL) and a 4 mol/L aqueous sodium hydroxide solution (2.0 mL) were added to the residue, and the mixture was stirred at room temperature for one hour. Water was added to the mixture. The organic layer was extracted with ethyl acetate, dried over anhydrous sodium sulfate, and concentrated under reduced pressure. The residue was purified by silica gel column chromatography (heptane/ethyl acetate=90/10→50/50) to obtain compound 35-2 (1.63 g, 65%).

$^1$H NMR (400 MHz, CDCl$_3$, δ): 7.76 (d, J=8.2 Hz, 1H), 7.27 (d, J=8.2 Hz, 1H), 4.67 (dd, J=8.6, 5.4 Hz, 1H), 4.16-4.12 (m, 4H), 2.38-2.31 (m, 1H), 2.18 (ddd, J=13.4, 6.8, 2.5 Hz, 1H), 2.07-1.98 (m, 1H), 1.90 (ddd, J=14.0, 11.1, 2.3 Hz, 1H);

ESIMS m/z: [M+H]$^+$ 242.

Step 3

2'-Chloro-8'-(4-chlorophenoxy)-7',8'-dihydro-6'H-spiro[[1,3]dioxolane-2,5'-quinolin]-8'-ol (Compound 35-3)

Compound 35-3 (68.5 mg) was obtained as a crude product in the same manner as step 4 of example 33, using compound 35-2 (110 mg, 0.455 mmol) and 4-chlorophenol (117 mg, 9.10 mmol).

ESIMS m/z: [M+H]$^+$ 352.

Step 4

2-Chloro-8-(4-chlorophenoxy)-7,8-dihydroquinolin-5(6H)-one (Compound 35-4)

Compound 35-4 (57.5 mg, 41% over two steps) was obtained in the same manner as step 5 of example 33, using compound 35-3 (422 mg) as a crude product.

$^1$H NMR (400 MHz, CDCl$_3$, δ): 8.29 (d, J=8.1 Hz, 1H), 7.46 (d, J=8.1 Hz, 1H), 7.29-7.28 (m, 2H), 7.08 (td, J=6.1, 3.8 Hz, 2H), 5.49 (t, J=3.5 Hz, 1H), 3.17-3.05 (m, 1H), 2.69-2.59 (m, 2H), 2.41-2.31 (m, 1H);

ESIMS m/z: [M+H]$^+$ 308.

Step 5

2-Chloro-8-(4-chlorophenoxy)-5,6,7,8-tetrahydroquinolin-5-amine (Compound 35-5)

Compound 35-5 (23.5 mg) was obtained as a crude product in the same manner as step 4 of example 1, using compound 35-4 (57.5 mg, 0.185 mmol).

ESIMS m/z: [M+H]$^+$ 309.

Step 6 cis-N-{2-Chloro-8-(4-chlorophenoxy)-5,6,7,8-tetrahydroquinolin-5-yl}acrylamide (Compound 70)

Compound 70 (10.2 mg, 15% over two steps) was obtained in the same manner as step 7 of example 33, using compound 35-5 (23.5 mg) as a crude product.

$^1$H NMR (400 MHz, CDCl$_3$, δ): 7.66 (d, J=8.6 Hz, 1H), 7.27 (d, J=5.4 Hz, 1H), 7.24 (t, J=2.9 Hz, 2H), 7.02 (td, J=6.2, 3.8 Hz, 2H), 6.39 (dd, J=16.8, 1.4 Hz, 1H), 6.16 (dd, J=16.8, 10.4 Hz, 1H), 5.95 (d, J=9.5 Hz, 1H), 5.75 (dd, J=10.4, 1.4 Hz, 1H), 5.36-5.33 (m, 1H), 5.28-5.28 (m, 1H), 2.42-2.33 (m, 1H), 2.08-2.01 (m, 3H);

ESIMS m/z: [M+H]$^+$ 363.

The following compound was synthesized in accordance with the synthesis method of compound 70.

cis-N-[2-Chloro-8-{(2-oxo-2H-chromen-7-yl)oxy}-5,6,7,8-tetrahydroquinolin-5-yl]acrylamide (Compound 75)

ESIMS m/z: [M+H]$^+$ 397.

Example 36

Step 1

8-(4-Chlorophenoxy)-2-methoxy-7,8-dihydroquinolin-5(6H)-one (Compound 36-1)

Compound 35-4 (50 mg, 0.162 mmol) was dissolved in methanol (0.5 mL), and a 28% sodium methoxide solution in methanol (1 mL) was added to the solution. The mixture was subjected to a reaction at a temperature of 120° C. for 3 minutes, using a microwave reactor manufactured by Biotage. The mixture was concentrated under reduced pressure, and water was added to the residue. The mixture was filtered with Presep ((R); diatomaceous earth, granular type M, 4.5 g/25 mL). The filtrate was concentrated under reduced pressure. The residue was purified by silica gel column chromatography (heptane/ethyl acetate=90/10→50/50) to obtain compound 36-1 (39 mg, 79%).

$^1$H NMR (400 MHz, CDCl$_3$, δ): 8.20 (d, J=8.6 Hz, 1H), 7.25 (td, J=6.1, 3.6 Hz, 2H), 7.13 (td, J=6.1, 3.6 Hz, 2H), 6.79 (d, J=8.6 Hz, 1H), 5.42 (dd, J=4.5, 3.6 Hz, 1H), 3.90 (s, 3H), 3.08-3.03 (m, 1H), 2.66-2.61 (m, 1H), 2.56-2.49 (m, 1H), 2.44-2.36 (m, 1H);

ESIMS m/z: [M+H]$^+$ 304.

Step 2

8-(4-Chlorophenoxy)-2-methoxy-5,6,7,8-tetrahydroquinolin-5-amine (Compound 36-2)

Compound 36-2 was obtained as a crude product in the same manner as step 4 of example 1, using compound 36-1 (39 mg, 0.128 mmol).

ESIMS m/z: [M+H]$^+$ 305,

Step 3 cis-N-{8-(4-Chlorophenoxy)-2-methoxy-5,6,7,8-tetrahydroquinolin-5-yl}acrylamide (Compound 71)

trans-N-{8-(4-Chlorophenoxy)-2-methoxy-5,6,7,8-tetrahydroquinolin-5-yl}acrylamide (Compound 81)

Compound 71 (9.2 mg, 20% over two steps) and compound 81 (1.8 mg, 4% over two steps) were obtained in the same manner as step 7 of example 33, using compound 36-2 as a crude product.

Compound 71: 1H NMR (400 MHz, CDCl$_3$, δ): 7.55 (d, J=8.6 Hz, 1H), 7.24-7.23 (m, 2H), 7.14 (td, J=6.2, 3.8 Hz, 2H), 6.70 (d, J=8.6 Hz, 1H), 6.36 (dd, J=17.2, 1.4 Hz, 1H), 6.12 (dd, J=17.2, 10.4 Hz, 1H), 5.74 (d, J=9.5 Hz, 1H), 5.72 (dd, J=10.4, 1.4 Hz, 1H), 5.31-5.29 (m, 1H), 5.23-5.22 (m, 1H), 3.82 (s, 3H), 2.32-2.28 (m, 1H), 2.18-2.01 (m, 3H);

ESIMS m/z: [M+H]$^+$ 359.

Compound 81: $^1$H NMR (400 MHz, CDCl$_3$, δ): 7.55 (d, J=8.6 Hz, 1H), 7.24-7.23 (m, 2H), 7.12 (td, J=6.1, 3.9 Hz, 2H), 6.70 (d, J=8.6 Hz, 1H), 6.34 (dd, J=16.8, 1.4 Hz, 1H), 6.06 (dd, J=16.8, 10.4 Hz, 1H), 5.69 (dd, J=10.4, 1.4 Hz, 1H), 5.63 (d, J=8.2 Hz, 1H), 5.34-5.32 (m, 1H), 5.26-5.24 (m, 1H), 3.79 (s, 3H), 2.48-2.38 (m, 1H), 2.26-2.08 (m, 2H), 1.95-1.88 (m, 1H);

ESIMS m/z: [M+H]⁺ 359.

The following compounds were synthesized in accordance with the synthesis method of compound 71.

cis-N-{8-(4-Chlorophenoxy)-2-(dimethylamino)-5,6,7,8-tetrahydroquinolin-5-yl}acrylamide (Compound 72)

ESIMS m/z: [M+H]⁺ 372.

cis-N-{8-(4-Chlorophenoxy)-2-(3,3-difluoroazetidin-1-yl)-5,6,7,8-tetrahydroquinolin-5-yl}acrylamide (Compound 73)

ESIMS m/z: [M+H]⁺ 420.

cis-N-{8-(4-Chlorophenoxy)-2-morpholino-5,6,7,8-tetrahydroquinolin-5-yl}acrylamide (Compound 74)

ESIMS m/z: [M+H]⁺ 414.

cis-N-{2-(Dimethylamino)-8-[{6-(trifluoromethyl)pyridin-3-yl}oxy]-5,6,7,8-tetrahydroquinolin-5-yl}acrylamide (Compound 78)

ESIMS m/z: [M+H]⁺ 407.

Example 37

Step 1

2'-Chloro-8'{4-(trifluoromethyl)phenoxy}-7',8'-dihydro-6'H-spiro[[1,3]dioxolane-2,5'-quinoline] (Compound 37-1)

Compound 37-1 was obtained as a crude product in the same manner as step 4 of example 33, using compound 35-2 (250 mg, 1.03 mmol) and 4-(trifluoromethyl)phenol (335 mg, 2.07 mmol).

ESIMS m/z: [M+H]⁺ 386.

Step 2

2-Chloro-8-{4-(trifluoromethyl)phenoxy}-7,8-dihydroquinolin-5(6H)-one (Compound 37-2)

Compound 37-2 was obtained as a crude product in the same manner as step 5 of example 33, using compound 37-1 (339 mg) as a crude product.

ESIMS m/z: [M+H]⁺ 342.

Step 3

2-Chloro-8-{4-(trifluoromethyl)phenoxy}-5,6,7,8-tetrahydroquinolin-5-amine (Compound 37-3)

Compound 37-3 was obtained as a crude product in the same manner as step 2 of example 3, using compound 37-2 (70 mg) as a crude product.

ESIMS m/z: [M+H]⁺ 343.

Step 4 cis-N-[2-Chloro-8-{4-(trifluoromethyl)phenoxy}-5,6,7,8-tetrahydroquinolin-5-yl]acrylamide (Compound 76)

trans-N-[2-Chloro-8-{4-(trifluoromethyl)phenoxy}-5,6,7,8-tetrahydroquinolin-5-yl]acrylamide (Compound 82)

Compound 76 (33.7 mg, 52% in four stages) and compound 82 (21.6 mg, 33% in four stages) were obtained in the same manner as step 3 of example 17, using compound 37-3 as a crude product.

Compound 76: ¹H NMR (400 MHz, CDCl₃, δ): 7.70 (d, J=8.5 Hz, 1H), 7.57 (dt, J=9.3, 2.4 Hz, 2H), 7.31 (d, J=8.5 Hz, 1H), 7.17 (dt, J=9.3, 2.4 Hz, 2H), 6.41 (dd, J=17.1, 1.3 Hz, 1H), 6.16 (dd, J=17.1, 10.3 Hz, 1H), 5.82 (d, J=9.4 Hz, 1H), 5.77 (dd, J=10.3, 1.3 Hz, 1H), 5.41-5.38 (m, 2H), 2.43-2.41 (m, 1H), 2.20-2.00 (m, 3H);

ESIMS m/z: [M+H]⁺ 397.

Compound 82: ¹H NMR (400 MHz, CDCl₃, δ): 7.73 (d, J=8.5 Hz, 1H), 7.57 (d, J=8.5 Hz, 2H), 7.31 (d, J=8.5 Hz, 1H), 7.17 (d, J=8.5 Hz, 2H), 6.37 (dd, J=16.6, 1.3 Hz, 1H), 6.08 (dd, J=16.6, 10.5 Hz, 1H), 5.73 (dd, J=10.5, 1.3 Hz, 1H), 5.72 (d, J=9.0 Hz, 1H), 5.45-5.42 (m, 2H), 2.47-2.42 (m, 1H), 2.31-2.28 (m, 1H), 2.19-2.10 (m, 1H), 1.94-1.90 (m, 1H);

ESIMS m/z: [M+H]⁺ 397.

The following compound was synthesized in accordance with the synthesis method of compound 76.

cis-N-(2-Chloro-8-[{6-(trifluoromethyl)pyridin-3-yl}oxy]-5,6,7,8-tetrahydroquinolin-5-yl)acrylamide (Compound 77)

ESIMS m/z: [M+H]⁺ 398,

Example 38

Step 1

6-(4-Chlorophenoxy)pyridin-2-amine (Compound 38-1)

2-Amino-6-chloropyridine (100 mg, 0.778 mmol) was dissolved in DMF (4.00 mL), and 4-chlorophenol (150 ng, 1.17 mmol) and cesium carbonate (507 mg, 1.56 mmol) were added to the solution. The mixture was heated to 180° C. and stirred for one hour using a microwave reactor, Initiator, manufactured by Biotage. A saturated aqueous sodium bicarbonate solution was added to the mixture. The organic layer was extracted with ethyl acetate, washed with saturated saline, dried over anhydrous magnesium sulfate, and concentrated under reduced pressure. The residue was purified using a preparative HPLC [Waters Xbridge Prep C18 OBD column, 5 μm silica, diameter 19 mm, length 100 mm; acetonitrile/0.05% aqueous TFA solution (30/70→40/60)] to obtain compound 38-1 (92.0 mg, 54%).

¹H NMR (400 MHz, CDCl₃, δ): 7.41 (t, J=8.2 Hz, 1H), 7.34-7.29 (m, 2H), 7.08-7.02 (m, 2H), 6.20 (d, J=8.2 Hz, 1H), 6.13 (d, J=8.2 Hz, 1H), 4.35 (br, 2H);

ESIMS m/z: [M+H]⁺ 221,

Step 2

N-{6-(4-Chlorophenoxy)pyridin-2-yl}acrylamide (Compound 83)

Compound 38-1 (47.0 mg, 0.213 mmol) was dissolved in dichloromethane (2.00 mL), and triethylamine (0.0890 mL, 0.639 mmol) and acryloyl chloride (0.0270 mL, 0.320 mmol) were added to the solution under ice cooling. The mixture was stirred at room temperature for 1.5 hours. Water and ethyl acetate were added to the mixture. The mixture was filtered with Presep ((R); diatomaceous earth, granular type M, 4.5 g/25 mL), and the filtrate was concentrated under reduced pressure. The residue was purified by silica gel column chromatography (heptane/ethyl acetate=100/0→60/40) to obtain compound 83 (34.0 mg, 58%).

$^1$H NMR (400 MHz, CDCl$_3$, δ): 7.99 (d, J=7.7 Hz, 1H), 7.76-7.65 (m, 2H), 7.38-7.32 (m, 2H), 7.09-7.02 (m, 2H), 6.63 (d, J=7.7 Hz, 1H), 6.43 (dd, J=16.8, 1.1 Hz, 1H), 6.18 (dd, J=16.8, 10.2 Hz, 1H), 5.79 (dd, J=10.2, 1.1 Hz, 1H);

ESIMS m/z: [M+H]$^+$ 275.

The following compounds were synthesized in accordance with the synthesis method of compound 83.

N-{2-(4-Chlorophenoxy)pyridin-4-yl}acrylamide (Compound 85)

ESIMS m/z: [M+H]$^+$ 275.

N-{6-(4-Chlorophenoxy)-5-methylpyridin-2-yl}acrylamide (Compound 86)

ESIMS m/z: [M+H]$^+$ 289.

N-{6-(4-Chlorophenoxy)-4-methylpyridin-2-yl}acrylamide (Compound 87)

ESIMS m/z: [M+H]$^+$ 289.

N-{4-(4-Chlorophenoxy)-6-methylpyridin-2-yl}acrylamide (Compound 88)

ESIMS m/z: [M+H]$^+$ 289.

N-{4-(4-Chlorophenoxy)-5-methylpyridin-2-yl}acrylamide (Compound 89)

ESIMS m/z: [M+H]$^+$ 289.

N-{2-(4-Chlorophenoxy)-6-methylpyridin-4-yl}acrylamide (Compound 91)

ESIMS m/z: [M+H]$^+$ 289.

N-{5-(4-Chlorophenoxy)-6-methylpyridin-3-yl}acrylamide (Compound 92)

ESIMS m/z: [M+H]$^+$ 289.

N-{5-(4-Chlorophenoxy)-2-methylpyridin-3-yl}acrylamide (Compound 93)

ESIMS m/z: [M+H]$^+$ 289.

N-{5-(4-chlorophenoxy)pyridin-3-yl}acrylamide (Compound 94)

ESIMS m/z: [M+H]$^+$ 275.

Example 39

N-{4-(4-Chlorophenoxy)pyridin-2-yl}acrylamide (Compound 84)

Step 1

4-(4-Chlorophenoxy)pyridin-2-amine (Compound 39-1)

Compound 39-1 (38.0 mg, 44%) was obtained in the same manner as step 1 of example 38, using 2-amino-4-chloropyridine.

$^1$H NMR (400 MHz, CDCl$_3$, δ): 7.95 (d, J=5.9 Hz, 1H), 7.39-7.33 (m, 2H), 7.05-6.99 (m, 2H), 6.27 (dd, J=5.9, 2.3 Hz, 1H), 5.95 (d, J=2.3 Hz, 1H), 4.39 (br, 2H);

ESIMS m/z: [M+H]$^+$ 221.

Step 2

Compound 84 (18.0 mg, 38%) was obtained in the same manner as step 2 of example 38, using compound 39-1.

$^1$H NMR (400 MHz, CDCl$_3$, δ): 8.14 (d, J=5.9 Hz, 1H), 8.01 (br, 1H), 7.90 (d, J=2.3 Hz, 1H), 7.41-7.36 (m, 2H), 7.09-7.03 (m, 2H), 6.62 (dd, J=5.9, 2.3 Hz, 1H), 6.43 (dd, J=17.0, 1.1 Hz, 1H), 6.22 (dd, J=16.8, 10.4 Hz, 1H), 5.81 (dd, J=10.4, 1.1 Hz, 1H);

ESIMS m/z: [M+H]$^+$ 275.

Example 40

(E)-N-{4-(4-Chlorophenoxy)pyridin-2-yl}-2-butenamide (Compound 90)

Compound 90 (16.0 mg, 25%) was obtained in the same manner as step 2 of example 38, using compound 39-1 and (E)-2-butenoyl chloride.

$^1$H NMR (400 MHz, CDCl$_3$, δ): 8.12 (d, J=5.4 Hz, 1H), 7.88 (d, J=2.3 Hz, 1H), 7.82 (br, 1H), 7.40-7.36 (m, 2H), 7.08-6.95 (m, 3H), 6.60 (dd, J=5.4, 2.3 Hz, 1H), 5.91 (dd, J=15.0, 1.6 Hz, 1H), 1.92 (dd, J=7.0, 1.6 Hz, 3H);

ESIMS m/z: [M+H]$^+$ 289.

Example 41

Step 1

5-(3-(Trifluoromethyl)phenoxy)pyridin-3-amine (Compound 41-1)

In DMSO (2.00 mL), 3-iodobenzotrifluoride (0.0530 mL, 0.357 mmol) was dissolved, and copper(I) iodide (3.40 mg, 0.0180 mmol), picolinic acid (4.39 mg, 0.0360 mm ol), tripotassium phosphate (151 mg, 0.713 m mol), and 3-amino-5-hydroxypyridine (47.0 mg, 0.428 mm ol) were added to the solution. The mixture was stirred at 80° C. for 4 hours. A saturated aqueous sodium bicarbonate solution was added to the mixture. The organic layer was extracted with ethyl acetate, washed with saturated saline, dried over anhydrous magnesium sulfate, and concentrated under reduced pressure. The residue was purified using a preparative HPLC [Waters Xbridge Prep C18 OBD column, 5 μm silica, diameter 19 mm, length 100 mm; acetonitrile/0.05% aqueous TFA solution (30/70→40/60)] to obtain compound 41-1 (36.0 mg, 40%).

$^1$H NMR (400 MHz, CDCl$_3$, δ): 7.92 (s, 1H), 7.82 (s, 1H), 7.51-7.35 (m, 2H), 7.30-7.16 (m, 2H), 6.63 (s, 1H), 3.79 (br, 2H)

ESIMS m/z: [M+H]$^+$ 255.

Step 2

N-[5-{3-(Trifluoromethyl)phenoxy}pyridin-3-yl]acrylamide (Compound 95)

Compound 95 (26.0 mg, 60%) was obtained in the same manner as step 2 of example 38, using compound 41-1.

$^1$H NMR (400 MHz, CDCl$_3$, δ): 8.37 (s, 1H), 8.17 (s, 1H), 8.08 (s, 1H), 7.56-7.17 (m, 5H), 6.46 (d, J=16.8 Hz, 1H), 6.25 (dd, J=16.8, 10.0 Hz, 1H), 5.85 (d, J=10.0 Hz, 1H); ESIMS m/z: [M+H]$^+$ 309,

Example 42

Step 1

5-(4-(Trifluoromethyl)phenoxy)pyridin-3-amine (Compound 42-1)

Compound 42-1 (30.0 mg, 33%) was obtained in the same manner as step 1 of example 41, using 4-iodobenzotrifluoride.

$^1$H NMR (400 MHz, CDCl$_3$, δ): 7.93 (d, J=2.3 Hz, 1H), 7.84 (d, J=2.3 Hz, 1H), 7.60 (d, J=8.2 Hz, 2H), 7.08 (d, 1=8.2 Hz, 2H), 6.65 (t, J=2.3 Hz, 1H), 3.79 (br, 2H); ESIMS m/z: [M+H]$^+$ 255,

Step 2

N-[5-{4-(Trifluoromethyl)phenoxy}pyridin-3-yl]acrylamide (Compound 96)

Compound 96 (24.0 mg, 66%) was obtained in the same manner as step 2 of example 38, using compound 42-1.

$^1$H NMR (400 MHz, DMSO-d$_6$, δ): 10.55 (br, 1H), 8.64 (d, J=2.3 Hz, 1H), 8.21 (d, J=2.3 Hz, 1H), 7.94 (t, J=2.3 Hz, 1H), 7.80 (d, J=8.6 Hz, 2H), 7.28 (d, J=8.6 Hz, 2H), 6.41 (dd, J=16.8, 10.0 Hz, 1H), 6.28 (dd, J=16.8, 1.8 Hz, 1H), 5.82 (dd, J=10.0, 1.8 Hz, 1H); ESIMS m/z: [M+H]$^+$ 309.

Example 43

Step 1

5-(4-(Trifluoromethoxy)phenoxy)pyridin-3-amine (Compound 43-1)

Compound 43-1 (33.0 mg, 36%) was obtained in the same manner as step 1 of example 41, using 1-iodo-4-(trifluoromethoxy)benzene.

$^1$H-NMR (400 MHz, CDCl$_3$, δ): 7.88 (d, J=2.3 Hz, 1H), 7.80 (d, J=2.3 Hz, 1H), 7.24-7.17 (m, 2H), 7.06-7.00 (m, 2H), 6.59 (t, J=2.3 Hz, 1H), 3.75 (br, 2H); ESIMS m/z: [M+H]$^+$ 271.

Step 2

N-[5-{4-(Trifluoromethoxy)phenoxy}pyridin-3-yl]acrylamide (Compound 100)

Compound 100 (26.0 mg, 66%) was obtained in the same manner as step 2 of example 38, using compound 43-1.

$^1$H NMR (400 MHz, DMSO-d$_6$, δ): 10.50 (br, 1H), 8.61 (d, J=2.3 Hz, 1H), 8.15 (d, J=2.3 Hz, 1H), 7.84 (t, J=2.3 Hz, 1H), 7.45 (d, J=8.6 Hz, 2H), 7.24 (d, J=8.6 Hz, 2H), 6.40 (dd, J=16.8, 10.0 Hz, 1H), 6.27 (dd, J=16.8, 1.8 Hz, 1H), 5.81 (dd, J=10.0, 1.8 Hz, 1H); ESIMS m/z: [M+H]$^+$ 325.

Example 44

Step 1

5-(4-Ethoxyphenoxy)pyridin-3-amine (Compound 44-1)

Compound 44-1 (15.0 mg, 17%) was obtained in the same manner as step 1 of example 41, using 1-ethoxy-4-iodobenzene.

$^1$H NMR (400 MHz, CDCl$_3$, δ): 7.79 (d, J=2.3 Hz, 1H), 7.77 (d, J=2.3 Hz, 1H), 7.00-6.95 (m, 2H), 6.91-6.86 (m, 2H), 6.50 (t, J=2.3 Hz, 1H), 4.02 (q, J=7.0 Hz, 2H), 3.67 (br, 2H), 1.42 (t, J=7.0 Hz, 3H); ESIMS m/z: [M+H]$^+$ 231.

Step 2

N-{5-(4-Ethoxyphenoxy)pyridin-3-yl}acrylamide (Compound 102)

Compound 102 (9.90 mg, 54%) was obtained in the same manner as step 2 of example 38, using compound 44-1.

$^1$H NMR (400 MHz, DMSO-d$_6$, δ): 10.41 (br, 1H), 8.52 (d, J=2.3 Hz, 1H), 8.06 (d, J=2.3 Hz, 1H), 7.68 (t, J=2.3 Hz, 1H), 7.10-7.05 (m, 2H), 7.02-6.96 (m, 2H), 6.38 (dd, J=17.0, 10.0 Hz, 1H), 6.25 (dd, J=17.0, 1.8 Hz, 1H), 5.79 (dd, J=10.0, 1.8 Hz, 1H), 4.03 (q, J=7.0 Hz, 2H), 1.34 (t, J=7.0 Hz, 3H)

ESIMS m/z: [M+H]$^+$ 285.

Example 45

Step 1

5-((5-(Trifluoromethyl)pyridin-3-yl)oxy)pyridin-3-amine (Compound 45-1)

Compound 45-1 (31.0 mg, 34%) was obtained in the same manner as step 1 of example 41, using 3-iodo-5-(trifluoromethyl)pyridine.

$^1$H NMR (400 MHz, CDCl$_3$, δ): 8.66 (br, 1H), 8.59 (d, J=2.3 Hz, 1H), 7.98 (d, J=2.3 Hz, 1H), 7.84 (d, J=2.3 Hz, 1H), 7.50 (br, 1H), 6.66 (t, J=2.3 Hz, 1H), 3.86 (br, 2H); ESIMS m/z: [M+H]$^+$ 256.

Step 2

N-(5-[{5-(Trifluoromethyl)pyridin-3-yl}oxy]pyridin-3-yl)acrylamide (Compound 107)

Compound 107 (13.0 mg, 34%) was obtained in the same manner as step 2 of example 38, using compound 45-1.

$^1$H NMR (DMSO-d$_6$, δ): 10.56 (br, 1H), 8.84 (br, 1H), 8.79 (d, J=2.3 Hz, 1H), 8.65 (d, J=2.3 Hz, 1H), 8.23 (d, J=2.7 Hz, 1H), 8.05 (br, 1H), 7.94 (t, J=2.3 Hz, 1H), 6.42 (dd, J=17.2, 10.0 Hz, 1H), 6.28 (dd, J=17.2, 1.8 Hz, 1H), 5.82 (dd, J=10.0, 1.8 Hz, 1H); ESIMS m/z: [M+H]$^+$ 310.

Example 46

Step 1

5-((2-(Trifluoromethyl)pyridin-4-yl)oxy)pyridin-3-amine (Compound 46-1)

Compound 46-1 (53.0 mg, 43%) was obtained in the same manner as step 1 of example 41, using 4-iodo-2-(trifluoromethyl)pyridine.

¹H NMR (400 MHz, CDCl₃, δ): 8.59 (d, J=5.9 Hz, 1H), 8.05 (d, J=2.3 Hz, 1H), 7.87 (d, J=2.3 Hz, 1H), 7.28-7.24 (m, 1H), 7.01 (dd, J=5.9, 2.3 Hz, 1H), 6.72 (t, J=2.3 Hz, 1H), 3.91 (br, 2H);
ESIMS m/z: [M+H]⁺ 256.
Step 2

N-(5-[{2-(Trifluoromethyl)pyridin-4-yl}oxy]pyridin-3-yl)acrylamide (Compound 108)

Compound 108 (40.0 mg, 63%) was obtained in the same manner as step 2 of example 38, using compound 46-1.
¹H NMR (400 MHz, DMSO-d₆, δ): 10.64 (br, 1H), 8.72 (d, J=2.3 Hz, 1H), 8.68 (d, J=5.4 Hz, 1H), 8.30 (d, J=2.3 Hz, 1H), 8.11 (t, J=2.3 Hz, 1H), 7.59 (d, J=2.3 Hz, 1H), 7.29 (dd, J=5.4, 2.3 Hz, 1H), 6.44 (dd, J=17.0, 10.0 Hz, 1H), 6.30 (dd, J=17.0, 1.8 Hz, 1H), 5.84 (dd, J=10.0, 1.8 Hz, 1H);
ESIMS m/z: [M+H]⁺ 310.

Example 47

Step 1

5-[{5-(Trifluoromethyl)pyridin-2-yl}oxy]pyridin-3-amine (Compound 47-1)

Compound 47-1 (99.0 mg, 73%) was obtained in the same manner as step 1 of example 41, using 2-iodo-5-(trifluoromethyl)pyridine.
¹H NMR (400 MHz, CDCl₃, δ): 8.44 (br, 1H), 8.00 (br, 1H), 7.95-7.89 (m, 2H), 7.06 (d, J=8.6 Hz, 1H), 6.83 (t, J=2.3 Hz, 1H), 3.81 (br, 2H);
ESIMS m/z: [M+H]⁺ 256.
Step 2

N-(5-[{5-(Trifluoromethyl)pyridin-2-yl}oxy]pyridin-3-yl)acrylamide (Compound 109)

Compound 109 (82.0 mg, 68%) was obtained in the same manner as step 2 of example 38, using compound 47-1.
¹H NMR (400 MHz, DMSO-d₆, δ): 10.57 (br, 1H), 8.66 (d, J=2.3 Hz, 1H), 8.59 (br, 1H), 8.33-8.23 (m, 2H), 8.10 (t, 3=2.3 Hz, 1H), 7.38 (d, J=8.6 Hz, 1H), 6.44 (dd, J=16.8, 10.0 Hz, 1H), 6.29 (dd, J=16.8, 1.8 Hz, 1H), 5.83 (dd, J=10.0, 1.8 Hz, 1H);
ESIMS m/z: [M+H]⁺ 310.

Example 48

Step 1

5-((6-Isopropoxypyridin-3-yl)oxy)pyridin-3-amine (Compound 48-1)

Compound 48-1 (26.0 mg, 23%) was obtained in the same manner as step 1 of example 41, using 5-iodo-2-(isopropoxy)pyridine.
¹H NMR (400 MHz, CDCl₃, δ): 7.95 (d, J=3.2 Hz, 1H), 7.82 (d, J=2.3 Hz, 1H), 7.77 (d, J=2.3 Hz, 1H), 7.33-7.26 (m, 1H), 6.69 (d, J=8.6 Hz, 1H), 6.52 (t, J=2.3 Hz, 1H), 5.29-5.20 (m, 1H), 3.71 (br, 2H); 1.36 (d, J=6.8 Hz, 6H);
ESIMS m/z: [M+H]⁺ 246.
Step 2

N-[5-{(6-Isopropoxypyrdin-3-yl)oxy}pyridin-3-yl]acrylamide (Compound 110)

Compound 110 (17.0 mg, 54%) was obtained in the same manner as step 2 of example 38, using compound 48-1.
¹H-NMR (400 MHz, DMSO-d₆, δ): 10.45 (br, 1H), 8.56 (d, J=2.3 Hz, 1H), 8.11 (d, J=2.3 Hz, 1H), 8.07 (d, J=2.7 Hz, 1H), 7.71 (t, 3=2.3 Hz, 1H), 7.59 (dd, J=9.1, 2.7 Hz, 1H), 6.84 (d, J=9.1 Hz, 1H), 6.39 (dd, J=16.8, 10.0 Hz, 1H), 6.26 (dd, J=16.8, 1.8 Hz, 1H), 5.80 (dd, J=10.0, 1.8 Hz, 1H), 5.26-5.15 (m, 1H), 1.31 (d, J=5.9 Hz, 6H);
ESIMS m/z: [M+H]⁺ 300.

The following compounds were synthesized in accordance with the synthesis method of compound 95.

N-{5-(3-Methoxyphenoxy)pyridin-3-yl}acrylamide (Compound 97)

ESIMS m/z: [M+H]⁺ 271.

N-{5-(4-Methoxyphenoxy)pyridin-3-yl}acrylamide (Compound 98)

ESIMS m/z: [M+H]⁺ 271.

N-{5-(4-Cyanophenoxy)pyridin-3-yl}acrylamide (Compound 99)

ESIMS m/z: [M+H]⁺ 266.

N-{5-(3-Ethoxyphenoxy)pyridin-3-yl}acrylamide (Compound 101)

ESIMS m/z: [M+H]⁺ 285.

N-{5-(4-Isopropoxyphenoxy)pyridin-3-yl}acrylamide (Compound 103)

ESIMS m/z: [M+H]⁺ 299.

N-[5-{4-(Benzyloxy)phenoxy}pyridin-3-yl]acrylamide (Compound 104)

ESIMS m/z: [M+H]⁺ 347.

N-{5-(3,4-Dichlorophenoxy)pyridin-3-yl}acrylamide (Compound 105)

ESIMS m/z: [M+H]⁺ 309.

N-[5-{3-Fluoro-4-(trifluoromethyl)phenoxy}pyridin-3-yl]acrylamide (Compound 106)

ESIMS m/z: [M+H]⁺ 327.

Example 49

Step 1

8-Phenoxyquinolin-5-amine (Compound 49-1)

Compound 49-1 (17.9 mg, 10%) was obtained in the same manner as step 4 of example 4, using 5-aminoquinolin-8-ol.
¹H NMR (300 MHz, CDCl₃, δ): 8.94 (dd, J=4.0, 1.5 Hz, 1H), 8.22 (dd, 3=8.6, 1.6 Hz, 1H), 7.44-7.40 (m, 2H), 7.12 (d, J=8.1 Hz, 1H), 7.06-7.00 (m, 4H), 6.77 (d, J=8.4 Hz, 1H)
ESIMS m/z: [M+H]⁺ 237.
Step 2

N-(8-Phenoxyquinolin-5-yl)acrylamide (Compound 111)

Compound 111 (8.3 mg, 40%) was obtained in the same manner as step 5 of example 1, using compound 49-1.

$^1$H NMR (300 MHz, CDCl$_3$, δ): 9.02 (s, 1H), 8.23 (d, J=7.3 Hz, 1H), 7.70-7.62 (m, 1H), 7.54-7.46 (m, 2H), 7.39 (t, J=7.7 Hz, 2H), 7.21-7.13 (m, 3H), 7.05 (d, J=8.4 Hz, 1H), 6.57-6.43 (m, 2H), 5.87 (d, J=9.9 Hz, 1H)

ESIMS m/z: [M+H]$^+$ 291.

Example 50

Step 1

8-Chloro-2-methyl-5-nitroquinoline (Compound 50-1)

8-Chloro-2-methylquinoline (0.50 g, 2.28 mmol) was added to a liquid mixture of concentrated sulfuric acid (2.5 mL), concentrated nitric acid (5.0 mL), and fuming nitric acid (1.0 mL) under ice cooling. The mixture was slowly stirred at 65° C. for 16 hours. The mixture was cooled to room temperature, and water was added to the mixture. The organic layer was extracted with tert-butyl methyl ether, washed with saturated saline, dried over anhydrous sodium sulfate, and concentrated under reduced pressure. The residue was purified by silica gel column chromatography (hexane/ethyl acetate=100/0→80/20) to obtain compound 50-1 (0.35 g, 56%).

$^1$H NMR (400 MHz, DMSO-d$_6$, δ): 8.77 (d, J=8.8 Hz, 1H), 8.34 (d, J=8.4 Hz, 1H), 8.10 (d, J=8.8 Hz, 1H), 7.78 (d, J=9.2 Hz, 1H), 2.76 (s, 3H).

Step 2

2-Methyl-5-nitro-8-phenoxyquinoline (Compound 50-2)

Compound 50-1 (0.35 g, 1.57 mmol) was dissolved in DMF (5.0 mL), and phenol (0.11 g, 1.89 mmol) and cesium carbonate (1.20 g, 3.94 mmol) were added to the solution. The mixture was stirred at 90° C. for 3 hours. The mixture was cooled to room temperature, and water was added to the mixture. The organic layer was extracted with tert-butyl methyl ether, washed with saturated saline, dried over anhydrous sodium sulfate, and concentrated under reduced pressure. The residue was purified by silica gel column chromatography (hexane/ethyl acetate=80/20→70/30) to obtain compound 50-2 (0.29 g, 56%).

$^1$H NMR (400 MHz, DMSO-d6, δ): 8.91 (d, J=9.2 Hz, 1H), 8.38 (d, J=8.8 Hz, 1H), 7.78 (d, J=9.2 Hz, 1H), 7.52 (t, J=8.0 Hz, 2H), 7.32 (t, J=7.2 Hz, 1H), 7.25 (d, J=7.6 Hz, 2H), 6.99 (d, J=8.8 Hz, 1H), 2.72 (s, 3H).

Step 3

2-Methyl-8-phenoxyquinolin-5-amine (Compound 50-3)

Compound 50-2 (0.28 g, 1.00 mmol) was suspended in ethanol (5.0 mL) and water (2.5 mL), and iron (0.27 g, 5.00 mmol) and ammonium chloride (0.26 g, 5.00 mmol) were added to the suspension. The mixture was refluxed for 2 hours. The mixture was cooled to room temperature, and dichloromethane (30 mL) was added to the mixture. The mixture was filtered with Celite®. The organic layer was washed with water (10 mL), dried over anhydrous sodium sulfate, and concentrated under reduced pressure to obtain compound 50-3 (0.16 g, 66%).

$^1$H NMR (400 MHz, DMSO-d6, δ): 8.43 (d, J=8.8 Hz, 1H), 7.29-7.20 (m, 3H), 7.12 (d, J=8.4 Hz, 1H), 6.92 (t, J=7.6 Hz, 1H), 6.77 (d, J=8.0 Hz, 2H), 6.62 (d, J=8.0 Hz, 1H), 5.81 (s, 2H), 2.50 (s, 3H).

Step 4

N-(2-Methyl-8-phenoxyquinolin-5-yl)acrylamide (Compound 112)

Compound 112 (51.0 mg, 28%) was obtained in the same manner as step 5 of example 1, using compound 50-3 (0.15 g, 0.60 mmol).

$^1$H NMR (400 MHz, DMSO-d6, δ): 10.16 (s, 1H), 8.36 (d, J=8.7 Hz, 1H), 7.71 (d, J=8.1 Hz, 1H), 7.51 (d, J=8.7 Hz, 1H), 7.38-7.33 (m, 2H), 7.23 (d, J=8.4 Hz, 1H), 7.09 (t, J=7.2 Hz, 1H), 6.97 (d, J=7.8 Hz, 2H), 6.66 (dd, J=16.8, 10.2 Hz, 1H), 6.31 (dd, J=17.1, 1.8 Hz, 1H), 5.82 (dd, J=10.2, 1.5 Hz, 1H), 2.60 (s, 3H)

ESIMS m/z: [M+H]$^+$ 305.

The following compounds were synthesized in accordance with the synthesis method of compound 112.

N-{8-(3-Chlorophenoxy)-2-methylquinolin-5-yl}acrylamide (Compound 115)

ESIMS m/z: [M+H]$^+$ 339.

N-{8-(4-Chlorophenoxy)-2-methylquinolin-5-yl}acrylamide (Compound 117)

ESIMS m/z: [M+H]$^+$ 339.

Example 51

Step 1

8-(2-Chlorophenoxy)-5-nitroquinoline (Compound 51-1)

Compound 51-1 (30.0 mg, 40%) was obtained in the same manner as step 2 of example 50, using 8-fluoro-5-nitroquinoline.

$^1$H NMR (400 MHz, CDCl$_3$, δ): 9.24 (dd, J=9.2, 1.6 Hz, 1H), 9.14 (dd, J=4.0, 1.2 Hz, 1H), 8.37 (d, J=8.8 Hz, 1H), 7.76 (dd, J=8.8, 4.0 Hz, 1H), 7.58-7.55 (m, 1H), 7.40-7.38 (m, 1H), 7.32-7.26 (m, 2H), 6.74 (d, J=8.8 Hz, 1H).

Step 2

8-(2-Chlorophenoxy)quinolin-5-amine (Compound 51-2)

Compound 51-2 (20.0 mg, 60%) was obtained in the same manner as step 3 of example 50, using compound 51-1.

$^1$H NMR (400 MHz, CDCl$_3$, δ): 8.95 (dd, J=4.4, 1.6 Hz, 1H), 8.21 (dd, J=8.4, 1.2 Hz, 1H), 7.47-7.41 (m, 2H), 7.12-7.10 (m, 1H), 7.04-7.00 (m, 2H), 6.84-6.82 (m, 1H), 6.73 (d, J=8.4 Hz, 1H), 4.11 (bs, 2H).

Step 3

N-{8-(2-Chlorophenoxy)quinolin-5-yl}acrylamide (Compound 113)

Compound 113 (150 mg, 70%) was obtained in the same manner as step 5 of example 1, using compound 51-2.

$^1$H-NMR (400 MHz, DMSO-d$_6$, δ): 10.22 (s, 1H), 8.90-8.89 (m, 1H), 8.51-8.49 (m, 1H), 7.82 (d, J=8.0 Hz, 1H), 7.66-7.58 (m, 2H), 7.29-7.21 (m, 2H), 7.15-7.11 (m, 1H), 6.77-6.75 (m, 1H), 6.67 (dd, J=16.8, 10.0 Hz, 1H), 6.33 (dd, J=16.8, 1.6 Hz, 1H), 5.85-5.82 (m, 1H)

ESIMS m/z: [M+H]$^+$ 325.

The following compounds were synthesized in accordance with the synthesis method of compound 113.

N-{8-(3-Chlorophenoxy)quinolin-5-yl}acrylamide (Compound 114)

ESIMS m/z: [M+H]+ 325.

N-{8-(4-Chlorophenoxy)quinolin-5-yl}acrylamide (Compound 116)

ESIMS m/z: [M+H]+ 325.

N-{8-(3,4-Dichlorophenoxy)quinolin-5-yl}acrylamide (Compound 118)

ESIMS m/z: [M+H]+ 359.

N-[8-{(4,4-Difluorocyclohexyl)oxy}quinolin-5-yl]acrylamide (Compound 120)

ESIMS m/z: [M+H]+ 333.

N-[8-{(Tetrahydro-2H-pyran-4-yl)oxy}quinolin-5-yl]acrylamide (Compound 121)

ESIMS m/z: [M+H]+ 299.

N-[8-{(Tetrahydro-2H-pyran-3-yl)oxy}quinolin-5-yl]acrylamide (Compound 122)

ESIMS m/z: [M+H]+ 299,

N-[8-{(4-Ethynylbenzyl)oxy}quinolin-5-yl]acrylamide (Compound 124)

ESIMS m/z: [M+H]+ 329.

cis-N-(8-[{4-(Trifluoromethyl)cyclohexyl}methoxy]quinolin-5-yl)acrylamide (Compound 127)

ESIMS m/z: [M+H]+ 379, trans-N-(8-[{4-(Trifluoromethyl)cyclohexyl}methoxy]quinolin-5-yl)acrylamide (Compound 128)

ESIMS m/z: [M+H]+ 379.

N-[8-{(Tetrahydro-2H-pyran-4-yl)methoxy}quinolin-5-yl]acrylamide (Compound 129)

ESIMS m/z: [M+H]+ 313.

N-[8-{(Tetrahydro-2H-pyran-3-yl)methoxy}quinolin-5-yl]acrylamide (Compound 130)

ESIMS m/z: [M+H]+ 313.

N-[8-{(Tetrahydro-2H-pyran-2-yl)methoxy}quinolin-5-yl]acrylamide (Compound 131)

ESIMS n/z: [M+H]+ 313.

N-[8-{(2,2-Dimethyltetrahydro-2H-pyran-4-yl)methoxy}quinolin-5-yl]acrylamide (Compound 132)

ESIMS m/z: [M+H]+ 341.

Example 52

Step 1

8-(Cyclohexyloxy)-5-nitroquinoline (Compound 52-1)

5-Nitroquinolin-8-ol (0.25 g, 1.31 mmol) was dissolved in DMF (5.0 mL), and cyclohexyl bromide (0.42 g, 2.63 mmol) and cesium carbonate (1.20 g, 3.94 mmol) were added to the liquid mixture. The liquid mixture was stirred at 90° C. for 16 hours. The mixture was cooled to room temperature, and water was added to the mixture. The organic layer was extracted with methyl tert-butyl ether, dried over anhydrous sodium sulfate, and concentrated under reduced pressure. The residue was purified by silica gel column chromatography (hexane/ethyl acetate=100/0→80/20) to obtain compound 52-1 (0.24 g, 67%).
$^1$H-NMR (300 MHz, DMSO-$d_6$, δ): 9.05-9.00 (m, 2H), 8.52 (d, J=9.0 Hz, 1H), 7.85-7.81 (m, 1H), 7.42 (d, J=9.0 Hz, 1H), 4.84-4.78 (m, 1H), 2.06-1.37 (m, 10H).

Step 2

8-(Cyclohexyloxy)quinolin-5-amine (Compound 52-2)

Compound 52-2 (0.17 g, 83%) was obtained in the same manner as step 3 of example 50, using compound 52-1.
$^1$H-NMR (300 MHz, DMSO-$d_6$, δ): 8.78 (dd, J=3.9, 1.5 Hz, 1H), 8.44 (dd, J=8.4, 1.2 Hz, 1H), 7.37 (dd, J=8.7, 4.2 Hz, 1H), 7.02 (d, J=8.4 Hz, 1H), 6.62 (d, J=8.1 Hz, 1H), 5.47 (s, 2H), 4.35-4.29 (m, 1H), 1.98-1.90 (m, 2H), 1.78-1.75 (m, 2H), 1.52-1.46 (m, 3H), 1.33-1.23 (m, 3H).

Step 3

N-{8-(Cyclohexyloxy)quinolin-5-yl}acrylamide (Compound 119)

Compound 119 (89 mg, 46%) was obtained in the same manner as step 5 of example 1, using compound 52-2.
$^1$H-NMR (300 MHz, DMSO-$d_6$, δ): 10.04 (s, 1H), 8.88 (dd, J=3.9, 1.5 Hz, 1H), 8.30 (dd, J=8.7, 1.8 Hz, 1H), 7.63-7.55 (m, 2H), 7.24 (d, J=8.7 Hz, 1H), 6.62 (dd, J=17.1, 10.2 Hz, 1H), 6.28 (dd, J=17.1, 1.8 Hz, 1H), 5.80 (dd, J=10.2, 1.8 Hz, 1H), 4.62-4.56 (m, 1H), 2.05-2.01 (m, 2H), 1.81-1.77 (m, 2H), 1.60-1.23 (m, 6H)
ESIMS m/z: [M+H]+ 297.

The following compounds were synthesized in accordance with the synthesis method of compound 119.

N-{8-(Benzyloxy)quinolin-5-yl}acrylamide (Compound 123)

ESIMS m/z: [M+H]+ 305,

N-{8-(Cyclohexylmethoxy)quinolin-5-yl}acrylamide (Compound 125)

ESIMS m/z: [M+H]+ 311.

Example 53

Step 1

8-{(4,4-Difluorocyclohexyl)methoxy}-5-nitroquinoline (Compound 53-1)

Compound 53-1 (0.25 g, 38%) was obtained in the same manner as step 2 of example 50, using 8-fluoro-5-nitroquinoline.

¹H-NMR (400 MHz, DMSO-d₆, δ): 9.04-9.02 (m, 2H), 8.54 (d, J=9.2 Hz, 1H), 7.85-7.82 (m, 1H), 7.36 (d, J=8.8 Hz, 1H), 4.22 (d, J=6.8 Hz, 2H), 2.10-1.86 (m, 7H), 1.45-1.41 (m, 2H).
Step 2

8-{(4,4-Difluorocyclohexyl)methoxy}quinolin-5-amine (Compound 53-2)

Compound 53-2 (0.17 g, 78%) was obtained in the same manner as step 3 of example 50, using compound 53-1.
¹H-NMR (400 MHz, DMSO-d₆, δ): 8.79-8.78 (m, 1H), 8.45 (dd, J=8.4, 1.6 Hz, 1H), 7.41-7.38 (m, 1H), 6.99 (d, J=8.4 Hz, 1H), 6.63 (d, J=8.4 Hz, 1H), 5.40 (s, 2H), 3.92 (d, J=6.0 Hz, 2H), 2.07-1.78 (m, 7H), 1.40-1.31 (m, 2H).
Step 3

N-[8-{(4,4-Difluorocyclohexyl)methoxy}quinolin-5-yl]acrylamide (Compound 126)

Compound 126 (78 mg, 38%) was obtained in the same manner as step 5 of example 1, using compound 53-2.
¹H-NMR (400 MHz, DMSO-d₆, δ): 8.89 (dd, J=4.0, 1.2 Hz, 1H), 8.31 (d, J=7.6 Hz, 1H), 7.63 (d, J=8.4 Hz, 1H), 7.60-7.57 (m, 1H), 7.20 (d, J=8.4 Hz, 1H), 6.61 (dd, J=17.2, 10.4 Hz, 1H), 6.28 (dd, J=17.2, 2.0 Hz, 1H), 5.79 (d, J=10.8 Hz, 1H), 4.06 (d, J=6.4 Hz, 2H), 2.07-1.81 (m, 7H), 1.44-1.36 (m, 2H); ESIMS m/z: [M+H]⁺ 347.

Example 54

Step 1

8-Fluoroquinoline-5-carbonitrile (Compound 54-1)

5-Bromo-8-fluoroquinoline (0.50 g, 2.21 mmol) was dissolved DMF (11 mL), and tetrakis(triphenylphosphine)palladium(0) (0.26 g, 0.22 mmol) and zinc cyanide (0.39 g, 3.32 mmol) were added to the solution. The mixture was subjected to a reaction at a temperature of 15° C. for 30 minutes using a microwave reactor, Initiator, manufactured by Biotage. The mixture was cooled to room temperature, and a saturated aqueous sodium bicarbonate solution was added to the mixture. The mixture was filtered with Celite®. The organic layer was extracted with ethyl acetate, washed with saturated saline, dried over anhydrous magnesium sulfate, and concentrated under reduced pressure. The residue was purified by silica gel column chromatography (heptane/ethyl acetate=90/10→60/40) to obtain compound 54-1 (0.36 g, 94%).
¹H NMR (400 MHz, CDCl₃, δ): 9.12 (dd, J=4.5, 1.5 Hz, 1H), 8.58 (dt, J=8.5, 1.5 Hz, 1H), 7.99 (dd, J=8.3, 4.5 Hz, 1H), 7.72 (dd, J=8.5, 4.0 Hz, 1H), 7.50 (dd, J=9.6, 8.3 Hz, 1H)
ESIMS m/z: [M+H]⁺ 173.
Step 2

8-(3-Chlorophenoxy)quinoline-5-carbonitrile (Compound 54-2)

Compound 54-2 (73.9 mg, 91%) was obtained in the same manner as step 2 of example 50, using compound 54-1 (50.0 mg, 0.29 mmol).
¹H NMR (400 MHz, CDCl₃, δ): 9.12 (dd, J=4.0, 1.8 Hz, 1H), 8.59 (dd, J=8.5, 1.8 Hz, 1H), 7.88 (d, J=8.5 Hz, 1H), 7.72 (dd, J=8.5, 4.0 Hz, 1H), 7.40 (t, J=8.1 Hz, 1H), 7.28 (dd, J=1.9, 1.0 Hz, 1H), 7.22 (q, J=1.9 Hz, 1H), 7.11 (dq, J=8.1, 1.0 Hz, 1H), 7.02 (d, J=8.1 Hz, 1H)
ESIMS m/z: [M+H]⁺ 281.
Step 3

{8-(3-Chlorophenoxy)quinolin-5-yl}methanamine (Compound 54-3)

Lithium aluminum hydride (35.2 mg, 0.93 mmol) was suspended in THF (4.0 mL), and compound 54-2 (86.8 mg, 0.31 mmol) dissolved in THF (1.0 mL) was added to the suspension under ice cooling. The mixture was stirred at 60° C. for 2 hours. The mixture was cooled to 0° C., and water (0.04 mL), a 4 mol/L aqueous sodium hydroxide solution (0.04 mL), and water (0.12 mL) were sequentially added to the mixture. The mixture was stirred at room temperature for 30 minutes. The mixture was filtered with Celite®. The organic layer was extracted with ethyl acetate, washed with saturated saline, dried over anhydrous sodium sulfate, and concentrated under reduced pressure. The residue was purified by aminosilica gel column chromatography (chloroform/methanol=100/0→95/5) to obtain compound 54-3 as a crude product, which was used as it is in the next reaction.
Step 4

N-[{8-(3-chlorophenoxy)quinolin-5-yl}methyl]acrylamide (Compound 133)

Compound 133 (3.0 mg, 3% over two steps) was obtained in the same manner as step 3 of example 17, using compound 54-3.
¹H NMR (400 MHz, CDCl₃, δ): 8.99 (dd, J=4.0, 1.3 Hz, 1H), 8.47 (dd, 3=8.5, 1.8 Hz, 1H), 7.54 (dd, J=8.5, 4.5 Hz, 1H), 7.44 (d, J=8.1 Hz, 1H), 7.30 (d, J=8.1 Hz, 1H), 7.13-7.10 (m, 2H), 7.06 (t, 3=2.0 Hz, 1H), 7.03-7.00 (m, 1H), 6.37 (dd, J=16.9, 1.3 Hz, 1H), 6.09 (dd, J=17.1, 10.3 Hz, 1H), 5.81 (br, 1H), 5.70 (dd, J=10.3, 1.3 Hz, 1H), 4.96 (d, J=5.8 Hz, 2H)
ESIMS m/z: [M+H]⁺ 339,

Example 55

Step 1

8-(4-Chlorophenoxy)quinoline-5-carbonitrile (Compound 55-1)

Compound 55-1 (0.64 g, 98%) was obtained in the same manner as step 2 of example 50, using compound 54-1 (0.40 g, 2.32 mmol) and 4-chlorophenol.
¹H NMR (400 MHz, CDCl₃, δ): 9.12 (dd, J=4.5, 1.8 Hz, 1H), 8.58 (dd, J=8.5, 1.8 Hz, 1H), 7.85 (d, J=8.1 Hz, 1H), 7.72 (dd, J=8.5, 4.5 Hz, 1H), 7.44 (dq, J=12.6, 2.8 Hz, 2H), 7.16 (dq, J=12.6, 2.8 Hz, 2H), 6.96 (d, J=8.5 Hz, 1H)
ESIMS m/z: [M+H]⁺ 281.
Step 2

{8-(4-Chlorophenoxy)quinolin-5-yl}methanamine (Compound 55-2)

Compound 55-2 was obtained as a crude product in the same manner as step 3 of example 54, using compound 55-1 (20.0 mg, 0.071 mmol), and used as it is in the next reaction.

Step 3

N-[{8-(4-Chlorophenoxy)quinolin-5-yl}methyl] acrylamide (Compound 134)

Compound 134 (2.2 mg, 9% over two steps) was obtained in the same manner as step 3 of example 17, using compound 55-2.

$^1$H NMR (400 MHz, CDCl$_3$, δ): 9.00 (dd, J=4.0, 1.3 Hz, 1H), 8.46 (dd, J=8.8, 1.6 Hz, 1H), 7.54 (dd, J=8.5, 4.0 Hz, 1H), 7.40 (d, J=8.1 Hz, 1H), 7.34-7.33 (m, 2H), 7.06-7.02 (m, 3H), 6.36 (dd, J=16.9, 1.0 Hz, 1H), 6.08 (dd, J=16.9, 10.3 Hz, 1H), 5.79 (br, 1H), 5.70 (dd, J=10.3, 1.0 Hz, 1H), 4.94 (d, J=5.8 Hz, 2H)

ESIMS m/z: [M+H]$^+$ 339,

Example 56

(E)-N-[{8-(4-Chlorophenoxy)quinolin-5-yl}methyl]-4,4,4-trifluoro-2-buten amide (Compound 135)

Compound 135 (60.0 mg, 60%) was obtained in the same manner as step 3 of example 17, using compound 55-2 (70.0 mg, 0.25 mmol) and commercially available (E)-4,4,4-trifluoro-2-butenoyl chloride (46.8 mg, 0.30 mmol).

$^1$H NMR (400 MHz, CDCl$_3$, δ): 8.96 (dd, J=4.0, 1.8 Hz, 1H), 8.39 (dd, J=8.5, 1.8 Hz, 1H), 7.52 (dd, J=8.5, 4.0 Hz, 1H), 7.40 (d, J=8.1 Hz, 1H), 7.33 (dd, J=7.0, 2.0 Hz, 2H), 7.04-7.00 (m, 3H), 6.88-6.79 (m, 1H), 6.46 (dd, J=15.3, 1.8 Hz, 1H), 6.15 (br, 1H), 4.95 (d, J=5.4 Hz, 2H)

ESIMS m/z: [M+H]$^+$ 407.

Example 57

Step 1

8-(4-Bromophenoxy)quinoline-5-carbonitrile (Compound 57-1)

Compound 57-1 (0.12 g, 94%) was obtained in the same manner as step 2 of example 50, using compound 54-1 (70.0 mg, 0.41 mmol) and 4-bromophenol (84.0 mg, 0.49 mmol).

$^1$H NMR (400 MHz, CDCl$_3$, δ): 9.12 (dd, J=4.3, 1.6 Hz, 1H), 8.58 (dd, J=8.5, 1.3 Hz, 1H), 7.85 (d, J=8.1 Hz, 1H), 7.72 (dd, J=8.3, 4.3 Hz, 1H), 7.59-7.57 (m, 2H), 7.12-7.08 (m, 2H), 6.97 (d, J=8.1 Hz, 1H)

ESIMS m/z: [M+H]$^+$ 324.

Step 2

{8-(4-Bromophenoxy)quinolin-5-yl}methanamine (Compound 57-2)

Compound 57-1 (125.0 mg, 0.38 mmol) was dissolved in a 2 mol/L ammonia solution in methanol (12 mL), and the solution was subjected to a reaction using Raney Nickel CatCart® (manufactured by ThalesNano Technologies, Inc., 30 mm) in the full H$_2$ mode of H-Cube® at 25° C. The solvent was concentrated under reduced pressure to obtain compound 57-2 as a crude product.

Step 3

N-[{8-(4-Bromophenoxy)quinolin-5-yl}methyl] acrylamide (Compound 57-3)

Compound 57-3 (0.10 g, 70% over two steps) was obtained in the same manner as step 3 of example 17, using compound 57-2.

$^1$H NMR (400 MHz, CDCl$_3$, δ): 8.99 (dd, J=4.0, 1.8 Hz, 1H), 8.46 (dd, J=8.5, 1.8 Hz, 1H), 7.54 (dd, J=8.5, 4.0 Hz, 1H), 7.48-7.47 (m, 2H), 7.41 (d, J=8.1 Hz, 1H), 7.04-6.95 (m, 3H), 6.36 (dd, J=17.0, 1.3 Hz, 1H), 6.07 (dd, J=17.0, 10.3 Hz, 1H), 5.75 (br, 1H), 5.70 (dd, J=10.3, 1.3 Hz, 1H), 4.95 (d, J=5.8 Hz, 2H)

ESIMS m/z: [M+H]$^+$ 383.

Step 4

N-[{8-(4-Cyclopropylphenoxy)quinolin-5-yl}methyl]acrylamide (Compound 136)

Compound 57-3 (50.0 mg, 0.13 mmol) was dissolved in 1,4-dioxane (1.0 mL), and added to the solution were bis(triphenylphosphine)palladium(II) chloride dichloromethane adduct (10.7 mg, 0.013 mmol), cyclopropylboronic acid (33.6 mg, 0.391 mmol), cesium carbonate (0.26 g, 0.783 mmol), and water (0.1 mL). The mixture was fluxed for 1.5 hours. The mixture was cooled to room temperature, and saturated saline was added to the mixture. The mixture was filtered with Presep ((R); diatomaceous earth, granular type M, 4.5 g/25 mL), and concentrated under reduced pressure. The residue was purified by silica gel column chromatography (heptane/ethyl acetate=90/10→50/50) to obtain compound 136 (12.8 mg, 28%).

$^1$H NMR (400 MHz, CDCl$_3$, δ): 9.02 (dd, J=4.1, 1.4 Hz, 1H), 8.44 (dd, J=8.6, 1.4 Hz, 1H), 7.53 (dd, J=8.6, 4.1 Hz, 1H), 7.35 (d, J=7.7 Hz, 1H), 7.11-7.04 (m, 4H), 6.90 (d, J=8.2 Hz, 1H), 6.35 (dd, J=17.2, 1.4 Hz, 1H), 6.06 (dd, J=17.2, 10.2 Hz, 1H), 5.73 (br, 1H), 5.69 (dd, J=10.2, 1.4 Hz, 1H), 4.92 (d, J=5.9 Hz, 2H), 1.92 (tt, J=8.4, 3.9 Hz, 1H), 0.98-0.96 (m, 2H), 0.70-0.69 (m, 2H)

ESIMS m/z: [M+H]$^+$ 345.

Example 58

Step 1

8-{3-(Trifluoromethyl)phenoxy}quinoline-5-carbonitrile (Compound 58-1)

Compound 58-1 (86.4 mg, 95%) was obtained in the same manner as step 2 of example 50, using compound 54-1 (50.0 mg, 0.29 nmol) and 3-(trifluoromethyl)phenol (56.0 mg, 0.35 mmol).

$^1$H NMR (400 MHz, CDCl$_3$, δ): 9.12 (dd, J=4.0, 1.5 Hz, 1H), 8.60 (dd, J=8.5, 1.5 Hz, 1H), 7.89 (d, J=8.5 Hz, 1H), 7.73 (dd, J=8.5, 4.0 Hz, 1H), 7.61-7.53 (m, 2H), 7.47 (s, 1H), 7.39 (dt, J=8.2, 1.7 Hz, 1H), 7.02 (d, J=8.1 Hz, 1H)

ESIMS m/z: [M+H]$^+$ 315.

Step 2

[8-{3-(Trifluoromethyl)phenoxy}quinolin-5-yl] methanamine (Compound 58-2)

Compound 58-2 was obtained as a crude product in the same manner as step 2 of example 57, using compound 58-1 (86.4 mg, 0.28 mmol), ESIMS m/z: [M+H]$^+$ 319.

Step 3

N-([8-{3-(Trifluoromethyl)phenoxy}quinolin-5-yl] methyl)acrylamide (Compound 137)

Compound 137 (65.3 mg, 64% over two steps) was obtained in the same manner as step 3 of example 17, using compound 58-2.

¹H NMR (400 MHz, CDCl₃, δ): 8.98 (dd, J=4.4, 1.6 Hz, 1H), 8.48 (dd, J=8.8, 1.6 Hz, 1H), 7.55 (dd, J=8.8, 4.4 Hz, 1H), 7.46-7.44 (m, 2H), 7.40 (d, J=8.1 Hz, 1H), 7.34 (br, 1H), 7.26-7.26 (m, 1H), 7.12 (d, J=7.6 Hz, 1H), 6.38 (dd, J=16.9, 1.3 Hz, 1H), 6.09 (dd, J=16.9, 10.3 Hz, 1H), 5.82 (br, 1H), 5.71 (dd, J=10.3, 1.3 Hz, 1H), 4.97 (d, J=5.8 Hz, 2H)
ESIMS m/z: [M+H]⁺ 373.

The following compounds were synthesized in accordance with the synthesis method of compound 137.

N-[{8-(3,4-Dichlorophenoxy)quinolin-5-yl}methyl]acrylamide (Compound 140)

ESIMS m/z: [M+H]⁺ 373.

N-[{8-(3,5-Dichlorophenoxy)quinolin-5-yl}methyl]acrylamide (Compound 141)

ESIMS m/z: [M+H]⁺ 373.

Example 59

Step 1

8-{4-(Trifluoromethyl)phenoxy}quinoline-5-carbonitrile (Compound 59-1)

Compound 59-1 (91.1 mg, 100%) was obtained in the same manner as step 2 of example 50, using compound 54-1 (50.0 mg, 0.29 mmol) and 4-(trifluoromethyl)phenol (56.0 mg, 0.35 mmol).
ESIMS m/z: [M+H]⁺ 315.

Step 2

[8-{4-(Trifluoromethyl)phenoxy}quinolin-5-yl]methanamine (Compound 59-2)

Compound 59-2 was obtained as a crude product in the same manner as step 2 of example 57, using compound 59-1 (91.1 mg, 0.29 mmol),
ESIMS m/z: [M+H]⁺ 319.

Step 3

N-([8-{4-(Trifluoromethyl)phenoxy}quinolin-5-yl]methyl)acrylamide (Compound 138)

Compound 138 (22.8 mg, 21% over two steps) was obtained in the same manner as step 3 of example 17, using compound 59-2.
¹H NMR (400 MHz, CDCl₃, δ): 8.97 (dd, J=4.0, 1.5 Hz, 1H), 8.49 (dd, J=8.5, 1.5 Hz, 1H), 7.59 (d, J=8.5 Hz, 2H), 7.54 (dd, J=8.8, 4.3 Hz, 1H), 7.47 (d, J=8.1 Hz, 1H), 7.19 (d, J=7.6 Hz, 1H), 7.12 (d, J=8.5 Hz, 2H), 6.38 (dd, J=17.1, 1.3 Hz, 1H), 6.09 (dd, J=17.1, 10.3 Hz, 1H), 5.79 (br, 1H), 5.71 (dd, J=10.3, 1.3 Hz, 1H), 4.98 (d, J=5.4 Hz, 2H)
ESIMS m/z: [M+H]⁺ 373.

Example 60

Step 1

5-Cyano-8-{4-(trifluoromethyl)phenoxy}quinoline 1-oxide (Compound 60-1)

Compound 59-1 (0.15 g, 0.48 mmol) was dissolved in dichloromethane (5.0 mL), and m-chloroperoxybenzoic acid (0.13 g, 0.57 mmol) was added to the solution. After the mixture was stirred at room temperature overnight, m-chloroperoxybenzoic acid (0.13 g, 0.57 mmol) was further added to the mixture. The mixture was stirred at room temperature overnight. The mixture was basified by the addition of a 4 mol/L aqueous sodium hydroxide solution, and a saturated aqueous sodium thiosulfate solution to the mixture for quenching. The organic layer was extracted with chloroform, dried over anhydrous sodium sulfate, and concentrated under reduced pressure to obtain compound 60-1 as a crude product.

Step 2

2-Chloro-8-{4-(trifluoromethyl)phenoxy}quinoline-5-carbonitrile (Compound 60-2)

Compound 60-1 was dissolved in toluene (4.8 mL), and phosphoryl chloride (0.22 mL, 2.39 mmol) and diisopropylethylamine (0.42 mL, 2.39 mmol) were added to the solution. The mixture was subjected to a reaction at 80° C. for one hour. The mixture was cooled to room temperature, diluted with acetonitrile, and added dropwise to ice-cooled water. A saturated aqueous sodium bicarbonate solution was added to the mixture. The organic layer was extracted with ethyl acetate, dried over anhydrous sodium sulfate, and concentrated under reduced pressure. The residue was purified by silica gel column chromatography (heptane/ethyl acetate=90/10→80/20) to obtain compound 60-2 (31.8 mg, 19% over two steps).
¹H NMR (400 MHz, CDCl₃, δ): 8.52 (d, J=9.0 Hz, 1H), 7.87 (d, J=8.1 Hz, 1H), 7.72 (d, J=8.5 Hz, 2H), 7.69 (d, J=8.5 Hz, 1H), 7.30-7.28 (m, 2H), 7.06 (d, J=8.5 Hz, 1H)
ESIMS m/z: [M+H]⁺ 349.

Step 3

[2-Chloro-8-{4-(trifluoromethyl)phenoxy}quinolin-5-yl]methanamine (Compound 60-3)

Compound 60-3 was obtained as a crude product in the same manner as step 2 of example 57, using compound 60-2 (31.8 mg, 0.091 mmol).
ESIMS m/z: [M+H]⁺ 353.

Step 4

N-([2-Chloro-8-{4-(trifluoromethyl)phenoxy}quinolin-5-yl]methyl)acrylamide (Compound 139)

Compound 139 (27.5 mg, 29% over two steps) was obtained in the same manner as step 3 of example 17, using compound 60-3.
¹H NMR (400 MHz, CDCl₃, δ): 8.45 (d, J=9.1 Hz, 1H), 7.61 (d, J=8.6 Hz, 2H), 7.51 (d, J=9.1 Hz, 1H), 7.44 (d, J=8.2 Hz, 1H), 7.14 (dd, J=9.7, 7.9 Hz, 3H), 6.37 (dd, J=17.0, 1.1 Hz, 1H), 6.08 (dd, J=17.0, 10.4 Hz, 1H), 5.80 (br, 1H), 5.72 (dd, J=10.4, 1.1 Hz, 1H), 4.94 (d, J=5.9 Hz, 2H)
ESIMS m/z: [M+H]⁺ 407.

Example 61

Step 1

8-{(6-Chloropyridin-3-yl)oxy}quinoline-5-carbonitrile (Compound 61-1)

Compound 61-1 (71.9 mg, 88%) was obtained in the same manner as step 2 of example 50, using compound 54-1 (50.0 mg, 0.29 mmol) and 6-chloropyridin-3-ol (45.0 mg, 0.35 mmol).

¹H NMR (400 MHz, CDCl₃, δ): 9.10 (dd, J=4.0, 1.8 Hz, 1H), 8.60 (dd, J=8.5, 1.8 Hz, 1H), 8.32 (d, J=2.2 Hz, 1H), 7.91 (d, J=8.1 Hz, 1H), 7.74 (dd, J=8.5, 4.0 Hz, 1H), 7.49 (dd, J=8.8, 2.9 Hz, 1H), 7.41 (d, J=8.5 Hz, 1H), 7.07 (d, J=8.1 Hz, 1H)
ESIMS m/z: [M+H]⁺ 282.

Step 2

[8-{(6-Chloropyridin-3-yl)oxy}quinolin-5-yl]methanamine (Compound 61-2)

Compound 61-2 was obtained as a crude product in the same manner as step 2 of example 57, using compound 61-1 (71.0 mg, 0.25 mmol).
ESIMS m/z: [M+H]⁺ 286.

Step 3

N-([8-{(6-Chloropyridin-3-yl)oxy}quinolin-5-yl]methyl)acrylamide (Compound 142)

Compound 142 (27.7 mg, 32% over two steps) was obtained in the same manner as step 3 of example 17, using compound 61-2.
¹H NMR (400 MHz, CDCl₃, δ): 8.97 (dd, J=4.3, 1.3 Hz, 1H), 8.49 (dd, J=8.5, 1.3 Hz, 1H), 8.21 (d, J=2.7 Hz, 1H), 7.56 (dd, J=8.5, 4.0 Hz, 1H), 7.46 (d, J=7.6 Hz, 1H), 7.36 (dd, J=8.8, 2.9 Hz, 1H), 7.30-7.29 (m, 1H), 7.15 (d, J=7.6 Hz, 1H), 6.38 (dd, J=16.8, 1.3 Hz, 1H), 6.09 (dd, J=16.8, 10.3 Hz, 1H), 5.81 (s, 1H), 5.71 (dd, J=10.3, 1.3 Hz, 1H), 4.97 (d, J=5.8 Hz, 2H); ESIMS m/z: [M+H]⁺ 340.

Example 62

Step 1

8-[{6-(Trifluoromethyl)pyridin-3-yl}oxy]quinoline-5-carbonitrile (Compound 62-1)

Compound 62-1 (71.0 mg, 78%) was obtained in the same manner as step 2 of example 50, using compound 54-1 (50.0 mg, 0.29 mmol) and 6-(trifluoromethyl)pyridin-3-ol (57.0 mg, 0.35 mmol).
¹H NMR (400 MHz, CDCl₃, δ): 9.06 (dd, J=4.0, 0.9 Hz, 1H), 8.62 (dd, J=8.5, 0.9 Hz, 1H), 8.58 (d, J=2.7 Hz, 1H), 7.74-7.72 (m, 2H), 7.52 (dd, J=8.7, 2.9 Hz, 1H), 7.30-7.29 (m, 1H)
ESIMS m/z: [M+H]⁺ 316.

Step 2

(8-[{6-(Trifluoromethyl)pyridin-3-yl}oxy]quinolin-5-yl)methanamine (Compound 62-2)

Compound 62-2 was obtained as a crude product in the same manner as step 2 of example 57, using compound 62-1 (71.0 mg, 0.23 mmol).
ESIMS m/z: [M+H]⁺ 320, Step 3

N-{(8-[{6-(Trifluoromethyl)pyridin-3-yl}oxy]quinolin-5-yl)methyl}acrylamide (Compound 143)

Compound 143 (26.7 mg, 32% over two steps) was obtained in the same manner as step 3 of example 17, using compound 62-2.
¹H NMR (400 MHz, CDCl₃, δ): 8.93 (dd, J=3.8, 1.6 Hz, 1H), 8.52-8.50 (m, 2H), 7.61 (d, J=8.5 Hz, 1H), 7.56-7.52 (m, 2H), 7.34-7.29 (m, 2H), 6.38 (d, J=17.1 Hz, 1H), 6.10 (dd, J=17.1, 10.1 Hz, 1H), 5.81 (br, 1H), 5.72 (d, J=10.1 Hz, 1H), 5.00 (d, J=5.8 Hz, 2H) ESIMS m/z: [M+H]⁺ 374.

Example 63

Step 1

2-(4-Chlorophenoxy)quinoline-4-carbonitrile (Compound 63-1)

2-Chloroquinoline-4-carbonitrile (0.10 g, 0.53 mmol) was dissolved in DMF (2 mL), and 4-chlorophenol (0.082 g, 0.64 mmol) was added to the solution. The mixture was stirred using a microwave reactor at 150° C. for 30 minutes. Water was added to the mixture. Precipitated crystals were filtered off, washed with water, and dried under reduced pressure to obtain compound 63-1 (145 mg, 97%).
¹H NMR (400 MHz, CDCl₃, δ): 8.13 (d, J=8.3 Hz, 1H), 7.83 (d, J=8.3 Hz, 1H), 7.75 (t, J=7.6 Hz, 1H), 7.62 (t, J=7.6 Hz, 1H), 7.50-7.40 (m, 2H), 7.24-7.18 (m, 3H).

Step 2

2-{4-(Chlorophenoxy)quinolin-4-yl}methanamine (Compound 63-2)

Compound 63-2 (148 mg, quantitatively) was obtained in the same manner as step 3 of example 15, using compound 63-1.
¹H NMR (400 MHz, CDCl₃, δ): 7.91 (d, J=7.8 Hz, 1H), 7.80 (d, J=7.8 Hz, 1H), 7.62 (t, J=7.8 Hz, 1H), 7.46 (t, J=7.8 Hz, 1H), 7.38 (t, J=8.8 Hz, 2H), 7.21-7.20 (m, 3H), 4.36 (s, 2H).

Step 3

N-[{2-(4-Chlorophenoxy)quinolin-4-yl}methyl]acrylamide (Compound 144)

Compound 144 (118 mg, 68%) was obtained in the same manner as step 5 of example 1, using compound 63-2.
¹H-NMR (400 MHz, DMSO-d₆, δ): 8.81 (s, 1H), 8.09 (d, J=8.3 Hz, 1H), 7.67 (s, 2H), 7.52 (d, J=8.8 Hz, 3H), 7.30 (d, J=8.8 Hz, 2H), 7.09 (s, 1H), 6.36 (dd, J=17.1, 10.2 Hz, 1H), 6.19 (d, J=17.1 Hz, 1H), 5.69 (d, J=10.2 Hz, 1H), 4.87 (d, J=5.4 Hz, 2H)
ESIMS m/z: [M+H]⁺ 339.

The following compounds were synthesized in accordance with the synthesis method of compound 144.

(E)-N-[{2-(4-Chlorophenoxy)quinolin-4-yl}methyl]-4,4,4-trifluoro-2-buten amide (Compound 145)

ESIMS m/z: [M+H]⁺ 407.

N-([2-{(6-Chloropyridin-3-yl)oxy}quinolin-4-yl]methyl)acrylamide (Compound 148)

ESIMS m/z: [M+H]⁺ 340.

Example 64

Step 1

2-{4-(Trifluoromethyl)phenoxy}quinoline-4-carbonitrile (Compound 64-1)

Compound 64-1 (129 mg, 52%) was obtained in the same manner as step 1 of example 63, using 2-chloroquinoline-4-carbonitrile.

¹H NMR (400 MHz, CDCl₃, δ): 8.16-8.12 (m, 1H), 7.86-7.71 (m, 4H), 7.66-7.62 (m, 1H), 7.52 (s, 1H), 7.39 (d, J=8.8 Hz, 2H).

Step 2

[2-{4-(Trifluoromethyl)phenoxy}quinolin-4-yl]methanamine (Compound 64-2)

Compound 64-2 (127 mg, quantitatively) was obtained in the same manner as step 3 of example 15, using compound 64-1.

¹H NMR (400 MHz, CDCl₃, δ): 7.92 (d, J=8.5 Hz, 1H), 7.81 (d, J=8.5 Hz, 1H), 7.68-7.61 (m, 3H), 7.47 (t, J=7.6 Hz, 1H), 7.36 (d, J=8.5 Hz, 1H), 7.29-7.26 (m, 2H), 4.43-4.40 (m, 2H).

Step 3

N-([2-{4-(Trifluoromethyl)phenoxy}quinolin-4-yl]methyl)acrylamide (Compound 146)

Compound 146 (29 mg, 41%) was obtained in the same manner as step 5 of example 1, using compound 64-2.

¹H NMR (400 MHz, CDCl₃, δ): 7.94 (d, J=8.3 Hz, 1H), 7.80 (d, J=8.3 Hz, 1H), 7.68-7.64 (m, 3H), 7.49 (t, J=8.3 Hz, 1H), 7.37 (d, J=8.8 Hz, 2H), 7.08 (s, 1H), 6.40 (d, J=17.1 Hz, 1H), 6.18 (dd, J=17.1, 10.2 Hz, 1H), 5.98 (s, 1H), 5.75 (d, J=10.2 Hz, 1H), 5.01 (d, J=6.3 Hz, 2H)

ESIMS m/z: [M+H]⁺ 373.

Example 65

(E)-4,4,4-Trifluoro-N-([2-{4-(trifluoromethyl)phenoxy}quinolin-4-yl]meth yl)-2-butenamide (Compound 147)

Compound 147 (19 mg, 23%) was obtained in the same manner as in example 18, using compound 64-2.

¹H NMR (400 MHz, CDCl₃, δ): 7.90 (d, J=8.1 Hz, 1H), 7.81 (d, J=8.1 Hz, 1H), 7.71-7.64 (m, 3H), 7.50 (t, J=8.1 Hz, 1H), 7.37 (d, J=8.8 Hz, 2H), 7.08 (s, 1H), 6.90-6.85 (m, 1H), 6.54 (dd, J=15.1, 2.0 Hz, 1H), 6.16 (br, 1H), 5.03 (d, J=5.9 Hz, 2H)

ESIMS m/z: [M+H]⁺ 441.

Example 66

Step 1

2-[{6-(Trifluoromethyl)pyridin-3-yl}oxy]quinoline-4-carbonitrile (Compound 66-1)

Compound 66-1 (76 mg, 91%) was obtained in the same manner as step 1 of example 63, using 2-chloroquinoline-4-carbonitrile.

¹H NMR (400 MHz, CDCl₃, δ): 8.76 (d, J=2.4 Hz, 1H), 8.17 (d, J=8.8 Hz, 1H), 7.85-7.80 (m, 4H), 7.69-7.65 (m, 1H), 7.58 (s, 1H).

Step 2

(2-[{6-(Trifluoromethyl)pyridin-3-yl}oxy]quinolin-4-yl)methanamine (Compound 66-2)

Compound 66-2 (70 mg, 91%) was obtained in the same manner as step 3 of example 15, using compound 66-1.

¹H NMR (400 MHz, CDCl₃, δ): 8.75 (d, J=2.3 Hz, 1H), 7.94 (dd, J=8.4, 1.2 Hz, 1H), 7.86 (dd, J=8.4, 2.3 Hz, 1H), 7.81-7.75 (m, 2H), 7.68-7.63 (m, 1H), 7.50 (td, J=7.7, 1.2 Hz, 1H), 7.34 (s, 1H).

Step 3

N-{(2-[{6-(Trifluoromethyl)pyridin-3-yl}oxy]quinolin-4-yl)methyl}acrylamide (Compound 149)

Compound 149 (72 mg, 90%) was obtained in the same manner as step 5 of example 1, using compound 66-2.

¹H NMR (400 MHz, CDCl₃, δ): 8.73 (d, J=2.4 Hz, 1H), 7.96 (d, J=8.3 Hz, 1H), 7.86 (dd, J=8.3, 2.4 Hz, 1H), 7.78-7.77 (m, 2H), 7.67 (t, J=7.8 Hz, 1H), 7.54-7.51 (m, 1H), 7.14 (s, 1H), 6.42 (dd, J=17.1, 1.5 Hz, 1H), 6.21 (dd, J=17.1, 10.2 Hz, 1H), 5.99 (br, 1H), 5.78 (dd, J=10.2, 1.5 Hz, 1H), 5.04 (d, J=5.9 Hz, 2H)

ESIMS m/z: [M+H]⁺ 374.

Example 67

Step 1

2-{(2-Chloropyridin-4-yl)oxy}quinoline-4-carbonitrile (Compound 67-1)

Compound 67-1 (75 mg, quantitatively) was obtained in the same manner as step 1 of example 63, using 2-chloroquinoline-4-carbonitrile.

¹H NMR (400 MHz, CDCl₃, δ): 8.45 (d, J=5.8 Hz, 1H), 8.19 (d, J=7.8 Hz, 1H), 7.92 (d, J=7.8 Hz, 1H), 7.83 (td, J=7.8, 1.3 Hz, 1H), 7.72-7.69 (m, 1H), 7.54 (s, 1H), 7.37 (d, J=2.1 Hz, 1H), 7.23 (dd, J=5.8, 2.1 Hz, 1H).

Step 2

[2-{(2-Chloropyridin-4-yl)oxy}quinolin-4-yl]methanamine (Compound 67-2)

Compound 67-2 (72 mg, 94%) was obtained in the same manner as step 3 of example 15, using compound 67-1.

¹H NMR (400 MHz, CDCl₃, δ): 8.37 (d, J=5.4 Hz, 1H), 7.96 (d, J=8.5 Hz, 1H), 7.89 (d, J=8.5 Hz, 1H), 7.70 (t, J=7.6 Hz, 1H), 7.54 (t, J=7.6 Hz, 1H), 7.31 (d, J=5.9 Hz, 2H), 7.19 (d, J=5.9 Hz, 1H), 4.42 (s, 2H).

Step 3

N-([2-{(2-Chloropyridin-4-yl)oxy}quinolin-4-yl]methyl)acrylamide (Compound 150)

Compound 150 (63 mg, 75%) was obtained in the same manner as step 5 of example 1, using compound 67-2.

¹H NMR (400 MHz, CDCl₃, δ): 8.38 (d, J=5.8 Hz, 1H), 7.98 (d, J=8.8 Hz, 1H), 7.88 (d, J=8.3 Hz, 1H), 7.74-7.69 (m, 1H), 7.58-7.54 (m, 1H), 7.32 (d, J=2.1 Hz, 1H), 7.20 (dd, J=5.8, 2.1 Hz, 1H), 7.10 (s, 1H), 6.41 (dd, J=17.1, 1.3 Hz, 1H), 6.20 (dd, J=17.1, 10.2 Hz, 1H), 6.00 (br, 1H), 5.77 (dd, J=10.2, 1.3 Hz, 1H), 5.04 (d, J=5.8 Hz, 2H)

ESIMS m/z: [M+H]⁺ 340.

Example 68

Step 1

2-[{2-(Trifluoromethyl)pyridin-4-yl}oxy]quinoline-4-carbonitrile (Compound 68-1)

Compound 68-1 (73 mg, 87%) was obtained in the same manner as step 1 of example 63, using 2-chloroquinoline-4-carbonitrile.

¹H NMR (400 MHz, CDCl₃, δ): 8.79 (d, J=5.5 Hz, 1H), 8.19 (d, J=8.5 Hz, 1H), 7.90 (d, J=8.5 Hz, 1H), 7.86-7.81 (m, 1H), 7.72-7.70 (m, 2H), 7.57 (s, 1H), 7.51 (dd, J=5.5, 2.2 Hz, 1H).

Step 2

(2-[{2-(Trifluoromethyl)pyridin-4-yl}oxy]quinolin-4-yl]methanamine (Compound 68-2)

Compound 62-2 (69 mg, 94%) was obtained in the same manner as step 3 of example 15, using compound 68-1.

¹H NMR (400 MHz, CDCl₃, δ): 8.72 (d, J=5.5 Hz, 1H), 7.97 (d, J=7.8 Hz, 1H), 7.87 (d, J=7.8 Hz, 1H), 7.71-7.69 (m, 2H), 7.54 (t, J=7.8 Hz, 1H), 7.47 (dd, J=5.5, 2.2 Hz, 1H), 7.34 (s, 1H), 4.43 (s, 2H).

Step 3

N-{(2-[{2-(Trifluoromethyl)pyridin-4-yl}oxy]quinolin-4-yl)methyl}acrylamide (Compound 151)

Compound 151 (65 mg, 83%) was obtained in the same manner as step 5 of example 1, using compound 68-2.

¹H NMR (400 MHz, CDCl₃, δ): 8.72 (d, J=5.4 Hz, 1H), 7.99 (dd, J=8.3, 1.0 Hz, 1H), 7.86 (d, J=7.8 Hz, 1H), 7.74-7.70 (m, 1H), 7.68 (d, J=2.2 Hz, 1H), 7.59-7.55 (m, 1H), 7.47 (dd, J=5.4, 2.2 Hz, 1H), 7.13 (s, 1H), 6.42 (dd, J=16.9, 1.3 Hz, 1H), 6.20 (dd, J=16.9, 10.2 Hz, 1H), 5.99 (br, 1H), 5.78 (dd, J=10.2, 1.3 Hz, 1H), 5.05 (d, J=5.9 Hz, 2H)

ESIMS m/z: [M+H]⁺ 374.

Example 69

Step 1

8-(4-Chlorophenoxy)chroman-4-ol (Compound 69-1)

Compound 69-1 (0.40 g, 80%) was obtained in the same manner as step 1 of example 15, using compound 25-4.

¹H NMR (400 MHz, DMSO-d₆, δ): 7.34 (d, J=8.8 Hz, 2H), 7.22 (d, J=7.2 Hz, 1H), 6.97-6.89 (m, 2H), 6.83 (d, J=8.8 Hz, 2H), 5.47 (d, J=5.2 Hz, 1H), 4.68-4.64 (m, 1H), 4.14-4.12 (m, 2H), 2.02-1.88 (n, 2H).

Step 2

8-(4-Chlorophenoxy)chromane-4-carbonitrile (Compound 69-2)

Compound 69-2 (0.02 g, 20%) was obtained in the same manner as step 2 of example 15, using compound 69-1.

¹H NMR (400 MHz, DMSO-d₆, δ): 7.36 (d, J=8.8 Hz, 2H), 7.22 (d, J=7.6 Hz, 1H), 7.06-6.97 (m, 2H), 6.88 (d, J=8.8 Hz, 2H), 4.53 (t, J=6.0 Hz, 1H), 4.18-4.14 (m, 2H), 2.33-2.24 (m, 2H).

Step 3

{8-(4-Chlorophenoxy)chroman-4-yl}methanamine (Compound 69-3)

Compound 69-3 (0.12 g, 79%) was obtained in the same manner as step 3 of example 15, using compound 69-2.

¹H NMR (400 MHz, DMSO-d₆, δ): 7.33 (d, J=8.8 Hz, 2H), 7.10 (dd, J=6.4, 2.8 Hz, 1H), 6.87-6.81 (m, 4H), 4.10-3.98 (m, 2H), 2.93-2.89 (m, 1H), 2.75-2.64 (m, 2H), 2.03-1.89 (n, 2H).

Step 4

N-[{8-(4-Chlorophenoxy)chroman-4-yl}methyl]acrylamide (Compound 152)

Compound 152 (0.09 g, 69%) was obtained in the same manner as step 5 of example 1, using compound 69-3.

¹H NMR (400 MHz, DMSO-d₆, δ): 8.37 (br, 1H), 7.34 (d, J=8.8 Hz, 2H), 7.10-7.08 (m, 1H), 6.93-6.83 (m, 4H), 6.26 (dd, J=16.8, 10.0 Hz, 1H), 6.11 (dd, J=17.2, 2.0 Hz, 1H), 5.62 (dd, J=10.0, 1.6 Hz, 1H), 4.14-4.02 (m, 2H), 3.54-3.48 (m, 1H), 3.36-3.29 (m, 1H), 2.98-2.97 (m, 1H), 1.93-1.78 (n, 2H);

ESIMS m/z: [M+H]⁺ 344.

Example 70

N-(6-Bromo-8-[{6-(trifluoromethyl)pyridin-3-yl}oxy]chroman-3-yl) acrylamide (Compound 153)

Compound 51 (50 mg, 0.137 mmol) was dissolved in acetonitrile (1 mL), and N-bromosuccinimide (26.9 mg, 0.151 mmol) was added to the solution. The mixture was stirred at room temperature for 72 hours. Methanol was added to the reaction liquid, and the mixture was concentrated under reduced pressure. The residue was purified using a preparative HPLC [Waters Xbridge Prep C18 OBD column, 5 μm silica, diameter 19 mm, length 100 mm; acetonitrile/0.05% aqueous TFA solution (30/70→40/60)] to obtain compound 153 (26.9 mg, 47%).

¹H NMR (400 MHz, CDCl₃, δ): 8.33 (d, J=2.7 Hz, 1H), 7.56 (d, J=8.6 Hz, 1H), 7.23 (dd, J=8.6, 2.7 Hz, 1H), 7.06 (dd, J=13.1, 2.3 Hz, 2H), 6.23 (dd, J=17.0, 1.1 Hz, 1H), 5.98 (dd, J=17.0, 10.2 Hz, 1H), 5.80 (d, J=7.2 Hz, 1H), 5.61 (dd, J=10.4, 1.4 Hz, 1H), 4.51-4.48 (m, 1H), 4.12-4.10 (m, 1H), 4.04-4.01 (m, 1H), 3.10 (dd, J=17.2, 5.4 Hz, 1H), 2.85-2.80 (m, 1H).

ESIMS m/z: [M+H]⁺ 443, 445.

Example 71

Step 1

8-[{2-(Trifluoromethyl)pyrimidin-5-yl}oxy]chroman-3-amine (Compound 71-1)

Compound 71-1 was obtained as a crude product in the same manner as step 4 of example 4, using compound 28-2 and commercially available 5-bromo-2-(trifluoromethyl)pyrimidine, and was used as it is in the next reaction.

ESIMS m/z: [M+H]⁺ 312.

Step 2

N-(8-[{2-(Trifluoromethyl)pyrimidin-5-yl}oxy]chroman-3-yl)acrylamide (Compound 155)

Compound 155 (130 mg, 44% over two steps) was obtained in the same manner as step 5 of example 1, using compound 71-1.

¹H NMR (400 MHz, CDCl₃, δ): 8.37 (s, 2H), 6.94-6.90 (m, 3H), 6.26-6.17 (m, 2H), 6.00 (dd, J=17.0, 10.2 Hz, 1H), 5.56 (dd, J=10.4, 1.4 Hz, 1H), 4.50-4.44 (m, 1H), 4.05-4.02 (m, 2H), 3.12 (dd, J=17.0, 5.2 Hz, 1H), 2.82 (dd, J=17.2, 4.1 Hz, 1H).

ESIMS m/z: [M+H]⁺ 366.

Example 72

Step 1

8-[{6-(Trifluoromethyl)pyridazin-3-yl}oxy]chroman-3-amine (Compound 72-1)

Compound 72-1 was obtained as a crude product in the same manner as step 4 of example 4, using compound 28-2 and commercially available 3-chloro-6-(trifluoromethyl)pyridazine, and was used as it is in the next reaction.
ESIMS m/z: [M+H]$^+$ 312.

Step 2

N-(8-[{6-(trifluoromethyl)pyridazin-3-yl}oxy]chroman-3-yl)acrylamide (Compound 156)

Compound 156 (158 mg, 53% over two steps) was obtained in the same manner as step 5 of example 1, using compound 72-1.
$^1$H NMR (400 MHz, CDCl$_3$, δ): 7.74 (d, J=9.1 Hz, 1H), 7.29 (d, J=9.1 Hz, 1H), 6.97-6.83 (m, 3H), 6.44 (d, J=8.2 Hz, 1H), 6.18 (dd, J=17.2, 1.4 Hz, 1H), 6.05 (dd, J=17.0, 10.2 Hz, 1H), 5.53 (dd, J=10.0, 1.4 Hz, 1H), 4.47-4.46 (m, 1H), 3.98-3.93 (m, 2H), 3.06 (dd, J=16.8, 5.4 Hz, 1H), 2.74 (dd, J=16.8, 3.2 Hz, 1H).
ESIMS m/z: [M+H]$^+$ 366,

Example 73

Step 1

8-[{5-(Trifluoromethyl)pyrazin-2-yl}oxy]chroman-3-amine (Compound 73-1)

Compound 73-1 was obtained as a crude product in the same manner as step 4 of example 4, using compound 28-2 and commercially available 2-chloro-5-(trifluoromethyl)pyrazine, and was used as it is in the next reaction.
ESIMS m/z: [M+H]$^+$ 312.

Step 2

N-(8-[{5-(Trifluoromethyl)pyrazin-2-yl}oxy]chroman-3-yl)acrylamide (Compound 157)

Compound 157 (89 mg, 29% over two steps) was obtained in the same manner as step 5 of example 1, using compound 73-1.
$^1$H NMR (400 MHz, CDCl$_3$, δ): 8.45 (s, 1H), 8.29 (s, 1H), 6.97-6.95 (m, 2H), 6.89 (dd, J=9.1, 6.3 Hz, 1H), 6.18 (dd, J=17.7, 12.2 Hz, 2H), 5.98 (dd, J=16.8, 10.4 Hz, 1H), 5.57 (d, J=10.9 Hz, 1H), 4.48-4.48 (m, 1H), 4.02-3.99 (m, 2H), 3.12 (dd, J=16.8, 5.4 Hz, 1H), 2.80 (d, J=16.8 Hz, 1H).
ESIMS m/z: [M+H]$^+$ 366.

Example 74

Step 1

8-[{4-(Trifluoromethyl)thio}phenoxy]chroman-3-amine (Compound 74-1)

Compound 74-1 was obtained as a crude product in the same manner as step 4 of example 4, using compound 28-2 and commercially available (4-bromophenyl)(trifluoromethyl)sulfane, and was used as it is in the next reaction.
ESIMS m/z: [M+H]$^+$ 342.

Step 2

N-(8-[{4-(Trifluoromethyl)thio}phenoxy]chroman-3-yl)acrylamide (Compound 158)

Compound 158 (48 mg, 15% over two steps) was obtained in the same manner as step 5 of example 1, using compound 74-1.
$^1$H NMR (400 MHz, CDCl$_3$, δ): 7.50 (d, J=11.6 Hz, 2H), 6.87-6.84 (m, 5H), 6.22 (d, J=16.8 Hz, 1H), 5.97 (dd, J=17.0, 10.2 Hz, 2H), 5.59 (d, J=10.9 Hz, 1H), 4.52-4.49 (m, 1H), 4.14 (dt, J=11.2, 2.8 Hz, 1H), 4.03 (dd, J=11.3, 1.4 Hz, 1H), 3.13 (dd, J=17.0, 5.2 Hz, 1H), 2.83 (dt, J=17.2, 2.5 Hz, 1H).
ESIMS m/z: [M+H]$^+$ 396.

Example 75

Step 1

8-[{4-(Trifluoromethyl)sulfonyl}phenoxy]chroman-3-amine (Compound 75-1)

Compound 75-1 was obtained as a crude product in the same manner as step 4 of example 4, using compound 28-2 and commercially available 1-bromo-4-{(trifluoromethyl)sulfonyl}benzene, and was used as it is in the next reaction.
ESIMS m/z: [M+H]$^+$ 374.

Step 2

N-(8-[{4-(Trifluoromethyl)sulfonyl}phenoxy]chroman-3-yl)acrylamide (Compound 159)

Compound 159 (34 mg, 10% over two steps) was obtained in the same manner as step 5 of example 1, using compound 75-1.
$^1$H NMR (400 MHz, CDCl$_3$, δ): 7.87 (d, J=9.3 Hz, 2H), 7.02 (dt, J=9.5, 2.5 Hz, 2H), 6.98-6.88 (m, 3H), 6.23 (dd, J=16.8, 1.4 Hz, 1H), 5.97 (dd, J=17.0, 10.2 Hz, 1H), 5.86 (d, J=7.7 Hz, 1H), 5.61 (dd, J=10.4, 1.4 Hz, 1H), 4.53-4.48 (m, 1H), 4.11 (dq, J=11.1, 2.0 Hz, 1H), 4.02 (dd, J=10.9, 1.8 Hz, 1H), 3.14 (dd, J=17.2, 5.4 Hz, 1H), 2.85 (dt, J=16.9, 2.8 Hz, 1H).
ESIMS m/z: [M+H]$^+$ 428,

Example 76

Step 1

N-(8-Hydroxychroman-3-yl)acrylamide (Compound 76-1)

Compound 28-2 (0.20 g, 0.81 mmol) was dissolved in THF (4 mL) and water (4 mL), and sodium hydrogen carbonate (0.34 g, 4.06 mmol) and acryloyl chloride (0.079 mL, 0.98 mmol) were added to the solution. The mixture was stirred at room temperature for 1.5 hours. Water was added to the mixture. The organic layer was extracted with ethyl acetate, washed with a 1 mol/L aqueous hydrochloric acid solution and saturated saline, dried over anhydrous magnesium sulfate, and concentrated under reduced pressure to obtain compound 76-1 (0.17 g, 93%). $^1$H NMR (400 MHz, DMSO-d$_6$, δ): 8.90 (s, 1H), 8.27 (d, J=6.8 Hz, 1H), 6.68-6.59 (m, 2H), 6.51 (d, J=7.8 Hz, 1H), 6.35-6.23 (m, 1H), 6.12 (dd, J=17.1, 2.0 Hz, 1H), 5.62-5.57 (m, 1H), 4.27-4.10 (m, 2H), 3.92 (dd, J=9.5, 6.6 Hz, 1H), 3.01 (dd, J=16.5, 6.2 Hz, 1H), 2.69 (dd, J=16.5, 6.2 Hz, 1H);
ESIMS m/z: [M+H]$^+$ 220.

Step 2

N-[8-{(4,4-Difluorocyclohexyl)methoxy}chroman-3-yl]acrylamide (Compound 160)

Compound 76-1 (165 mg, 0.753 mmol), triphenylphosphine (237.0 m g, 0.903 mmol), and (4,4-difluorocyclohexyl)methanol (136.0 mg, 0.347 mmol) were dissolved in THF (4 mL). Diisopropyl azodicarboxylate (0.19 mL) was added to the solution under cooling at 0° C. The mixture was stirred at room temperature for 2 hours. Magnesium chloride hexahydrate (612 mg, 3.01 mmol) and heptane (3.8 mL) were added to the mixture. The mixture was stirred at 60° C. for 2 hours. Water was added to the mixture. The organic layer was extracted with ethyl acetate, washed with saturated saline, dried over anhydrous magnesium sulfate, and concentrated under reduced pressure. The residue was purified by silica gel column chromatography (chloroform/methanol=99/1→96/4) to obtain a crude product. The crude product obtained was purified using a preparative HPLC [Waters Xbridge Prep C18 OBD column, 5 μm silica, diameter 19 mm, length 100 mm; acetonitrile/0.05% aqueous TFA solution (30/70→40/60)] to obtain compound 160 (37.0 ng, 13%).

$^1$H NMR (400 MHz, CDCl$_3$, δ): 6.84 (t, J=7.6 Hz, 1H), 6.74 (d, J=7.6 Hz, 1H), 6.68 (d, J=7.6 Hz, 1H), 6.31 (dd, J=17.1, 1.3 Hz, 1H), 6.10-6.01 (m, 2H), 5.64 (dd, J=10.3, 1.3 Hz, 1H), 4.63-4.56 (m, 1H), 4.35-4.28 (m, 1H), 4.15 (dd, J=11.0, 2.0 Hz, 1H), 3.87-3.80 (m, 2H), 3.16 (dd, J=17.1, 5.4 Hz, 1H), 2.87-2.78 (m, 1H), 2.21-2.08 (m, 2H), 2.07-1.92 (m, 3H), 1.87-1.66 (m, 2H), 1.47-1.32 (n, 2H);

ESIMS m/z: [M+H]$^+$ 352.

Example 77

Step 1

8-{(5-Chloropyrimidin-2-yl)oxy}chroman-3-amine hydrochloride (Compound 77-1)

Compound 28-2 (0.20 g, 0.81 mmol) was dissolved in DMF (8 mL), and potassium carbonate (0.56 g, 4.06 mmol) and 2,5-dichloropyrimidine (0.13 g, 0.89 mmol) were added to the solution. The mixture was stirred at 100° C. for 17 hours. Water was added to the mixture. The organic layer was extracted with ethyl acetate, washed with saturated saline, dried over anhydrous magnesium sulfate, and concentrated under reduced pressure to obtain compound 77-1 as a crude product, which was used as it is in the next reaction.

Step 2

N-[8-{(5-Chloropyrimidin-2-yl)oxy}chroman-3-yl]acrylamide (Compound 161)

Compound 161 (10.0 mg, 5% over two steps) was obtained in the same manner as step 5 of example 1, using compound 77-1.

$^1$H NMR (400 MHz, CDCl$_3$, δ): 8.46 (s, 2H), 7.08 (dd, J=7.7, 1.6 Hz, 1H), 7.04-6.94 (m, 2H), 6.29 (dd, J=17.2, 1.5 Hz, 1H), 6.08-5.95 (m, 2H), 5.66 (dd, J=10.4, 1.5 Hz, 1H), 4.62-4.56 (m, 1H), 4.17-4.01 (m, 2H), 3.20 (dd, J=17.0, 5.0 Hz, 1H), 2.87 (d, J=17.0 Hz, 1H);

ESIMS m/z: [M+H]$^+$ 332.

Example 78

Step 1

2-Hydroxy-5-iodo-3-methoxybenzaldehyde (Compound 78-1)

Commercially available 2-hydroxy-3-methoxybenzaldehyde (2.00 g, 13.15 mmol) was dissolved in chloroform (40 mL) and pyridine (20 mL), and silver nitrate (2.10 g, 13.15 mmol) was added to the solution. The mixture was stirred at room temperature for 10 minutes. Iodine monochloride (2.10 g, 12.15 mmol) was added to the mixture. The mixture was stirred at room temperature for 3 hours. A saturated aqueous sodium thiosulfate solution (50 mL) and a 2 mol/L aqueous hydrochloric acid solution (50 mL) were added to the mixture. The organic layer was extracted with dichloromethane, dried over anhydrous sodium sulfate, and concentrated under reduced pressure to obtain compound 78-1 (1.80 g, 50%).

$^1$H NMR (300 MHz, DMSO-d$_6$, δ): 10.42 (s, 1H), 10.18 (s, 1H), 7.49 (d, J=1.8 Hz, 1H), 7.45 (d, J=2.1 Hz, 1H), 3.86 (s, 3H).

Step 2

6-Iodo-8-methoxy-2H-chromene-3-carbonitrile (Compound 78-2)

Compound 78-2 (0.50 g, 22%) was obtained in the same manner as step 1 of example 23, using compound 78-1.

$^1$H NMR (300 MHz, DMSO-d$_6$, δ): 7.52 (s, 1H), 7.31 (s, 1H), 7.25 (d, J=1.5 Hz, 1H), 4.87 (s, 2H), 3.77 (s, 3H).

Step 3

8-Methoxy-6-(trifluoromethyl)-2H-chromene-3-carbonitrile (Compound 78-3)

Compound 78-2 (1.50 g, 4.80 mmol) was dissolved in DMF (15 mL), and added to the solution were methyl 2,2-difluoro-2-(fluorosulfonyl)acetate (4.50 g, 24.03 mmol), hexamethylphosphoric triamide (4.20 g, 24.03 mmol), and copper(I) iodide (0.76 g, 4.80 mmol). The mixture was stirred at 90° C. for 16 hours. Water was added to the mixture. The organic layer was extracted with ethyl acetate, dried over anhydrous sodium sulfate, and concentrated under reduced pressure. The residue was purified by silica gel column chromatography (hexane/ethyl acetate=80/20→70/30) to obtain compound 78-3 (0.65 g, 53%).

$^1$H NMR (300 MHz, DMSO-d$_6$, δ): 7.63 (s, 1H), 7.31 (d, J=4.2 Hz, 2H), 4.99 (d, J=1.2 Hz, 2H), 3.85 (s, 3H).

Step 4

8-Methoxy-5-(trifluoromethyl)-2H-chromene-3-carboxylic acid (Compound 78-4)

Compound 78-4 (0.60 g, 86%) was obtained in the same manner as step 2 of example 23, using compound 78-3.

$^1$H NMR (400 MHz, DMSO-d$_6$, δ): 13.01 (bs, 1H), 7.50 (s, 1H), 7.38 (d, J=1.2 Hz, 1H), 7.25 (d, J=2.0 Hz, 1H), 4.99 (d, J=1.6 Hz, 2H), 3.84 (s, 3H).

Step 5 tert-Butyl {8-methoxy-6-(trifluoromethyl)-2H-chromen-3-yl)carbamate (Compound 78-5)

Compound 78-5 (0.60 g, 79%) was obtained in the same manner as step 3 of example 23, using compound 78-4.

¹H NMR (400 MHz, DMSO-d₆, δ): 9.17 (s, 1H), 6.99 (d, J=0.8 Hz, 2H), 6.60 (s, 1H), 4.75 (d, J=1.2 Hz, 2H), 3.80 (s, 3H), 1.45 (s, 9H).

Step 6 tert-Butyl {8-methoxy-6-(trifluoromethyl)chroman-3-yl)carbamate (Compound 78-6)

Compound 78-6 (0.55 g, 91%) was obtained in the same manner as step 4 of example 23, using compound 78-5.

¹H NMR (400 MHz, CDCl₃, δ): 6.95 (d, J=9.2 Hz, 2H), 4.85-4.83 (m, 1H), 4.33-4.16 (m, 3H), 3.92 (s, 3H), 3.15-3.10 (m, 1H), 2.80-2.76 (m, 1H), 1.43 (s, 9H).

Step 7

3-Amino-6-(trifluoromethyl)chroman-8-ol hydrobromide (Compound 78-7)

Compound 78-7 (0.35 g, 86%) was obtained in the same manner as step 6 of example 27, using compound 78-6.

ESIMS m/z: [M+H]⁺ 234.

Step 8

N-{8-Hydroxy-6-(trifluoromethyl)chroman-3-yl}acrylamide (Compound 78-8)

Compound 78-8 (0.07 g, 25%) was obtained in the same manner as step 1 of example 76, using compound 78-7.

¹H NMR (300 MHz, DMSO-d₆, δ): 9.65 (s, 1H), 8.28 (d, J=6.6 Hz, 1H), 6.90 (d, J=12.9 Hz, 2H), 6.29 (dd, J=17.1, 9.9 Hz, 1H), 6.12 (dd, J=17.1, 2.4 Hz, 1H), 5.60 (dd, J=9.9, 2.4 Hz, 1H), 4.25-4.18 (m, 2H), 4.04 (dd, J=11.1, 6.3 Hz, 1H), 3.11 (dd, J=16.5, 5.1 Hz, 1H), 2.75 (dd, J=16.8, 6.0 Hz, 1H).

Step 9

N-{6-(Trifluoromethyl)-8-[{6-(trifluoromethyl)pyridin-3-yl}oxy]chroman-3-yl}acrylamide (Compound 162)

Compound 162 (0.03 g, 34%) was obtained in the same manner as step 1 of example 3, using compound 78-8.

¹H NMR (400 MHz, DMSO-d₆, δ): 8.51 (d, J=2.8 Hz, 1H), 8.30 (d, J=6.8 Hz, 1H), 7.82 (d, J=8.8 Hz, 1H), 7.54 (d, J=8.4 Hz, 2H), 7.46 (dd, J=8.4, 2.4 Hz, 1H), 6.26 (dd, J=16.8, 10.0 Hz, 1H), 6.10 (dd, J=16.8, 2.0 Hz, 1H), 5.60 (dd, J=10.4, 2.4 Hz, 1H), 4.29-4.27 (m, 1H), 4.16 (dd, J=10.8, 2.0 Hz, 1H), 4.06 (dd, J=10.0, 6.4 Hz, 1H), 3.21 (dd, J=16.4, 4.8 Hz, 1H), 2.87 (dd, J=17.6, 6.0 Hz, 1H);

ESIMS m/z: [M+H]⁺ 433.

Example 79

Step 1

8-Methoxy-7-[{6-(trifluoromethyl)pyridin-3-yl}oxy] chroman-4-one (Compound 79-1)

Compound 79-1 (0.11 g, 64%) was obtained in the same manner as step 1 of example 3, using compound 21-3.

¹H NMR (400 MHz, CDCl₃, δ): 8.50 (d, J=2.5 Hz, 1H), 7.72 (d, J=8.6 Hz, 1H), 7.66 (d, J=8.6 Hz, 1H), 7.34 (dd, J=8.6, 2.5 Hz, 1H), 6.73 (d, J=8.6 Hz, 1H), 4.68 (t, J=6.3 Hz, 2H), 3.84 (s, 3H), 2.87 (t, J=6.3 Hz, 2H).

ESIMS m/z: [M+H]⁺ 340.

Step 2

8-Methoxy-7-[{6-(trifluoromethyl)pyridin-3-yl}oxy] chroman-4-amine (Compound 79-2)

Compound 79-2 was obtained as a crude product in the same manner as step 2 of example 3, using compound 79-1, and used as it is in the next reaction.

Step 3

N-(8-Methoxy-7-[{6-(trifluoromethyl)pyridin-3-yl}oxy]chroman-4-yl)acryl amide (Compound 163)

Compound 163 (0.013 g, 14% over two steps) was obtained in the same manner as step 3 of example 17, using compound 79-2.

¹H NMR (400 MHz, CDCl₃, δ): 8.44 (d, J=2.7 Hz, 1H), 7.58 (d, J=8.6 Hz, 1H), 7.23 (dd, J=8.6, 2.7 Hz, 1H), 7.02 (d, J=8.6 Hz, 1H), 6.66 (d, J=8.6 Hz, 1H), 6.37 (dd, J=17.1, 1.4 Hz, 1H), 6.13 (dd, J=17.1, 10.3 Hz, 1H), 6.01 (d, J=7.7 Hz, 1H), 5.73 (dd, J=10.3, 1.4 Hz, 1H), 5.31-5.24 (m, 1H), 4.45-4.37 (m, 1H), 4.32-4.22 (m, 1H), 3.77 (s, 3H), 2.34-2.22 (m, 1H), 2.21-2.10 (m, 1H);

ESIMS m/z: [M+H]⁺ 395.

Example 80

Step 1

7-(3,4-Difluorophenoxy)-8-methoxychroman-4-one (Compound 80-1)

Compound 80-1 (0.12 g, 79%) was obtained in the same manner as step 1 of example 3, using compound 21-3.

¹H NMR (400 MHz, CDCl₃, δ): 7.64 (d, J=9.2 Hz, 1H), 7.15 (q, J=9.2 Hz, 1H), 6.91-6.84 (m, 1H), 6.79-6.73 (m, 1H), 6.56 (d, J=9.2 Hz, 1H), 4.65 (t, J=6.6 Hz, 2H), 3.89 (s, 3H), 2.84 (t, J=6.6 Hz, 2H);

ESIMS m/z: [M+H]⁺ 307.

Step 2

7-(3,4-Difluorophenoxy)-8-methoxychroman-4-amine (Compound 80-2)

Compound 80-2 was obtained as a crude product in the same manner as step 2 of example 3, using compound 80-1, and used as it is in the next reaction.

Step 3

N-{7-(3,4-Difluorophenoxy)-8-methoxychroman-4-yl}acrylamide (Compound 164)

Compound 164 (0.052 g, 39% over two steps) was obtained in the same manner as step 3 of example 17, using compound 80-2.

¹H NMR (400 MHz, CDCl₃, δ): 7.08 (q, J=9.2 Hz, 1H), 6.94 (dd, J=8.5, 0.9 Hz, 1H), 6.81-6.74 (m, 1H), 6.71-6.66 (m, 1H), 6.56 (d, J=9.2 Hz, 1H), 6.37 (dd, J=17.1, 1.3 Hz, 1H), 6.11 (dd, J=17.1, 10.3 Hz, 1H), 5.82 (d, J=7.2 Hz, 1H), 5.72 (dd, J=10.3, 1.3 Hz, 1H), 5.27-5.20 (m, 1H), 4.44-4.37 (m, 1H), 4.28-4.20 (m, 1H), 3.81 (s, 3H), 2.33-2.22 (m, 1H), 2.18-2.09 (m, 1H);

ESIMS m/z: [M+H]⁺ 362.

Example 81

Step 1

7-{(4,4-Difluorocyclohexyl)methoxy}-8-methoxy-chroman-4-one (Compound 81-1)

Compound 81-1 (0.16 g, 93%) was obtained in the same manner as step 2 of example 76, using compound 21-3.

$^1$H NMR (400 MHz, CDCl$_3$, δ): 7.67 (d, J=8.6 Hz, 1H), 6.61 (d, J=8.6 Hz, 1H), 4.59 (t, J=6.3 Hz, 2H), 3.93 (d, J=6.3 Hz, 2H), 3.86 (s, 3H), 2.78 (t, J=6.3 Hz, 2H), 2.18-2.13 (m, 2H), 2.03-1.95 (m, 3H), 1.88-1.71 (m, 2H), 1.53-1.42 (m, 2H);
ESIMS m/z: [M+H]$^+$ 327.

Step 2

7-{(4,4-Difluorocyclohexyl)methoxy}-8-methoxy-chroman-4-amine (Compound 81-2)

Compound 81-2 was obtained as a crude product in the same manner as step 2 of example 3, using compound 81-1, and used as it is in the next reaction.

Step 3

N-[7-{(4,4-Difluorocyclohexyl)methoxy}-8-methoxychroman-4-yl]acrylamide (Compound 165)

Compound 165 (0.039 g, 24% over two steps) was obtained in the same manner as step 3 of example 17, using compound 81-2.

$^1$H NMR (400 MHz, CDCl$_3$, δ): 6.87 (d, J=8.5 Hz, 1H), 6.46 (d, J=8.5 Hz, 1H), 6.34 (dd, J=17.1, 1.3 Hz, 1H), 6.11 (dd, J=17.1, 10.3 Hz, 1H), 6.03 (d, J=7.2 Hz, 1H), 5.69 (dd, J=10.3, 1.3 Hz, 1H), 5.19-5.12 (m, 1H), 4.39-4.29 (m, 1H), 4.23-4.13 (m, 1H), 3.85-3.80 (m, 5H), 2.26-2.04 (m, 4H), 2.01-1.91 (m, 3H), 1.86-1.67 (m, 2H), 1.50-1.36 (m, 2H);
ESIMS m/z: [M+H]$^+$ 382.

Example 82

Step 1

7-(Benzyloxy)-8-fluorochroman-4-one (Compound 82-1)

Compound 19-3 (0.50 g, 2.74 mmol) was dissolved in DMF (14 mL), and potassium carbonate (0.76 g, 5.49 mmol) and benzyl bromide (0.39 mL, 3.29 mmol) were added to the solution. The mixture was stirred at room temperature for 4 hours. Water was added to the mixture. Precipitated crystals were filtered off, washed with water, and dried under reduced pressure to obtain compound 82-1 (0.73 g, 98%).

$^1$H NMR (400 MHz, CDCl$_3$, δ): 7.64 (dd, J=8.9, 2.2 Hz, 1H), 7.46-7.32 (m, 5H), 6.70 (dd, J=8.9, 7.0 Hz, 1H), 5.22 (s, 2H), 4.62 (t, J=6.4 Hz, 2H), 2.81 (t, J=6.4 Hz, 2H);
ESIMS m/z: [M+H]$^+$ 273.

Step 2

7-(Benzyloxy)-8-fluorochroman-4-amine (Compound 82-2)

Compound 82-2 (0.053 g, 53%) was obtained in the same manner as step 4 of example 1, using compound 82-1.

$^1$H NMR (400 MHz, CDCl$_3$, δ): 7.46-7.28 (m, 5H), 6.93 (dd, J=8.7, 2.0 Hz, 1H), 6.56 (dd, J=8.7, 7.6 Hz, 1H), 5.12 (s, 2H), 4.37-4.26 (m, 2H), 4.00 (t, J=5.2 Hz, 1H), 2.18-2.09 (m, 1H), 1.86-1.77 (m, 1H), 1.69-1.58 (m, 2H).

Step 3

N-{7-(Benzyloxy)-8-fluorochroman-4-yl}acrylamide (Compound 166)

Compound 82-2 (0.014 g, 27%) was obtained in the same manner as step 3 of example 17, using compound 82-2.

$^1$H NMR (400 MHz, CDCl$_3$, δ): 7.46-7.30 (m, 5H), 7.12 (d, J=7.6 Hz, 1H), 6.88-6.85 (m, 1H), 6.58 (t, J=8.1 Hz, 1H), 6.32 (d, J=17.1 Hz, 1H), 6.13 (dd, J=17.1, 10.3 Hz, 1H), 5.69 (dd, J=10.3, 1.3 Hz, 1H), 5.19-5.11 (m, 3H), 4.40-4.32 (m, 1H), 4.28-4.18 (m, 1H), 2.26-2.17 (m, 1H), 2.12-2.03 (m, 1H);
ESIMS m/z: [M+H]$^+$ 328,

The following compound was synthesized in accordance with the synthesis method of compound 31.

N-{8-Fluoro-7-(4-fluorophenoxy)chroman-4-yl}acrylamide (Compound 167)

ESIMS m/z: [M+H]$^+$ 332,

Example 83

Step 1

3-Chloro-1-(3-chloro-2,4-dihydrophenyl)propan-1-one (Compound 83-1)

Compound 83-1 (0.30 g, 38%) was obtained in the same manner as step 1 of example 1, using 2-chlorobenzene-1,3-diol.

$^1$H NMR (300 MHz, DMSO-d$_6$, δ): 13.09 (s, 1H), 11.52 (s, 1H), 7.82 (d, J=9.0 Hz, 1H), 6.61 (d, J=8.7 Hz, 1H), 3.92 (t, J=6.3 Hz, 2H), 3.54 (t, J=6.0 Hz, 2H).

Step 2

8-Chloro-7-hydroxychroman-4-one (Compound 83-2)

Compound 83-2 (0.15 g, 60%) was obtained in the same manner as step 2 of example 1, using compound 83-1.

$^1$H NMR (300 MHz, DMSO-d$_6$, δ): 11.29 (s, 1H), 7.58 (d, J=9.0 Hz, 1H), 6.69 (d, J=8.7 Hz, 1H), 4.59 (t, J=6.6 Hz, 2H), 2.71 (t, J=6.6 Hz, 2H).

Step 3

8-Chloro-7-{(4-methoxybenzyl)oxy}chroman-4-one (Compound 83-3)

Compound 83-3 (0.35 g, 73%) was obtained in the same manner as step 1 of example 82, using compound 83-2.

$^1$H NMR (300 MHz, DMSO-d$_6$, δ): 7.71 (d, J=8.7 Hz, 1H), 7.39 (d, J=8.7 Hz, 2H), 7.03-6.95 (m, 3H), 5.22 (s, 2H), 4.62 (t, J=6.3 Hz, 2H), 3.75 (s, 3H), 2.77 (t, J=6.3 Hz, 2H).

Step 4

8-Chloro-7-{(4-methoxybenzyl)oxy}chroman-4-amine (Compound 83-4)

Compound 83-4 (0.33 g, 94%) was obtained in the same manner as step 4 of example 1, using compound 83-3.

$^1$H NMR (300 MHz, DMSO-d$_6$, δ): 7.36 (d, J=8.4 Hz, 2H), 7.22 (d, J=8.4 Hz, 1H), 6.94 (d, J=8.4 Hz, 2H), 6.75 (d,

J=8.4 Hz, 1H), 5.23-5.01 (m, 3H), 4.35-4.18 (m, 2H), 3.74 (s, 3H), 2.08-1.92 (m, 1H), 1.85-1.69 (m, 1H).

Step 5

4-Amino-8-chlorochroman-7-ol hydrochloride (Compound 83-5)

Compound 83-4 (0.33 g, 1.03 mmol) was dissolved in dichloromethane (10 mL), and a 4 mol/L hydrochloric acid solution in dioxane (1.81 mL, 7.24 mmol) was added to the solution. The mixture was stirred at room temperature for 18 hours. The mixture was concentrated under reduced pressure. The solid obtained was washed with dichloromethane to obtain compound 83-5 (0.20 g, 82%).

$^1$H NMR (400 MHz, DMSO-$d_6$, δ): 10.41 (br, 1H), 8.58 (br, 3H), 7.28 (d, J=8.8 Hz, 1H), 6.64 (d, J=8.8 Hz, 1H), 4.41-4.31 (m, 3H), 2.26-2.15 (m, 2H).

Step 6

N-(8-Chloro-7-hydroxychroman-4-yl)acrylamide (Compound 83-6)

Compound 83-6 (0.10 g, 93%) was obtained in the same manner as step 1 of example 76, using compound 83-5.

ESIMS m/z: [M+H]$^+$ 254.

Step 7

N-(8-Chloro-7-[{6-(trifluoromethyl)pyridin-3-yl}oxy]chroman-4-yl)acrylamide (Compound 168)

Compound 168 (0.13 g, 41%) was obtained in the same manner as step 1 of example 3, using compound 83-6.

$^1$H NMR (400 MHz, DMSO-$d_6$, δ): 8.64 (d, J=8.0 Hz, 1H), 8.54 (d, J=2.4 Hz, 1H), 7.90 (d, J=8.8 Hz, 1H), 7.41 (dd, J=8.4, 2.4 Hz, 1H), 7.24 (d, J=8.4 Hz, 1H), 6.92 (d, J=8.4 Hz, 1H), 6.29-6.19 (m, 2H), 5.66 (dd, J=9.6, 2.4 Hz, 1H), 5.17-5.14 (m, 1H), 4.44-4.32 (m, 2H), 2.16-2.12 (m, 1H), 1.99-1.96 (m, 1H);

ESIMS m/z: [M+H]$^+$ 328.

Example 84

Step 1

1-(3-Bromo-2,4-dihydrophenyl)-3-chloropropan-1-one (Compound 84-1)

Compound 84-1 (0.15 g, 21%) was obtained in the same manner as step 1 of example 1, using 2-bromobenzene-1,3-diol.

$^1$H NMR (300 MHz, DMSO-$d_6$, δ): 11.99 (br, 1H), 11.35 (br, 1H), 7.62 (d, J=8.7 Hz, 1H), 6.68 (d, J=8.7 Hz, 1H), 4.59 (t, J=6.3 Hz, 2H), 2.72 (t, J=6.3 Hz, 2H).

Step 2

8-Bromo-7-hydroxychroman-4-one (Compound 84-2)

Compound 84-2 (0.080 g, 62%) was obtained in the same manner as step 2 of example 1, using compound 84-1.

$^1$H NMR (400 MHz, DMSO-$d_6$, δ): 11.34 (s, 1H), 7.62 (d, J=8.8 Hz, 1H), 6.68 (d, J=8.8 Hz, 1H), 4.59 (t, J=6.4 Hz, 2H), 2.72 (t, J=6.4 Hz, 2H).

Step 3

8-Bromo-7-{(4-methoxybenzyl)oxy}chroman-4-one (Compound 84-3)

Compound 84-3 (0.55 g, 73%) was obtained in the same manner as step 1 of example 82, using compound 84-2.

$^1$H NMR (300 MHz, CDCl$_3$, δ): 7.85 (d, J=9.0 Hz, 1H), 7.37 (d, J=8.7 Hz, 2H), 6.93-6.88 (m, 3H), 5.17 (s, 2H), 4.63 (t, J=6.6 Hz, 2H), 3.81 (s, 3H), 2.79 (t, J=6.3 Hz, 2H).

Step 4

8-Bromo-7-{(4-methoxybenzyl)oxy}chroman-4-amine (Compound 84-4)

Compound 84-4 (0.50 g, 90%) was obtained in the same manner as step 4 of example 1, using compound 84-3.

ESIMS m/z: [M+H]$^+$ 364.

Step 5

4-Amino-8-bromochroman-7-ol hydrochloride (Compound 84-5)

Compound 84-5 (0.25 g, 65%) was obtained in the same manner as step 5 of example 83, using compound 84-4.

ESIMS m/z: [M+H]$^+$ 244.

Step 6

N-(8-Bromo-7-hydroxychroman-4-yl)acrylamide (Compound 84-6)

Compound 84-6 (0.15 g, 61%) was obtained in the same manner as step 1 of example 76, using compound 84-5.

$^1$H NMR (400 MHz, DMSO-$d_6$, δ): 10.12 (s, 1H), 8.51 (d, J=8.0 Hz, 1H), 6.93 (d, J=8.8 Hz, 1H), 6.52 (d, J=8.4 Hz, 1H), 6.26-6.11 (m, 2H), 5.61 (dd, J=9.6, 2.4 Hz, 1H), 5.01-4.96 (m, 1H), 4.34-4.29 (m, 1H), 4.22-4.00 (m, 1H), 2.07-1.98 (m, 1H), 1.87-1.83 (m, 1H).

Step 7

N-(8-Bromo-7-[{6-(trifluoromethyl)pyridin-3-yl}oxy]chroman-4-yl)acrylamide (Compound 169)

Compound 169 (0.055 g, 23%) was obtained in the same manner as step 1 of example 3, using compound 84-6.

$^1$H NMR (300 MHz, DMSO-$d_6$, δ): 8.64 (d, J=8.1 Hz, 1H), 8.53 (d, J=2.4 Hz, 1H), 7.90 (d, J=8.7 Hz, 1H), 7.38 (dd, J=8.7, 2.4 Hz, 1H), 7.28 (d, J=8.4 Hz, 1H), 6.90 (d, J=8.4 Hz, 1H), 6.30-6.13 (m, 2H), 5.65 (dd, J=9.3, 2.7 Hz, 1H), 5.18-5.14 (m, 1H), 4.46-4.30 (m, 2H), 2.17-1.95 (m, 2H);

ESIMS m/z: [M+H]$^+$ 443.

Example 85

Step 1

4-Amino-7-[{6-(trifluoromethyl)pyridin-3-yl}oxy]chroman-8-ol hydrobromide (Compound 85-1)

Compound 85-1 was obtained as a crude product in the same manner as step 6 of example 27, using compound 79-2.

ESIMS m/z: [M−16]$^+$ 310.

Step 2

N-(8-Hydroxy-7-[{6-(trifluoromethyl)pyridin-3-yl}oxy]chroman-4-yl)acryl amide (Compound 170)

Compound 170 (0.030 g, 16%) was obtained in the same manner as step 1 of example 76, using compound 85-1.

$^1$H NMR (400 MHz, DMSO-$d_6$, δ): 9.20 (s, 1H), 8.61 (d, J=8.0 Hz, 1H), 8.44 (d, J=2.8 Hz, 1H), 7.85 (d, J=8.8 Hz, 1H), 7.26 (dd, J=8.4, 2.4 Hz, 1H), 6.74-6.69 (m, 2H), 6.27 (dd, J=16.8, 7.2 Hz, 1H), 6.19-6.12 (m, 1H), 5.64 (dd, J=9.6, 2.4 Hz, 1H), 5.11-5.09 (m, 1H), 4.34-4.32 (m, 1H), 4.27-4.25 (m, 1H), 2.16-2.08 (m, 1H), 1.98-1.91 (m, 1H);
ESIMS m/z: [M+H]$^+$ 381.

Example 86

Step 1

4-Amino-8-fluorochroman-7-ol (Compound 86-1)

Compound 82-1 (1.33 g, 4.87 mmol) was dissolved in ethanol (100 mL), and the solution was subjected to a reaction using Pd/C CatCart® (manufactured by ThalesNano Technologies, Inc., 70 mm) in the full H$_2$ mode of H-Cube® at 35° C. The solvent was concentrated under reduced pressure to obtain compound 86-1 as a crude product, which was used as it is in the next reaction.

Step 2

N-(8-Fluoro-7-hydroxychroman-4-yl)acrylamide (Compound 86-2)

Compound 86-2 (0.35 g, 29% over two steps) was obtained in the same manner as step 3 of example 17, using compound 86-1.
$^1$H NMR (400 MHz, CDCl$_3$, δ): 6.83 (d, J=10.1 Hz, 1H), 6.55 (t, J=8.4 Hz, 1H), 6.34 (t, J=8.4 Hz, 1H), 6.13-6.07 (m, 2H), 5.70 (dd, J=10.1, 1.3 Hz, 1H), 5.17-5.13 (m, 1H), 4.38-4.32 (m, 1H), 4.23-4.16 (m, 1H), 2.28-2.18 (m, 1H), 2.15-2.07 (m, 1H);
ESIMS m/z: [M−H]$^+$236.

Step 3

N-(8-Fluoro-7-[{2-(trifluoromethyl)pyrimidin-5-yl}oxy]chroman-4-yl)acryl amide (Compound 171)

Compound 171 (6.00 mg, 7%) was obtained in the same manner as step 3 of example 1, using compound 86-2.
$^1$H NMR (400 MHz, CDCl$_3$, δ): 8.54 (s, 2H), 7.10 (dd, J=8.8, 1.4 Hz, 1H), 6.75 (dd, J=8.8, 7.0 Hz, 1H), 6.40 (dd, J=17.0, 1.4 Hz, 1H), 6.13 (dd, J=17.0, 10.3 Hz, 1H), 5.80-5.75 (m, 2H), 5.34 (dd, J=13.5, 5.8 Hz, 1H), 4.48-4.40 (m, 1H), 4.36-4.27 (m, 1H), 2.37-2.27 (m, 1H), 2.22-2.13 (m, 1H);
ESIMS m/z: [M+H]$^+$ 384.

Example 87

N-(8-Ethoxy-7-[{6-(trifluoromethyl)pyridin-3-yl}oxy]chroman-4-yl)acrylamide (Compound 172)

Compound 170 (0.05 g, 0.131 mmol) was dissolved in DMF (2 mL), and potassium carbonate (0.037 g, 0.263 mmol) and iodoethane (0.050 mL, 0.657 mmol) were added to the solution. The mixture was stirred at 70° C. for one hour. The mixture was cooled to room temperature, and water was added to the mixture. The organic layer was extracted with ethyl acetate, washed with water, dried over anhydrous sodium sulfate, and concentrated under reduced pressure. The residue was purified by silica gel column chromatography (hexane/ethyl acetate=80/20→40/60) to obtain compound 172 (0.030 g, 56%).
$^1$H NMR (400 MHz, DMSO-d$_6$, δ): 8.64 (d, J=8.0 Hz, 1H), 8.50 (d, J=2.7 Hz, 1H), 7.87 (d, J=8.8 Hz, 1H), 7.36 (d, J=8.4 Hz, 1H), 6.98 (d, J=8.4 Hz, 1H), 6.81 (d, J=8.4 Hz, 1H), 6.30-6.15 (m, 2H), 5.66-5.63 (m, 1H), 5.12-5.10 (m, 1H), 4.34-4.22 (m, 2H), 3.93-3.86 (m, 2H), 2.13-2.09 (m, 1H), 1.95-1.92 (m, 1H), 1.03 (t, J=7.2 Hz, 3H);
ESIMS m/z: [M+H]$^+$ 409.

Example 88

Step 1

2-Aminobenzene-1,3-diol (Compound 88-1)

2-Nitrobenzene-1,3-diol (12.0 g, 77.41 mmol) was dissolved in ethanol (100 mL), and 10% palladium carbon (2.0 g) was added to the solution. The mixture was stirred under hydrogen atmosphere at room temperature for 18 hours. The mixture was filtered with Celite®, and the filtrate was concentrated under reduced pressure to obtain compound 88-1 (8.0 g, 83%).
$^1$H NMR (400 MHz, DMSO-d$_6$, δ): 8.83 (br, 2H), 6.25 (br, 2H), 6.23-6.20 (m, 3H).

Step 2

2-(Dimethylamino)benzene-1,3-diol (Compound 88-2)

Compound 88-1 (3.0 g, 24.0 mmol) was dissolved in THF (40 mL), and the solution was cooled to 0° C. Formaldehyde (2.10 mL, 72.0 mmol) and sodium cyanoborohydride (2.20 g, 36.0 mmol) were added to the solution, and the mixture was stirred at room temperature for 18 hours. Water (50 mL) was added to the mixture. The organic layer was extracted with ethyl acetate, washed with water, dried over anhydrous sodium sulfate, and concentrated under reduced pressure. The residue was purified by silica gel column chromatography (hexane/ethyl acetate=90/10→70/30) to obtain compound 88-2 (1.80 g, 38%).
$^1$H NMR (300 MHz, DMSO-d$_6$, δ): 9.44 (br, 2H), 6.82 (t, J=8.1 Hz, 1H), 6.29 (d, J=8.1 Hz, 2H), 2.77 (s, 6H).

Step 3

3-Chloro-1-{3-(dimethylamino)-2,4-dihydrophenyl}propan-1-one (Compound 88-3)

Compound 88-3 (0.92 g, 33%) was obtained in the same manner as step 1 of example 1, using compound 88-2.
ESIMS m/z: [M+H]$^+$ 244.

Step 4

8-(Dimethylamino)-7-hydroxychroman-4-one (Compound 88-4)

Compound 88-4 (0.35 g, 46%) was obtained in the same manner as step 2 of example 1, using compound 88-3.
$^1$H NMR (400 MHz, DMSO-d$_6$, δ): 9.49 (br, 1H), 7.47 (d, J=8.4 Hz, 1H), 6.52 (d, J=8.4 Hz, 1H), 4.52 (t, J=6.0 Hz, 2H), 2.68-2.67 (m, 8H).

Step 5

8-(Dimethylamino)-7-{(4-methoxybenzyl)oxy}chroman-4-one (Compound 88-5)

Compound 88-5 (0.30 g, 54%) was obtained in the same manner as step 1 of example 82, using compound 88-4.
$^1$H NMR (300 MHz, DMSO-d$_6$, δ): 7.51 (d, J=8.7 Hz, 1H), 7.39 (d, J=8.4 Hz, 2H), 6.96 (d, J=8.4 Hz, 2H), 6.83 (d, J=9.0 Hz, 1H), 5.10 (s, 2H), 4.49 (t, J=6.3 Hz, 2H), 3.75 (s, 3H), 2.70-2.67 (m, 8H).

Step 6

7-{(4-Methoxybenzyl)oxy}-N⁸,N⁸-dimethylchromane-4,8-diamine (Compound 88-6)

Compound 88-6 (0.22 g, 73%) was obtained in the same manner as step 4 of example 1, using compound 88-5.

¹H NMR (300 MHz, DMSO-$d_6$, δ): 7.36 (d, J=8.4 Hz, 2H), 6.95-6.92 (m, 3H), 6.56 (d, J=8.4 Hz, 1H), 4.96 (s, 2H), 4.23-4.10 (m, 2H), 3.81-3.78 (m, 1H), 3.74 (s, 3H), 2.64 (s, 6H), 1.95-1.89 (m, 1H), 1.68-1.63 (m, 1H).

Step 7

4-Amino-8-(dimethylamino)chroman-7-ol hydrochloride (Compound 88-7)

Compound 88-7 (0.10 g, 65%) was obtained in the same manner as step 5 of example 83, using compound 88-6.

ESIMS m/z: [M+H]⁺ 209.

Step 8

4-Acrylanide-8-(dimethylamino)chroman-7-yl acrylate (Compound 88-8)

Compound 88-8 (0.10 g, 65%) was obtained in the same manner as step 1 of example 76, using compound 88-7.

ESIMS m/z: [M+H]⁺ 317.

Step 9

N-{8-(Dimethylamino)-7-hydroxychroman-4-yl}acrylamide (Compound 88-9)

Compound 88-8 (0.12 g, 0.38 mmol) was dissolved in methanol (5 mL), and potassium carbonate (0.10 g, 0.75 mmol) were added to the solution. The mixture was stirred at 80° C. for one hour. The mixture was left to cool to room temperature. Water (20 mL) was added to the mixture. The organic layer was extracted with ethyl acetate, dried over anhydrous sodium sulfate, and concentrated under reduced pressure to obtain compound 88-9 (0.085 g, 85%).

¹H NMR (300 MHz, DMSO-$d_6$, δ): 8.52 (d, J=8.0 Hz, 1H), 8.35 (br, 1H), 7.22 (d, J=8.8 Hz, 1H), 6.76 (d, J=9.2 Hz, 1H), 6.25 (dd, J=17.2, 10.0 Hz, 1H), 6.13 (dd, J=17.2, 2.8 Hz, 1H), 5.59 (dd, J=9.6, 2.4 Hz, 1H), 4.95-4.91 (m, 1H), 4.28-4.11 (m, 2H), 2.65 (s, 6H), 2.08-1.96 (m, 1H), 1.87-1.81 (m, 1H).

Step 10

N-{8-(Dimethylamino)-7-[{6-(trifluoromethyl)pyridin-3-yl}oxy]chroman-4-yl}acrylamide (Compound 173)

Compound 173 (0.019 g, 15%) was obtained in the same manner as step 1 of example 3, using compound 88-9.

¹H NMR (400 MHz, DMSO-$d_6$, δ): 8.40 (d, J=2.4 Hz, 1H), 7.58 (d, J=8.8 Hz, 1H), 7.22 (dd, J=8.4, 2.4 Hz, 1H), 6.98 (d, J=8.4 Hz, 1H), 6.57 (d, J=8.4 Hz, 1H), 6.36 (dd, J=16.8, 1.2 Hz, 1H), 6.11 (dd, J=16.8, 10.0 Hz, 1H), 5.82 (d, J=7.2 Hz, 1H), 5.72 (dd, J=10.0, 0.8 Hz, 1H), 5.26-5.21 (m, 1H), 4.42-4.37 (m, 1H), 4.25-4.19 (m, 1H), 2.65 (s, 6H), 2.31-2.23 (m, 1H), 2.17-2.09 (m, 1H);

ESIMS m/z: [M+H]⁺ 408.

Example 89

Step 1

4-(4-Chlorophenoxy)-3-methoxybenzonitrile (Compound 89-1)

Compound 89-1 (0.50 g, 58%) was obtained in the same manner as step 2 of example 50, using commercially available 4-fluoro-3-methoxybenzonitrile.

¹H NMR (400 MHz, DMSO-$d_6$, δ): 7.67 (d, J=2.0 Hz, 1H), 7.46-7.41 (m, 3H), 7.11 (d, J=8.4 Hz, 1H), 6.99 (d, J=8.8 Hz, 2H), 3.83 (s, 3H).

Step 2

4-(4-Chlorophenoxy)-3-hydroxybenzonitrile (Compound 89-2)

Compound 89-2 (0.40 g, 85%) was obtained in the same manner as step 1 of example 19, using compound 89-1.

¹H NMR (400 MHz, DMSO-$d_6$, δ): 10.46 (s, 1H), 7.42 (d, J=9.2 Hz, 2H), 7.32-7.31 (m, 2H), 7.09 (d, J=8.0 Hz, 1H), 6.98 (d, J=8.8 Hz, 2H).

Step 3

3-(Allyloxy)-4-(4-chlorophenoxy)benzonitrile (Compound 89-3)

Compound 89-2 (1.00 g, 4.08 mmol) was dissolved in DMF (10 mL), and potassium carbonate (1.12 g, 8.16 mmol) and allyl chloride (0.40 mL, 4.89 mmol) were added to the solution. The mixture was stirred at 80° C. for one hour. The mixture was cooled to room temperature, and water was added to the mixture. The organic layer was extracted with tert-butyl methyl ether, dried over anhydrous sodium sulfate, and concentrated under reduced pressure. The residue was purified by silica gel column chromatography (hexane/ethyl acetate=100/0→80/20) to obtain compound 89-3 (1.00 g, 86%).

¹H NMR (400 MHz, DMSO-$d_6$, δ): 7.67 (d, J=1.8 Hz, 1H), 7.43-7.40 (m, 3H), 7.16 (d, J=8.4 Hz, 1H), 7.00 (d, J=9.0 Hz, 2H), 5.97-5.84 (m, 1H), 5.25-5.17 (m, 2H), 4.65 (d, J=5.1 Hz, 2H).

Step 4

2-Allyl-4-(4-chlorophenoxy)-3-hydroxybenzonitrile (Compound 89-4)

Compound 89-3 (0.50 g, 1.75 mmol) was stirred using a microwave reactor at 180° C. for one hour. The mixture was cooled to room temperature, and ethyl acetate was added to the mixture. The organic layer was washed with water, dried over anhydrous sodium sulfate, and concentrated under reduced pressure to obtain compound 89-4 (0.45 g, 90%).

¹H NMR (400 MHz, DMSO-$d_6$, δ): 9.99 (s, 1H), 7.46 (d, J=9.2 Hz, 2H), 7.26 (d, J=8.4 Hz, 1H), 7.08 (d, J=9.2 Hz, 2H), 6.85 (d, J=8.4 Hz, 1H), 5.99-5.89 (m, 1H), 5.07-4.98 (m, 2H), 3.55 (d, J=6.4 Hz, 2H).

Step 5

2-Allyl-6-(4-chlorophenoxy)-3-cyanophenyl acetate (Compound 89-5)

Compound 89-4 (0.50 g, 1.75 mmol) was dissolved in dichloromethane (10 mL), and triethylamine (0.50 mL, 3.50 mmol) and acetic anhydride (0.35 mL, 3.50 mmol) were added to the solution. The mixture was stirred at room temperature for 2 hours. Dichloromethane was added to the mixture. The organic layer was washed with a saturated aqueous sodium hydrogen carbonate solution, dried over anhydrous sodium sulfate, and concentrated under reduced pressure. The residue was purified by silica gel column chromatography (hexane/ethyl acetate=100/0→90/10) to obtain compound 89-5 (0.45 g, 78%).

$^1$H NMR (400 MHz, DMSO-$d_6$, δ): 7.74 (d, J=8.8 Hz, 1H), 7.50 (d, J=8.8 Hz, 2H), 7.10 (d, J=8.8 Hz, 2H), 6.96 (d, J=8.8 Hz, 1H), 5.88-5.78 (m, 1H), 5.11-5.04 (m, 2H), 3.52 (d, J=6.4 Hz, 2H), 2.30 (s, 3H).

Step 6

6-(4-Chlorophenoxy)-3-cyano-2-(oxiran-2-ylmethyl) phenyl acetate (Compound 89-6)

Compound 89-5 (0.40 g, 1.22 mmol) was dissolved in dichloromethane (10 mL), and m-chloroperoxybenzoic acid (0.45 g, 1.83 mmol) was added to the solution. The mixture was stirred at room temperature for 24 hours. Dichloromethane was added to the mixture. The organic layer was washed with a 4 mol/L aqueous sodium hydroxide solution and a saturated aqueous sodium sulfate solution, dried over anhydrous sodium sulfate, and concentrated under reduced pressure. The residue was purified by silica gel column chromatography (hexane/ethyl acetate=100/0→80/20) to obtain compound 89-6 (0.35 g, 74%).

$^1$H NMR (400 MHz, DMSO-$d_6$, δ): 7.75 (d, J=8.8 Hz, 1H), 7.51 (d, J=9.2 Hz, 2H), 7.11 (d, J=9.2 Hz, 2H), 6.98 (d, J=8.4 Hz, 1H), 3.12-3.04 (m, 3H), 2.76-2.74 (m, 2H), 2.33 (s, 3H).

Step 7

1-Chloro-3-{3-(4-chlorophenoxy)-6-cyano-2-hydroxyphenyl}propan-2-yl acetate (Compound 89-7)

Compound 89-6 (6.00 g, 17.49 mmol) was dissolved in dioxane (50 mL), and a 20/a hydrochloric acid solution in dioxane (15.96 mL, 87.46 mmol) was added to the solution. The mixture was stirred at room temperature for 72 hours. Water was added to the mixture. The organic layer was extracted with ethyl acetate, dried over anhydrous sodium sulfate, and concentrated under reduced pressure. The residue was purified by silica gel column chromatography (hexane/ethyl acetate=90/10→80/20) to obtain compound 89-7 (4.70 g, 70%).

$^1$H NMR (300 MHz, DMSO-$d_6$, δ): 10.19 (s, 1H), 7.45 (d, J=9.0 Hz, 2H), 7.24 (d, J=8.4 Hz, 1H), 7.05 (d, J=8.7 Hz, 2H), 6.88 (d, J=8.4 Hz, 1H), 5.40-5.35 (m, 1H), 4.04-3.92 (m, 1H), 3.82-3.66 (m, 1H), 3.24-3.03 (m, 2H), 1.99 (s, 3H).

Step 8

8-(4-Chlorophenoxy)-5-cyanochroman-3-yl acetate (Compound 89-8)

Compound 89-7 (0.24 g, 0.63 mmol) was dissolved in DMF (3.0 mL), and potassium carbonate (0.10 g, 0.76 mmol) was added to the solution. The mixture was stirred at room temperature for one hour. Water was added to the mixture. The organic layer was extracted with tert-butyl methyl ether, dried over anhydrous sodium sulfate, and concentrated under reduced pressure. The residue was purified by silica gel column chromatography (hexane/ethyl acetate=100/0→80/20) to obtain compound 89-8 (0.16 g, 75%).

$^1$H NMR (400 MHz, DMSO-$d_6$, δ): 7.45-7.42 (m, 3H), 7.03-6.97 (m, 3H), 5.32-5.30 (m, 1H), 4.32-4.16 (m, 2H), 3.38-3.33 (m, 1H), 2.99-2.94 (m, 1H), 2.02 (s, 3H).

Step 9

5-(Aminomethyl)-8-(4-chlorophenoxy)chroman-3-yl acetate (Compound 89-9)

Compound 89-9 (0.12 g) was obtained as a crude product in the same manner as step 3 of example 15, using compound 89-8.

ESIMS m/z: [M+H]$^+$ 348.

Step 10

5-(Acrylamidemethyl)-8-(4-chlorophenoxy)chroman-3-yl acetate (Compound 174)

Compound 174 (0.09 g, 71% over two steps) was obtained in the same manner as step 1 of example 76, using compound 89-9.

$^1$H NMR (300 MHz, DMSO-$d_6$, δ): 8.48 (t, J=5.4 Hz, 1H), 7.34 (d, J=9.0 Hz, 2H), 6.94 (d, J=8.4 Hz, 1H), 6.87-6.83 (m, 3H), 6.30 (dd, J=17.1, 10.2 Hz, 1H), 6.13 (dd, J=17.1, 2.1 Hz, 1H), 5.63 (dd, J=9.9, 2.1 Hz, 1H), 5.25 (br, 1H), 4.32-4.26 (m, 2H), 4.15-4.01 (m, 2H), 3.15-3.07 (m, 1H), 2.84-2.73 (m, 1H), 2.01 (s, 3H);

ESIMS m/z: [M+H]$^+$ 402.

Step 11

N-[{8-(4-Chlorophenoxy)-3-hydroxychroman-5-yl}methyl]acrylamide (Compound 175)

Compound 174 (0.27 g, 0.66 mmol) was dissolved in THF (2 mL), methanol (2 mL), and water (2 mL), and sodium hydroxide (0.04 g, 0.99 mmol) was added to the solution. The mixture was stirred at room temperature for 2 hours. The mixture was concentrated under reduced pressure. Water and a 2 mol/L aqueous hydrochloric acid solution were added to the residue. The mixture was extracted with dichloromethane, dried over anhydrous sodium sulfate, and concentrated under reduced pressure. The residue was purified by silica gel column chromatography (hexane/ethyl acetate=100/0→80/20) to obtain compound 175 (0.12 g, 46%).

$^1$H NMR (400 MHz, DMSO-$d_6$, δ): 8.45 (t, J=5.6 Hz, 1H), 7.33 (d, J=9.2 Hz, 2H), 6.89 (d, J=8.0 Hz, 1H), 6.83-6.81 (m, 3H), 6.30 (dd, J=17.2, 10.4 Hz, 1H), 6.13 (dd, J=17.2, 2.4 Hz, 1H), 5.62 (dd, J=10.0, 2.0 Hz, 1H), 5.17 (d, J=4.0 Hz, 1H), 4.28 (d, J=5.6 Hz, 2H), 4.03-3.96 (m, 2H), 3.76-3.72 (m, 1H), 2.97-2.92 (m, 1H), 2.60-2.56 (m, 1H);

ESIMS m/z: [M+H]$^+$ 360.

Example 90

Step 1

8-(4-Chlorophenoxy)-3-hydroxychromane-5-carbonitrile (Compound 90-1)

Compound 90-1 (0.30 g, 68%) was obtained in the same manner as step 11 of example 89, using compound 89-8.

$^1$H NMR (400 MHz, DMSO-$d_6$, δ): 7.41 (d, J=8.8 Hz, 2H), 7.37 (d, J=8.4 Hz, 1H), 6.99 (d, J=8.8 Hz, 2H), 6.94 (d, J=8.4 Hz, 1H), 5.30 (d, J=3.6 Hz, 1H), 4.17-4.00 (m, 2H), 3.99-3.96 (m, 1H), 3.17-3.11 (m, 1H), 2.82-2.77 (m, 1H).

Step 2

8-(4-Chlorophenoxy)-2H-chromene-5-carbonitrile (Compound 90-2)

Compound 90-1 (0.25 g, 0.83 mmol) was dissolved in toluene (5.0 mL), and methyl N-(triethylammoniumsulfonyl)carbamate (0.39 g, 1.65 mmol) was added to the solution. The mixture was stirred at 100° C. for 3 hours. The mixture was cooled to 0° C., and sodium hydride (0.074 g, 1.63 mm ol) was added to the mixture. The mixture was stirred at 100° C. for 3 hours. The mixture was cooled to 0° C., and water was added to the mixture. The organic layer was extracted with ethyl acetate, dried over anhydrous sodium sulfate, and concentrated under reduced pressure. The residue was purified by silica gel column chromatography (hexane/ethyl acetate=80/20→50/50) to obtain compound 90-2 (0.075 g, 32%).

$^1$H NMR (300 MHz, DMSO-$d_6$, δ): 7.43-7.36 (m, 3H), 7.04-6.99 (m, 3H), 6.66 (d, J=10.2 Hz, 1H), 6.27-6.22 (m, 1H), 4.87-4.86 (m, 2H).

Step 3

{8(4-Chlorophenoxy)chroman-5-yl}methanamine (Compound 90-3)

Compound 90-3 (0.025 g) was obtained as a crude product in the same manner as step 3 of example 15, using compound 90-2.

ESIMS m/z: [M−16]$^+$ 273.

Step 4

N-[{8-(4-Chlorophenoxy)chroman-5-yl}methyl]acrylamide (Compound 176)

Compound 176 (0.025 g, 31% over two steps) was obtained in the same manner as step 5 of example 1, using compound 90-3.

$^1$H NMR (400 MHz, DMSO-$d_6$, δ): 8.44 (br, 1H), 7.32 (d, J=8.0 Hz, 2H), 6.89-6.80 (m, 4H), 6.30 (dd, J=17.6, 10.4 Hz, 1H), 6.15-6.11 (m, 1H), 5.63-5.61 (m, 1H), 4.29 (d, J=3.2 Hz, 2H), 4.03 (br, 2H), 2.72 (br, 2H), 1.92 (br, 2H);

ESIMS m/z: [M+H]$^+$ 344.

The following compound was synthesized in accordance with the synthesis method of compound 152.

N-[{6-(4-Chlorophenoxy)chroman-4-yl}methyl]acrylamide (Compound 177)

ESIMS m/z: [M+H]$^+$ 344.
ESIMS m/z: [M+H]$^+$ 397.

Example 91

Step 1

2-Methoxy-8-{4-(trifluoromethyl)phenoxy}-7,8-dihydroquinolin-5(6H)-one (Compound 91-1)

Compound 37-2 (0.20 g, 0.59 mmol) was dissolved in methanol (0.6 mL), and sodium methoxide (37.9 mg, 0.70 mmol) was added to the solution. The mixture was stirred at 60° C. overnight. A saturated aqueous sodium bicarbonate solution was added to the mixture. The organic layer was extracted with ethyl acetate, washed with saturated saline, dried over anhydrous magnesium sulfate, and concentrated under reduced pressure to obtain compound 91-1 (0.20 g) as a crude product, which was used as it is in the next reaction.

ESIMS m/z: [M+H]$^+$ 338.

Step 2

2-Methoxy-8-{4-(trifluoromethyl)phenoxy}-5,6,7,8-tetrahydroquinolin-5-amine (Compound 91-2)

Compound 91-2 (0.23 g) was obtained as a crude product in the same manner as step 2 of example 3, using compound 91-1, and used as it is in the next reaction.

ESIMS m/z: [M+H]$^+$ 339.

Step 3 cis-N-[2-Methoxy-8-{4-(trifluoromethyl)phenoxy}-5,6,7,8-tetrahydroquinolin-5-yl]acrylamide (Compound 179)

Compound 179 (4.70 mg, 2.1% in three stages) was obtained in the same manner as step 1 of example 76, using compound 91-2.

$^1$H NMR (400 MHz, CDCl$_3$, δ): 7.56 (d, J=8.5 Hz, 3H), 7.28 (d, J=7.4 Hz, 2H), 6.71 (d, J=8.5 Hz, 1H), 6.38 (dd, J=16.9, 1.3 Hz, 1H), 6.13 (dd, J=16.9, 10.2 Hz, 1H), 5.75 (br, 1H), 5.74 (dd, J=10.2, 1.3 Hz, 1H), 5.38-5.32 (m, 2H), 3.80 (s, 3H), 2.36-2.29 (m, 1H), 2.17-2.09 (m, 3H).

ESIMS m/z: [M+H]$^+$ 393.

Example 92

Step 1

2-[{2-(Dimethylamino)ethyl}(methyl)amino]-8-{4-(trifluoromethyl)phenoxy}-7,8-dihydroquinolin-5(6H)-one (Compound 92-1)

Compound 37-2 (0.10 g, 0.29 mmol) was dissolved in DMF (1.5 mL), and N1,N1,N2-trimethylethane-1,2-diamine (44.9 mg, 0.44 mmol) was added to the solution. The mixture was stirred at 80° C. for 3 hours. The mixture was cooled to room temperature, and concentrated under reduced pressure. The residue was purified by aminosilica gel column chromatography (hexane/ethyl acetate=70/30→40/60) to obtain compound 92-1 (88.4 ng, 74%).

$^1$H NMR (400 MHz, CDCl$_3$, δ): 8.07 (d, J=9.0 Hz, 1H), 7.54 (d, J=8.5 Hz, 2H), 7.25 (d, J=8.5 Hz, 2H), 6.52 (d, J=9.0 Hz, 1H), 5.45 (dd, J=5.4, 3.6 Hz, 1H), 3.64-3.63 (m, 2H), 3.07 (s, 3H), 3.04-2.95 (m, 1H), 2.60 (ddd, J=17.4, 6.2, 5.0 Hz, 1H), 2.52-2.36 (m, 4H), 2.20 (s, 6H).

ESIMS m/z: [M+H]$^+$ 408.

Step 2

N2-{2-(Dimethylamino)ethyl}-N2-methyl-8-{4-(trifluoromethyl)phenoxy}-5,6,7,8-tetrahydroquinoline-2,5-diamine (Compound 92-2)

Compound 92-2 was obtained as a crude product in the same manner as step 2 of example 17, using compound 92-1 (88.4 mg, 0.22 mmol), and used as it is in the next reaction.

ESIMS m/z: [M+H]$^+$ 409.

Step 3 cis-N-(2-[{2-(Dimethylamino)ethyl}(methyl)amino]-8-{4-(trifluoromethyl)phenoxy}-5,6,7,8-tetrahydroquinolin-5-yl)acrylamide (Compound 180)

Compound 180 (10.2 mg, 10% over two steps) was obtained in the same manner as step 3 of example 17, using compound 92-2.

$^1$H NMR (400 MHz, CDCl$_3$, δ): 7.54 (d, J=9.0 Hz, 2H), 7.41 (d, J=8.5 Hz, 1H), 7.25 (d, J=8.5 Hz, 2H), 6.47 (d, J=9.0 Hz, 1H), 6.35 (dd, J=17.0, 1.2 Hz, 1H), 6.11 (dd, J=17.0, 10.3 Hz, 1H), 5.72 (br, 1H), 5.71 (dd, J=10.3, 1.2 Hz, 1H), 5.30-5.24 (m, 2H), 3.62-3.59 (m, 1H), 3.54-3.47 (m, 1H), 2.97 (s, 3H), 2.37-2.03 (m, 6H), 2.18 (s, 6H).
ESIMS m/z: [M+H]$^+$ 463.

Example 93

Step 1

2-Chloro-8-{(5,6-dichloropyridin-3-yl)oxy}-7,8-dihydro-6H-spiro[quinoline-5,2'-[1,3]dioxolane] (Compound 93-1)

Compound 93-1 (0.20 g) was obtained as a crude product in the same manner as step 4 of example 33, using compound 33-3 (0.10 g, 0.41 mmol) and 5,6-dichloropyridin-3-ol (70.0 mg, 0.41 mmol), and used as it is in the next reaction.
$^1$H NMR (300 MHz, DMSO-d$_6$, δ): 8.13 (d, J=2.7 Hz, 1H), 7.82 (d, J=8.4 Hz, 1H), 7.67 (d, J=2.7 Hz, 1H), 7.34 (d, J=8.4 Hz, 1H), 5.30 (t, J=3.6 Hz, 1H), 4.28-4.04 (m, 4H), 2.35-2.22 (m, 3H), 2.03-2.00 (m, 1H).

Step 2

2-Chloro-8-{(5,6-dichloropyridin-3-yl)oxy}-7,8-dihydroquinolin-5(6H)-one (Compound 93-2)

Compound 93-2 (0.18 g) was obtained as a crude product in the same manner as step 5 of example 33, using compound 93-1, and used as it is in the next reaction.
$^1$H NMR (300 MHz, DMSO-d$_6$, δ): 8.28 (d, J=8.4 Hz, 1H), 8.19 (d, J=2.4 Hz, 1H), 7.76 (d, J=2.7 Hz, 1H), 7.47 (d, J=8.4 Hz, 1H), 5.15 (t, J=3.6 Hz, 1H), 3.15-3.03 (m, 1H), 2.77-2.45 (m, 3H).

Step 3

2-Chloro-8-{(5,6-dichloropyridin-3-yl)oxy}-5,6,7,8-tetrahydroquinolin-5-amine (Compound 93-3)

Compound 93-3 (50.0 mg, 35% in three stages) was obtained in the same manner as step 4 of example 1, using compound 93-2.
$^1$H NMR (400 MHz, DMSO-d$_6$, δ): 8.23-8.22 (m, 1H), 8.16 (d, J=8.4 Hz, 0.7H), 8.10-8.09 (m, 1H), 8.00 (d, J=8.4 Hz, 0.3H), 7.53-7.47 (m, 1H), 5.63-5.62 (m, 0.3H), 5.60-5.56 (m, 0.7H), 3.98-3.95 (m, 0.3H), 3.83-3.78 (m, 0.7H), 2.41-2.21 (m, 3H), 2.18-2.04 (m, 1H).

Step 4 cis-N-[2-Chloro-8-{(5,6-dichloropyridin-3-yl)oxy}-5,6,7,8-tetrahydroquinolin-5-yl]acrylamide (Compound 181)

Compound 181 (0.22 g, 40%) was obtained in the same manner as step 5 of example 1, using compound 93-3 (0.48 mg, 0.14 mmol),
$^1$H NMR (300 MHz, CDCl3, δ): 8.14 (d, J=3.0 Hz, 1H), 7.74 (d, J=2.4 Hz, 1H), 7.70 (d, J=8.1 Hz, 1H), 7.31 (d, J=8.4 Hz, 1H), 6.41 (dd, J=16.8, 1.2 Hz, 1H), 6.16 (dd, J=17.1, 10.2 Hz, 1H), 5.82-5.76 (m, 2H), 5.43-5.31 (m, 2H), 2.42-2.37 (m, 1H), 2.31-2.13 (m, 3H).
ESIMS m/z: [M+H]$^+$ 400.

Example 94

Step 1

5-Oxo-8-{4-(trifluoromethyl)phenoxy}-5,6,7,8-tetrahydroquinoline-2-carbonitrile (Compound 94-1)

Compound 94-1 (65.2 mg, 75%) was obtained in the same manner as step 1 of example 54, using compound 37-2 (90.0 mg, 0.26 mmol).
$^1$H NMR (400 MHz, CDCl$_3$, δ): 8.50 (d, J=7.7 Hz, 1H), 7.85 (d, J=7.7 Hz, 1H), 7.60 (d, J=9.0 Hz, 2H), 7.25 (d, J=9.0 Hz, 2H), 5.70 (t, J=3.4 Hz, 1H), 3.21 (ddd, J=18.1, 13.1, 4.8 Hz, 1H), 2.80 (dt, J=18.1, 4.8 Hz, 1H), 2.72-2.65 (m, 1H), 2.49-2.40 (m, 1H).
ESIMS m/z: [M+H]$^+$ 333.

Step 2

5-Amino-8-{4-(trifluoromethyl)phenoxy}-5,6,7,8-tetrahydroquinoline-2-carbonitrile (Compound 94-2)

Compound 94-2 was obtained as a crude product in the same manner as step 2 of example 3, using compound 94-1 (65.2 mg, 0.20 mmol), and used as it is in the next reaction.

Step 3 cis-N-[2-Cyano-8-{4-(trifluoromethyl)phenoxy}-5,6,7,8-tetrahydroquinolin-5-yl]acrylamide (Compound 182)

Compound 182 (20.4 mg, 27% over two steps) was obtained in the same manner as step 1 of example 76, using compound 94-2.
$^1$H NMR (400 MHz, CDCl3, δ): 7.90 (dd, J=8.1, 1.0 Hz, 1H), 7.66 (d, J=8.1 Hz, 1H), 7.59 (d, J=8.5 Hz, 2H), 7.20 (d, J=8.5 Hz, 2H), 6.44 (dd, J=16.7, 1.0 Hz, 1H), 6.17 (dd, J=16.7, 10.3 Hz, 1H), 5.87 (d, J=9.0 Hz, 1H), 5.81 (dd, J=10.3, 1.0 Hz, 1H), 5.51-5.44 (m, 2H), 2.50-2.46 (m, 1H), 2.24-2.05 (m, 3H).
ESIMS m/z: [M+H]$^+$ 388.

Example 95

N-[(5R*,8S*)-2-Methyl-8-{4-(trifluoromethyl)phenoxy}-5,6,7,8-tetrahydroquinolin-5-yl]acrylamide (Compound 183)

Compound 242 (30.0 mg, 0.076 mmol) was dissolved in toluene (1.0 mL), and added to the solution were palladium acetate (1.7 mg, 7.60 µmol), trimethylboroxine (38.0 mg, 0.30 mmol), dicyclohexyl(2',6'-diisopropoxy-[1,1'-biphenyl]-2-yl)phosphate (7.1 mg, 15.0 µmol), cesium carbonate (0.74 g, 0.23 mmol), and water (0.3 mL). The mixture was stirred at 100° C. overnight. The mixture was cooled to room temperature, and added to the mixture were palladium acetate (1.7 mg, 7.60 µmol), trimethylboroxine (19.0 mg, 0.15 mmol), dicyclohexyl(2',6'-diisopropoxy-[1,1'-biphenyl]-2-yl)phosphate (7.1 mg, 15.0 µmol), and cesium carbonate (0.74 g, 0.23 mmol). The mixture was again stirred at 100° C. for 1.5 hours. The mixture was cooled to room temperature and filtered with Presep ((R); diatomaceous earth, granular type M, 4.5 g/25 mL). The filtrate was concentrated under reduced pressure. The residue was purified by silica gel column chromatography (heptane/ethyl acetate=80/20→40/60) to obtain compound 183 (30.0 mg, quantitatively).

¹H NMR (400 MHz, CDCl3, δ): 7.60 (d, J=7.8 Hz, 1H), 7.56 (d, J=8.5 Hz, 2H), 7.20 (d, J=8.5 Hz, 2H), 7.14 (d, J=7.8 Hz, 1H), 6.40 (dd, J=17.1, 1.3 Hz, 1H), 6.15 (dd, J=17.1, 10.3 Hz, 1H), 5.80 (br, 1H), 5.75 (dd, J=10.3, 1.3 Hz, 1H), 5.45 (t, J=2.5 Hz, 1H), 5.38 (dd, J=15.7, 9.0 Hz, 1H), 2.54 (s, 3H), 2.44-2.38 (m, 1H), 2.18-2.11 (m, 1H), 2.07-2.02 (m, 2H).

ESIMS m/z: [M+H]⁺ 377.

Example 96 cis-N-[2-Methyl-8-{4-(trifluoromethyl)phenoxy}-5,6,7,8-tetrahydroquinolin-5-yl]acrylamide (Compound 184)

Compound 184 (18.2 mg, 64%) was obtained in the same manner as step 1 of example 95, using compound 76 (30.0 mg, 0.076 mmol).

¹H NMR (400 MHz, CDCl3, δ): 7.60 (d, J=8.1 Hz, 1H), 7.56 (d, J=8.5 Hz, 2H), 7.20 (d, J=8.5 Hz, 2H), 7.15 (d, J=8.1 Hz, 1H), 6.40 (dd, J=17.0, 1.3 Hz, 1H), 6.15 (dd, J=17.0, 10.3 Hz, 1H), 5.79 (br, 1H), 5.75 (dd, J=10.3, 1.3 Hz, 1H), 5.45 (t, J=2.7 Hz, 1H), 5.38 (dd, J=16.2, 9.0 Hz, 1H), 2.54 (s, 3H), 2.44-2.39 (m, 1H), 2.16-2.14 (m, 1H), 2.08-2.01 (n, 2H).

ESIMS m/z: [M+H]⁺ 377.

Example 97 cis-N-[2-Cyclopropyl-8-{4-(trifluoromethyl)phenoxy}-5,6,7,8-tetrahydroquinolin-5-yl]acrylamide (Compound 185)

Compound 185 (17.8 mg, 59%) was obtained in the same manner as step 1 of example 95, using compound 76 (30.0 mg, 0.076 mmol) and potassium cyclopropyltrifluoroborate (55.9 mg, 0.38 mmol).

¹H NMR (400 MHz, CDCl3, δ): 7.56 (d, J=10.4 Hz, 2H), 7.53 (d, J=8.1 Hz, 1H), 7.27 (d, J=10.4 Hz, 2H), 7.09 (d, J=8.1 Hz, 1H), 6.38 (dd, J=16.9, 1.3 Hz, 1H), 6.14 (dd, J=16.9, 10.3 Hz, 1H), 5.79 (br, 1H), 5.74 (dd, 3=10.3, 1.3 Hz, 1H), 5.37-5.33 (m, 2H), 2.36-2.35 (m, 1H), 2.20-2.14 (m, 1H), 2.12-2.06 (m, 2H), 2.01-1.94 (m, 1H), 1.02-0.88 (m, 3H), 0.86-0.79 (m, 1H).

ESIMS m/z: [M+H]⁺ 403,
Step 1 cis-N-[2-ethyl-8-{4-(trifluoromethyl)phenoxy}-5,6,7,8-tetrahydroquinolin-5-yl]acrylamide (Compound 186)

Compound 186 (7.5 mg, 25%) was obtained in the same manner as step 1 of example 95, using compound 76 (30.0 mg, 0.076 mmol) and ethylboronic acid (5.6 mg, 0.076 mmol).

¹H NMR (400 MHz, CDCl3, δ): 7.63 (d, J=8.1 Hz, 1H), 7.56 (d, J=8.5 Hz, 2H), 7.25 (d, J=8.5 Hz, 2H), 7.15 (d, J=8.1 Hz, 1H), 6.39 (dd, J=16.9, 1.3 Hz, 1H), 6.15 (dd, J=16.9, 10.1 Hz, 1H), 5.80 (d, J=9.4 Hz, 1H), 5.75 (dd, J=10.1, 1.3 Hz, 1H), 5.46 (t, J=2.5 Hz, 1H), 5.39 (dd, J=16.2, 9.9 Hz, 1H), 2.80 (q, J=7.6 Hz, 2H), 2.44-2.39 (m, 1H), 2.20-2.14 (m, 1H), 2.10-2.05 (m, 2H), 1.26 (t, J=7.6 Hz, 3H).

ESIMS m/z: [M+H]⁺ 391.

Example 99

Step 1

2-Chloro-8-{3-fluoro-4-(trifluoromethyl)phenoxy}-7,8-dihydro-6H-spiro[quinoline-5,2'-[1,3]dioxolane] (Compound 99-1)

Compound 99-1 (0.13 g, 38%) was obtained in the same manner as step 4 of example 33, using compound 33-3 (0.20 g, 0.83 mmol) and 3-fluoro-4-(trifluoromethyl)phenol (0.18 g, 0.99 mmol).

¹H NMR (400 MHz, CDCl₃, δ): 7.84 (d, J=8.5 Hz, 1H), 7.51 (t, 3=8.1 Hz, 1H), 7.36 (d, J=8.5 Hz, 1H), 6.92 (d, J=10.3 Hz, 2H), 5.39 (t, J=3.4 Hz, 1H), 4.29-4.14 (m, 3H), 4.11-4.08 (m, 1H), 2.32-2.27 (m, 3H), 2.01-1.96 (m, 1H).
ESIMS m/z: [M+H]⁺ 404.
Step 2

2-Chloro-8-{3-fluoro-4-(trifluoromethyl)phenoxy}-7,8-dihydroquinolin-5(6H)-one (Compound 99-2)

Compound 99-2 (0.11 g, quantitatively) was obtained in the same manner as step 5 of example 33, using compound 99-1 (0.13 g, 0.32 mmol).

¹H NMR (400 MHz, CDCl3, δ): 8.31 (d, J=8.1 Hz, 1H), 7.54 (t, J=8.5 Hz, 1H), 7.49 (d, J=8.1 Hz, 1H), 7.04-7.01 (m, 2H), 5.59 (t, J=3.6 Hz, 1H), 3.11 (ddd, J=17.5, 12.1, 4.9 Hz, 1H), 2.74 (dt, J=17.5, 4.0 Hz, 1H), 2.64-2.60 (m, 1H), 2.48-2.39 (m, 1H).

ESIMS m/z: [M+H]⁺ 360.
Step 3

2-Chloro-8-{3-fluoro-4-(trifluoromethyl)phenoxy}-5,6,7,8-tetrahydroquinolin-5-amine (Compound 99-3)

Compound 99-3 (0.11 g) was obtained as a crude product in the same manner as step 2 of example 3, using compound 99-2 (0.11 g, 0.32 mmol), and used as it is in the next reaction.

ESIMS m/z: [M+H]⁺ 361.
Step 4 cis-N-[2-Chloro-8-{3-fluoro-4-(trifluoromethyl)phenoxy}-5,6,7,8-tetrahydroquinolin-5-yl]acrylamide (Compound 187)

Compound 187 (33.3 mg, 25% over two steps) was obtained in the same manner as step 3 of example 17, using compound 99-3.

¹H NMR (400 MHz, CDCl3, δ): 7.71 (d, J=8.1 Hz, 1H), 7.53 (t, J=8.3 Hz, 1H), 7.32 (d, J=8.1 Hz, 1H), 6.96-6.93 (m, 2H), 6.42 (dd, J=16.9, 1.3 Hz, 1H), 6.16 (dd, J=16.9, 10.3 Hz, 1H), 5.79 (dd, J=10.3, 1.3 Hz, 1H), 5.77 (d, J=9.0 Hz, 1H), 5.42-5.38 (m, 2H), 2.42-2.41 (m, 1H), 2.19-2.17 (m, 1H), 2.08-2.02 (m, 2H).

ESIMS m/z: [M+H]⁺ 415.

Example 100

Step 1

2-Ethoxy-8-{4-(trifluoromethyl)phenoxy}-7,8-dihydro-6H-spiro[quinoline-5,2'-[1,3]dioxolane] (Compound 100-1)

Compound 37-1 (0.20 g, 0.52 mmol) was dissolved in ethanol (5 mL), and a 20% sodium ethoxide solution in ethanol (0.41 mL, 1.04 mmol) was added to the solution. The mixture was stirred at 80° C. for a week. Water was added to the mixture. The organic layer was extracted with ethyl acetate, washed with saturated saline, dried over anhydrous magnesium sulfate, and concentrated under reduced pressure to obtain compound 100-1 (0.13 g) as a crude product, which was used as it is in the next reaction.

$^1$H NMR (400 MHz, CDCl$_3$, δ): 7.71 (d, J=8.5 Hz, 1H), 7.54 (d, J=8.8 Hz, 2H), 7.23 (d, J=8.8 Hz, 2H), 6.70 (d, J=8.5 Hz, 1H), 5.37 (t, J=4.0 Hz, 1H), 4.27-4.05 (m, 6H), 2.35-2.28 (m, 3H), 2.02-1.98 (m, 1H), 1.23 (t, J=7.2 Hz, 3H).

ESIMS m/z: [M+H]$^+$ 396.

Step 2

2-Methoxy-8-{4-(trifluoromethyl)phenoxy}-7,8-dihydroquinolin-5(6H)-one (Compound 100-2)

Compound 100-2 (0.12 g) was obtained as a crude product in the same manner as step 5 of example 33, using compound 100-1 (0.13 g, 0.33 mmol), and used as it is in the next reaction.

ESIMS m/z: [M+H]$^+$ 352.

Step 3

2-Ethoxy-8-{4-(trifluoromethyl)phenoxy}-5,6,7,8-tetrahydroquinolin-5-amine (Compound 100-3)

Compound 100-3 (71.0 mg) was obtained as a crude product in the same manner as step 4 of example 1, using compound 100-2, and used as it is in the next reaction.

ESIMS m/z: [M+H]$^+$ 353.

Step 4 cis-N-[2-Ethoxy-8-{4-(trifluoromethyl)phenoxy}-5,6,7,8-tetrahydroquinolin-5-yl]acrylamide (Compound 188)

Compound 188 (25.6 mg, 31% in four stages) was obtained in the same manner as step 3 of example 17, using compound 100-3.

$^1$H NMR (400 MHz, CDCl3, δ): 7.57-7.54 (m, 3H), 7.26 (d, J=8.5 Hz, 2H), 6.68 (d, J=8.5 Hz, 1H), 6.38 (dd, J=17.1, 1.3 Hz, 1H), 6.13 (dd, J=17.1, 10.3 Hz, 1H), 5.74 (dd, J=10.3, 1.3 Hz, 1H), 5.73 (br, 1H), 5.36 (t, J=3.6 Hz, 1H), 5.30 (dd, J=8.8, 6.1 Hz, 1H), 4.22-4.16 (m, 2H), 2.34-2.26 (m, 1H), 2.15-2.07 (m, 3H), 1.27 (t, J=7.2 Hz, 3H).

ESIMS m/z: [M+H]$^+$ 407.

Example 101

Step 1

2-Chloro-8-[{5-(trifluoromethyl)pyridin-2-yl}oxy]-7,8-dihydro-6H-spiro[quinoline-5,2'-[1,3]dioxolane] (Compound 101-1)

Compound 101-1 (0.15 g, 47%) was obtained as a crude product in the same manner as step 4 of example 33, using compound 33-3 (0.20 g, 0.83 mmol) and 5-(trifluoromethyl)pyridin-2-ol (0.16 g, 0.99 mmol), and used as it is in the next reaction.

$^1$H NMR (400 MHz, CDCl$_3$, δ): 8.47 (s, 1H), 7.83 (d, J=8.1 Hz, 1H), 7.78 (dd, J=8.6, 2.5 Hz, 1H), 7.34 (d, J=8.1 Hz, 1H), 6.83 (d, J=8.6 Hz, 1H), 6.30 (t, J=4.5 Hz, 1H), 4.28-4.09 (m, 4H), 2.41-2.36 (m, 2H), 2.24-2.19 (m, 1H), 2.01-1.97 (m, 1H).

ESIMS m/z: [M+H]$^+$ 387.

Step 2

2-Chloro-8-[{5-(trifluoromethyl)pyridin-2-yl}oxy]-7,8-dihydroquinolin-5(6H)-one (Compound 101-2)

Compound 101-2 (0.13 g, 97%) was obtained in the same manner as step 5 of example 33, using compound 101-1 (0.15 g, 0.39 mmol).

$^1$H NMR (400 MHz, CDCl$_3$, δ): 8.49 (dd, J=1.8, 0.9 Hz, 1H), 8.31 (d, J=8.3 Hz, 1H), 7.83 (dd, J=8.8, 1.8 Hz, 1H), 7.47 (d, J=8.3 Hz, 1H), 6.87 (d, J=8.8 Hz, 1H), 6.54 (dd, J=4.9, 3.6 Hz, 1H), 3.01-2.97 (m, 1H), 2.77-2.62 (m, 2H), 2.53-2.45 (m, 1H).

ESIMS m/z: [M+H]$^+$ 343.

Step 3

2-Chloro-8-[{5-(trifluoromethyl)pyridin-2-yl}oxy]-5,6,7,8-tetrahydroquinolin-5-amine (Compound 101-3)

Compound 101-3 (0.14 g) was obtained as a crude product in the same manner as step 2 of example 3, using compound 101-2 (0.13 g, 0.38 mmol), and used as it is in the next reaction.

ESIMS m/z: [M+H]$^+$ 344.

Step 4 cis-N-(2-Chloro-8-[{5-(trifluoromethyl)pyridin-2-yl}oxy]-5,6,7,8-tetrahydroquinolin-5-yl)acrylamide (Compound 189)

Compound 189 (25.7 mg, 17%) was obtained in the same manner as step 3 of example 17, using compound 101-3.

$^1$H NMR (400 MHz, CDCl3, δ): 8.47 (s, 1H), 7.79 (dd, J=8.8, 2.5 Hz, 1H), 7.69 (d, J=8.5 Hz, 1H), 7.30 (d, J=8.8 Hz, 1H), 6.81 (d, J=8.5 Hz, 1H), 6.41 (dd, J=16.9, 1.0 Hz, 1H), 6.25 (t, J=3.6 Hz, 1H), 6.15 (dd, J=16.9, 10.3 Hz, 1H), 5.82 (d, J=9.0 Hz, 1H), 5.77 (dd, J=10.3, 1.0 Hz, 1H), 5.39 (td, J=9.5, 5.5 Hz, 1H), 2.49-2.45 (m, 1H), 2.20-2.11 (m, 2H), 2.03-1.94 (m, 1H).

ESIMS m/z: [M+H]$^+$ 398.

Example 102

Step 1

3-Chloro-7,8-dihydroquinolin-5(6H)-one (Compound 102-1)

To a cyclohexane-1,3-dione (0.824 g, 7.35 mmol) solution in THF (20 mL), a 1 mol/L potassium tert-butoxide/tetrahydrofuran solution (8.00 mL, 8.00 mmol) was added dropwise at 0° C. After the mixture was stirred at room temperature for 30 minutes, 2-chloro-N,N-dimethylaminotrimethynium hexafluorophosphate (1.50 g, 4.89 mmol) was added to the mixture. The mixture was stirred at 50° C. for one hour. Next, ammonium acetate (1.70 g, 22.05 mmol) was added to the mixture, and the mixture was stirred at 100° C. for 1.5 hours. After the reaction liquid was concentrated under reduced pressure, ethyl acetate was added to the residue. The mixture was washed with water and saturated saline and dried over anhydrous magnesium sulfate. The residue was purified by silica gel column chromatography (heptane/ethyl acetate=100/0→70/30) to obtain compound 102-1 (257.4 mg, 29%).

¹H NMR (400 MHz, CDCl₃, δ): 8.64 (d, J=2.7 Hz, 1H), 8.24 (d, J=2.7 Hz, 1H), 3.14 (t, J=6.3 Hz, 2H), 2.70 (dd, J=7.2, 5.9 Hz, 2H), 2.21 (m, 2H).

Step 2

3-Chloro-5,6,7,8-tetrahydroquinolin-5-ol (Compound 102-2)

To a methanol solution (10 mL) of compound 102-1 (322.6 mg, 1.776 mmol), sodium borohydride (160.0 mg, 4.230 mmol) was added in small portions at 0° C. After the mixture was stirred at room temperature for 15 minutes, water was added to the mixture. The mixture was extracted with chloroform. After the extracted liquid was dried over anhydrous magnesium sulfate, the residue was purified by silica gel column chromatography (heptane/ethyl acetate=100/0→50/50) to obtain compound 102-2 (296.7 mg, 91%).

¹H NMR (400 MHz, CDCl₃, δ): 8.25 (d, J=2.7 Hz, 1H), 7.80 (d, J=2.7 Hz, 1H), 4.74 (m, 1H), 4.62 (br d, J=6.3 Hz, 1H), 2.83 (m, 2H), 2.05 (m, 2H), 1.80 (m, 2H);

ESIMS m/z: [M+H]⁺ 184, 186.

Step 3

5-Azido-3-chloro-5,6,7,8-tetrahydroquinoline (Compound 102-3)

Compound 102-2 (296.7 mg, 1.616 mmol) was dissolved in a toluene (8 mL)-tetrahydrofuran (2 mL) mixed solvent, and 1,8-diazabicyclo[5.4.0]-7-undecene (0.370 mL, 2.455 mmol) and diphenylphosphorylazide (0.530 mL, 2.459 mmol) were sequentially added to the mixture. The mixture was stirred at room temperature for 2 hours. The reaction liquid was concentrated under reduced pressure. A saturated aqueous sodium hydrogen carbonate was added to the residue, and the mixture was extracted with chloroform. The extracted liquid was washed with saturated saline and dried over anhydrous magnesium sulfate. The residue was purified by silica gel column chromatography (heptane/ethyl acetate=100/0→80/20) to obtain compound 102-3 (337.0 mg, 100%).

¹H NMR (400 MHz, CDCl₃, δ): 8.43 (d, J=2.3 Hz, 1H), 7.64 (d, J=2.3 Hz, 1H), 4.54 (m, 1H), 2.91 (m, 2H), 2.07 (m, 2H), 2.00-1.83 (m, 2H);

ESIMS m/z: [M+H]⁺ 209, 211.

Step 4 tert-Butyl (3-chloro-5,6,7,8-tetrahydroquinolin-5-yl) carbamate (Compound 102-4)

In ethyl acetate (15 mL), 10% palladium/carbon (140 mg) was suspended, and the suspension was stirred under hydrogen atmosphere for 15 minutes. Compound 102-3 (447.8 mg, 2.146 m mol) and an ethyl acetate solution (2 mL) of di-tert-butyl dicarbonate (937.0 mg, 4.290 mm ol) were added to the suspension. The mixture was stirred at room temperature for 30 minutes. The reaction liquid was filtered using Celite®. The residue obtained by concentrating the filtrate was purified by silica gel column chromatography (heptane/ethyl acetate=100/0→50/50) to obtain compound 102-4 (296.1 mg, 49%).

¹H NMR (400 MHz, CDCl₃, δ): 8.37 (br, 1H), 7.66 (br, 1H), 4.87 (br, 1H), 4.77 (br, 1H), 2.89 (m, 2H), 2.10 (m, 1H), 1.94 (m, 2H), 1.71 (m, 1H), 1.50 (s, 9H);

ESIMS m/z: [M+H]⁺ 283, 285.

Step 5 tert-Butyl (3-chloro-8-hydroxy-5,6,7,8-tetrahydroquinolin-5-yl)carbamate (Compound 102-5)

3-Chloroperoxybenzoic acid (300.0 mg, 1.738 mmol) was added to a methylene chloride solution (5 mL) of compound 102-4 (296.1 mg, 1.047 mmol). The mixture was stirred at room temperature for one hour. A saturated aqueous sodium hydrogen carbonate solution was added to the reaction liquid, and the mixture was extracted with chloroform. The extracted liquid was washed with a saturated aqueous sodium thiosulfate solution and dried over anhydrous magnesium sulfate to obtain N-oxide (373.2 mg). N-Oxide obtained was dissolved in methylene chloride (3 mL). Trifluoroacetic anhydride (0.400 mL, 2.83 nmol) was added to the solution at 0° C. The mixture was stirred at 0° C. for 20 minutes, and then at room temperature for 16 hours. A 4 N aqueous sodium hydroxide solution (2 mL, 8 mmol) was added to the mixture at 0° C. The mixture was stirred at room temperature for 40 minutes. A 2 N aqueous hydrochloric acid solution was added dropwise to the mixture under cooling at 0° C. pH was adjusted to 2-3, and the mixture was extracted with chloroform. The extracted liquid was washed with saturated saline and dried over anhydrous magnesium sulfate. The residue was purified by silica gel column chromatography (chloroform/methanol=100/0→85/15) to obtain compound 102-5 (122.5 mg, 39%).

¹H NMR (400 MHz, CDCl₃, cis/trans-diastereomer mixture, δ): 8.10 (d, J=1.8 Hz, 1H), 7.68 (d, J=1.8 Hz, 1H), 7.65 (br, 1H), 7.31 (br, 1H), 5.54 (d, J=9.1 Hz, 1H), 5.38 (d, J=9.5 Hz, 1H), 4.89 (m, 1H), 4.82 (m, 2H), 4.65 (m, 3H), 2.85-2.65 (m, 2H), 2.32 (m, 1H), 2.11-1.95 (m, 3H), 1.81 (m, 1H), 1.68 (m, 1H), 1.49 (s, 18H);

ESIMS m/z: [M+H]⁺ 299, 301.

Step 6 tert-Butyl (3-chloro-8-(4-(trifluoromethyl)phenoxy)-5,6,7,8-tetrahydroquinolin-5-yl) carbamate (Compound 102-6)

To a tetrahydrofuran solution (4 mL) of compound 102-5 (122.5 mg, 0.410 mmol), 4-(trifluoromethyl)phenol (140 mg, 0.864 mmol), triphenylphosphine (250 mg, 0.953 mmol), and a 2.2 mol/L diethyl azodicarboxylate/toluene solution (0.400 mL, 0.880 mmol) were sequentially added. The mixture was stirred at room temperature for 2 hours. After the reaction liquid was concentrated under reduced pressure, the residue was purified by silica gel column chromatography (heptane/ethyl acetate=100/0→70/30) to obtain compound 102-6 (182.0 mg, 100%).

¹H NMR (400 MHz, CDCl₃, cis/trans-diastereo mixture, δ): 8.51 (m, 2H), 7.80 (m, 2H), 7.52 (m, 4H), 7.10 (m, 4H), 5.47 (m, 2H), 5.01-4.85 (m, 3H), 3.75 (m, 1H), 2.38 (m, 2H), 2.21 (m, 2H), 2.12 (m, 1H), 1.99 (m, 2H), 1.85 (m, 1H), 1.52 (s, 9H), 1.50 (s, 9H);

ESIMS m/z: [M+H]⁺ 443, 445.

Step 7

N-((5R*,8S*)-3-Chloro-8-(4-(trifluoromethyl)phenoxy)-5,6,7,8-tetrahydro quinolin-5-yl)acrylamide (Compound 190)

Trifluoroacetic acid (1.0 mL, 12.98 mmol) was added to a methylene chloride solution (2 mL) of compound 102-6 (191.5 mg, 0.432 mmol). The solution was stirred at room temperature for one hour. After the reaction liquid was concentrated under reduced pressure, the residue was dissolved in methylene chloride (2 mL). Triethylamine (0.150 mL, 1.076 mmol) and acryloyl chloride (0.100 mL, 1.231 mmol) were added dropwise to the solution. The mixture was stirred at room temperature for 30 minutes. The reaction liquid was poured onto a 1 N aqueous hydrochloric acid solution and the mixture was extracted with chloroform. The extracted liquid was washed with saturated saline and dried over anhydrous magnesium sulfate. The residue was purified by silica gel column chromatography (heptane/ethyl acetate=100/0→55/45) to obtain compound 190 (cis isomer, 24.8 mg, 15%) and the trans isomer (17.0 mg, 9.9%).

$^1$H NMR (400 MHz, CDCl$_3$, δ): 8.49 (d, J=1.8 Hz, 1H), 7.70 (d, J=1.8 Hz, 1H), 7.56 (d, J=8.6 Hz, 2H), 7.15 (d, J=8.6 Hz, 2H), 6.42 (dd, J=16.8, 1.4 Hz, 1H), 6.19 (dd, J=16.8, 10.4 Hz, 1H), 6.08 (d, J=9.5 Hz, 1H), 5.78 (dd, J=10.4, 1.4 Hz, 1H), 5.47 (br t, J=2.3 Hz, 1H), 5.37 (m, 1H), 2.46-2.35 (m, 1H), 2.18-2.00 (m, 3H);

ESIMS m/z: [M+H]$^+$ 397, 399.

Example 103

Step 1

2-{4-(Trifluoromethyl)phenoxy}-7,8-dihydroquinolin-5(6H)-one (Compound 103-1)

Commercially available 2-chloro-7,8-dihydroquinolin-5 (6H)-one (0.20 g, 1.10 mmol) was dissolved in DMF (5.5 mL), and cesium carbonate (0.72 g, 2.20 mmol) and 4-(trifluoromethyl)phenol (0.72 g, 1.65 nmol) were added to the solution. The mixture was subjected to a reaction at a temperature of 120° C. for 30 minutes using a microwave reactor manufactured by Biotage. Water was added to the mixture. The organic layer was extracted with ethyl acetate, washed with saturated saline, dried over anhydrous magnesium sulfate, and concentrated under reduced pressure. The residue was purified by silica gel column chromatography (heptane/ethyl acetate=90/10→60/40) to obtain compound 103-1 (0.23 g, 68%).

$^1$H NMR (400 MHz, CDCl3, δ): 8.32 (d, J=8.6 Hz, 1H), 7.68 (d, J=8.6 Hz, 2H), 7.29 (d, J=8.6 Hz, 2H), 6.85 (d, J=8.6 Hz, 1H), 2.96 (t, J=6.1 Hz, 2H), 2.65 (t, J=6.6 Hz, 2H), 2.15 (tt, J=6.6, 6.1 Hz, 2H).

ESIMS m/z: [M+H]$^+$ 308.

Step 2

2-{4-(Trifluoromethyl)phenoxy}-5,6,7,8-tetrahydroquinolin-5-amine (Compound 103-2)

Compound 103-2 was obtained as a crude product in the same manner as step 2 of example 3, using compound 103-1 (0.23 g, 0.75 mmol), and used as it is in the next reaction.

ESIMS m/z: [M+H]$^+$ 309.

Step 3

N-[2-{4-(Trifluoromethyl)phenoxy}-5,6,7,8-tetrahydroquinolin-5-yl]acrylamide (Compound 191)

Compound 191 (71.4 mg, 26%) was obtained in the same manner as step 3 of example 17, using compound 103-2.

$^1$H NMR (400 MHz, CDCl3, δ): 7.65 (d, J=8.1 Hz, 1H), 7.62 (d, J=8.7 Hz, 2H), 7.20 (d, J=8.7 Hz, 2H), 6.73 (d, J=8.1 Hz, 1H), 6.37 (dd, J=17.0, 1.1 Hz, 1H), 6.10 (dd, J=17.0, 10.3 Hz, 1H), 5.72 (dd, J=10.3, 1.1 Hz, 1H), 5.70 (d, J=8.5 Hz, 1H), 5.32 (dd, J=14.8, 6.3 Hz, 1H), 2.88-2.73 (m, 2H), 2.12-2.08 (m, 1H), 1.91-1.83 (m, 3H).

ESIMS m/z: [M+H]$^+$ 363.

Example 104

Step 1

5-[(4,4-Difluorocyclohexyl)methoxy]pyridin-3-amine (Compound 192)

Compound 104-1 (78.0 mg, 44%) was obtained in the same manner as step 4 of example 33, using 4,4-difluorocyclohexanemethanol (110 mg, 0.733 mmol) and 3-amino-5-hydroxypiperidine (161 mg, 1.47 mmol).

$^1$H NMR (400 MHz, CDCl$_3$, δ): 7.73 (d, J=1.8 Hz, 2H), 6.52-6.48 (m, 1H), 3.82 (d, J=5.9 Hz, 2H), 3.67 (br, 2H), 2.22-2.08 (m, 2H), 1.99-1.66 (m, 5H), 1.50-1.35 (m, 2H).

ESIMS m/z: [M+H]$^+$ 243.

Step 2

Compound 192 (28.0 mg, yield 29%) was obtained in the same manner as in step 5 of example 1, using compound 104-1 (78.0 mg, 0.322 mmol) obtained in step 1.

$^1$H NMR (400 MHz, CDCl$_3$, δ): 8.09-8.05 (m, 3H), 7.38 (br, 1H), 6.48 (dd, J=16.8, 0.9 Hz, 1H), 6.26 (dd, J=16.8, 10.4 Hz, 1H), 5.85 (dd, J=10.2, 1.1 Hz, 1H), 3.88 (d, J=6.3 Hz, 2H), 2.22-2.09 (m, 2H), 2.01-1.67 (m, 5H), 1.52-1.36 (m, 2H).

ESIMS m/z: [M+H]$^+$ 297.

The following compound was synthesized in accordance with the synthesis method of compound 95.

N-(5-{[4-(Trifluoromethyl)pyrimidin-2-yl]oxy}pyridin-3-yl)acrylamide (Compound 193)

ESIMS m/z: [M+H]$^+$ 311.

The following compound was synthesized in accordance with the synthesis method of compound 192.

N-{5-[(4,4-Difluorocyclohexyl)oxy]pyridin-3-yl}acrylamide (Compound 194)

ESIMS m/z: [M+H]$^+$ 283.

The following compounds were synthesized in accordance with the synthesis method of compound 137.

N-([8-{(4,4-Difluorocyclohexyl)methoxy}quinolin-5-yl]methyl)acrylamide (Compound 195)

ESIMS m/z: [M+H]$^+$ 361.

N-{(8-[{5-(Trifluoromethyl)pyridin-2-yl}oxy]quinolin-5-yl)methyl}acrylamide (Compound 197)

ESIMS r/z: [M+H]$^+$ 374.

N-{(8-[{5-(Trifluoromethyl)pyrazin-2-yl}oxy]quinolin-5-yl)methyl}acrylamide (Compound 198)

ESIMS m/z: [M+H]$^+$ 375.

Example 105

Step 1

8-[{2-(Trifluoromethyl)pyrimidin-5-yl}oxy]quinoline-5-carbonitrile (Compound 105-1)

Compound 105-1 (0.059 g, 66%) was obtained in the same manner as step 2 of example 50, using compound 54-1.

¹H NMR (400 MHz, CDCl₃, δ): 8.99 (dd, J=4.1, 1.8 Hz, 1H), 8.65 (dd, J=8.6, 1.8 Hz, 1H), 8.59 (s, 2H), 8.06 (d, J=8.2 Hz, 1H), 7.74 (dd, J=8.6, 4.1 Hz, 1H), 7.50 (d, J=8.2 Hz, 1H);
ESIMS m/z: [M+H]⁺ 317.
Step 2

(8-[{2-(Trifluoromethyl)pyrimidin-5-yl}oxy]quinolin-5-yl)methanamine (Compound 105-2)

Compound 105-2 (0.063 g) was obtained as a crude product in the same manner as step 2 of example 57, using compound 105-1.
ESIMS m/z: [M+H]⁺ 321.
Step 3

N-{(8-[{2-(Trifluoromethyl)pyrimidin-5-yl}oxy]quinolin-5-yl)methyl}acryl amide (Compound 196)

Compound 196 (0.025 g, 36% over two steps) was obtained in the same manner as step 5 of example 1, using compound 105-2.
¹H NMR (400 MHz, CDCl₃, δ): 8.88 (dd, J=4.3, 1.5 Hz, 1H), 8.54 (dd, 3=8.5, 1.5 Hz, 1H), 8.49 (s, 2H), 7.60-7.54 (m, 2H), 7.47 (d, J=7.6 Hz, 1H), 6.40 (dd, J=17.0, 1.2 Hz, 1H), 6.11 (dd, J=17.0, 10.3 Hz, 1H), 5.87 (br, 1H), 5.74 (dd, J=10.3, 1.2 Hz, 1H), 5.03 (d, J=5.8 Hz, 2H);
ESIMS m/z: [M+H]⁺ 375.

Example 106

Step 1

3-Iodo-8-{4-(trifluoromethyl)phenoxy}quinoline-5-carbonitrile (Compound 106-1)

Compound 59-1 (0.10 g, 0.32 mmol) was dissolved in acetonitrile (5.0 mL), and iodine (0.12 g, 0.48 mmol) and tert-butyl hydroperoxide (0.44 mL, 3.18 mmol) were added to the solution. The mixture was stirred at 80° C. for five days. The mixture was cooled to room temperature, and sodium thiosulfate was added to the mixture. The organic layer was extracted with ethyl acetate, washed with saturated saline, dried over anhydrous magnesium sulfate, and concentrated under reduced pressure. The residue was purified by silica gel column chromatography (heptane/ethyl acetate=80/20→50/50) to obtain compound 106-1 (0.051 g, 36%).
¹H NMR (400 MHz, CDCl₃, δ): 9.21 (d, J=1.8 Hz, 1H), 8.96 (d, J=1.8 Hz, 1H), 7.89 (d, J=8.3 Hz, 1H), 7.72 (d, J=8.1 Hz, 2H), 7.27-7.26 (m, 2H), 7.07 (d, J=8.3 Hz, 1H).
Step 2

3-Methyl-8-{4-(trifluoromethyl)phenoxy}quinoline-5-carbonitrile (Compound 106-2)

Compound 106-1 (0.06 g, 0.14 mmol) was dissolved in toluene (1.0 mL) and water (0.25 mL), and added to the solution were cesium carbonate (0.22 g, 0.68 mmol), trimethylboroxine (0.095 mL, 0.68 mmol), 2-dicyclohexylphosphino-2',6'-diisopropoxy-1,1'-biphenyl (0.013 g, 0.027 mmol), and palladium acetate (0.003 g, 0.014 mmol). The mixture was stirred under argon atmosphere at 100-C for 0.5 hours. The mixture was filtered with Presep ((R); diatomaceous earth, granular type M, 4.5 g/25 mL), and the filtrate was concentrated under reduced pressure. The residue was purified by silica gel column chromatography (heptane/ethyl acetate=80/20→50/50) to obtain compound 106-2 (0.044 g, 98%).
¹H NMR (400 MHz, CDCl₃, δ): 8.93 (s, 1H), 8.34 (s, 1H), 7.86 (d, J=8.1 Hz, 1H), 7.70 (d, J=8.3 Hz, 2H), 7.27-7.26 (m, 2H), 7.00 (d, J=8.1 Hz, 1H), 2.65 (s, 3H).
Step 3

[3-Methyl-8-{4-(trifluoromethyl)phenoxy}quinolin-5-yl]methanamine (Compound 106-3)

Compound 106-3 (0.039 g, 96%) was obtained in the same manner as step 2 of example 57, using compound 106-2.
¹H NMR (400 MHz, CDCl₃, δ): 8.80 (d, J=2.0 Hz, 1H), 8.26 (s, 1H), 7.57 (d, J=8.8 Hz, 2H), 7.46 (d, J=7.8 Hz, 1H), 7.16 (d, J=7.8 Hz, 1H), 7.09 (d, J=8.8 Hz, 2H), 4.31 (s, 2H), 2.57 (s, 3H).
Step 4

N-([3-Methyl-8-{4-(trifluoromethyl)phenoxy}quinolin-5-yl]methyl)acrylamide (Compound 199)

Compound 199 (0.032 g, 80%) was obtained in the same manner as step 3 of example 17, using compound 106-3.
¹H NMR (400 MHz, CDCl₃, δ): 8.80 (d, J=2.0 Hz, 1H), 8.19 (s, 1H), 7.58 (d, J=9.3 Hz, 2H), 7.43 (d, J=7.8 Hz, 1H), 7.11-7.10 (m, 3H), 6.38 (dd, J=17.0, 1.1 Hz, 1H), 6.10 (dd, J=17.0, 10.2 Hz, 1H), 5.80 (br, 1H), 5.71 (dd, J=10.2, 1.1 Hz, 1H), 4.94 (d, J=5.4 Hz, 2H), 2.55 (s, 3H);
ESIMS m/z: [M+H]⁺ 387.

Example 107

Step 1

3-Iodo-8-[{6-(Trifluoromethyl)pyridin-3-yl}oxy]quinoline-5-carbonitrile (Compound 107-1)

Compound 107-1 (0.22 g, 91%) was obtained in the same manner as step 1 of example 106, using compound 62-1.
¹H NMR (400 MHz, CDCl₃, δ): 9.16 (d, J=2.0 Hz, 1H), 8.98 (d, J=2.0 Hz, 1H), 8.57 (d, J=2.5 Hz, 1H), 7.96 (d, J=8.4 Hz, 1H), 7.74 (d, J=8.8 Hz, 1H), 7.52 (dd, J=8.4, 2.5 Hz, 1H), 7.26-7.25 (m, 1H).
Step 2

3-Methyl-8-[{6-(trifluoromethyl)pyridin-3-yl}oxy]quinoline-5-carbonitrile (Compound 107-2)

Compound 107-2 (0.040 g, 90%) was obtained in the same manner as step 2 of example 106, using compound 107-1.
¹H NMR (400 MHz, CDCl₃, δ): 8.89 (d, J=2.4 Hz, 1H), 8.57 (d, J=2.4 Hz, 1H), 8.36 (s, 1H), 7.93 (d, J=8.1 Hz, 1H), 7.73 (d, J=8.7 Hz, 1H), 7.51 (dd, J=8.7, 2.7 Hz, 1H), 7.17 (d, J=8.1 Hz, 1H), 2.65 (s, 3H).
Step 3

(3-Methyl-8-[{6-(trifluoromethyl)pyridin-3-yl}oxy]quinolin-5-yl)methanamine (Compound 107-3)

Compound 107-3 (0.065 g) was obtained as a crude product in the same manner as step 2 of example 57, using compound 107-2.
ESIMS m/z: [M+H]⁺ 334.

Step 4

N-{(3-Methyl-8-[{6-(trifluoromethyl)pyridin-3-yl}oxy]quinolin-5-yl)methyl}acrylamide (Compound 200)

Compound 200 (0.025 g, 54% over two steps) was obtained in the same manner as step 5 of example 1, using compound 107-3.

$^1$H NMR (400 MHz, CDCl$_3$, δ): 8.72 (s, 1H), 8.43 (d, J=2.7 Hz, 1H), 8.20 (s, 1H), 7.59 (d, J=8.5 Hz, 1H), 7.47 (d, J=7.6 Hz, 1H), 7.30 (dd, J=8.5, 2.7 Hz, 1H), 7.21 (d, J=7.6 Hz, 1H), 6.37 (dd, J=17.1, 1.3 Hz, 1H), 6.19 (br, 1H), 6.12 (dd, J=17.1, 10.3 Hz, 1H), 5.70 (d, J=10.3 Hz, 1H), 4.94 (d, J=5.4 Hz, 2H), 2.53 (s, 3H);

ESIMS m/z: [M+H]$^+$ 388.

Example 108

Step 1

5-Bromo-8-fluoro-4-methylquinoline (Compound 108-1)

5-Bromo-2-fluoroaniline (0.20 g, 1.05 mmol) was dissolved in toluene (3.0 mL), and a 6 mol/L aqueous hydrochloric acid solution (0.53 mL, 3.16 mmol) and methyl vinyl ketone (0.17 mL, 2.11 mmol) were added to the solution. The mixture was stirred at 120° C. for 1.5 hours. The mixture was left to cool to room temperature, and water was added to the mixture. The aqueous layer was washed with ethyl acetate. A 2 mol/L aqueous sodium hydroxide solution was added to the aqueous layer, and the aqueous layer was extracted with ethyl acetate, dried over anhydrous magnesium sulfate, and concentrated under reduced pressure. The residue was purified by silica gel column chromatography (heptane/ethyl acetate=90/10→80/20) to obtain compound 108-1 (0.040 g, 16%).

$^1$H NMR (400 MHz, CDCl$_3$, δ): 8.79 (d, J=4.2 Hz, 1H), 7.81 (dd, J=8.3, 5.4 Hz, 1H), 7.34 (d, J=4.2 Hz, 1H), 7.23 (t, J=9.0 Hz, 1H), 3.14 (s, 3H).

Step 2

8-Fluoro-4-methylquinoline-5-carbonitrile (Compound 108-2)

Compound 108-2 (0.047 g, 48%) was obtained in the same manner as step 1 of example 54, using compound 108-1.

$^1$H NMR (400 MHz, CDCl$_3$, δ): 8.90 (d, J=4.4 Hz, 1H), 8.01 (dd, J=8.1, 5.1 Hz, 1H), 7.49-7.42 (m, 2H), 3.12 (s, 3H).

Step 3

4-Methyl-8-{4-(trifluoromethyl)phenoxy}quinoline-5-carbonitrile (Compound 108-3)

Compound 108-3 (0.051 g, 66%) was obtained in the same manner as step 2 of example 50, using compound 108-2.

$^1$H NMR (400 MHz, CDCl$_3$, δ): 8.90 (d, J=4.4 Hz, 1H), 7.93 (d, J=8.3 Hz, 1H), 7.70 (d, J=9.3 Hz, 2H), 7.44 (d, J=4.4 Hz, 1H), 7.26-7.22 (m, 2H), 7.06 (d, J=8.3 Hz, 1H), 3.14 (s, 3H).

Step 4

[4-Methyl-8-{4-(trifluoromethyl)phenoxy}quinolin-5-yl]methanamine (Compound 108-4)

Compound 108-4 (0.043 g) was obtained as a crude product in the same manner as step 2 of example 57, using compound 108-3.

Step 5

N-([4-Methyl-8-{4-(trifluoromethyl)phenoxy}quinolin-5-yl]methyl)acrylamide (Compound 201)

Compound 201 (0.013 g, 22% over two steps) was obtained in the same manner as step 5 of example 1, using compound 108-4.

$^1$H NMR (400 MHz, CDCl$_3$, δ): 8.71 (d, J=4.4 Hz, 1H), 7.57 (d, J=8.8 Hz, 2H), 7.47 (d, J=7.8 Hz, 1H), 7.28-7.24 (m, 1H), 7.16 (d, J=7.8 Hz, 1H), 7.05 (d, J=8.8 Hz, 2H), 6.37 (d, J=17.1 Hz, 1H), 6.12 (dd, J=17.1, 10.2 Hz, 1H), 6.02 (br, 1H), 5.69 (d, J=10.2 Hz, 1H), 5.04 (d, J=4.9 Hz, 2H), 2.92 (s, 3H);

ESIMS m/z: [M+H]$^+$ 387.

Example 109

Step 1

8-[{4-(Trifluoromethyl)phenyl}thio]quinoline-5-carbonitrile (Compound 109-1)

Compound 109-1 (0.40 g, 42%) was obtained in the same manner as step 2 of example 50, using compound 54-1.

ESIMS m/z: [M+H]$^+$ 331.

Step 2

(8-[{4-(Trifluoromethyl)phenyl}thio]quinolin-5-yl)methanamine (Compound 109-2)

Compound 109-2 (0.20 g) was obtained as a crude product in the same manner as step 2 of example 57, using compound 109-1.

ESIMS m/z: [M+H]$^+$ 335.

Step 3

N-{(8-[{4-(Trifluoromethyl)phenyl}thio]quinolin-5-yl)methyl}acrylamide (Compound 202)

Compound 202 (0.10 g, 34% over two steps) was obtained in the same manner as step 1 of example 76, using compound 109-2.

$^1$H NMR (400 MHz, DMSO-d$_6$, δ): 8.96 (dd, J=4.0, 1.6 Hz, 1H), 8.67 (t, J=5.6 Hz, 1H), 8.61 (dd, J=8.8, 1.6 Hz, 1H), 7.76 (d, J=8.0 Hz, 2H), 7.70-7.67 (m, 1H), 7.58 (d, J=8.0 Hz, 2H), 7.47 (d, J=7.6 Hz, 1H), 7.37 (d, J=7.6 Hz, 1H), 6.29-6.22 (m, 1H), 6.17-6.12 (m, 1H), 5.62 (dd, J=10.0, 2.4 Hz, 1H), 4.80 (d, J=5.6 Hz, 2H);

ESIMS m/z: [M+H]$^+$ 389.

Example 110

Step 1

8-[{4-(Trifluoromethyl)phenyl}amino]quinoline-5-carbonitrile (Compound 110-1)

Compound 110-1 (0.25 g, 46%) was obtained in the same manner as step 2 of example 50, using compound 54-1.

ESIMS m/z: [M+H]$^+$ 314.

Step 2

5-(Aminomethyl)-N-{4-(trifluoromethyl)phenyl}quinolin-8-amine (Compound 110-2)

Compound 110-2 (0.20 g) was obtained as a crude product in the same manner as step 2 of example 57, using compound 110-1.

ESIMS m/z: [M+H]⁺ 318.

Step 3

N-{(8-[{4-(Trifluoromethyl)phenyl}amino]quinolin-5-yl)methyl}acrylamide (Compound 203)

Compound 203 (0.020 g, 8% over two steps) was obtained in the same manner as step 1 of example 76, using compound 110-2.

$^1$H NMR (400 MHz, DMSO-d6, δ): 9.13 (s, 1H), 8.92 (d, J=3.9 Hz, 1H), 8.60-8.51 (m, 2H), 7.69-7.46 (m, 7H), 6.30-6.21 (m, 1H), 6.18-6.11 (m, 1H), 6.62 (dd, J=9.6, 2.4 Hz, 1H), 4.75 (d, J=5.4 Hz, 2H);

ESIMS m/z: [M+H]⁺ 372.

Example 111

N-{(8-[{4-(Trifluoromethyl)phenyl}sulfonyl]quinolin-5-yl)methyl}acrylamide (Compound 204)

Compound 202 (0.050 g, 0.12 mmol) was dissolved in dichloroethane (10 mL), and Oxone (0.29 g, 1.93 mmol) was added to the solution. The mixture was stirred at 80° C. for 12 hours. The mixture was cooled to room temperature, and water (10 mL) was added to the mixture. The organic layer was extracted with dichloromethane, dried over anhydrous sodium sulfate, and concentrated under reduced pressure. The residue was purified by silica gel column chromatography (hexane/ethyl acetate=80/20→40/60) to obtain compound 204 (0.050 g, 85%).

$^1$H NMR (300 MHz, DMSO-d6, δ): 8.91 (d, J=3.3 Hz, 1H), 8.80-7.79 (m, 1H), 8.69-8.64 (m, 2H), 8.27 (d, J=7.8 Hz, 2H), 7.93 (d, J=8.1 Hz, 2H), 7.78 (d, J=7.5 Hz, 1H), 7.66 (dd, J=8.4, 4.2 Hz, 1H), 6.33-6.24 (m, 1H), 6.19-6.13 (m, 1H), 5.68-5.64 (m, 1H), 4.90 (d, J=5.7 Hz, 2H);

ESIMS m/z: [M+H]⁺ 421.

Example 112

Step 1

8-[Methyl{4-(trifluoromethyl)phenyl}amino]quinoline-5-carbonitrile (Compound 112-1)

Compound 112-1 (0.12 g, 21%) was obtained in the same manner as step 2 of example 50, using compound 54-1.

$^1$H NMR (400 MHz, CDCl₃, δ): 9.12 (dd, J=4.4, 1.6 Hz, 1H), 8.94 (dd, J=4.4 Hz, 2.0 Hz, 1H), 7.96 (d, J=8.0 Hz, 1H), 7.74-7.71 (m, 1H), 7.62 (d, J=8.0 Hz, 1H), 7.43 (d, J=8.8 Hz, 2H), 6.86 (d, J=8.8 Hz, 2H), 3.58 (s, 3H).

Step 2

5-(Aminomethyl)-N-methyl-N-{4-(trifluoromethyl)phenyl}quinolin-8-amine (Compound 112-2)

Compound 112-2 (0.10 g) was obtained as a crude product in the same manner as step 2 of example 57, using compound 112-1.

ESIMS m/z: [M+H]⁺ 332.

Step 3

N-{(8-[Methyl{4-(trifluoromethyl)phenyl}amino]quinolin-5-yl)methyl}acrylamide (Compound 205)

Compound 205 (0.030 g, 21% over two steps) was obtained in the same manner as step 1 of example 76, using compound 112-2.

$^1$H NMR (400 MHz, CDCl₃, δ): 8.91 (dd, J=4.4, 1.6 Hz, 1H), 8.48 (dd, J=8.8, 1.6 Hz, 1H), 7.59-7.47 (m, 3H), 7.35 (d, J=8.8 Hz, 2H), 6.68 (d, J=8.8 Hz, 2H), 6.39 (dd, J=17.2, 1.2 Hz, 1H), 6.10 (dd, J=16.8, 10.4 Hz, 1H), 5.83-5.82 (m, 1H), 5.72 (dd, J=10.4, 1.2 Hz, 1H), 5.01 (d, J=5.6 Hz, 2H), 3.48 (s, 3H);

ESIMS m/z: [M+H]⁺ 386.

Example 113

Step 1

(5-Bromoquinolin-8-yl){4-(trifluoromethyl)phenyl}methano (Compound 113-1)

Magnesium (turnings) (0.08 g, 3.41 mmol) was dissolved in THF (10 mL), and iodine (10 mg) was added to the solution. The mixture was stirred at room temperature for 5 minutes. 1-Bromo-4-(trifluoromethyl)benzene (0.38 g, 1.70 mmol) was added to the mixture. The mixture was stirred at room temperature for 45 minutes. Thereafter, the mixture was cooled to 0° C., and a THF (5.0 mL) solution of 5-bromoquinoline-8-carboaldehyde (0.20 g, 0.85 mmol) was added to the mixture. The mixture was stirred at 0° C. for 30 minutes. A saturated aqueous ammonium chloride solution was added to the mixture. The organic layer was extracted with ethyl acetate, dried over anhydrous sodium sulfate, and concentrated under reduced pressure. The residue was purified by silica gel column chromatography (hexane/ethyl acetate=90/10→70/30) to obtain compound 113-1 (0.15 g, 46%).

$^1$H NMR (400 MHz, DMSO-d₆, δ): 9.02 (dd, J=4.0, 1.6 Hz, 1H), 8.53 (dd, J=8.8, 1.6 Hz, 1H), 8.03 (d, J=8.0 Hz, 1H), 7.89 (dd, J=8.0 Hz, 1H), 7.73-7.70 (m, 1H), 7.65 (d, J=8.4 Hz, 2H), 7.60 (d, J=8.4 Hz, 2H), 7.00 (d, J=4.4 Hz, 1H), 6.26 (d, J=4.4 Hz, 1H).

Step 2

8-[Hydroxy{4-(trifluoromethyl)phenyl}methyl]quinoline-5-carbonitrile (Compound 113-2)

Compound 113-2 (0.020 g, 58%) was obtained in the same manner as step 1 of example 54, using compound 113-1.

$^1$H NMR (300 MHz, CDCl₃, δ): 8.99 (d, J=3.9 Hz, 1H), 8.61 (d, J=8.4 Hz, 1H), 7.95 (d, J=7.5 Hz, 1H), 7.70-7.65 (m, 1H), 7.63-7.57 (m, 5H), 6.55 (d, J=6.6 Hz, 1H), 6.04 (d, J=6.9 Hz, 1H).

Step 3

{5-(Aminomethyl)quinolin-8-yl}{4-(trifluoromethyl)phenyl}methanol (Compound 113-3)

Compound 113-3 (0.025 g) was obtained as a crude product in the same manner as step 2 of example 57, using compound 113-2.

¹H NMR (300 MHz, DMSO-d6, δ): 8.93 (d, J=3.6 Hz, 1H), 8.59 (d, J=8.4 Hz, 1H), 7.87 (d, J=7.5 Hz, 1H), 7.67-7.53 (m, 6H), 7.01 (br, 1H), 6.17 (br, 1H), 4.18 (s, 2H).

Step 4

N-{(8-[Hydroxy{4-(trifluoromethyl)phenyl}methyl]quinolin-5-yl)methyl}acrylamide (Compound 206)

Compound 206 (0.13 g, 51%) was obtained in the same manner as step 1 of example 76, using compound 113-3.

¹H NMR (400 MHz, DMSO-d6, δ): 8.96 (dd, J=4.0, 1.2 Hz, 1H), 8.61 (t, J=5.6 Hz, 1H), 8.52 (dd, J=8.8, 1.6 Hz, 1H), 7.90 (d, J=7.2 Hz, 1H), 7.66 (d, J=8.0 Hz, 2H), 7.67-7.56 (m, 4H), 7.01 (d, J=4.4 Hz, 1H), 6.27-6.11 (m, 3H), 5.61 (dd, J=10.0, 2.4 Hz, 1H), 4.86-4.72 (m, 2H);

Example 114

Step 1

Triphenyl{4-(trifluoromethyl)benzyl}phosphonium bromide (Compound 114-1)

In toluene (10 mL), 1-(bromomethyl)-4-(trifluoromethyl)benzene (1.00 g, 4.18 mmol) was dissolved, and triphenylphosphine (1.64 g, 6.27 mmol) was added to the solution. The mixture was refluxed for 8 hours. The mixture was cooled to room temperature. The precipitated solid was filtered off and washed with hexane to obtain compound 114-1 (1.75 g, 99%).

ESIMS m/z: [M+H]⁺ 422.

Step 2

(E)-5-Bromo-8-{4-(trifluoromethyl)styryl}quinoline (Compound 114-2)

Compound 114-1 (1.90 g, 4.51 mmol) was dissolved in THF (20 mL), and the mixture was cooled to −78° C. Potassium tert-butoxide (1.01 g, 9.02 mmol) was added to the mixture, and the mixture was stirred under argon atmosphere at −30° C. for 30 minutes. 5-Bromoquinoline-8-carboaldehyde (1.17 g, 4.96 mmol) was added to the mixture. The mixture was stirred at room temperature for one hour. Water (10 mL) was added to the mixture. The organic layer was extracted with ethyl acetate, dried over anhydrous sodium sulfate, and concentrated under reduced pressure. The residue was purified by silica gel column chromatography (hexane/ethyl acetate=80/20→40/60) to obtain compound 114-2 (1.20 g, 70%).

ESIMS m/z: [M+H]⁺ 378.

Step 3

(E)-8-{4-(Trifluoromethyl)styryl}quinoline-5-carbonitrile (Compound 114-3)

Compound 114-3 (0.80 g, 78%) was obtained in the same manner as step 1 of example 54, using compound 114-2.

ESIMS m/z: [M+H]⁺ 325.

Step 4

(E)-[8-{4-(Trifluoromethyl)styryl}quinolin-5-yl]methanamine (Compound 114-4)

Compound 114-4 (0.10 g) was obtained as a crude product in the same manner as step 3 of example 54, using compound 114-3.

ESIMS m/z: [M+H]⁺ 329.

Step 5

(E)-N-([8-{4-(Trifluoromethyl)styryl}quinolin-5-yl]methyl)acrylamide (Compound 207)

Compound 207 (0.040 g, 22% over two steps) was obtained in the same manner as step 1 of example 76, using compound 114-4.

¹H NMR (400 MHz, DMSO-d₆, δ): 8.97 (dd, J=4.0, 1.6 Hz, 1H), 8.65 (t, J=5.2 Hz, 1H), 8.57 (dd, J=8.4, 1.6 Hz, 1H), 7.66-7.63 (m, 1H), 7.58-7.52 (m, 3H), 7.46 (d, J=7.2 Hz, 1H), 7.38-7.35 (m, 3H), 6.90 (d, J=12.4 Hz, 1H), 6.30-6.23 (m, 1H), 6.17-6.12 (m, 1H), 5.62 (dd, J=10.0, 2.4 Hz, 1H), 4.81 (d, J=6.0 Hz, 2H);

ESIMS m/z: [M+H]⁺ 383.

Example 115

N-([8-{4-(Trifluoromethyl)benzoyl}quinolin-5-yl]methyl)acrylamide (Compound 208)

Compound 206 (0.20 g, 0.52 mmol) was dissolved in dichloromethane (10 mL), and pyridinium chlorochromate (0.22 g, 1.03 mmol) was added to the solution. The mixture was stirred at room temperature for 3 hours. The mixture was filtered with Celite®, and the filtrate was washed with dichloromethane (20 mL). The organic layer was concentrated under reduced pressure. The residue was purified by silica gel column chromatography (hexane/ethyl acetate=80/20→20/80) to obtain compound 208 (0.055 g, 24%).

¹H NMR (400 MHz, DMSO-d6, δ): 8.79-8.77 (m, 2H), 8.66 (dd, J=8.4, 1.2 Hz, 1H), 7.88-7.81 (m, 5H), 7.68 (d, J=7.2 Hz, 1H), 7.64-7.61 (m, 1H), 6.31 (dd, J=16.8, 10.0 Hz, 1H), 6.18 (dd, J=17.2, 2.4 Hz, 1H), 5.66 (dd, J=10.0, 2.4 Hz, 1H), 4.92 (d, J=5.6 Hz, 2H);

ESIMS m/z: [M+H]⁺ 385.

Example 116

Step 1

[8-{4-(Trifluoromethyl)phenethyl}quinolin-5-yl]methanamine (Compound 116-1)

Compound 114-4 (0.05 g, 1.15 mmol) was dissolved in ethanol (20 mL), and 10% palladium carbon (0.05 g) was added to the solution. The mixture was stirred under hydrogen atmosphere at room temperature for 2 hours. The mixture was filtered with Celite®. The filtrate was concentrated under reduced pressure to obtain compound 116-1 (0.05 g) as a crude product.

ESIMS m/z: [M+H]⁺ 331.

Step 2

N-([8-{4-(Trifluoromethyl)phenethyl}quinolin-5-yl]methyl)acrylamide (Compound 209)

Compound 209 (0.040 g, 7% over two steps) was obtained in the same manner as step 1 of example 76, using compound 116-1.

¹H NMR (400 MHz, DMSO-d₆, δ): 8.98 (dd, J=4.0, 1.6 Hz, 1H), 8.26 (t, J=5.6 Hz, 1H), 8.52 (dd, J=8.4, 1.6 Hz, 1H), 7.64 (d, J=8.4 Hz, 2H), 7.61-7.56 (m, 2H), 7.49 (d, J=8.0 Hz, 2H), 7.44 (d, J=7.2 Hz, 1H), 6.29-6.23 (m, 1H), 6.17-6.12 (m, 1H), 5.62 (dd, J=10.0, 2.4 Hz, 1H), 4.79 (d, J=5.6 Hz, 2H), 3.51 (t, J=8.4 Hz, 2H), 3.11 (t, J=8.4 Hz, 2H);

ESIMS m/z: [M+H]⁺ 385.

Example 117

Step 1

5-Bromoquinolin-8-amine (Compound 117-1)

Quinolin-8-amine (0.20 g, 1.38 mmol) was dissolved in acetonitrile (20 mL), and N-bromosuccinimide (0.26 g, 1.43 mmol) was added to the solution. The mixture was stirred at room temperature for 30 minutes. Water was added to the mixture. The organic layer was extracted with ethyl acetate, dried over anhydrous sodium sulfate, and concentrated under reduced pressure. The residue was purified by silica gel column chromatography (hexane/ethyl acetate=90/10→70/30) to obtain compound 117-1 (0.15 g, 50%).

$^1$H NMR (300 MHz, DMSO-d$_6$, δ): 8.76 (d, J=3.3 Hz, 1H), 8.42 (d, J=8.1 Hz, 1H), 7.56 (d, J=8.4 Hz, 1H), 7.48 (dd, J=8.4, 4.2 Hz, 1H), 6.80 (d, J=8.1 Hz, 1H), 5.04 (br, 2H).

Step 2

N-(5-Bromoquinolin-8-yl)-4-(trifluoromethyl)benzamide (Compound 117-2)

Compound 117-1 (0.15 g, 1.20 mmol) was dissolved in DMF (5 mL), and added to the solution were O-(7-azabenzotriazol-1-yl)-N,N,N',N'-tetramethyluronium hexafluorophosphate (0.38 g, 1.45 mmol), diisopropylethylamine (0.45 mL, 2.41 mmol), and 4-(trifluoromethyl)benzoic acid (0.34 g, 1.81 mmol). The mixture was stirred at room temperature for 18 hours. Water was added to the mixture. The organic layer was extracted with ethyl acetate, dried over anhydrous sodium sulfate, and concentrated under reduced pressure to obtain compound 117-2 (0.15 g, 57%).

$^1$H NMR (300 MHz, CDCl$_3$, δ): 10.76 (br, 1H), 8.88 (d, J=3.6 Hz, 1H), 8.82 (d, J=8.4 Hz, 1H), 8.58 (d, J=8.4 Hz, 1H), 8.18 (d, J=8.4 Hz, 2H), 7.88 (d, J=8.4 Hz, 1H), 7.83 (d, J=8.4 Hz, 2H), 7.64-7.60 (m, 1H).

Step 3

N-(5-Cyanoquinolin-8-yl)-4-(trifluoromethyl)benzamide (Compound 117-3)

Compound 117-3 (0.52 g, 72%) was obtained in the same manner as step 1 of example 54, using compound 117-2.

ESIMS m/z: [M+H]$^+$ 342.

Step 4

N-{5-(Aminomethyl)quinolin-8-yl}-4-(trifluoromethyl)benzamide (Compound 117-4)

Compound 117-4 (0.09 g) was obtained as a crude product in the same manner as step 2 of example 57, using compound 117-3.

ESIMS m/z: [M+H]$^+$ 346.

Step 5

N-{5-(Acrylamide methyl)quinolin-8-yl}-4-(trifluoromethyl)benzamide (Compound 210)

Compound 210 (0.15 g, 32% over two steps) was obtained in the same manner as step 1 of example 76, using compound 117-4.

$^1$H NMR (300 MHz, DMSO-d6, δ): 10.79 (s, 1H), 9.00 (d, J=3.6 Hz, 1H), 8.67-8.62 (m, 3H), 8.24 (d, J=8.1 Hz, 2H), 8.00 (d, J=7.8 Hz, 2H), 7.76-7.72 (m, 1H), 7.62 (d, J=7.8 Hz, 1H), 6.32-6.13 (m, 2H), 5.63 (dd, J=9.6, 2.1 Hz, 1H), 4.82 (d, J=5.4 Hz, 2H);

ESIMS m/z: [M+H]$^+$ 400.

Example 118

Step 1

8-[Chloro{4-(trifluoromethyl)phenyl}methyl]quinoline-5-carbonitrile (Compound 118-1)

Compound 113-2 (0.28 g, 0.85 mmol) was dissolved in toluene (5 mL), and thionyl chloride (0.53 g, 4.48 mmol) was added to the solution. The mixture was stirred at room temperature for 3 hours. The toluene in the mixture was concentrated under reduced pressure. The residue was purified by silica gel column chromatography (hexane/ethyl acetate=100/0→85/15) to obtain compound 118-1 (0.17 g, 57%).

$^1$H NMR (300 MHz, CDCl$_3$, δ): 9.05 (d, J=3.9 Hz, 1H), 8.56 (d, J=8.4 Hz, 1H), 8.11-8.02 (m, 2H), 7.69-7.64 (m, 4H), 7.57 (d, J=8.1 Hz, 2H).

Step 2

[8-{4-(Trifluoromethyl)benzyl}quinolin-5-yl]methanamine (Compound 118-2)

Compound 118-2 (0.09 g) was obtained as a crude product in the same manner as step 2 of example 57, using compound 118-1.

$^1$H NMR (400 MHz, DMSO-d$_6$, δ): 8.94 (dd, J=4.4, 2.0 Hz, 1H), 8.59 (dd, J=8.4, 1.6 Hz, 1H), 7.63-7.55 (m, 5H), 7.49 (d, J=8.0 Hz, 2H), 4.65 (s, 2H), 4.21 (s, 2H).

Step 3

N-([8-{4-(Trifluoromethyl)benzyl}quinolin-5-yl]methyl)acrylamide (Compound 211)

Compound 211 (0.11 g, 6% over two steps) was obtained in the same manner as step 1 of example 76, using compound 118-2.

$^1$H NMR (400 MHz, DMSO-d6, δ): 8.96 (dd, J=4.0, 1.6 Hz, 1H), 8.62 (br, 1H), 8.52 (dd, J=8.4, 1.6 Hz, 1H), 7.65-7.58 (m, 4H), 7.50-7.48 (m, 3H), 6.24 (dd, J=17.2, 10.0 Hz, 1H), 6.14 (dd, J=17.2, 2.8 Hz, 1H), 5.61 (dd, J=10.0, 2.8 Hz, 1H), 4.79 (d, J=5.60 Hz, 2H), 4.65 (s, 2H);

ESIMS m/z: [M+H]$^+$ 371.

Example 119

Step 1

2-Methyl-8-{4-(trifluoromethyl)phenoxy}quinoline-5-carbonitrile (Compound 119-1)

Compound 119-1 (0.050 g, 89%) was obtained in the same manner as step 2 of example 106, using compound 60-1.

$^1$H NMR (400 MHz, CDCl$_3$, δ): 8.45 (d, J=8.5 Hz, 1H), 7.81 (d, J=8.3 Hz, 1H), 7.70 (d, J=8.5 Hz, 2H), 7.58 (d, J=8.5 Hz, 1H), 7.29-7.24 (m, 2H), 7.01 (d, J=8.3 Hz, 1H), 2.83 (s, 3H).

Step 2

[2-Methyl-8-{4-(trifluoromethyl)phenoxy}quinolin-5-yl]methanamine (Compound 119-2)

Compound 119-2 (0.051 g) was obtained as a crude product in the same manner as step 2 of example 57, using compound 119-1.
ESIMS m/z: [M+H]$^+$ 333.

Step 3

N-([2-Methyl-8-{4-(trifluoromethyl)phenoxy}quinolin-5-yl]methyl)acrylamide (Compound 212)

Compound 212 (0.029 g, 49% over two steps) was obtained in the same manner as step 5 of example 1, using compound 119-2.
$^1$H NMR (400 MHz, CDCl$_3$, δ): 8.33 (d, J=8.5 Hz, 1H), 7.58 (d, J=8.5 Hz, 2H), 7.38 (t, J=8.0 Hz, 2H), 7.11 (dd, J=8.0, 2.7 Hz, 3H), 6.37 (dd, J=16.9, 1.3 Hz, 1H), 6.09 (dd, J=16.9, 10.3 Hz, 1H), 5.85 (br, 1H), 5.70 (dd, J=10.3, 1.3 Hz, 1H), 4.94 (d, J=5.8 Hz, 2H), 2.71 (s, 3H);
ESIMS m/z: [M+H]$^+$ 387.

Example 120

Step 1

2-Hydroxy-8-{4-(trifluoromethyl)phenoxy}quinoline-5-carbonitrile (Compound 120-1)

Compound 60-2 (0.050 g, 0.14 mmol) was dissolved in DMSO (3 mL), and N-hydroxyacetamide (0.022 g, 0.29 mmol) and potassium carbonate (0.059 g, 0.43 mmol) were added to the solution. The mixture was stirred at 80° C. for 2 hours. The mixture was cooled to room temperature, and water was added to the mixture. The organic layer was extracted with ethyl acetate, washed with saturated saline, dried over anhydrous magnesium sulfate, and concentrated under reduced pressure. The residue was purified by silica gel column chromatography (heptane/ethyl acetate=100/0→50/50) to obtain compound 120-1 (0.043 g, 91%).
ESIMS m/z: [M+H]$^+$ 331.

Step 2

5-(Aminomethyl)-8-{4-(trifluoromethyl)phenoxy}quinolin-2-ol (Compound 120-2)

Compound 120-2 (0.045 g) was obtained as a crude product in the same manner as step 2 of example 57, using compound 120-1.

Step 3

N-([2-Hydroxy-8-{4-(trifluoromethyl)phenoxy}quinolin-5-yl]methyl)acrylamide (Compound 213)

Compound 213 (7.0 mg, 13% over two steps) was obtained in the same manner as step 5 of example 1, using compound 120-2.
$^1$H NMR (400 MHz, CDCl$_3$, δ): 8.15 (d, J=9.9 Hz, 1H), 7.65 (d, J=8.5 Hz, 2H), 7.16 (dd, J=7.9, 6.1 Hz, 3H), 7.03 (d, J=8.1 Hz, 1H), 6.77 (d, J=9.9 Hz, 1H), 6.35 (dd, J=17.0, 1.3 Hz, 1H), 6.14 (dd, J=17.0, 10.2 Hz, 1H), 5.70 (dd, J=10.2, 1.3 Hz, 1H), 4.76 (s, 2H);
ESIMS m/z: [M+H]$^+$ 389.

Example 121

Step 1

8-Fluoroquinoline-6-carbonitrile (Compound 121-1)

Compound 121-1 (0.15 g, 83%) was obtained in the same manner as step 1 of example 54, using 6-bromo-8-fluoroquinoline.
$^1$H NMR (400 MHz, CDCl$_3$, δ): 9.13 (dd, J=4.4, 1.6 Hz, 1H), 8.59-8.54 (m, 2H), 8.09 (dd, J=10.4, 1.6 Hz, 1H), 7.82 (dd, J=8.4, 4.0 Hz, 1H).

Step 2

8-{4-(Trifluoromethyl)phenoxy}quinoline-6-carbonitrile (Compound 121-2)

Compound 121-2 (0.16 g, 27%) was obtained in the same manner as step 2 of example 50, using compound 121-1.
ESIMS m/z: [M+H]$^+$ 315.

Step 3

[8-{4-(Trifluoromethyl)phenoxy}quinolin-6-yl]methanamine (Compound 121-3)

Compound 121-3 (0.16 g) was obtained as a crude product in the same manner as step 2 of example 57, using compound 121-2.
ESIMS m/z: [M+H]$^+$ 319.

Step 4

N-([8-{4-(Trifluoromethyl)phenoxy}quinolin-6-yl]methyl)acrylamide (Compound 214)

Compound 214 (0.010 g, 6% over two steps) was obtained in the same manner as step 1 of example 76, using compound 121-3.
$^1$H NMR (400 MHz, CDCl$_3$, δ): 8.91 (dd, J=4.0, 1.6 Hz, 1H), 8.18 (dd, J=8.4, 1.6 Hz, 1H), 7.59-7.57 (m, 3H), 7.49-7.46 (m, 1H), 7.19 (d, J=1.6 Hz, 1H), 7.10 (d, J=8.4 Hz, 2H), 6.33 (dd, J=16.8, 1.2 Hz, 1H), 6.12 (dd, J=16.8, 10.0 Hz, 1H), 5.96 (bs, 1H), 5.72 (dd, J=10.4, 1.6 Hz, 1H), 4.66 (d, J=6.0 Hz, 2H);
ESIMS m/z: [M+H]$^+$ 373.

Example 122

Step 1

4-Bromo-8-{4-(trifluoromethyl)phenoxy}quinoline (Compound 122-1)

Compound 122-1 (0.030 g, 37%) was obtained in the same manner as step 1 of example 3, using 4-bromoquinolin-8-ol.
ESIMS m/z: [M+H]$^+$ 369.

Step 2

8-{4-(Trifluoromethyl)phenoxy}quinoline-4-carbonitrile (Compound 122-2)

Compound 122-2 (0.018 g, 70%) was obtained in the same manner as step 1 of example 54, using compound 122-1.
ESIMS m/z: [M+H]$^+$ 315.

Step 3

[8-{4-(Trifluoromethyl)phenoxy}quinolin-4-yl]methanamine (Compound 122-3)

Compound 122-3 (0.30 g) was obtained as a crude product in the same manner as step 2 of example 57, using compound 122-2.
ESIMS m/z: [M+H]$^+$ 319.

Step 4

N-([8-{4-(Trifluoromethyl)phenoxy}quinolin-4-yl]methyl)acrylamide (Compound 215)

Compound 215 (0.040 g, 11% over two steps) was obtained in the same manner as step 1 of example 76, using compound 122-3.
$^1$H NMR (300 MHz, DMSO-d$_6$, δ): 8.82 (t, J=5.4 Hz 1H), 8.77 (t, J=4.2 Hz, 1H), 8.12 (d, J=8.4 Hz, 1H), 7.27 (t, J=7.8 Hz, 1H), 7.70-7.61 (m, 3H), 7.42 (d, J=4.2 Hz, 1H), 6.98 (d, J=8.4 Hz, 2H), 6.39-6.30 (m, 1H), 6.21-6.15 (m, 1H), 5.68 (dd, J=9.9, 1.8 Hz, 1H), 4.89 (d, J=5.7 Hz, 2H);
ESIMS m/z: [M+H]$^+$ 373.

Example 123

Step 1

5-Fluoroquinoline-8-carbonitrile (Compound 123-1)

Compound 123-1 (0.15 g, 65%) was obtained in the same manner as step 1 of example 54, using 8-bromo-5-fluoroquinoline.
$^1$H NMR (300 MHz, CDCl$_3$, δ): 9.17 (dd, J=4.2, 1.5 Hz, 1H), 8.51 (dd, J=8.4, 1.5 Hz, 1H), 8.11 (dd, J=8.1, 5.7 Hz, 1H), 7.63 (dd, J=8.4, 4.2 Hz, 1H), 7.31 (t, J=8.7 Hz, 1H).

Step 2

5-{4-(Trifluoromethyl)phenoxy}quinoline-8-carbonitrle (Compound 123-2)

Compound 123-2 (0.10 g, 36%) was obtained in the same manner as step 2 of example 50, using compound 123-1.
$^1$H NMR (400 MHz, DMSO-d$_6$, δ): 9.17 (dd, J=4.0, 1.6 Hz, 1H), 8.69 (dd, J=8.8, 2.0 Hz, 1H), 8.03 (d, J=8.0 Hz, 1H), 7.73 (d, J=8.8 Hz, 2H), 7.61 (dd, J=8.4, 4.4 Hz, 1H), 7.25 (d, J=8.8 Hz, 2H), 6.88 (d, J=8.4 Hz, 1H).

Step 3

[5-{4-(Trifluoromethyl)phenoxy}quinolin-8-yl]methanamine (Compound 123-3)

Compound 123-3 (0.060 g) was obtained as a crude product in the same manner as step 2 of example 57, using compound 123-2.
ESIMS m/z: [M+H]$^+$ 319.

Step 4

N-([5-{4-(Trifluoromethyl)phenoxy}quinolin-8-yl]methyl)acrylamide (Compound 216)

Compound 216 (0.010 g, 17% over two steps) was obtained in the same manner as step 1 of example 76, using compound 123-3.
$^1$H NMR (300 MHz, CDCl$_3$, δ): 8.97 (dd, J=3.9, 1.5 Hz, 1H), 8.44 (dd, J=8.7, 1.5 Hz, 1H), 7.72 (d, J=7.8 Hz, 1H), 7.60 (d, J=8.7 Hz, 2H), 7.47 (dd, J=8.4, 4.2 Hz, 1H), 7.10-7.01 (m, 4H), 6.28 (dd, J=16.8, 1.2 Hz, 1H), 6.09 (dd, J=16.8, 10.2 Hz, 1H), 5.61 (dd, J=9.9, 1.2 Hz, 1H), 5.05 (d, J=6.3 Hz, 2H);
ESIMS m/z: [M+H]$^+$ 373.

Example 124

Step 1

8-Bromo-4-chloroquinoline (Compound 124-1)

Phosphorus oxychloride (2.0 mL) was added to 8-bromoquinolin-4-ol (0.10 g, 0.44 mmol) at 0° C., and the solution was stirred at 120° C. for 2 hours. The mixture was cooled to room temperature and added dropwise to ice water (30 mL). The organic layer was extracted with ethyl acetate, dried over anhydrous sodium sulfate, and concentrated under reduced pressure to obtain compound 124-1 (0.070 g, 65%).
$^1$H NMR (400 MHz, CDCl$_3$, δ): 8.93 (d, J=4.8 Hz, 1H), 8.25 (dd, J=8.4, 1.2 Hz, 1H), 8.13 (dd, J=7.2, 1.2 Hz, 1H), 7.58 (d, J=4.8 Hz, 1H), 7.53-7.49 (m, 1H).

Step 2

8-Bromo-4-{4-(trifluoromethyl)phenoxy}quinoline (Compound 124-2)

Compound 124-2 (0.050 g, 33%) was obtained in the same manner as step 2 of example 50, using compound 124-1.
$^1$H NMR (300 MHz, CDCl$_3$, δ): 8.87 (d, J=5.1 Hz, 1H), 8.31 (d, J=8.4 Hz, 1H), 8.13 (d, J=7.5 Hz, 1H), 7.75 (d, J=8.7 Hz, 2H), 7.48-7.42 (m, 1H), 7.29 (d, J=8.4 Hz, 2H), 6.70 (d, J=5.4 Hz, 1H).

Step 3

4-{4-(Trifluoromethyl)phenoxy}quinoline-8-carbonitrile (Compound 124-3)

Compound 124-3 (0.15 g, 58%) was obtained in the same manner as step 1 of example 54, using compound 124-2.
$^1$H NMR (400 MHz, CDCl$_3$, δ): 8.91 (d, J=5.2 Hz, 1H), 8.59 (dd, J=8.4, 1.2 Hz, 1H), 8.20 (dd, J=7.2, 1.6 Hz, 1H), 7.79 (d, J=8.4 Hz, 2H), 7.69-7.65 (m, 1H), 7.32 (d, J=8.4 Hz, 2H), 6.72 (d, J=5.2 Hz, 1H).

Step 4

[4-{4-(Trifluoromethyl)phenoxy}quinolin-8-yl]methanamine (Compound 124-4)

Compound 124-4 (0.27 g) was obtained as a crude product in the same manner as step 2 of example 57, using compound 124-3.
ESIMS m/z: [M+H]$^+$ 319.

Step 5

N-([4-{4-(Trifluoromethyl)phenoxy}quinolin-8-yl]methyl)acrylamide (Compound 217)

Compound 217 (0.050 g, 31% over two steps) was obtained in the same manner as step 1 of example 76, using compound 124-4.
$^1$H NMR (300 MHz, CDCl$_3$, δ): 8.75 (d, J=5.1 Hz, 1H), 8.25 (d, J=8.4 Hz, 1H), 7.83 (d, J=6.9 Hz, 1H), 7.73 (d, J=8.7 Hz, 2H), 7.56-7.51 (m, 1H), 7.30 (dd, J=8.7 Hz, 2H), 7.13

(br, 1H), 6.68 (d, J=5.1 Hz, 1H), 6.27 (d, J=16.5 Hz, 1H), 6.09 (dd, J=17.1, 10.2 Hz, 1H), 5.59 (d, J=10.2 Hz, 1H), 5.07 (d, J=6.3 Hz, 2H);
ESIMS m/z: [M+H]$^+$ 373.

Example 125

Step 1

4-{4-(Trifluoromethyl)phenoxy}quinoline-2-carbonitrile (Compound 125-1)

Compound 125-1 (0.30 g, 60%) was obtained in the same manner as step 2 of example 50, using 4-chloroquinoline-2-carbonitrile.
$^1$H NMR (400 MHz, CDCl$_3$, δ): 8.38 (dd, J=8.4, 0.8 Hz, 1H), 8.18 (d, J=8.8 Hz, 1H), 7.92-7.88 (m, 1H), 7.81 (d, J=8.4 Hz, 2H), 7.77-7.73 (m, 1H), 7.32 (d, J=8.4 Hz, 2H), 6.85 (s, 1H).
Step 2

[4-{4-(Trifluoromethyl)phenoxy}quinolin-2-yl]methanamine (Compound 125-2)

Compound 125-2 (0.12 g) was obtained as a crude product in the same manner as step 2 of example 57, using compound 125-1.
ESIMS m/z: [M+H]$^+$ 319,
Step 3

N-([4-{4-(Trifluoromethyl)phenoxy}quinolin-2-yl]methyl)acrylamide (Compound 218)

Compound 218 (0.030 g, 13% over two steps) was obtained in the same manner as step 1 of example 76, using compound 125-2.
$^1$H NMR (400 MHz, CDCl$_3$, δ): 8.27 (dd, J=8.4, 0.8 Hz, 1H), 8.07 (d, J=8.4 Hz, 1H), 7.81-7.73 (m, 3H), 7.61-7.57 (m, 1H), 7.28-7.23 (m, 3H), 6.57 (s, 1H), 6.36-6.24 (m, 2H), 5.69 (dd, J=9.6, 2.4 Hz, 1H), 4.66 (d, J=4.4 Hz, 2H);
ESIMS m/z: [M+H]$^+$ 373.

Example 126

Step 1

5-[{6-(Trifluoromethyl)pyridin-3-yl}oxy]quinoline-8-carbonitrile (Compound 126-1)

Compound 126-1 (0.20 g, 54%) was obtained in the same manner as step 2 of example 50, using compound 123-1.
ESIMS m/z: [M+H]$^+$ 316.
Step 2

(5-[{6-(Trifluoromethyl)pyridin-3-yl}oxy]quinolin-8-yl)methanamine (Compound 126-2)

Compound 126-2 (0.020 g) was obtained as a crude product in the same manner as step 2 of example 57, using compound 126-1.
ESIMS m/z: [M+H]$^+$ 320.
Step 3

N-{(5-[{6-(Trifluoromethyl)pyridin-3-yl}oxy]quinolin-8-yl)methyl}acrylamide (Compound 219)

Compound 219 (0.055 g, 20% over two steps) was obtained in the same manner as step 1 of example 76, using compound 126-2.
$^1$H NMR (400 MHz, DMSO-d$_6$, δ): 9.00 (dd, J=4.2 Hz, 1H), 8.57 (d, J=2.4 Hz, 1H), 8.42 (dd, J=8.4, 1.5 Hz, 1H), 7.75 (d, J=7.8 Hz, 1H), 7.63 (d, J=8.4 Hz, 1H), 7.50 (dd, J=8.7, 4.2 Hz, 1H), 7.39-7.30 (m, 1H), 7.08-7.01 (m, 2H), 6.28 (dd, J=16.8, 1.5 Hz, 1H), 6.09 (dd, J=17.1, 10.2 Hz, 1H), 5.62 (dd, J=10.2, 1.5 Hz, 1H), 5.06 (d, J=6.3 Hz, 2H);
ESIMS m/z: [M+H]$^+$ 374.

Example 127

Step 1

5-Bromo-7-fluoroquinoline (Compound 127-1-1)

7-Bromo-5-fluoroquinoline (Compound 127-1-2)

3-Bromo-5-fluoroaniline hydrochloride (4.00 g, 17.66 mmol) and glycerol (3.26 g, 35.50 mmol) were dissolved in nitrobenzene (2 mL). Iron(II) sulfate heptahydrate (0.24 g, 0.06 mmol) and concentrated sulfuric acid (4.8 mL) were added to the solution. The mixture was stirred at 80° C. for 12 hours. The mixture was cooled to room temperature and neutralized with a saturated aqueous sodium hydrogen carbonate solution. The organic layer was extracted with ethyl acetate, dried over anhydrous sodium sulfate, and concentrated under reduced pressure. The residue was purified by silica gel column chromatography (hexane/ethyl acetate=95/5→90/10) to obtain a mixture (2.4 g) of compound 127-1-1 and compound 127-1-2.
ESIMS m/z: [M+H]$^+$ 226.
Step 2

7-Fluoroquinoline-5-carbonitrile (Compound 127-2-1)

5-Fluoroquinoline-7-carbonitrile (Compound 127-2-2)

The mixture (0.17 g) of compound 127-2-1 and compound 127-2-2 was obtained in the same manner as step 2 of example 50, using the mixture (0.27 g, 1.21 mmol) of compound 127-1-1 and compound 127-1-2.
ESIMS m/z: [M+H]$^+$ 173.
Step 3

7-Methoxyquinoline-5-carbonitrile (Compound 127-3-1)

5-Methoxyquinoline-7-carbonitrile (Compound 127-3-2)

The mixture (1.2 g, 6.97 mmol) of compound 127-2-1 and compound 127-2-2 was dissolved in THF (10 mL), and a 25% methanol solution of sodium methoxide (0.73 mL, 13.94 mmol) was added to the solution. The mixture was stirred at 100° C. for 30 minutes. The mixture was left to cool to room temperature, and water (50 mL) was added to the mixture. The organic layer was extracted with dichloromethane, dried over anhydrous sodium sulfate, and concentrated under reduced pressure. The residue was purified by silica gel column chromatography (hexane/ethyl acetate=80/20→70/30) to obtain compound 127-3-1 (0.50 g, 38%) and compound 127-3-2 (0.40 g, 31%).
Compound 127-3-1: $^1$H NMR (300 MHz, CDCl$_3$, δ): 8.95 (d, J=3.3 Hz, 1H), 8.45 (d, J=8.4 Hz, 1H), 7.65 (d, J=6.6 Hz, 2H), 7.49-7.45 (m, 1H), 3.99 (s, 3H).

Compound 127-3-2: $^1$H NMR (400 MHz, CDCl$_3$, δ): 9.01 (d, J=2.4 Hz, 1H), 8.60 (d, J=8.0 Hz, 1H), 8.07 (s, 1H), 7.54-7.50 (m, 1H), 6.96 (s, 1H), 4.05 (s, 3H).

Step 4

(7-Methoxyquinolin-5-yl)methanamine (Compound 127-4)

Compound 127-4 (0.45 g, 88%) was obtained in the same manner as step 2 of example 57, using compound 127-3-1.
ESIMS m/z: [M+H]$^+$ 189.

Step 5

5-(Aminomethyl)quinolin-7-ol (Compound 127-5)

Pyridine hydrochloride (0.15 g) was added to compound 127-4 (0.45 g, 2.39 mmol). The mixture was stirred at 180° C. for one hour using a microwave reactor. The mixture was left to cool to room temperature. A saturated aqueous sodium hydrogen carbonate solution (20 mL) was added to the mixture. The organic layer was extracted with dichloromethane, dried over anhydrous sodium sulfate, concentrated under reduced pressure to obtain compound 127-5 (0.40 g, 54%).
ESIMS m/z: [M+H]$^+$ 175.

Step 6

5-(Acrylamidemethyl)quinolin-7-yl acrylate (Compound 127-6)

Compound 127-6 (0.35 g, 54%) was obtained in the same manner as step 1 of example 76, using compound 127-5.
$^1$H NMR (300 MHz, DMSO-d$_6$, δ): 8.84 (dd, J=4.0, 1.2 Hz, 1H), 8.33 (d, J=8.0 Hz, 1H), 7.73 (d, J=2.0 Hz, 1H), 7.38-7.35 (m, 1H), 7.26 (d, J=2.4 Hz, 1H), 6.60 (dd, J=17.2, 0.8 Hz, 1H), 6.34-6.26 (m, 2H), 6.08-5.99 (m, 3H), 5.61 (dd, J=10.4, 1.2 Hz, 1H), 4.88 (d, J=6.0 Hz, 2H).

Step 7

N-{(7-Hydroxyquinolin-5-yl)methyl}acrylamide (Compound 127-7)

Compound 127-6 (0.11 g, 0.38 nmol) was dissolved in methanol (5 mL), and potassium carbonate (0.10 g, 0.77 mmol) was added to the solution. The mixture was stirred at 80° C. for 30 minutes. The mixture was left to cool to room temperature, and water (20 mL) was added to the mixture. The organic layer was extracted with dichloromethane, dried over anhydrous sodium sulfate, concentrated under reduced pressure to obtain compound 127-7 (0.20 g, 70%).
$^1$H NMR (400 MHz, DMSO-d$_6$, δ): 10.15 (s, 1H), 8.75-8.73 (m, 1H), 8.67-8.66 (m, 1H), 8.35 (d, J=8.0 Hz, 1H), 7.31 (dd, J=8.4, 4.4 Hz, 1H), 7.16-7.10 (m, 2H), 6.29 (dd, J=16.8, 10.0 Hz, 1H), 6.15 (dd, J=16.8, 2.0 Hz, 1H), 5.64 (dd, J=10.0, 2.4 Hz, 1H), 4.75 (d, J=6.0 Hz, 2H).

Step 8

N-([7-{4-(Trifluoromethyl)phenoxy}quinolin-5-yl]methyl)acrylamide (Compound 220)

Compound 220 (0.023 g, 14%) was obtained in the same manner as step 1 of example 3, using compound 127-7.
$^1$H NMR (400 MHz, CDCl$_3$, δ): 8.98 (s, 1H), 8.75-8.70 (m, 2H), 7.84 (d, J=7.6 Hz, 2H), 7.66 (bs, 1H), 7.43 (s, 2H), 7.35 (d, J=7.6 Hz, 2H), 6.30-6.12 (m, 2H), 5.64 (d, J=9.2 Hz, 1H), 4.87 (d, J=4.0 Hz, 2H);
ESIMS m/z: [M+H]$^+$ 373.

Example 128

Step 1

6-Fluoroquinoline-8-carbonitrile (Compound 128-1)

Compound 128-1 (0.25 g, 82%) was obtained in the same manner as step 2 of example 50, using 8-bromo-6-fluoroquinoline.
$^1$H NMR (300 MHz, CDCl$_3$, δ): 9.09 (d, J=3.0 Hz, 1H), 8.21 (dd, J=8.1, 1.2 Hz, 1H), 7.92 (dd, J=7.8, 2.7 Hz, 1H), 7.72 (dd, J=8.1, 2.7 Hz, 1H), 7.58 (dd, J=8.4, 4.2 Hz, 1H).

Step 2

6-Methoxyquinoline-8-carbonitrile (Compound 128-2)

Compound 128-2 (0.75 g, 64%) was obtained in the same manner as step 3 of example 127, using compound 128-1.
$^1$H NMR (400 MHz, CDCl$_3$, δ): 8.95 (dd, J=4.4, 2.0 Hz, 1H), 8.12 (dd, J=8.4, 1.6 Hz, 1H), 7.79 (d, J=2.8 Hz, 1H), 7.51-7.49 (m, 1H), 7.32 (d, J=2.8 Hz, 1H), 3.97 (s, 3H).

Step 3

(6-Methoxyquinolin-8-yl)methanamine (Compound 128-3)

Compound 128-3 (0.60 g, 90%) was obtained in the same manner as step 2 of example 57, using compound 128-2.
$^1$H NMR (300 MHz, CDCl3, δ): 8.76 (dd, J=4.0, 1.6 Hz, 1H), 8.04 (dd, J=8.4, 1.6 Hz, 1H), 7.38-7.26 (m, 2H), 6.96 (d, J=2.8 Hz, 1H), 4.37 (s, 2H), 3.92 (s, 3H).

Step 4

8-(Aminomethyl)quinolin-6-ol (Compound 128-4)

Compound 128-4 (0.20 g, 78%) was obtained in the same manner as step 5 of example 127, using compound 128-3.
ESIMS m/z: [M+H]$^+$ 175.

Step 5

8-(Acrylamidemethyl)quinolin-6-yl acrylate (Compound 128-5)

Compound 128-5 (0.11 g, 27%) was obtained in the same manner as step 1 of example 76, using compound 128-4.
ESIMS m/z: [M+H]$^+$ 283.

Step 6

N-{(6-Hydroxyquinolin-8-yl)methyl}acrylamide (Compound 128-6)

Compound 128-6 (0.070 g, 86%) was obtained in the same manner as step 7 of example 127, using compound 128-5.
ESIMS m/z: [M+H]$^+$ 229.

Step 7

N-([6-{4-(Trifluoromethyl)phenoxy}quinolin-8-yl]methyl)acrylamide (Compound 221)

Compound 221 (6.0 mg, 4%) was obtained in the same manner as step 1 of example 3, using compound 128-6.
$^1$H NMR (400 MHz, CDCl$_3$, δ): 8.90 (dd, J=4.4, 1.6 Hz, 1H), 8.11 (dd, J=8.4, 1.6 Hz, 1H), 7.65-7.52 (m, 3H), 7.49-7.46 (m, 1H), 7.31-7.24 (m, 2H), 7.14 (d, J=8.4 Hz, 2H), 6.26 (dd, J=16.8, 1.2 Hz, 1H), 6.10 (dd, J=16.8, 10.0 Hz, 1H), 5.61 (d, J=10.4, 1.6 Hz, 1H), 5.05 (d, J=6.0 Hz, 2H);

ESIMS m/z: [M+H]$^+$ 373.

Example 129

Step 1

4-Bromo-1-{4-(trifluoromethyl)phenoxy}isoquinoline (Compound 129-1)

Compound 129-1 (0.50 g) was obtained as a crude product in the same manner as step 2 of example 50, using 4-bromo-1-chloroisoquinoline.

ESIMS m/z: [M+H]$^+$ 369.

Step 2

1-{4-(Trifluoromethyl)phenoxy}isoquinoline-4-carbonitrile (Compound 129-2)

Compound 129-2 (0.20 g, 43% over two steps) was obtained in the same manner as step 1 of example 54, using compound 129-1.

$^1$H NMR (300 MHz, DMSO-d6, δ): 8.62 (s, 1H), 8.56 (d, J=8.1 Hz, 1H), 8.14-8.09 (m, 2H), 7.98-7.88 (m, 3H), 7.60 (d, J=8.7 Hz, 2H).

Step 3

[1-{4-(Trifluoromethyl)phenoxy}isoquinolin-4-yl]methanamine (Compound 129-3)

Compound 129-3 (0.15 g) was obtained as a crude product in the same manner as step 2 of example 57, using compound 129-2.

ESIMS m/z: [M+H]$^+$ 319.

Step 4

N-([1-{4-(Trifluoromethyl)phenoxy}isoquinolin-4-yl]methyl)acrylamide (Compound 222)

Compound 222 (0.070 g, 30% over two steps) was obtained in the same manner as step 1 of example 76, using compound 129-3.

$^1$H NMR (400 MHz, DMSO-d$_6$, δ): 8.58 (t, J=5.6 Hz, 1H), 8.42 (d, J=7 Hz, 1H), 8.12 (d, J=8.4 Hz, 1H), 7.95-7.91 (n, 2H), 7.84 (d, J=8.4 Hz, 2H), 7.78 (t, J=8.0 Hz, 1H), 7.49 (d, J=8.4 Hz, 2H), 6.25-6.11 (m, 2H), 5.61 (dd, J=9.6, 2.8 Hz, 1H), 4.71 (d, J=5.2 Hz, 2H);

ESIMS m/z: [M+H]$^+$ 373.

Example 130

Step 1

8-Fluoroisoquinoline-5-carbonitrile (Compound 130-1)

Compound 130-1 (0.30 g, 87%) was obtained in the same manner as step 1 of example 54, using 5-bromo-8-fluoroisoquinoline.

$^1$H NMR (400 MHz, DMSO-d6, δ): 9.64 (d, J=0.8 Hz, 1H), 8.88 (d, J=6.0 Hz, 1H), 8.53 (dd, J=8.0, 5.2 Hz, 1H), 8.03-8.01 (m, 1H), 7.75-7.71 (m, 1H).

Step 2

8-{4-(Trifluoromethyl)phenoxy}isoquinoline-5-carbonitrile (Compound 130-2)

Compound 130-2 (0.35 g, 76%) was obtained in the same manner as step 2 of example 50, using compound 130-1.

$^1$H NMR (400 MHz, DMSO-d$_6$, δ): 9.83 (s, 1H), 8.84 (d, J=6.0 Hz, 1H), 8.03 (dd, J=6.0 Hz, 1H), 7.88 (d, J=8.0 Hz, 1H), 7.77 (d, J=8.4 Hz, 2H), 7.31 (d, J=8.8 Hz, 2H), 6.86 (d, J=8.0 Hz, 1H).

Step 3

[8-{4-(Trifluoromethyl)phenoxy}isoquinolin-5-yl]methanamine (Compound 130-3)

Compound 130-3 (0.20 g, 66%) was obtained in the same manner as step 2 of example 57, using compound 130-2.

ESIMS m/z: [M+H]$^+$ 319,

Step 4

N-([8-{4-(Trifluoromethyl)phenoxy}isoquinolin-5-yl]methyl)acrylamide (Compound 223)

Compound 223 (0.028 g, 14%) was obtained in the same manner as step 1 of example 76, using compound 130-3.

$^1$H NMR (300 MHz, DMSO-d6, δ): 9.43 (d, J=0.8 Hz, 1H), 8.70-8.65 (m, 2H), 8.04 (dd, J=6.0, 1.2 Hz, 1H), 7.78 (d, J=8.8 Hz, 2H), 7.71 (d, J=8.0 Hz, 1H), 7.27-7.25 (m, 3H), 6.27 (dd, J=16.8, 10.0 Hz, 1H), 6.16 (dd, J=17.2, 2.4 Hz, 1H), 5.64 (dd, J=9.6, 2.0 Hz, 1H), 4.80 (d, J=6.0 Hz, 2H);

ESIMS m/z: [M+H]$^+$ 373.

Example 131

Step 1

1-Chloro-4-{4-(trifluoromethyl)phenoxy}isoquinoline (Compound 131-1)

Compound 131-1 (0.45 g, 25%) was obtained in the same manner as step 1 of example 3, using 1-chloroisoquinolin-4-ol.

ESIMS m/z: [M+H]$^+$ 324.

Step 2

4-{4-(Trifluoromethyl)phenoxy}isoquinoline-1-carbonitrile (Compound 131-2)

Compound 131-2 (0.32 g, 73%) was obtained in the same manner as step 1 of example 54, using compound 131-1.

$^1$H NMR (300 MHz, DMSO-d6, δ): 8.39 (s, 1H), 8.35-8.25 (m, 2H), 8.05-8.02 (m, 2H), 7.83 (d, J=8.7 Hz, 2H), 7.43 (d, J=8.4 Hz, 2H);

ESIMS m/z: [M+H]$^+$ 315.

Step 3

[4-{4-(Trifluoromethyl)phenoxy}isoquinolin-1-yl]methanamine (Compound 131-3)

Compound 131-2 (0.20 g, 0.63 mmol) was dissolved in ethanol (10 mL), and nickel chloride hexahydrate (0.010 g, 0.063 mmol) and sodium borohydride (0.070 g, 1.90 mmol) were added to the solution. The mixture was stirred at room temperature for 2 hours. The mixture was filtered with Celite®. The filtrate was concentrated under reduced pressure to obtain compound 131-3 (0.20 g) as a crude product.

ESIMS m/z: [M+H]$^+$ 319.

Step 4

N-([4-{4-(Trifluorophenyl)phenoxy}isoquinolin-1-yl]methyl)acrylamide (Compound 224)

Compound 224 (0.050 g, 22% over two steps) was obtained in the same manner as step 1 of example 76, using compound 131-3.

$^1$H NMR (400 MHz, DMSO-d6, δ): 8.75-8.74 (m, 1H), 8.40 (d, J=8.0 Hz, 1H), 8.33 (s, 1H), 7.94 (d, J=7.6 Hz, 1H), 7.86-7.77 (m, 2H), 7.74 (d, J=8.8 Hz, 2H), 7.17 (d, J=8.4 Hz, 2H), 6.39-6.32 (m, 1H), 6.19-6.14 (m, 1H), 5.63 (dd, J=10.0, 2.0 Hz, 1H), 5.03 (d, J=5.6 Hz, 2H);
ESIMS m/z: [M+H]$^+$ 373.

Example 132

Step 1

8-Bromo-5-methoxyisoquinoline (Compound 132-1)

5-Methoxyisoquinoline (0.20 g, 1.25 mmol) was dissolved in acetic acid (5 mL), and bromine (0.20 g, 1.25 mmol) was added to the solution at 0° C. The mixture was stirred at room temperature for 16 hours. Water (50 mL) was added to the mixture. The organic layer was extracted with ethyl acetate, dried over anhydrous sodium sulfate, and concentrated under reduced pressure. The residue was purified by silica gel column chromatography (heptane/ethyl acetate=80/20→70/30) to obtain compound 132-1 (0.10 g, 33%).

$^1$H NMR (300 MHz, CDCl$_3$, δ): 9.53 (s, 1H), 8.61 (d, J=5.7 Hz, 1H), 7.99 (d, J=5.7 Hz, 1H), 7.71 (d, J=8.1 Hz, 1H), 6.85 (d, J=8.1 Hz, 1H), 4.00 (s, 3H).

Step 2

5-Methoxyisoquinoline-8-carbonitrile (Compound 132-2)

Compound 132-2 (0.30 g, 77%) was obtained in the same manner as step 1 of example 54, using compound 132-1.

$^1$H NMR (400 MHz, CDCl$_3$, δ): 9.58 (s, 1H), 8.71 (d, J=6.0 Hz, 1H), 8.05 (d, J=5.6 Hz, 1H), 7.96 (d, J=8.4 Hz, 1H), 7.02 (d, J=8.4 Hz, 1H), 4.10 (s, 3H).

Step 3

{5-Methoxyisoquinolin-8-yl}methanamine (Compound 132-3)

Compound 132-3 (0.17 g, 66%) was obtained in the same manner as step 2 of example 57, using compound 132-2.
ESIMS m/z: [M+H]$^+$ 189.

Step 4

8-(Aminomethyl)isoquinolin-5-ol hydrobromide (Compound 132-4)

Compound 132-4 (0.20 g, 49%) was obtained in the same manner as step 6 of example 27, using compound 132-3.
ESIMS m/z: [M+H]$^+$ 175.

Step 5 tert-Butyl ([5-{(tert-butoxycarbonyl)oxy}isoquinolin-8-yl]methyl)carbamate (Compound 132-5)

Compound 132-4 (1.0 g, 3.93 mmol) was dissolved in dichloromethane (15 mL), and diisopropylethylamine (2.1 mL, 11.7 mmol) and di-tert-butyl dicarbonate (6.0 mL, 27.55 mmol) were added to the solution. The mixture was stirred at room temperature for 16 hours. Water (50 mL) was added to the mixture. The organic layer was extracted with tert-butyl methyl ether, dried over anhydrous sodium sulfate, and concentrated under reduced pressure. The residue was purified by silica gel column chromatography (heptane/ethyl acetate=60/40→50/50) to obtain compound 132-5 (0.60 g, 41%).

$^1$H NMR (400 MHz, DMSO-d6, δ): 9.61 (s, 1H), 8.62 (d, J=6.0 Hz, 1H), 7.69 (d, J=5.6 Hz, 1H), 7.64-7.62 (m, 2H), 7.54 (d, J=7.6 Hz, 1H), 4.70 (d, J=6.0 Hz, 2H), 1.53 (s, 9H), 1.39 (s, 9H).

Step 6 tert-Butyl {(5-hydroxyisoquinolin-8-yl)methyl}carbamate (Compound 132-6)

Compound 132-5 (0.60 g, 1.60 mmol) was dissolved in methanol (10 mL), and potassium carbonate (0.44 g, 3.20 mmol) was added to the solution. The mixture was stirred at 60° C. for 30 minutes. The mixture was left to cool to room temperature, and water (20 mL) was added to the mixture. The organic layer was extracted with dichloromethane, dried over anhydrous sodium sulfate, concentrated under reduced pressure to obtain compound 132-6 (0.50 g, 61%).

$^1$H NMR (400 MHz, DMSO-d6, δ): 10.50 (bs, 1H), 9.42 (s, 1H), 8.48 (d, J=5.6 Hz, 1H), 7.94 (d, J=5.6 Hz, 1H), 7.45-7.44 (m, 1H), 7.32 (d, J=7.6 Hz, 1H), 7.00 (d, J=8.0 Hz, 1H), 4.55 (d, J=5.6 Hz, 2H), 1.38 (s, 9H).

Step 7 tert-Butyl ([5-{4-(trifluoromethyl)phenoxy}isoquinolin-8-yl]methyl)carbamate (Compound 132-7)

Compound 132-7 (0.28 g, 36%) was obtained in the same manner as step 1 of example 3, using compound 132-6.
ESIMS m/z: [M+H]$^+$ 419.

Step 8

[5-{4-(Trifluoromethyl)phenyloxy}isoquinolin-8-yl]methanamine hydrochloride (Compound 132-8)

Compound 132-7 (0.30 g, 0.71 mmol) was dissolved in dichloromethane (10 mL), and a 4 mol/L hydrochloric acid solution in dioxane (0.04 mL, 1.43 mmol) was added to the solution at 0° C. The mixture was stirred for 16 hours. The mixture was concentrated under reduced pressure. The solid obtained was washed with tert-butyl methyl ether to obtain compound 132-8 (0.15 g, 59%).
ESIMS m/z: [M+H]$^+$ 319.

Step 9

N-([5-{4-(Trifluoromethyl)phenoxy}isoquinolin-8-yl]methyl)acrylamide (Compound 225)

Compound 132-8 (0.10 g, 0.28 mmol) was dissolved in DMF (5 mL), and added to the solution at 0° C. were diisopropylamine (0.10 mL, 0.56 mmol), O-(7-azabenzotriazol-1-yl)-N,N,N',N'-tetramethyluronium hexafluorophosphate (0.12 g, 0.33 mmol), and acrylic acid (0.040 g, 0.56 mmol). The mixture was stirred at room temperature for 16 hours. Water (10 mL) was added to the mixture. The organic layer was extracted with dichloromethane, dried over anhydrous sodium sulfate, and concentrated under reduced pressure. The residue was purified using a preparative HPLC to obtain compound 225 (6.0 mg, 6%).

$^1$H NMR (400 MHz, CDCl$_3$, δ): 9.47 (s, 1H), 8.55 (s, 1H), 7.86 (d, J=5.6 Hz, 1H), 7.55 (d, J=8.8 Hz, 2H), 7.45 (d, J=8.0 Hz, 1H), 7.09 (d, J=8.0 Hz, 1H), 7.02 (d, J=8.4 Hz, 2H), 6.30 (dd, J=16.8, 1.2 Hz, 1H), 6.05 (d, J=17.2, 10.4 Hz, 1H), 5.91 (bs, 1H), 5.64 (dd, J=10.0, 0.8 Hz, 1H), 5.04 (d, J=5.6 Hz, 2H);
ESIMS m/z: [M+H]$^+$ 373.

Example 133

Step 1

1,7-Naphthyridin-8-amine (Compound 133-1)

Commercially available pyridine-2,3-diamine (2.0 g, 18.34 mmol) was dissolved in concentrated sulfuric acid (10 mL) and water (20 mL), and glycerol (6.69 mL, 91.74 mmol) and sodium 3-nitrobenzenesulfonate (8.25 g, 36.69 mmol) were added to the solution. The mixture was stirred at 135° C. for 36 hours. The mixture was cooled, and a 6 mol/L aqueous sodium hydroxide solution was added to the mixture to bring pH to 10. Thereafter, the organic layer was extracted with ethyl acetate, dried over anhydrous sodium sulfate, and concentrated under reduced pressure. The residue was purified by silica gel column chromatography (dichloromethane/methanol=100/0→92/8) to obtain compound 133-1 (0.50 g, 20%).

$^1$H NMR (400 MHz, DMSO-d$_6$, δ): 8.78 (dd, J=4.0 Hz, 1.6 Hz, 1H), 8.16 (dd, J=6.8 Hz, 1.6 Hz, 1H), 7.85 (d, J=5.6 Hz, 1H), 7.66 (dd, J=8.4 Hz, 4.4 Hz, 1H), 6.94 (s, 2H), 6.91 (d, J=5.6 Hz, 1H).

Step 2

5-Bromo-1,7-naphthyridin-8-amine (Compound 133-2)

Compound 133-1 (0.50 g, 3.44 mmol) was dissolved in acetic acid (5 mL), and bromine (1.18 mL) was added to the solution. The mixture was stirred at 90° C. for 3 hours. The mixture was cooled, and ammonia water was added to the mixture to bring pH to 7. Thereafter, the precipitated solid was filtered off and dried under reduced pressure to obtain compound 133-2 (0.45 g, 53%).

$^1$H NMR (300 MHz, DMSO-d$_6$, δ): 8.87-8.86 (m, 1H), 8.24 (d, J=8.4 Hz, 1H), 8.05 (s, 1H), 7.84 (dd, J=7.8 Hz, 4.2 Hz, 1H), 7.23 (s, 2H).

Step 3

5-Bromo-8-chloro-1,7-naphthyridine (Compound 133-3)

Compound 133-2 (0.45 g, 3.10 mmol) was dissolved in concentrated hydrochloric acid (5 mL) and water (5 mL), and sodium nitrite (1.05 g, 15.51 mmol) dissolved in water (5 mL) was added dropwise to the solution at −10° C. The mixture was stirred at room temperature for one hour. The mixture was cooled, and a saturated aqueous sodium hydrogen carbonate solution was added to the mixture to bring pH to 8. The organic layer was extracted with dichloromethane, dried over anhydrous sodium sulfate, and concentrated under reduced pressure. The residue was purified by silica gel column chromatography (hexane/ethyl acetate=80/20→60/40) to obtain compound 133-3 (0.15 g, 30%/).

$^1$H NMR (400 MHz, DMSO-d$_6$, δ): 9.24 (dd, J=4.0 Hz, 1.2 Hz, 1H), 8.72 (s, 1H), 8.59 (dd, J=8.4 Hz, 1.6 Hz, 1H), 8.58 (dd, J=8.8 Hz, 4.4 Hz, 1H).

Step 4

5-Bromo-8-(4-chlorophenoxy)-1,7-naphthyridine (Compound 133-4)

Compound 133-3 (0.50 g, 2.05 mmol) was dissolved in dimethylformamide (10 mL), and 4-chlorophenol (0.31 g, 2.46 mmol) and potassium carbonate (0.56 g, 4.11 mmol) were added to the solution. The mixture was stirred at 100° C. for one hour using a microwave reactor. The mixture was cooled, and water was added to the mixture. The organic layer was extracted with ethyl acetate, dried over anhydrous sodium sulfate, and concentrated under reduced pressure. The residue was purified by silica gel column chromatography (hexane/ethyl acetate=90/10→50/50) to obtain compound 133-4 (0.50 g, 72%).

$^1$H NMR (400 MHz, DMSO-d$_6$, δ): 9.15 (dd, J=4.4 Hz, 1.6 Hz, 1H), 8.50 (dd, J=8.4 Hz, 1.6 Hz, 1H), 8.30 (s, 1H), 8.02 (dd, J=8.8 Hz, 4.4 Hz, 1H), 7.53 (dd, J=6.8 Hz, 2.0 Hz, 2H), 7.33 (dd, J=6.8 Hz, 2.4 Hz, 2H).

Step 5 tert-Butyl {8-(4-chlorophenoxy)-1,7-naphthyridin-5-yl}carbamate (Compound 133-5)

Compound 133-4 (0.25 g, 0.75 mmol) was dissolved in dimethylacetamide (5 mL), and tert-butyl carbamate (0.175 g, 1.501 mmol), sodium tert-butoxide (0.144 g, 1.501 mmol), and X-phos (0.035 g, 0.075 mmol) were added to the solution. The mixture was purged with nitrogen. Tris(dibenzylideneacetone)dipalladium (0.034 g, 0.037 mmol) was added to the mixture. The mixture was stirred at 150° C. for one hour using a microwave reactor. The mixture was cooled, and water was added to the mixture. The organic layer was extracted with ethyl acetate, dried over anhydrous sodium sulfate, and concentrated under reduced pressure. The residue was purified by silica gel column chromatography (hexane/ethyl acetate=90/10→10/90) to obtain compound 133-5 (0.11 g, 40%).

$^1$H NMR (400 MHz, DMSO-d$_6$, δ): 9.31 (s, 1H), 9.06 (d, J=2.8 Hz, 1H), 8.40 (d, J=7.6 Hz, 1H), 8.01 (s, 1H), 7.88 (dd, J=8.8 Hz, 4.4 Hz, 1H), 7.50 (d, J=8.8 Hz, 2H), 7.28 (d, J=8.8 Hz, 2H), 1.47 (s, 9H).

Step 6

8-(4-Chlorophenoxy)-1,7-naphthyridin-5-amine hydrochloride (Compound 133-6)

Compound 133-5 (0.110 g, 0.296 mmol) was dissolved in dichloromethane (10 mL), and a 4 mol/L hydrochloric acid solution in 1,4-dioxane (2.0 mL) was added to the solution at 0° C. The mixture was stirred at room temperature for 4 hours. The mixture was concentrated under reduced pressure, and the crystals obtained were washed with tert-butyl methyl ether to obtain compound 133-6 (0.05 g, 62%).

ESIMS m/z: [M+H]$^+$ 272.

Step 7

N-{8-(4-chlorophenoxy)-1,7-naphthyridin-5-yl}acrylamide (Compound 226)

Compound 226 (15 mg, 25%) was obtained in the same manner as step 5 of example 1, using compound 133-6.

¹H NMR (400 MHz, DMSO-d₆, δ): 10.23 (s, 1H), 9.09 (d, J=2.4 Hz, 1H), 8.41 (d, J=8.4 Hz, 1H), 8.20 (s, 1H), 7.92 (dd, J=8.4 Hz, 4.0 Hz, 1H), 7.52 (d, J=9.2 Hz, 2H), 7.31 (d, J=8.8 Hz, 2H), 6.62 (dd, J=17.2 Hz, 10.8 Hz, 1H), 6.30 (dd, J=17.2 Hz, 1.6 Hz, 1H), 5.86-5.84 (m, 1H).
ESIMS m/z: [M+H]⁺ 326.

Example 134

Step 1

8-(4-Chlorophenoxy)-1,7-naphthyridine-5-carbonitrile (Compound 134-1)

Compound 133-4 (0.25 g, 0.75 mmol) was dissolved in dimethylformamide (5 mL), and zinc cyanide (0.113 g, 1.12 mmol) was added to the solution. The mixture was purged with nitrogen. Tetrakis(triphenylphosphine)palladium (0.043 g, 0.037 mmol) was added to the mixture, and the mixture was stirred at 150° C. for one hour using a microwave reactor. The mixture was cooled, and water was added to the mixture. The organic layer was extracted with ethyl acetate, dried over anhydrous sodium sulfate, and concentrated under reduced pressure. The residue was purified by silica gel column chromatography (hexane/ethyl acetate=90/10→30/70) to obtain compound 134-1 (0.10 g, 47%).
ESIMS m/z: [M+H]⁺ 282.

Step 2

{8-(4-Chlorophenoxy)-1,7-naphthyridin-5-yl}methanamine (Compound 134-2)

Compound 134-1 (0.10 g, 0.35 mmol) was dissolved in ethanol (10 mL), and ammonia water (1.0 mL) and Raney nickel (0.050 g) were added to the solution. The mixture was stirred under hydrogen atmosphere at room temperature for 2 hours. The mixture was filtered with Celite®, and the filtrate was concentrated under reduced pressure to obtain compound 134-2 (0.08 g, 79%).
ESIMS m/z: [M+H]⁺ 286.

Step 3

N-[{8-(4-Chlorophenoxy)-1,7-naphthyridin-5-yl}methyl]acrylamide (Compound 227)

Compound 227 (18 mg, 19%) was obtained in the same manner as step 5 of example 1, using compound 134-2.
H NMR (300 MHz, DMSO-d₆, δ): 9.08-9.07 (m, 1H), 8.62 (t, J=5.1 Hz, 1H), 8.56-8.53 (m, 1H), 7.98 (s, 1H), 7.92 (dd, J=8.4 Hz, 4.2 Hz, 1H), 7.52 (d, J=8.7 Hz, 2H), 7.27 (d, J=9.0 Hz, 2H), 6.25-6.15 (m, 2H), 5.63-5.94 (m, 1H), 4.70 (d, J=5.4 Hz, 2H).
ESIMS m/z: [M+H]⁺ 340.

Example 135

Step 1

6,7-Dihydroisoquinolin-8(5H)-one (Compound 135-1)

Commercially available 5,6,7,8-tetrahydroisoquinoline (1.00 g, 7.51 mmol) was dissolved in water (33.4 mL) and acetic acid (0.56 mL), and potassium permanganate (2.67 g, 16.9 mmol) was added to the solution. The mixture was stirred at room temperature for 30 minutes. The mixture was filtered with Celite®, and a saturated aqueous sodium bicarbonate solution was added to the filtrate. The organic layer was extracted with dichloromethane, dried over anhydrous magnesium sulfate, and concentrated under reduced pressure. The residue was purified by silica gel column chromatography (heptane/ethyl acetate=80/20→50/50) to obtain compound 135-1 (0.17 g, 16%).
¹H NMR (400 MHz, CDCl3, δ): 9.17 (s, 1H), 8.62 (d, J=5.1 Hz, 1H), 7.20 (dd, J=5.1, 0.7 Hz, 1H), 2.97 (t, J=6.1 Hz, 2H), 2.70 (t, J=6.5 Hz, 2H), 2.22-2.15 (m, 2H).
ESIMS m/z: [M+H]⁺ 148.

Step 2

5,6,7,8-Tetrahydroisoquinolin-8-ol (Compound 135-2)

Compound 135-2 (0.17 g, 95%) was obtained in the same manner as step 1 of example 15, using compound 135-1 (0.17 g, 1.17 mmol).
¹H NMR (400 MHz, CDCl3, δ): 8.63 (s, 1H), 8.35 (d, J=5.2 Hz, 1H), 7.01 (d, J=5.2 Hz, 1H), 4.87 (t, J=4.5 Hz, 1H), 2.85-2.78 (m, 1H), 2.72-2.68 (m, 1H), 2.17 (br, 1H), 2.07-1.90 (m, 3H), 1.85-1.76 (m, 1H).
ESIMS m/z: [M+H]⁺ 150.

Step 3

8-{4-(Trifluoromethyl)phenoxy}-5,6,7,8-tetrahydroisoquinoline (Compound 135-3)

Compound 135-3 (0.31 g, 95%) was obtained in the same manner as step 4 of example 33, using compound 135-2 (0.17 g, 1.11 mmol) and 4-(trifluoromethyl)phenol (0.22 g, 1.33 mmol).
¹H NMR (400 MHz, CDCl3, δ): 8.55 (s, 1H), 8.43 (d, J=4.9 Hz, 1H), 7.59 (d, J=8.5 Hz, 2H), 7.10 (d, J=4.9 Hz, 1H), 7.08 (d, J=8.5 Hz, 2H), 5.49 (t, J=3.8 Hz, 1H), 2.91 (dt, J=17.7, 4.6 Hz, 1H), 2.79-2.74 (m, 1H), 2.26-2.20 (m, 1H), 2.09-1.98 (m, 2H), 1.87-1.82 (m, 1H).
ESIMS m/z: [M+H]⁺ 294.

Step 4

8-{4-(Trifluoromethyl)phenoxy}-5,6,7,8-tetrahydroisoquinoline-2-oxide (Compound 135-4)

Compound 135-3 (0.31 g, 1.05 mmol) was dissolved in dichloromethane (5.2 mL), and m-chloroperoxybenzoic acid (0.62 g, 2.32 mmol) was added to the solution. The mixture was stirred at room temperature for one hour. The mixture was basified by the addition of a 4 mol/L aqueous sodium hydroxide solution, and a saturated aqueous sodium thiosulfate solution was added to the mixture. The organic layer was extracted with chloroform/methanol, dried over anhydrous sodium sulfate, and concentrated under reduced pressure. The residue was dried over anhydrous magnesium sulfate and concentrated under reduced pressure to obtain compound 135-4 as a crude product.
ESIMS m/z: [M+H]⁺ 310.

Step 5

8-{4-(Trifluoromethyl)phenoxy}-5,6,7,8-tetrahydroisoquinolin-5-ol (Compound 135-5)

Compound 135-4 as a crude product was dissolved in ethyl acetate (10.5 mL), and triethylamine (0.44 mL, 3.16 mmol) was added to the solution. Trifluoroacetic acid anhydride (0.30 mL, 2.11 mmol) was added to the mixture, and the mixture was stirred at room temperature for 4 hours. The mixture was concentrated under reduced pressure. Ethanol (5.0 mL) and a 2 mol/L aqueous sodium hydroxide solution (2.0 mL) were added to the residue, and the mixture was stirred at room temperature for one hour. Water was added to the mixture. The organic layer was extracted with ethyl acetate, dried over anhydrous magnesium sulfate, and concentrated under reduced pressure. The residue was amino-silica gel column chromatography (chloroform/methanol=100/0→90/10→85/15) to obtain compound 135-5 (145 mg) as a crude product.
ESIMS m/z: [M+H]$^+$ 310.
Step 6

8-{4-(Trifluoromethyl)phenoxy}-7,8-tetrahydroisoquinolin-5(6H)-one (Compound 135-6)

Compound 135-5 was dissolved in dichloromethane (4.7 mL), and Dess-Martin Periodinane (0.24 mg, 0.57 mmol) was added to the solution. The mixture was stirred at room temperature for 30 minutes. A saturated aqueous sodium bicarbonate solution was added to the mixture. The organic layer was extracted with chloroform, dried over anhydrous magnesium sulfate, and concentrated under reduced pressure. The residue was purified by silica gel column chromatography (chloroform/methanol=90/10→50/50) to obtain compound 135-6 (0.11 mg, 35% in three stages).
$^1$H NMR (400 MHz, CDCl3, δ): 8.87 (s, 1H), 8.84 (d, J=5.0 Hz, 1H), 7.85 (d, J=5.0 Hz, 1H), 7.63 (d, J=9.1 Hz, 2H), 7.12 (d, J=9.1 Hz, 2H), 5.68 (dd, J=5.9, 3.6 Hz, 1H), 3.05 (ddd, J=17.7, 9.3, 5.2 Hz, 1H), 2.73 (ddd, J=17.7, 6.8, 5.2 Hz, 1H), 2.56-2.49 (m, 2H).
ESIMS m/z: [M+H]$^+$ 308.
Step 7

8-{4-(Trifluoromethyl)phenoxy}-5,6,7,8-tetrahydroisoquinolin-5-amine (Compound 135-7)

Compound 135-7 was obtained as a crude product in the same manner as step 2 of example 3, using compound 135-6 (40.0 mg, 0.13 mmol).
ESIMS m/z: [M+H]$^+$ 309.
Step 8

N-[8-{4-(Trifluoromethyl)phenoxy}-5,6,7,8-tetrahydroisoquinolin-5-yl]acrylamide (Compound 228)

Compound 228 (1.00 mg, 2% over two steps) was obtained in the same manner as step 3 of example 17, using compound 135-7.
$^1$H NMR (400 MHz, CDCl3, δ): 8.59 (s, 1H), 8.55 (d, J=5.4 Hz, 1H), 7.60 (d, J=8.8 Hz, 2H), 7.30 (d, J=5.4 Hz, 1H), 7.06 (d, J=8.8 Hz, 2H), 6.42 (dd, J=16.7, 1.0 Hz, 1H), 6.18 (dd, J=16.7, 10.3 Hz, 1H), 5.85 (d, J=9.0 Hz, 1H), 5.79 (dd, J=10.3, 1.0 Hz, 1H), 5.48 (t, J=3.1 Hz, 1H), 5.34 (td, J=9.4, 5.4 Hz, 1H), 2.39-2.34 (m, 1H), 2.17-1.99 (m, 3H).
ESIMS m/z: [M+H]$^+$ 363.

Example 136

N-(8-[{6-(Trifluoromethyl)pyridin-3-yl}oxy]chroman-3-yl)acrylamide (Compounds 229 and 230)

Compound 51 was optically resolved under the following chiral preparative conditions to obtain compound 229 (137 mg, 45%) having a retention time of 2.61 minutes and compound 230 (135 mg, 44%) having a retention time of 3.28 minutes.
Compound 229: ESIMS m/z: [M+H]$^+$ 365.
Compound 230: ESIMS m/z: [M+H]$^+$ 365.
Chiral Preparative Conditions
  Apparatus used: SFC30 manufactured by Waters
  Column used: CHIRALPAK® IA/SFC 10 mmϕ×250 mm, 5 μM
  Temperature: 40° C.
  Liquid feeding condition: 88% carbon dioxide/12% isopropanol
  Preparative time: 5 minutes
  Flow rate: 30 mL/minute
  Retention time: 2.61 minutes (compound 229), 3.28 minutes (compound 230)

Example 137

N-(6-Bromo-8-[{6-(trifluoromethyl)pyridin-3-yl}oxy]chroman-3-yl)acrylamide (Compounds 231 and 232)

Compound 153 was optically resolved under the following chiral preparative conditions to obtain compound 231 (7.6 mg, 36%) having a retention time of 2.44 minutes and compound 232 (8.1 mg, 39%) having a retention time of 3.24 minutes.
Compound 231: ESIMS m/z: [M+H]$^+$ 443, 445.
Compound 232: ESIMS m/z: [M+H]$^+$ 443, 445.
Chiral Preparative Conditions
  Apparatus used: SFC30 manufactured by Waters
  Column used: CHIRALPAK® IA/SFC 10 mmϕ×250 mm, 5 μM
  Temperature: 40° C.
  Liquid feeding condition: 86% carbon dioxide/14% methanol
  Preparative time: 5 minutes
  Flow rate: 30 mL/minute
  Retention time: 2.44 minutes (compound 231), 3.24 minutes (compound 232)

Example 138

N-[4-Oxo-8-{4-(tolyloromethyl)phenoxy}chroman-3-yl]acrylamide (Compounds 233 and 234)

Compound 40 was optically resolved under the following chiral preparative conditions to obtain compound 233 (24 mg, 48%) having a retention time of 4.56 minutes and compound 234 (22 mg, 44%) having a retention time of 5.07 minutes.
Compound 233: ESIMS m/z: [M+H]$^+$ 378.
Compound 234: ESIMS m/z: [M+H]$^+$ 378.
Chiral Preparative Conditions
  Apparatus used: SFC30 manufactured by Waters
  Column used: CHIRALPAK® ID/SFC 10 mmϕ×250 mm, 5 μM
  Temperature: 40° C.
  Liquid feeding condition: 88% carbon dioxide/12% methanol
  Preparative time: 10 minutes
  Flow rate: 30 mL/minute
  Retention time: 4.56 minutes (compound 233), 5.07 minutes (compound 234)

Example 139

N-(6-Bromo-8-[{6-(trifluoromethyl)pyridin-3-yl}oxy]chroman-3-yl)acrylamide (Compounds 235 and 236)

Compound 153 was optically resolved under the following chiral preparative conditions to obtain compound 235

(13.5 mg, 45%) having a retention time of 3.67 minutes and compound 236 (12 mg, 40%) having a retention time of 4.35 minutes.

Compound 235: ESIMS m/z: [M+H]$^+$ 345.
Compound 236: ESIMS m/z: [M+H]$^+$ 345.

Chiral Preparative Conditions
Apparatus used: SFC30 manufactured by Waters
Column used: CHIRALPAK® IC/SFC 10 mmφ×250 mm, 5 μM
Temperature: 40° C.
Liquid feeding condition: 88% carbon dioxide/12% methanol
Preparative time: 10 minutes
Flow rate: 30 mL/minute
Retention time: 3.67 minutes (compound 235), 4.35 minutes (compound 236)

Example 140

N-[8-Methoxy-7-{4-(trifluoromethyl)phenoxy}chroman-4-yl]acrylamide (Compounds 237 and 238)

Compound 33 was optically resolved under the following chiral preparative conditions to obtain compound 237 having a retention time of 5.14 minutes and compound 238 having a retention time of 6.79 minutes.

Compound 237: ESIMS m/z: [M+H]$^+$ 394.
Compound 238: ESIMS m/z: [M+H]$^+$ 394.

Chiral Preparative Conditions
Apparatus used: SFC30 manufactured by Waters
Column used: CHIRALPAK® IA/SFC 10 mmφ×250 mm, 5 μM
Temperature: 40° C.
Liquid feeding condition: 95% carbon dioxide/5% methanol→93% carbon dioxide/7% methanol
Preparative time: 10 minutes
Flow rate: 30 mL/minute
Retention time: 5.14 minutes (compound 237), 6.79 minutes (compound 238)

Example 141

N-[8-Fluoro-7-{4-(trifluoromethyl)phenoxy}chroman-4-yl]acrylamide (Compounds 239 and 240)

Compound 31 was optically resolved under the following chiral preparative conditions to obtain compound 239 having a retention time of 6.19 minutes and compound 240 having a retention time of 7.43 minutes.

Compound 239: ESIMS m/z: [M+H]$^+$ 382.
Compound 240: ESIMS m/z: [M+H]$^+$ 382.

Chiral Preparative Conditions
Apparatus used: SFC30 manufactured by Waters
Column used: CHIRALPAK® IB/SFC 10 mmφ×250 mm, 5 μM
Temperature: 40° C.
Liquid feeding condition: 96% carbon dioxide/4% methanol
Preparative time: 10 minutes
Flow rate: 30 mL/minute
Retention time: 6.19 minutes (compound 239), 7.43 minutes (compound 240)

Example 142

Step 1 cis-N-[2-Chloro-8-{4-(trifluoromethyl)phenoxy}-5,6,7,8-tetrahydroquinolin-5-yl]acrylamide (Compounds 241 and 242)

Compound 76 was optically resolved under the following chiral preparative conditions to obtain compound 241 having a retention time of 2.73 minutes and compound 242 having a retention time of 3.41 minutes.

Compound 241: ESIMS m/z: [M+H]$^+$ 397.
Compound 242: ESIMS m/z: [M+H]$^+$ 397.

Chiral Preparative Conditions
Apparatus used: SFC30 manufactured by Waters
Column used: CHIRALPAK® IC/SFC 10 mmφ×250 mm, 5 μM
Temperature: 40° C.
Liquid feeding condition: 88% carbon dioxide/12% (chloroform:methanol=1:1)
Preparative time: 4 minutes
Flow rate: 30 mL/minute
Retention time: 2.73 minutes (compound 241), 3.41 minutes (Compound 242)

The invention claimed is:

1. An α,β-unsaturated amide compound or a pharmaceutically acceptable salt thereof represented by the following formula (I):

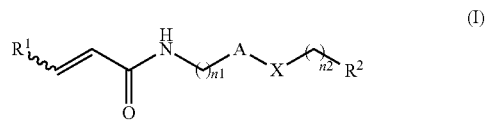

wherein
R$^1$ represents hydrogen atom,
R$^2$ represents optionally substituted aryl, optionally substituted cycloalkyl, optionally substituted aliphatic heterocyclic group or optionally substituted aromatic heterocyclic group,
X represents —O—, —S—, —SO$_2$—, —CHR$^{X2}$— wherein, R$^{X2}$ represents hydrogen atom or hydroxy, —CH=CH—, or —CO—,
n1 and n2 are the same or different, and each represents 0 or 1, and
"A" represents optionally substituted heterocyclic diyl, wherein the heterocyclic diyl in the optionally substituted heterocyclic diyl is heterocyclic diyl selected from the group consisting of the following formulae (A4-1), (A4-2), (A4-3), and (A4-4):

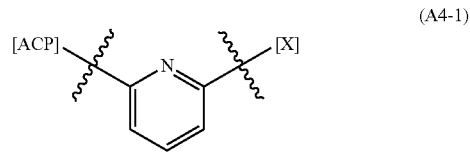

-continued

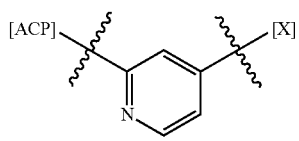 (A4-2)

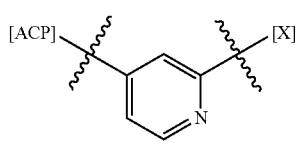 (A4-3)

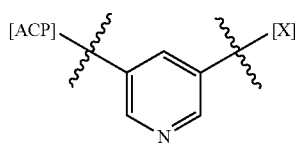 (A4-4)

wherein —[X] represents bonding position of the group represented in formula (A-1):

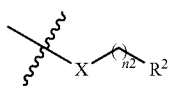 (A-1)

wherein X, R² and n2 are each the same as the definition described above,

[ACP] represents bonding position of the group represented in formula (A-2):

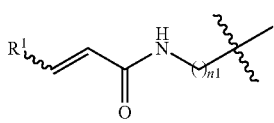 (A-2)

wherein R¹ and n1 are each the same as the definition described above.

2. A pharmaceutical composition comprising the α,β-unsaturated amide compound or a pharmaceutically acceptable salt thereof according to claim 1 and a carrier.

3. A method for the treatment of cancer, comprising:
administrating the α,β-unsaturated amide compound or a pharmaceutically acceptable salt thereof according to claim 1 to a subject.

* * * * *